United States Patent
Anish et al.

(10) Patent No.: US 10,596,272 B2
(45) Date of Patent: Mar. 24, 2020

(54) **VACCINES AGAINST *STREPTOCOCCUS PNEUMONIAE* SEROTYPE 5**

(71) Applicant: Max-Planck-Gesellschaft zur Förderung der Wissenschaften e.V., Munich (DE)

(72) Inventors: Chakkumkal Anish, The Hague (NL); Marilda Lisboa, Berlin (DE); Christopher Martin, Tuttlingen (DE); Claney Lebev Pereira, Berlin (DE); Peter H. Seeberger, Kleinmachnow (DE); Naeem Khan, Berlin (DE)

(73) Assignee: Max-Planck-Gesellschaft zur Förderung der Wissenschaften e.V., Munich (DE)

( * ) Notice: Subject to any disclaimer, the term of this patent is extended or adjusted under 35 U.S.C. 154(b) by 139 days.

(21) Appl. No.: 15/580,069

(22) PCT Filed: Jan. 26, 2016

(86) PCT No.: PCT/EP2016/051608
§ 371 (c)(1),
(2) Date: Dec. 6, 2017

(87) PCT Pub. No.: WO2016/198170
PCT Pub. Date: Dec. 15, 2016

(65) Prior Publication Data
US 2018/0296687 A1 Oct. 18, 2018

(30) Foreign Application Priority Data
Jun. 8, 2015 (EP) .................................. 15171079

(51) Int. Cl.
| | | |
|---|---|---|
| *A61K 31/702* | (2006.01) | |
| *A61K 31/7016* | (2006.01) | |
| *A61K 39/09* | (2006.01) | |
| *A61K 31/7028* | (2006.01) | |
| *A61K 39/00* | (2006.01) | |
| *A61K 47/64* | (2017.01) | |
| *C07H 15/04* | (2006.01) | |
| *A61K 45/06* | (2006.01) | |
| *C07H 15/06* | (2006.01) | |
| *A61P 31/04* | (2006.01) | |

(52) U.S. Cl.
CPC .......... *A61K 47/646* (2017.08); *A61K 31/702* (2013.01); *A61K 31/7016* (2013.01); *A61K 31/7028* (2013.01); *A61K 39/09* (2013.01); *A61K 39/092* (2013.01); *A61K 45/06* (2013.01); *A61K 47/6415* (2017.08); *A61P 31/04* (2018.01); *C07H 15/04* (2013.01); *C07H 15/06* (2013.01); *A61K 2039/55* (2013.01); *A61K 2039/55511* (2013.01); *A61K 2039/6037* (2013.01)

(58) Field of Classification Search
None
See application file for complete search history.

(56) References Cited

FOREIGN PATENT DOCUMENTS

| AU | 2004207647 | | 7/2010 | |
|---|---|---|---|---|
| FR | 2 850 106 A1 | | 7/2004 | |
| FR | 2850106 A1 | | 7/2004 | |
| JP | H05-178986 | * | 5/1993 | ............. C08G 69/10 |
| WO | WO 2004/067574 A1 | | 12/2004 | |
| WO | WO 2009/000826 A1 | | 12/2008 | |

OTHER PUBLICATIONS

Leonori et al., "De Novo Synthesis of the Bacterial 2-Amino-2,6-Dideoxy Sugar Building Blocks D-Fucosamine, D-Bacillosamine, and D-Xylo-6-deoxy-4-ketohexosamine" Organic Letters vol. 14 No. 18 pp. 4954-4957 (Year: 2012).*

AlonsoDeVelasco et al., "*Streptococcus pneumoniae*: Virulence Factors, Pathogenesis, and Vaccines" Microbiological Reviews (1995) 59(4):591-603.

Corsaro et al., "Highly Phosphorylated Core Oligosaccharide Structures from Cold-Adapted Psychromonas arctica" Chemistry—A European Journal (2008) 14(30):9368-9376.

Kim et al., "Determination of saccharide content in pneumococcal polysaccharides and conjugate vaccines by GC-MSD" Analytical Biochemistry (2005) 347(2):262-274.

Pieretti et al., "The complete structure of the core of the LPS from Plesiomonas shigelloides 302-73 and the identification of its O-antigen biological repeating unit" Carbohydrate Research (2010) 345(17):2523-2528.

International Search Report and Written Opinion dated May 10, 2016 for PCT Application No. PCT/EP2016/051608, filed Jan. 26, 2016.

Bedini et. al., "A Versatile Strategy for the Synthesis of N-Acetylbacillosamine-Containing Disaccharide Building Blocks Related to Bacterial O-Antigens" Synlett (2006) 6:825-830.

(Continued)

*Primary Examiner* — Eric Olson
(74) *Attorney, Agent, or Firm* — Knobbe Martens Olson & Bear LLP

(57) ABSTRACT

The present invention relates to well-defined synthetic saccharides of general formula (I) that are related to the repeating unit of *Streptococcus pneumoniae* serotype 5 capsular polysaccharide and conjugates thereof. The conjugates and pharmaceutical compositions containing said conjugates are useful for prevention and/or treatment of diseases associated with *Streptococcus pneumoniae*, and more specifically against diseases associated with *Streptococcus pneumoniae* serotype 5. Furthermore, the synthetic saccharides of general formula (I) are useful as marker in immunological assays for detection of antibodies against *Streptococcus pneumoniae* bacteria.

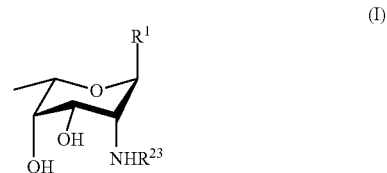

(I)

21 Claims, 12 Drawing Sheets

(56) References Cited

OTHER PUBLICATIONS

Khan et al., "Correlation between in vitro Complement Deposition and Passive Mouse Protection of Anti-Pneumococcal Surface Protein A Monoclonal Antibodies" Clin Vaccine Immunology (2015) 22(1):99-107.
Romero-Steiner et al., "Standardization of an opsonophagocytic assay for the measurement of functional antibody activity against *Streptococcus pneumoniae* using differentiated HL-60 cells" Clinical and Diagnostic Laboaratory Immunology (1997) 4(4):415-422.
Kawano, T., et al., "Natural killer-like nonspecific tumor cell lysis mediated by specific ligand-activated Va14 NKT cells," Proc. Natl Acad. Sci. USA (1998) 95:5690-5693.
International Preliminary Report on Patentability dated Dec. 12, 2017 for PCT Application No. PCT/EP2016/051608, filed Jan. 26, 2016.

\* cited by examiner

Figure 2

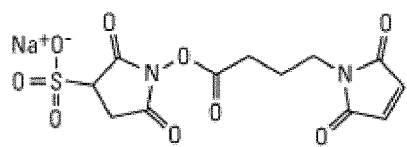

Sulfo-GMBS
N-(γ-Maleimidobutyryloxy) sulfosuccinimide ester
MW 382.28
Spacer Arm 7.3 Å

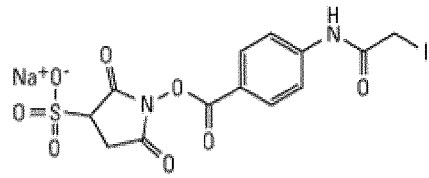

Sulfo-SIAB
Sulfosuccinimidyl (4-iodoacetyl) aminobenzoate
MW 504.19
Spacer Arm 10.6 Å

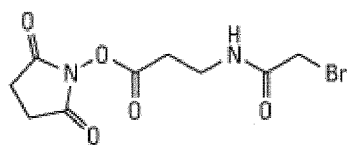

SBAP
Succinimidyl-3-(bromoacetamido)propionate
MW 307.10
Spacer Arm 6.2 Å

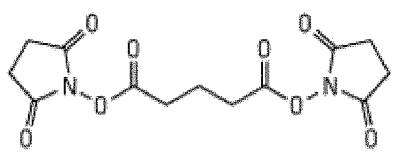

DSG
Disuccinimidyl glutarate
MW 326.26
Spacer Arm 7.7 Å

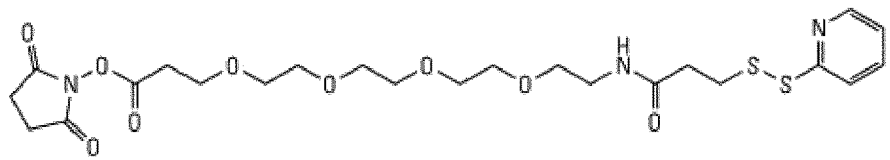

PEG4-SPDP
2-Pyridyldithiol-tetraoxatetradecane-N-hydroxysuccinimide
MW 559.17
Spacer Arm 25.7 Å

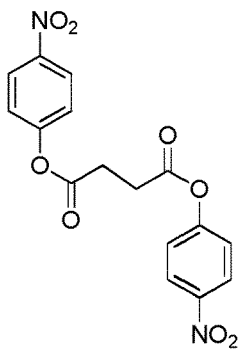

Bis-(4-nitrophenyl)succinate

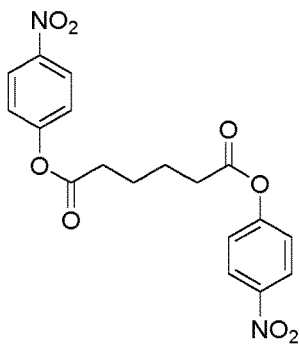

Bis-(4-nitrophenyl) adipate

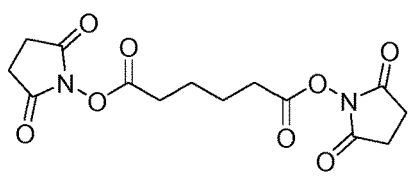

DSA
Disuccinimidyl adipate

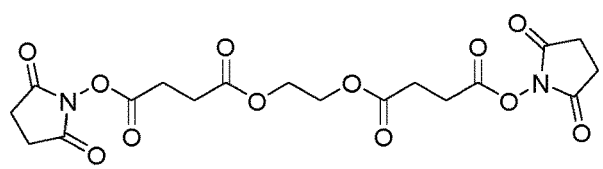

Ethylene glycol-bis(succinic acid
N-hydroxysuccinimide ester)

| Position | Saccharide | Position | Saccharide |
|---|---|---|---|
| 1 | 33* | 7 | 44* |
| 2 | 14* | 8 | 27* |
| 3 | 15* | 9 | 52* |
| 4 | 20* | 10 | 36* |
| 5 | 21* | 11 | 37* |
| 6 | 51* | | |

| Position | Saccharide | Position | Saccharide |
|---|---|---|---|
| 1 | 33* | 7 | 44* |
| 2 | 14* | 8 | 27* |
| 3 | 15* | 9 | 52* |
| 4 | 20* | 10 | 36* |
| 5 | 21* | 11 | 37* |
| 6 | 51* | | |

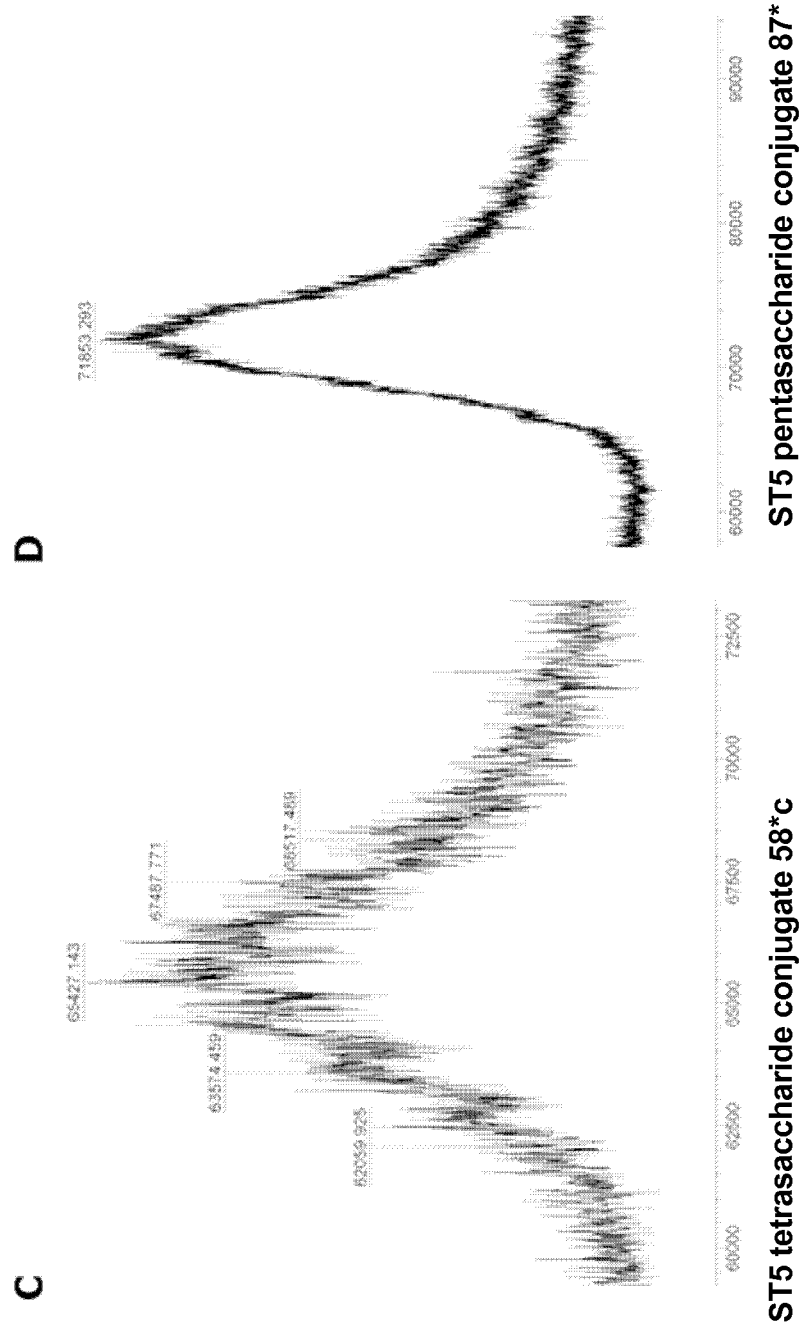

VACCINES AGAINST *STREPTOCOCCUS PNEUMONIAE* SEROTYPE 5

CROSS REFERENCE TO RELATED APPLICATIONS

This application is a U.S. National Phase Application of PCT International Application No. PCT/EP2016/051608, filed on Jan. 26, 2016, designating the United States of America and published in the English language, which claims priority to EP Application No. 15171079.5, filed Jun. 8, 2015. The disclosures of the above-referenced applications are hereby expressly incorporated by reference in their entireties.

FIELD OF THE INVENTION

The present invention relates to well-defined synthetic saccharides of general formula (I) that are related to the repeating unit of *Streptococcus pneumoniae* serotype 5 capsular polysaccharide and conjugates thereof. The conjugates and pharmaceutical compositions containing said conjugates are useful for prevention and/or treatment of diseases associated with *Streptococcus pneumoniae*, and more specifically against diseases associated with *Streptococcus pneumoniae* serotype 5. Furthermore, the synthetic saccharides of general formula (I) are useful as marker in immunological assays for detection of antibodies against *Streptococcus pneumoniae* bacteria

BACKGROUND OF THE INVENTION

*Streptococcus pneumoniae* is a Gram-positive, encapsulated bacterium that is a main cause of infections of the respiratory tract and can lead to severe invasive pneumococcal disease (IPD). More than 90 different pneumococcal serotypes have been described to date. These are classified by the structure of their capsular polysaccharide (CPS), which is unique to each serotype. Consequently, the immune response generated against the CPS varies between different serotypes. This is used to generate specific antibodies in rabbits against the antigen of each serotype. Cross-reactivity between these specific antibodies and other serotypes than those they were raised against is often observed, due to structural similarities of the CPS of different serotypes. Due to its immunological properties, CPS is used as the main component of *S. pneumoniae* vaccines.

The first efficient vaccine that contained the CPS of four different serotypes was described in 1945. It then took over thirty years until a vaccine was introduced that covered 14 serotypes, shortly followed by a 23-valent vaccine. However, these polysaccharide vaccines had several shortcomings. They were not able to elicit a long-lasting protection and were not effective in the populations most vulnerable to infection, namely children under two years of age as well as immunodeficient and elderly patients. These shortcomings result from the immunology of carbohydrates and were overcome by the introduction of carbohydrate-protein conjugate vaccines. The first pneumococcal conjugate vaccines were the seven-valent (PCV-7) and 10-valent (PCV-10) vaccine. PCV-7 was later replaced with the most recent vaccine (PCV-13), which contains the CPS-glycoconjugates of 13 different serotypes.

*S. pneumoniae* serotype 5 (SP5) is globally the fifth most prevalent IPD-causing serotype among young children, and the second most prevalent serotype amongst children in the poorest countries of the world, eligible to the support of the Global Alliance for Vaccines and Immunization (GAVI). Furthermore, SP5 was recently identified as the causative agent of an epidemic of severe pneumonia among young Israeli army recruits and community outbreaks of invasive infection in impoverished, urban populations in Canada. A very recent study showed that SP5 is a frequent cause of IPD outbreaks among children and adults in Spain. Although most SP5 subtypes are still susceptible to antibiotics, the emergence and dissemination of antibiotic-resistant SP5 bacteria is of concern.

The SP5 CPS is a component of the most recent PCV-10 and PCV-13 conjugate vaccines. The SP5 CPS consists of a branched pentasaccharide repeating unit with the sequence [→4)-β-D-Glcp-(1→4)-[α-L-PnepNAc-(1→2)-β-D-GlcpA-(1→3)]-α-L-FucpNAc-(1→3)-β-D-Sugp (1→], where Sugp is 4-keto-D-FucNAc (systematic name: 2-acetamido-2,5-dideoxy-D-xylo-hexos-4-ulose) and PneNAc is N-acetyl-L-pneumosamine (see FIG. 1).

The French patent application FR 2850106 A1 (AVENTIS PASTEUR, 23 Jul. 2004) describes conjugates obtained by reductive amination of SP5 CPS for use as vaccines against SP5. The saccharidic part of the conjugates are fragments of SP5 CPS isolated from bacterial sources containing in average 30 to 35 repeating units, wherein at least 85% of repeating units correspond to one of the following repeating units: [→4)-β-D-Glcp-(1→4)-[α-L-PnepNAc-(1→2)-β-D-GlcpA-(1→3)]-α-L-FucpNAc-(1→3)-β-D-Sugp (1→]; [→4)-β-D-Glcp-(1→4)-[α-L-PnepNAc-(1→2)-β-D-GlcpA-(1→3)]-α-L-FucpNAc-(1→3)-β-D-FucpNAc (1→]; and [→4)-β-D-Glcp-(1→4)-[α-L-PnepNAc-(1→2)-β-D-GlcpA-(1→3)]-α-L-FucpNAc-(1→3)-β-D-QuipNAc (1→]. The heterogenicity of the SP5 CPS fragments both in terms of size and structure is detrimental for the efficient manufacture of a well-defined vaccine.

It is the objective of the present invention to provide well-defined synthetic saccharides of general formula (I) that are related to the repeating unit of *Streptococcus pneumoniae* serotype 5 capsular polysaccharides. Said well-defined synthetic saccharides are suitable to be conjugated to an immunogenic carrier to provide conjugates and pharmaceutical compositions thereof that are useful for prevention and/or treatment of diseases associated with *Streptococcus pneumoniae*, and more specifically against diseases associated with *Streptococcus pneumoniae* serotype 5. Furthermore, the synthetic saccharides of general formula (I) are useful as marker in immunological assays for detection of antibodies against *Streptococcus pneumoniae* bacteria.

The objective of the present invention is solved by the teaching of the independent claims. Further advantageous features, aspects and details of the invention are evident from the dependent claims, the description, the figures, and the examples of the present application.

DESCRIPTION OF THE INVENTION

Definitions

The term "linker" as used herein encompasses molecular fragments capable of connecting the reducing-end monosaccharide of a saccharide with an immunogenic carrier or a solid support, optionally by binding to at least one interconnecting molecule. Thus, the function of the linker per se or together with the interconnecting molecule is to establish, keep and/or bridge a special distance between the reducing-end monosaccharide and an immunogenic carrier or a solid support. More specifically, one extremity of the linker is connected to the exocyclic oxygen atom at the anomeric center of the reducing-end monosaccharide and the other extremity is connected via the nitrogen atom with the interconnecting molecule, or directly with the immunogenic carrier or the solid support.

As used herein, the term "interconnecting molecule" refers to a bifunctional molecule containing functional group X and functional group Y, wherein functional group X is capable of reacting with the terminal amino group on the linker L and the functional group Y is capable of reacting with a functionality present on an immunogenic carrier or on a solid support. FIG. 2 displays examples of commercially available interconnecting molecules, but does not restrict the interconnecting molecules that can be used according to the present invention to the examples displayed herein.

The term "adjuvant" as used herein refers to an immunological adjuvant i.e. a material used in a vaccine composition that modifies or augments the effects of said vaccine by enhancing the immune response to a given antigen contained in the vaccine without being antigenically related to it. For the person skilled in the art, classically recognized examples of adjuvants include:

mineral-containing compositions, including calcium salts and aluminium salts (or mixtures thereof). Calcium salts include calcium phosphate. Aluminium salts include hydroxides, phosphates, sulfates, etc., with the salts taking any suitable form (e.g. gel, crystalline, amorphous, etc.). Adsorption to these salts is preferred. The mineral containing compositions may also be formulated as a particle of metal salt. The adjuvants known as aluminium hydroxide and aluminium phosphate may be also used. The invention can use any of the "hydroxide" or "phosphate" adjuvants that are in general used as adjuvants. The adjuvants known as "aluminium hydroxide" are typically aluminium oxyhydroxide salts, which are usually at least partially crystalline. The adjuvants known as "aluminium phosphate" are typically aluminium hydroxyphosphates, often also containing a small amount of sulfate (i. e. aluminium hydroxyphosphate sulfate). They may be obtained by precipitation, and the reaction conditions and concentrations during precipitation influence the degree of substitution of phosphate for hydroxyl in the salt. Mixtures of both an aluminium hydroxide and an aluminium phosphate can be employed in the formulation according to the present invention;

saponins, which are a heterologous group of sterol glycosides and triterpenoid glycosides that are found in the bark, leaves, stems, roots and even flowers of a wide range of plant species. Saponins from the bark of the *Quillaia saponaria*, Molina tree have been widely studied as adjuvants. Saponins can also be commercially obtained from *Smilax ornata* (sarsaprilla), *Gypsophilla paniculata* (brides veil), and *Saponaria oficianalis* (soap root). Saponin adjuvant formulations include purified formulations, such as QS21, as well as lipid formulations, such as ISCOMs. Saponin compositions have been purified using HPLC and RP-HPLC. Specific purified fractions using these techniques have been identified, including QS 7, QS 17, QS 18, QS2 1, QH-A, QH-B and QH-C. Saponin formulations may also comprise a sterol, such as cholesterol. Combinations of saponins and cholesterols can be used to form unique particles called immunostimulating complexes (ISCOMs). ISCOMs generally include a phospholipid such as phosphatidylethanolamine or phosphatidylcholine. Any known saponin can be used in ISCOMs. Preferably, the ISCOM includes one or more of QuilA, QHA & QHC;

microparticles (i.e. a particle of 100 nm to 150 pm in diameter, more preferably 200 nm to 30 pm in diameter, or 500 nm to 10 pm in diameter) formed from materials that are biodegradable and non-toxic. Such non-toxic and biodegradable materials include, but are not restricted to poly(α-hydroxy acid), polyhydroxybutyric acid, polyorthoester, polyanhydride, polycaprolactone;

CD1d ligands, such as an α-glycosylceramide, phytosphingosine-containing α-glycosylceramides, OCH, KRN7000 [(2S,3S,4R)-1-O-(α-D-galactopyranosyl)-2-(N-hexacosanoylamino)-1,3,4-octadecanetriol], CRONY-101, 3"-sulfo-galactosyl-ceramide;

immunostimulatory oligonucleotides, such CpG motif containing ones (a dinucleotide sequence containing an unmethylated cytosine residue linked by a phosphate bond to a guanosine residue), or CpI motif containing ones (a dinucleotide sequence containing cytosine linked to inosine), or a double-stranded RNA, or an oligonucleotide containing a palindromic sequence, or an oligonucleotide containing a poly(dG) sequence. Immunostimulatory oligonucleotides can include nucleotide modifications/analogs such as phosphorothioate modifications and can be double-stranded or (except for RNA) single-stranded;

compounds containing lipids linked to a phosphate-containing acyclic backbone, such as the TLR4 antagonist E5564;

oil emulsions (e.g. Freund's adjuvant).

Theoretically, each molecule or substance that is able to favor or amplify a particular situation in the cascade of immunological events, ultimately leading to a more pronounced immunological response, can be defined as an adjuvant.

In principle, through the use of adjuvants in vaccine formulations, one can direct and optimize immune responses that are appropriate or desirable for the vaccine;

enable mucosal delivery of vaccines, i.e. administration that results in contact of the vaccine with a mucosal surface such as buccal or gastric or lung epithelium and the associated lymphoid tissue;

promote cell-mediated immune responses;

enhance the immunogenicity of weaker immunogens, such as highly purified or recombinant antigens;

reduce the amount of antigen or the frequency of immunization required to provide protective immunity; and improve the efficacy of vaccines in individuals with reduced or weakened immune responses, such as newborns, the aged, and immunocompromised vaccine recipients.

Although little is known about their mode of action, it is currently believed that adjuvants augment immune responses by one of the following mechanisms:

increasing the biological or immunologic half-life of antigens;

improving antigen delivery to antigen-presenting cells (APCs), as well as antigen processing and presentation by the APCs e.g., by enabling antigen to cross endosomal membranes into the cytosol after ingestion of antigen-adjuvant complexes by APC;

mimicking danger inducing signals from stressed or damaged cells, which serve to initiate an immune response;

inducing the production of immunomodulatory cytokines;

biasing the immune response towards a specific subset of the immune system; and blocking the rapid dispersal of the antigen challenge.

Saccharides are known by the person skilled in the art as TI-2 (T cell independent-2) antigens and poor immunogens. Therefore, to produce a saccharide-based vaccine, said saccharides are conjugated to an immunogenic carrier to provide a conjugate, which presents an increased immunogenicity in comparison with the saccharide. In this context the term "immunogenic carrier" is defined as a structure, which is conjugated to the saccharide to form a conjugate that presents an increased immunity in comparison with the saccharide per se. Thus, the conjugation of the saccharides to the immunogenic carrier has as effect the stimulation of the immune response against said saccharide, without inducing an immune response against the said immunogenic carrier.

The present invention relates to saccharides of general formula (I):

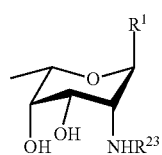

(I)

wherein
$R^1$ is selected from $R^2$, $R^4$,

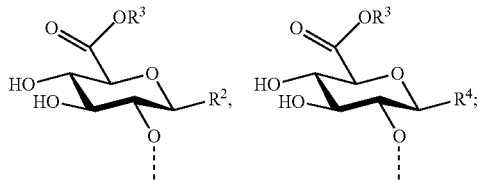

$R^2$ represents

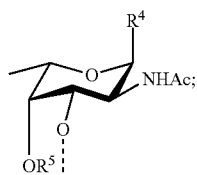

$R^3$ is selected from —H, —$CH_3$, —$C_2H_5$, —$C_3H_7$, —$C_4H_9$ and —$CF_3$;
$R^4$ represents $R^6$ or

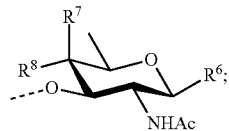

$R^5$ represents —H or

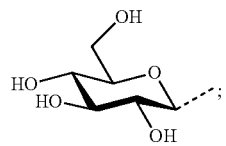

$R^6$ represents —O-L-$NH_2$;
$R^7$ and $R^8$ are independently of each other selected from —H and —OH and cannot be simultaneously —H;
$R^7$ and $R^8$ can form together a =O residue; or in other words $R^7$ and $R^8$ can form together with the carbon atom to which they are attached to a carbonyl group C=O;

$R^{23}$ is selected from —H, —C(O)$CH_3$, —C(O)$CF_3$ and —C(O)$CCl_3$;
-L- is a linker;
and pharmaceutically acceptable salts thereof.

-L- is defined as a linker and is part of the fragment —O-L-$NH_2$. Thus, the linker -L- is bound to an oxygen atom and to the nitrogen atom of the $NH_2$-group. It is preferred that at least two carbon atoms of the linker are between the oxygen atom and the $NH_2$-group, like —O—C—C—$NH_2$. The linker -L- can be an aliphatic chain, wherein the aliphatic chain can optionally include an aromatic chain inserted in it, or a number of heteroatoms oscillating from 0 to 10.

The linker L preferably contains between 2 and 40 carbon atoms (including the carbon atoms of optional side chains), more preferably between 2 and 30, more preferably between 2 and 20, more preferably between 2 and 14, more preferably between 2 and 12, and still more preferably between 2 and 10 carbon atoms.

The shortest atom chain between the oxygen (i.e. the oxygen of —O-L-$NH_2$) and the $NH_2$-group consists preferably of 2 to 14 atoms, more preferably of 2 to 12 atoms, more preferably of 2 to 10 atoms, more preferably of 2 to 8 atoms. In case the shortest chain (which is the shortest possible connection between the oxygen at the anomeric center and the $NH_2$-group) consists of 2 to 6 atoms, these are preferably carbon atoms. In case the shortest chain consists of 4 to 8 atoms, the chain may contain 1, or 2 heteroatoms selected from O, N and S. In case the shortest chain consists of 9 to 14 atoms, the chain may contain 1, 2, 3, or 4 heteroatoms selected from O, N and S. It is preferred that the shortest chain contains 0, 1, or 2 sulphur atoms and/or 0, 1, or 2 nitrogen atoms and/or 0, 1, 2, or 3 oxygen atoms.

It is also preferred that the linker -L-, or the shortest chain is fully or partially fluorinated. The linker -L- may contain a 3-membered or a 4-membered or a 5-membered or a 6-membered saturated carbocycle or a 5-membered partly unsaturated (and not aromatic) carbocycle or a 4-membered or a 5-membered or a 6-membered saturated oxygen heterocycle or a 4-membered or a 5-membered or a 6-membered saturated nitrogen heterocycle or a 6-membered aromatic carbocycle.

The linker -L- may also contain amide (—NH—CO—, —CO—NH—) and/or urea (—NH—CO—NH—) residues and preferably only one amide or urea residue. The linker may also contain substituents and preferably one substituent such as $R^{10}$ or two substituents such as $R^{10}$ and $R^{14}$, which have the meanings as defined herein and which are preferably selected from: —F, —Cl, —$CH_3$, —$C_2H_5$, —$C_3H_7$, —$C_5H_9$, —$C_6H_{13}$, —$OCH_3$, —$OC_2H_5$, —$CH_2F$, —$CHF_2$, —$CF_3$, —C(O)—$NH_2$, —$SCH_3$, —$SC_2H_5$, —NHC(O)$CH_3$, —N($CH_3$)$_2$, and —N($C_2H_5$)$_2$;

In case the linker is fluorinated, more than two substituents —F are preferred.

Preferably the linker -L- is selected from: —$CH_2$—, —($CH_2$)$_2$—, —($CH_2$)$_3$—, —($CH_2$)$_4$—, —($CH_2$)$_5$—, —($CH_2$)$_6$—, —($CH_2$)$_7$—, —($CH_2$)$_8$—, —($CH_2$)$_9$—, —($CH_2$)$_{10}$—, —$CF_2$—, —($CF_2$)$_2$—, —($CF_2$)$_3$—, —($CF_2$)$_4$—, —($CF_2$)$_5$—, —($CF_2$)$_6$—, —($CF_2$)$_7$—, —($CF_2$)$_8$—, —($CF_2$)$_9$—, —($CF_2$)$_{10}$—, —($CH_2$)$_2$—O—($CH_2$)$_2$—, —$CH_2$—O—($CH_2$)$_3$—, —($CH_2$)$_3$—O—$CH_2$—, —$CH_2$—O—($CH_2$)$_2$—, —($CH_2$)$_2$—O—$CH_2$—, —($CH_2$)$_3$—O—($CH_2$)$_2$—, —($CH_2$)$_2$—O—($CH_2$)$_3$—, —($CH_2$)$_4$—O—$CH_2$—, —$CH_2$—O—($CH_2$)$_4$—, -$L^a$-, -$L^a$-$L^e$-, -$L^a$-$L^b$-$L^e$-, -$L^a$-$L^b$-$L^d$-$L^c$-$L^e$-, -$L^a$-$L^d$-$L^e$-;

wherein

-$L^a$- is selected from: —$(CH_2)_m$—, —$(CF_2)_m$—, —$(CH_2$—$CH_2$—$O)_m$—$C_2H_4$—, —$(CH_2$—$CH_2$—$O)_m$—$CH_2$—, —$(CR^{10}R^{11})_m$—,

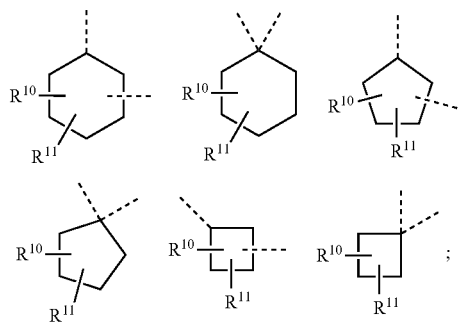

-$L^b$- and -$L^c$- are independently of each other selected from: —O—, —S—, —NH—C(O)—NH—, —NH—C(S)—NH—, —NH—C(O)—, —C(O)—NH—, —NH—C(O)—O—, —$NR^9$—, —$NR^{18}$—, —$SO_2$—,

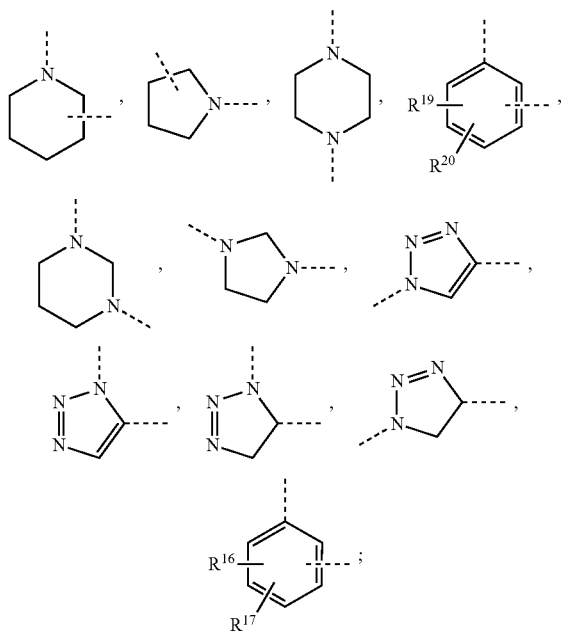

-$L^d$- represents —$(CH_2)_n$—, —$(CF_2)_n$—, —$(CR^{12}R^{13})_n$—, —$(CH_2$—$CH_2$—$O)_n$—$C_2H_4$—, —$(CH_2$—$CH_2$—$O)_n$—$CH_2$—,

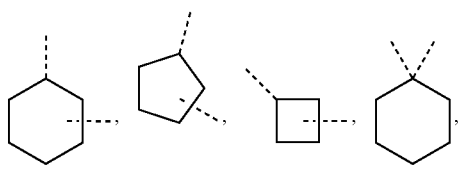

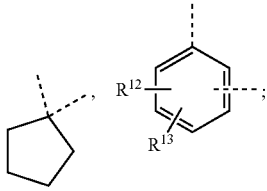

-$L^e$- is selected from: —$(CH_2)_{p1}$—, —$(CF_2)_{p1}$—, —$C_2H_4$—(O—$CH_2$—$CH_2)_{p1}$—, —$CH_2$—(O—$CH_2$—$CH_2)_{p1}$—, —$(CH_2)_{p1}$—O—$(CH_2)_{p2}$—, —$(CH_2)_{p1}$—S—$(CH_2)_{p2}$—, —$(CR^{14}R^{15})_{p1}$—, —$(CR^{14}R^{15})_{p1}$—O—$(CR^{21}R^{22})_{p2}$—, —$(CR^{14}R^{15})_{p1}$—S—$(CR^{21}R^{22})_{p2}$—,

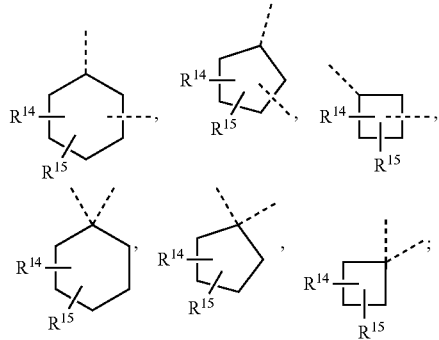

$R^9$ and $R^{18}$ are independently of each other selected from: —$CH_3$, —$C_2H_5$, —$C_3H_7$, and —$C(O)CH_3$;

$R^{10}$, $R^{11}$, $R^{12}$, $R^{13}$, $R^{14}$, $R^{15}$, $R^{16}$, $R^{17}$, $R^{19}$, $R^{20}$, $R^{21}$ and $R^{22}$ are independently of each other selected from: —H, —F, —Cl, —$CH_3$, —$C_2H_5$, —$C_3H_7$, —$C_5H_9$, —$C_6H_{13}$, —$OCH_3$, —$OC_2H_5$, —$CH_2F$, —$CHF_2$, —$CF_3$, —C(O)—$NH_2$, —$SCH_3$, —$SC_2H_5$, —$NHC(O)CH_3$, —$N(CH_3)_2$ and —$N(C_2H_5)_2$;

m, n, p1 and p2 are independently of each other an integer selected from 1, 2, 3, 4, 5, 6, 7, 8, 9, and 10.

The saccharides of the present invention bear basic and/or acidic substituents and they may form salts with organic or inorganic acids or bases.

Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphorsulfonic acid, china acid, mandelic acid, o-methylmandelic acid, hydrogen-benzenesulfonic acid, picric acid, adipic acid, d-o-tolyltartaric acid, tartronic acid, (o,m,p)-toluic acid, naphthylamine sulfonic acid, and other mineral or carboxylic acids well known to those skilled in the art. The salts are prepared by contacting the free base form with a sufficient amount of the desired acid to produce a salt in the conventional manner.

Examples of suitable inorganic or organic bases are, for example, NaOH, KOH, $NH_4OH$, tetraalkylammonium hydroxide, lysine or arginine and the like. Salts may be prepared in a conventional manner using methods well known in the art, for example by treatment of a solution of the compound of the general formula (I) with a solution of a base, selected out of the group mentioned above.

Further, it is also possible that the compounds of the present invention bear simultaneously basic and acid groups. Further, it may also occur that these basic and acid groups appear to be in close vicinity to one another enabling an intramolecular proton transfer from the acidic group to the basic group. Therefore, in a preferred embodiment of the present invention the compound of the formula (I) may be zwitter-ionic, bearing at least e.g. one —O⁻ and one —NH$_3^+$ group.

It is clear for the skilled person in the art of carbohydrate chemistry that the saccharides of general (I) are not containing —O—O— bonds and or sugar fragments connected or bound to each other via their anomeric or C-1 carbons.

Preferred are saccharides of general formulae (IV), (V), (VI) and (VII)

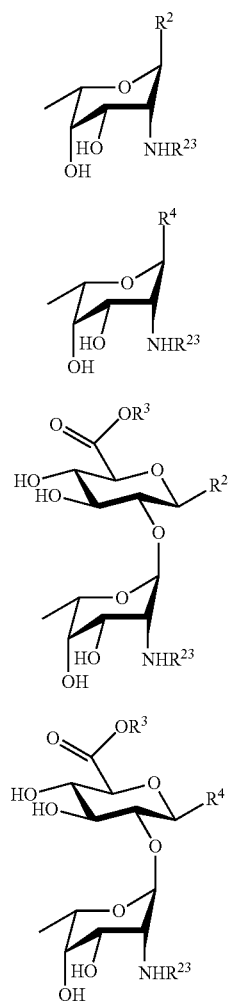

wherein $R^2$, $R^3$, $R^4$ and $R^{23}$ have the meanings defined above, and even more preferred are saccharides of general formulae (VI) and (VII).

Another preferred embodiment of the present invention is directed to saccharides of general formula (I), wherein $R^1$ represents:

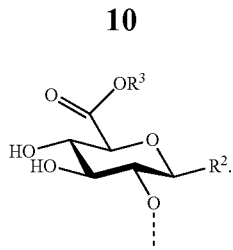

Especially preferred saccharides according to the present invention are saccharides wherein the residue $R^4$ represents $R^6$. Thus, saccharides of general formulae (I), (IV), (V), (VI) and (VII), with $R^4$ being $R^6$ are especially preferred.

A even more preferred embodiment of the present invention is directed to a saccharide of general formula (III)

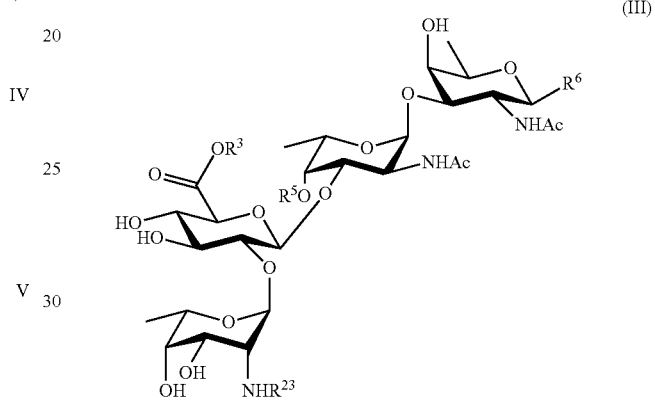

wherein residues $R^3$, $R^5$, $R^6$ and $R^{23}$ are having the meanings as defined herein.

Particularly preferred are saccharides according to the present invention wherein $R^3$ represents —H. Hence, saccharides of general formulae (I), (III), (VI) and (VII), with $R^3$ being —H are particularly preferred.

Preferably, the residue $R^{23}$ represents —C(O)CH$_3$. Thus, saccharides of general formula (I) with the residue $R^3$ representing —H and the residue $R^{23}$ representing —C(O)CH$_3$ are especially preferred.

Preferred saccharides according to the present invention are saccharides of general formulae (I), (III), (IV), (V) or (VII) wherein the linker -L- is selected from: -L$^a$-, -L$^a$-L$^e$-, -L$^a$-L$^b$-L$^e$-, -L$^a$-L$^b$-L$^d$-L$^c$-L$^e$-, -L$^a$-L$^d$-L$^e$-, and wherein -L$^a$- is selected from: —(CH$_2$)$_m$, —(CF$_2$)$_m$—, —(CH$_2$—CH$_2$—O)$_m$—C$_2$H$_4$—, —(CH$_2$—CH$_2$—O)$_m$—CH$_2$—, —(CR$^{10}$R$^{11}$)$_m$—;

-L$^b$- and -L$^c$- are independently of each other selected from: —O—, —S—, —NR$^9$—, —NH—C(O)—NH—, —NH—C(O)—, —C(O)—NH—, —NH—C(O)—O—, —NR$^{18}$—, —SO$_2$—,

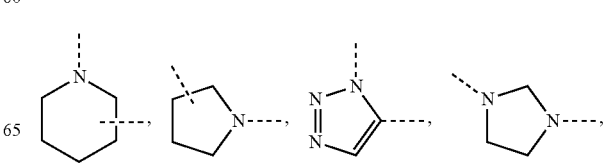

-continued

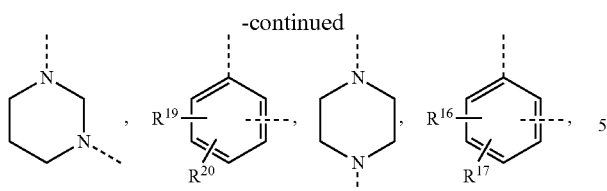

-L$^d$- represents —(CH$_2$)$_n$—, —(CF$_2$)$_n$—, —(CR$^{12}$R$^{13}$)$_n$—, —(CH$_2$—CH$_2$—O)$_n$—C$_2$H$_4$—, —(CH$_2$—CH$_2$—O)$_n$—CH$_2$—,

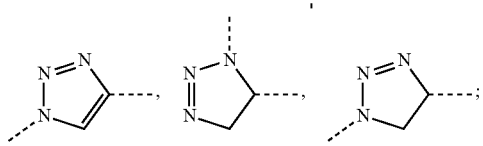

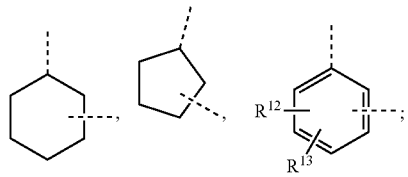

-L$^e$- is selected from: —(CH$_2$)$_{p1}$—, —(CF$_2$)$_{p1}$—, —C$_2$H$_4$—(O—CH$_2$—CH$_2$)$_{p1}$—, —CH$_2$—(O—CH$_2$—CH$_2$)$_{p1}$—, —(CH$_2$)$_{p1}$—O—(CH$_2$)$_{p2}$—, —(CH$_2$)$_{p1}$—S—(CH$_2$)$_{p2}$—, —(CR$^{14}$R$^{15}$)$_{p1}$—, —(CR$^{14}$R$^{15}$)$_{p1}$—O—(CR$^{21}$R$^{22}$)$_{p2}$—, —(CR$^{14}$R$^{15}$)$_{p1}$—S—(CR$^{21}$R$^{22}$)$_{p2}$—, R$^9$ and R$^{18}$ are independently of each other selected from: —CH$_3$, —C$_2$H$_5$, —C$_3$H$_7$, and —C(O)CH$_3$;

R$^{10}$, R$^{11}$, R$^{12}$, R$^{13}$, R$^{14}$, R$^{15}$, R$^{16}$, R$^{17}$, R$^{19}$, R$^{20}$, R$^{21}$ and R$^{22}$ are independently of each other selected from: —H, —F, —Cl, —CH$_3$, —C$_2$H$_5$, —C$_3$H$_7$, —C$_5$H$_9$, —C$_6$H$_{13}$, —OCH$_3$, —OC$_2$H$_5$, —CH$_2$F, —CHF$_2$, —CF$_3$, —C(O)—NH$_2$, —SCH$_3$, —SC$_2$H$_5$, —NHC(O)CH$_3$, —N(CH$_3$)$_2$, and —N(C$_2$H$_5$)$_2$;

m, n, p1 and p2 are independently of each other an integer selected from 1, 2, 3, 4, 5, and 6.

In a even more preferred embodiment, the linker -L- is selected from: -L$^a$-, -L$^a$-L$^b$-L$^e$- and -L$^a$-L$^d$-L$^e$-;
and -L$^a$- is selected from: —(CH$_2$)$_m$—, —(CF$_2$)$_m$—, —(CH$_2$—CH$_2$—O)$_m$—C$_2$H$_4$—, —(CH$_2$—CH$_2$—O)$_m$—CH$_2$—;

-L$^b$- is selected from: —O—, —S—, —NH—C(O)—NH—, —NH—C(O)—, and —C(O)—NH—;

-L$^d$- is selected from —(CH$_2$)$_n$— and —(CF$_2$)$_n$—;

-L$^e$- is selected from: —(CH$_2$)$_{p1}$—, —(CF$_2$)$_{p1}$—, —C$_2$H$_4$—(O—CH$_2$—CH$_2$)$_{p1}$—, —CH$_2$—(O—CH$_2$—CH$_2$)$_{p1}$—, —(CH$_2$)$_{p1}$—O—(CH$_2$)$_{p2}$—, and —(CH$_2$)$_{p1}$—S—(CH$_2$)$_{p2}$—, and m, n, p1 and p2 are independently of each other an integer selected from 1, 2, 3, 4, 5, 6, 7, 8, 9, and 10. Thus, a saccharide of general formulae (I), (III), (IV), (V) or (VII) wherein the linker -L- has the meaning defined above is especially preferred.

In the most preferred embodiment, the linker -L- represents —(CH$_2$)$_m$—, wherein m has the meaning defined herein and most preferably m is an integer selected from 1, 2, 3, 4, 5 and 6, or the linker -L- represents —(CH$_2$—CH$_2$—O)$_m$—C$_2$H$_4$— or —(CH$_2$—CH$_2$—O)$_m$—CH$_2$— and m is an integer selected from 1, 2 and 3.

Preferably the saccharides according to the present invention are selected from:

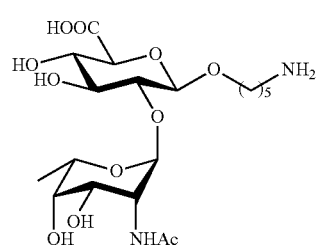

(27*)

5-amino-pentanyl 2-N-acetyl-α-L-pneumosaminopyranosyl-(1 → 2)-β-D-glucopyranosyluronate

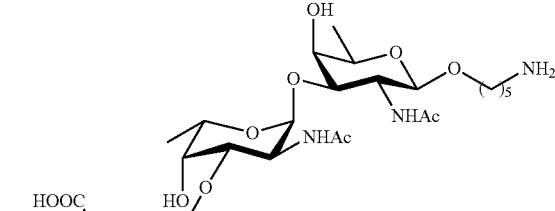

(33*)

5-amino-pentanyl 2-N-acetyl-α-L-pneumosaminopyranosyl-(1 → 2)-β-D-glucopyranosyluronate-(1 → 3)-2-N-acetyl-α-L-fucosaminopyranosyl-(1 → 3)-2-N-aceyl-β-D-fucosaminopyranoside

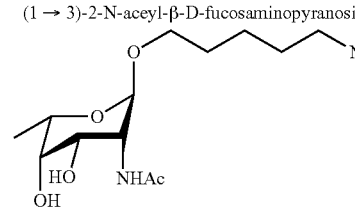

5-amino-pentanyl 2-N-acetyl-α-L-pneumosaminopyranoside

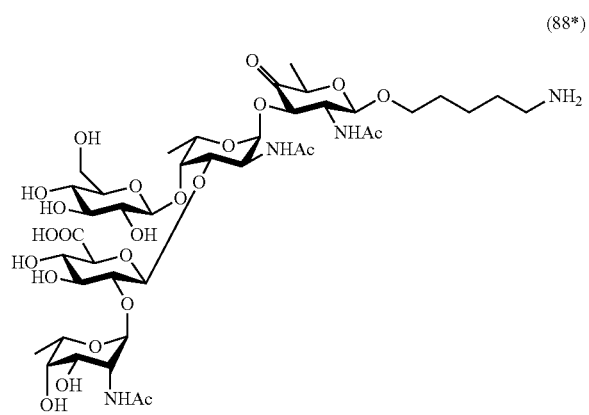

(88*)

5-amino-pentanyl 2-N-acetyl-α-L-pneumosaminopyranosyl-(1 → 2)-β-D-glucopyranosyluronate-(1 → 3)-2-N-acetyl-α-L-fucosaminopyranosyl-(1 → 3)-[β-D-glucopyranosyl-(1 → 4)]-2-acetamido-2,5-dideoxy-β-D-xylo-hexos-4-uloside

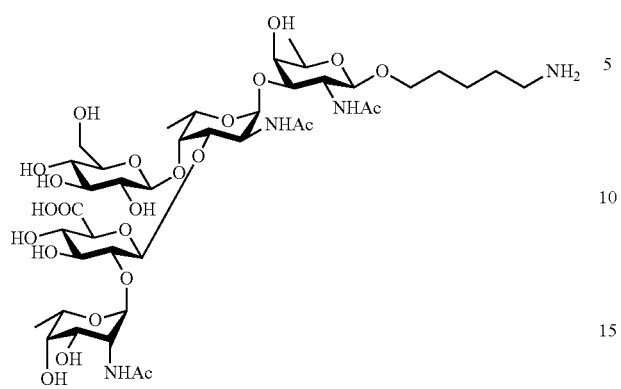

5-amino-pentanyl 2-N-acetyl-α-L-pneumosaminopyranosyl-(1 → 2)-β-D-glucopyranosyluronate-(1 → 3)-2-N-acetyl-α-L-fucosaminopyranosyl-(1 → 3)-[β-D-glucopyranosyl-(1 → 4)]-2-N-acetyl-β-D-fucosaminopyranoside (73*)

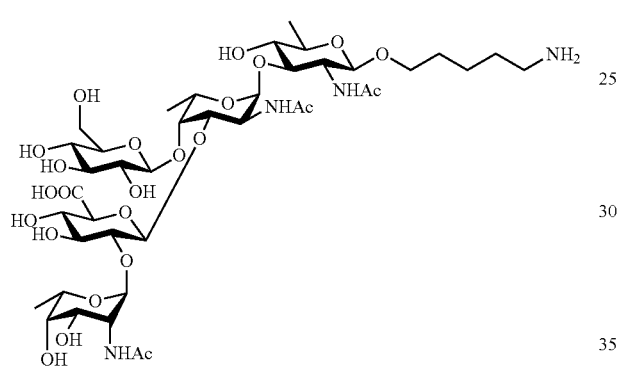

5-amino-pentanyl 2-N-acetyl-α-L-pneumosaminopyranosyl-(1 → 2)-β-D-glucopyranosyluronate-(1 → 3)-2-N-acetyl-α-L-fucosaminopyranosyl-(1 → 3)-[β-D-glucopyranosyl-(1 → 4)]-2-N-acetyl-β-D-quinovosaminopyranoside (85*)

The saccharides of general formula (I) are able to induce a protective immune response against *S. pneumoniae* serotype 5 bacteria in a human and/or animal host. The presence of the α-L-pneumosamine residue in the saccharides of general formula (I) is essential for achieving cross-reactivity towards the native *S. pneumoniae* type 5 capsular polysaccharides.

Another aspect of the present invention refers to intermediates of general formula (IX)

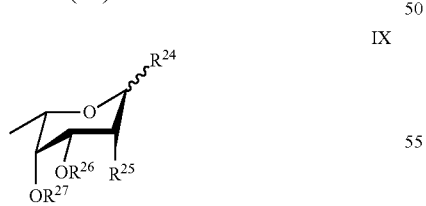

IX wherein
R²⁴ is selected from

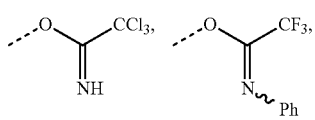

—F, —Cl, —Br, —I, —SR²⁸, —SeR²⁹, —OPO₃R³⁰₂;
R²⁵ is selected from —N₃, —NBn₂, —NBnCbz;

R²⁶ and R²⁷ are independently of each other selected from —H, -Bn,

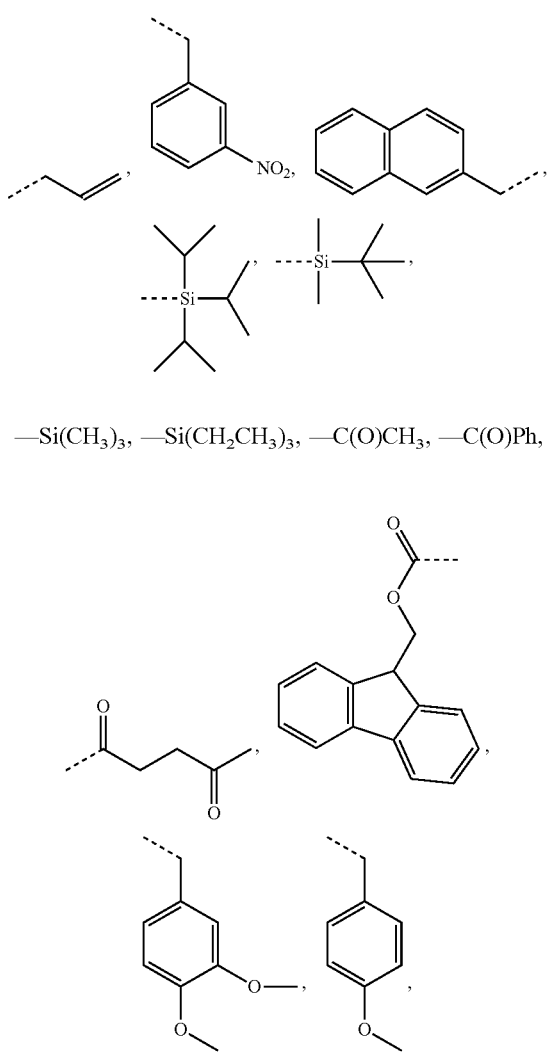

—Si(CH₃)₃, —Si(CH₂CH₃)₃, —C(O)CH₃, —C(O)Ph, or R²⁶ and R²⁷ can form together

R²⁸ is selected from: —CH₃, —CH₂CH₃, -Ph,

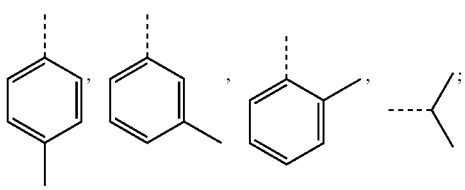

R²⁹ represents -Ph;
R³⁰ represents —CH₂CH₂CH₂CH₃; and intermediates of the formulae 36, 41, 63, 68*, 70 and 70a

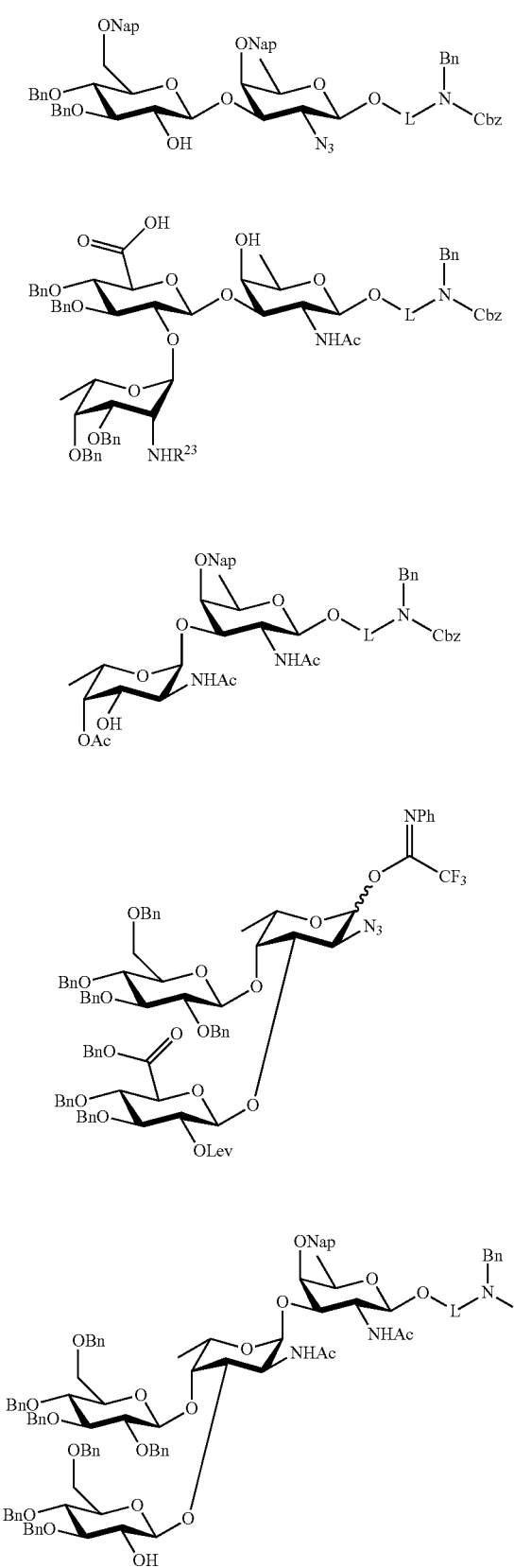

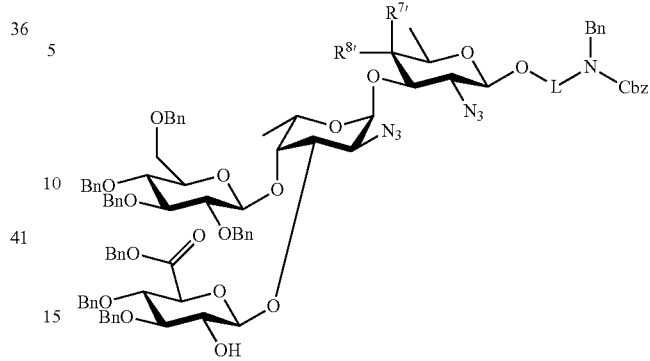

wherein L and $R^{23}$, and $R^{7'}$ and $R^{8'}$ are defined as disclosed herein, preferred L is —$C_5H_{10}$— and/or $R^{23}$ is $CH_3CO$—.

Glycoconjugates

Another aspect of the present invention refers to a conjugate comprising a saccharide according to the present invention. Said conjugate proved to be efficient as a vaccine for immunization against diseases associated with *Streptococcus pneumoniae* serotype 5 bacteria.

Saccharides are known by the person skilled in the art as generally TI-2 (T cell independent-2) antigens and poor immunogens. TI-2 antigens are antigens, which are recognized only by mature B cells through the cross linking of surface exposed immunoglobulin receptors. Without T cell help, no immunological memory is generated and neither isotype switching from IgM to other IgG subclasses, nor B cells affinity maturation occurs. Moreover, saccharides are known poor immunogens in humans due to the structural homology to human glycolipids and glycoproteins. Due to their poor immunogenic properties, saccharides manifest poor ability to produce both antibody production by B cells, as well as the formation of memory cells, features which are essential for the production of potent vaccines.

Therefore, to produce a potent saccharide-based vaccine, the saccharides of general formulae (I), (III), (IV), (V), (VI) and (VII) are conjugated to an immunogenic carrier to provide conjugates, which present increased immunogenicity in comparison with the saccharide. Surprisingly, it was found that immunization with a conjugate comprising a saccharide of general formula (I) covalently linked to an immunogenic carrier results in the production of high titers of antibodies specific to the carbohydrate part of the saccharide of general formula (I). Said antibodies are cross-reacting with the natural SP-5 CPS and present opsonophagocytosis and bactericidal activity, thus conferring protection against *S. pneumoniae* serotype 5 bacteria.

In this context the term "immunogenic carrier" is defined as a structure, which is conjugated to the saccharide to form a conjugate that presents an increased immunity in comparison with the saccharide per se. Thus, the conjugation of the saccharides of general formulae (I), (III), (IV), (V), (VI) and (VII) to the immunogenic carrier has as effect the stimulation of the immune response against the saccharide of general formulae (I), (III), (IV), (V), (VI) and (VII) without inducing an immune response against the said immunogenic carrier.

Preferred immunogenic carriers are carrier proteins or glycosphingolipids with immunomodulatory properties. For the person skilled in the art, a carrier protein is a protein selected from the group comprising or consisting of: a diphtheria toxoid, a mutated diphtheria toxoid, a modified diphtheria toxoid, a mutated and modified diphtheria toxoid, a tetanus toxoid, a modified tetanus toxoid, a mutated tetanus toxoid, outer membrane protein (OMP), bovine serum albumin (BSA), keyhole limpet hemocyanine (KLH) or cholera toxoid (CT). The term "toxoid" as used herein refers to a bacterial toxin (usually an exotoxin), whose toxicity has been inactivated or suppressed either by chemical (formalin) or heat treatment, while other properties, typically immunogenicity, are maintained. A mutated toxoid as used herein is a recombinant bacterial toxin, which has been amended to be less toxic or even non-toxic by amending the wild-type amino acid sequence. Such a mutation could be a substitution of one or more amino acids. Such a mutated toxoid presents on its surface a functionality that can react with the functional group Y of the interconnecting molecule to provide a modified toxoid. Said functionality is known to the person skilled in the art and includes, but is not restricted to the primary amino functionality of a lysine residue that can react with activated esters, an isocyanate group or an aldehyde in presence of a reducing agent, to the carboxylate functionality of a glutamate or aspartate residue that can be activated by carbodiimides or to the thiol functionality of a cysteine residue.

Activated esters include, but are not restricted to N-(γ-maleimidobutyryloxy) sulfosuccinimide ester (sulfo-GMBS), succinimidyl (4-iodoacetyl) aminobenzoate (sulfo-SIAB), succinimidyl-3-(bromoacetamido)propionate (SBAP), disuccinimidyl glutarat (DSG), disuccinimidyl adipate (DSA), 2-pyridyldithiol-tetraoxatetradecane-N-hydroxysuccinimide (PEG-4-SPDP) (see FIG. 2).

The cysteine residue on the carrier protein can be converted to the corresponding dehydroalanine that can be further reacted with a suitable interconnecting molecule to provide modified carrier protein having on their surface the functional group X of the interconnecting molecule.

It is especially preferred that the saccharides of general formulae (I), (III), (IV), (V), (VI) and (VII) and preferably saccharides 10, 11, 21, 24, 25, 26, 32, 42, 57, 61, 65, 72, 27*, 33*, 36*, 73*, 85*and 88* are conjugated to the non-toxic mutated diphtheria toxin $CRM_{197}$ presenting as a functionality a primary amine functionality of a lysine residue.

$CRM_{197}$ like wild-type diphtheria toxin is a single polypeptide chain of 535 amino acids (58 kD) consisting of two subunits linked by disulfide bridges having a single amino acid substitution of glutamic acid for glycine. It is utilized as a carrier protein in a number of approved conjugate vaccines for diseases such as Prevnar.

Thus, in a preferred embodiment of the present invention the carrier protein presents on its surface primary amino functionalities of lysine residues that are able to react with the functional group Y of the interconnecting molecule to provide modified carrier protein having on their surface said functional group X of the interconnecting molecule, which is able to react with the terminal amino group of the linker of the compounds of general formula (I).

Said functional group X of the interconnecting molecules is selected of the group comprising or consisting of maleimide; α-iodoacetyl; α-bromoacetyl; and N-hydroxysuccinimide ester (NHS), aldehyde, imidoester, carboxylic acid, alkyl sulfonate, sulfonyl chloride, epoxide, anhydride, carbonate (see FIG. 3).

Preferably, the saccharide of general formulae (I), (III), (IV), (V), (VI) and (VII) is conjugated to the non-toxic mutated diphtheria toxin $CRM_{197}$, which is modified by maleimide. In yet another preferred embodiment, the saccharide of general formulae (I), (III), (IV), (V), (VI) and (VII) is conjugated to the non-toxic mutated diphtheria toxin $CRM_{197}$, which is modified by α-bromoacetamide. In the most preferred embodiment, the saccharide of general formula I is conjugated to the non-toxic mutated diphtheria toxin $CRM_{197}$, which is modified by N-hydroxysuccinimide adipate.

More preferably, the $CRM_{197}$ glycoconjugate is selected from the group consisting of:

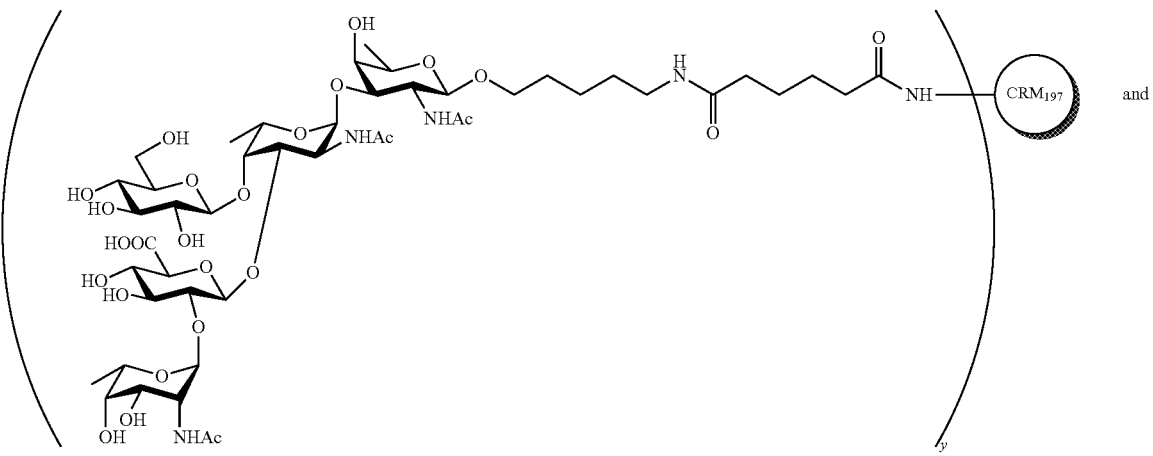
(XI)
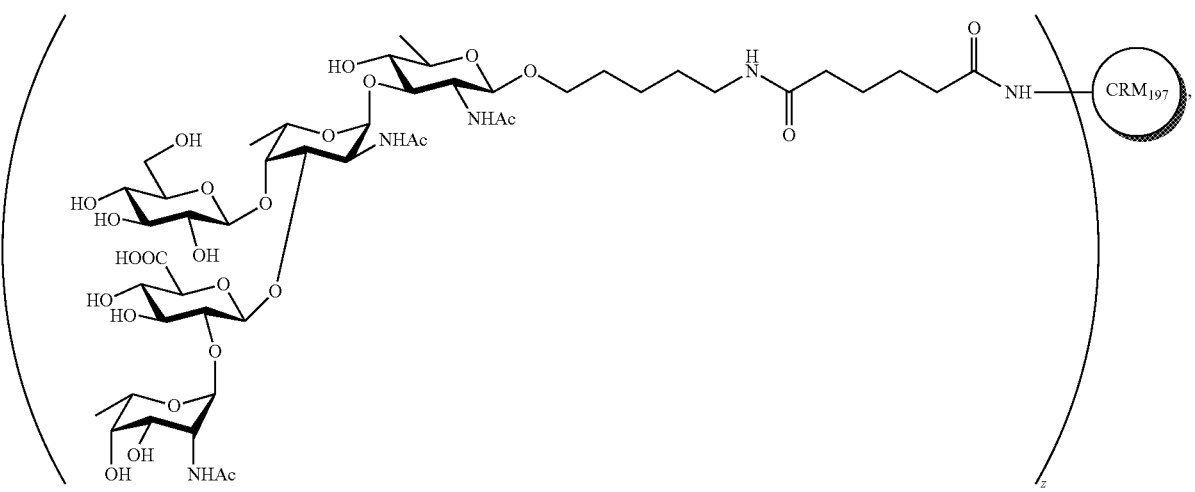
(XII)
wherein x, y and z are independently integer from 1 to 20; preferred integer from 1 to 15; more preferred integer from 5 to 14; more preferred integer from 7 to 13; more preferred integer from 8 to 12.
Most preferred is the conjugates 58a*, 58b*, 58c*, and 87*
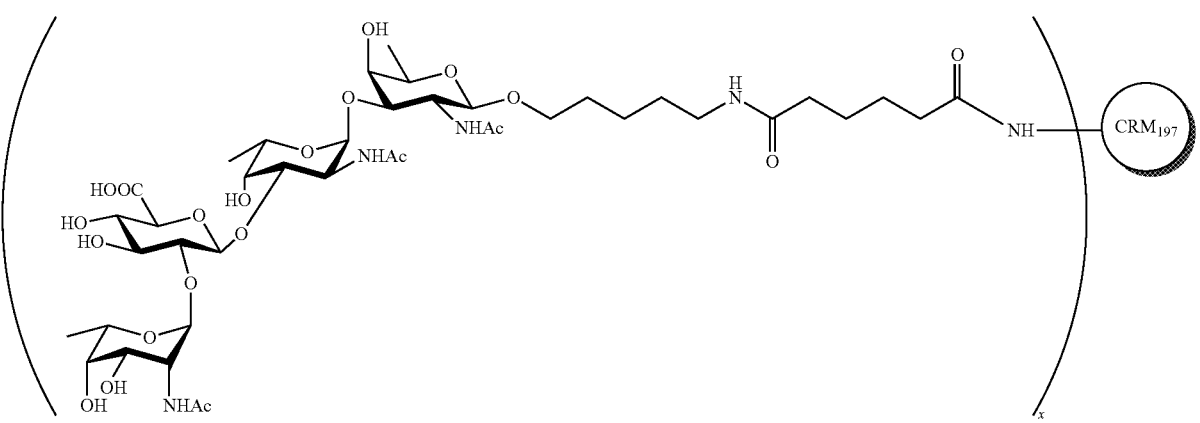
58*

58*a when x=7; 58*b when x=8; 58*c when x=11.2.

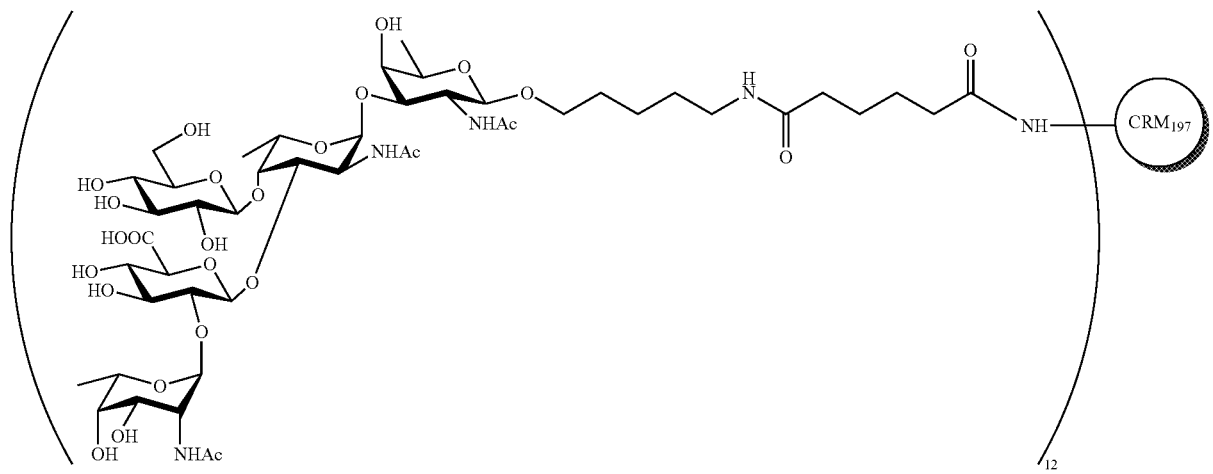

87*

In another embodiment, said immunogenic carrier is preferably a glycosphingolipid with immunomodulatory properties, and more preferably (2S,3S,4R)-1-(α-D-galactopyranosyl)-2-hexacosanoylaminooctadecane-3,4-diol. The term glycosphingolipid with immunomodulatory properties, as used herein, refers to a suitable glycosphingolipid capable of stimulating the immune system's response to a target antigen, but which does not in itself confer immunity as defined above.

Glycosphingolipids as used herein are compounds containing a carbohydrate moiety α-linked to a sphingolipid. Preferably, the carbohydrate moiety is a hexopyranose and most preferably is α-D-galactopyranose. For the person skilled in the art, sphingolipids are a class of lipids containing a C18 amino alcohol connected via an amide bond to a fatty acid. The C18 amino alcohol is preferably mono-, di- or polysubstituted with hydroxyl groups. Especially preferred, the C18 amino alcohol is phytosphingosine. The fatty acid is preferably a monocarboxylic acid having a saturated alkyl chain of a number of carbons ranging from 16 to 28 and more preferably from 18 to 26. Glycosphingolipids with immunomodulatory properties include, but they are not restricted to (2S,3S,4R)-1-(α-D-galactopyranosyl)-2-hexacosanoylaminooctadecane-3,4-diol, which can stimulate natural killer (NK) activity and cytokine production by natural killer T (NKT) cells and exhibits potent antitumor activity in vivo (*Proc. Natl Acad. Sci. USA,* 1998, 95, 5690).

The conjugates of the saccharides of general formulae (I), (III), (IV), (V), (VI) and (VII) with a glycosphingolipid with immunomodulatory properties have the advantage of being heat stable. To be suitable for conjugation, on the glycosphingolipid with immunomodulatory properties a functionality is introduced. Said functionality is prone to react directly with the terminal amino group of the linker of the saccharides of general formulae (I), (III), (IV), (V), (VI) and (VII) to provide conjugates of the saccharides of general formulae (I), (III), (IV), (V), (VI) and (VII), or with the functional group Y of the interconnecting molecule to provide the modified glycosphingolipid with immunomodulatory properties.

Preferably, said functionality is introduced at the C6 of the carbohydrate moiety of the glycosphingolipid with immunomodulatory properties. Thus, the glycosphingolipid with immunomodulatory properties is functionalized with a functionality, which is prone of reacting with the terminal amino group of the saccharides or with the functional group Y of the interconnecting molecule. A functionality prone to react with an amino group includes, but it is not restricted to activated ester, isocyanate group, aldehyde, epoxide, imidoester, carboxylic acid, alkyl sulfonate and sulfonyl chloride.

A functionality prone to react with the functional group Y of the interconnecting molecule so that to provide the modified glycosphingolipid with immunomodulatory properties presenting the functional group X of the interconnecting molecule includes, but it is not restricted to amine, alcohol, thiol, activated ester, isocyanate group, aldehyde, epoxide, vinyl, imidoester, carboxylic acid, alkyl sulfonate, sulfonyl chloride, vinyl group, alkynyl group and azido group.

Preferably, the functionality introduced at the C6 of the carbohydrate moiety of the glycosphingolipid with immunomodulatory properties is selected from the group comprising or containing an amine, a thiol, an alcohol, a carboxylic acid, a vinyl, maleimide, α-iodoacetyl, α-bromoacetyl, N-hydroxysuccinimide ester (NHS), 2-pyridyldithiols.

Said functional group X of the interconnecting molecules is selected from the group comprising or consisting of maleimide, α-iodoacetyl, α-bromoacetyl, N-hydroxysuccinimide ester (NHS), aldehyde, carboxylic acid, epoxyde alkyl sulfonate, sulfonyl chloride, anhydride, carbonate.

As used herein, the term "interconnecting molecule" refers to a bifunctional molecule containing functional group X and functional group Y, wherein functional group X is capable of reacting with the terminal amino group on the linker -L- and the functional group Y is capable of reacting with a functionality present on the immunogenic carrier or on the solid support.

It was found that the conjugates comprising the saccharides of the present invention, preferred the conjugates (X), (XI) and (XII), more preferred 58*a, 58*b, 58*c, 87*, are suitable for raising a protective immune response in a human and/or animal host, and therefore are useful for prevention and/or treatment of diseases associated with bacteria containing N-acetyl-L-pneumosamine in their capsular polysaccharide.

Preferably, the bacterium containing in the capsular polysaccharide N-acetyl-L-pneumosamine is *Streptococcus pneumoniae* serotype 5.

In a preferred embodiment, the conjugates comprising the saccharides of general formulae (I), (III), (IV), (V), (VI) or (VII) conjugated to an immunogenic carrier, preferred the conjugates (X), (XI) and (XII), more preferred 58*a, 58*b, 58*c, 87*, are useful for prevention and/or treatment of diseases associated with bacteria, and particularly with diseases associated with bacteria containing N-acetyl-L-pneumosamine in their capsular polysaccharide, and preferably with *Streptococcus pneumoniae* serotype 5, wherein said diseases include pneumonia, meningitis, otitis media, bacteremia and acute exacerbation of chronic bronchitis, sinusitis, arthritis and conjunctivitis.

One aspect of the present invention relates to pharmaceutical compositions, especially vaccines comprising a conjugate comprising a saccharide of general formula (I) conjugated to an immunogenic carrier, and/or one saccharide of general formula (I), together with at least one pharmaceutically acceptable cryoprotectant, lyoprotectant, excipient and/or diluent. Said pharmaceutical compositions can be used for raising a protective immune response in a human and/or animal host.

One aspect of the present invention relates to pharmaceutical compositions, especially vaccines further comprising at least one of antigens of other *Streptococcus pneumoniae* serotypes, preferred serotypes 2, 4, 8, 9A, 9V and 14.

Said vaccine may be prepared in the form of a suspension or may be lyophilized. The suspension form may be stored frozen. In the lyophilized form, it is preferable to add one or more stabilizers. Optionally, one or more adjuvants may be added as well. Any conventional stabilizers and adjuvants may be included in a vaccine according to this invention.

The term "adjuvant" as used herein refers to an immunological adjuvant i.e. a material used in a vaccine composition that modifies or augments the effects of said vaccine by enhancing the immune response to a given antigen contained in the vaccine without being antigenically related to it. For the persons skilled in the art, classically recognized examples immunological adjuvants include but are not restricted to oil emulsions (e.g. Freund's adjuvant), saponins, aluminium or calcium salts (e.g. alum), non-ionic block polymer surfactants, and many others.

Vaccination can be performed at any age. The vaccine many be administered subcutaneously, by spray, by injection, orally, intraocularly, intratracheally or nasally.

Another aspect of the present invention relates to pharmaceutical formulations and pharmaceutical compositions containing the vaccine as an active ingredient, together with at least one pharmaceutically acceptable carrier, excipient, solvent and/or diluents.

Further preferred, the pharmaceutical composition is formulated in the form of a lyophilisate or liquid buffer solution.

The vaccine can also be administered in form of its pharmaceutically active salt optionally using substantially nontoxic pharmaceutically acceptable carrier, excipients, adjuvants or diluents. The vaccine of the present invention is prepared in a conventional solid or liquid carrier or diluents and a conventional pharmaceutically-made adjuvant at suitable dosage level in a known way. The preferred preparations and formulations are in administrable form, which is suitable for oral application. These administrable forms, for example, include pills, tablets, film tablets, coated tablets, capsules, powders and deposits. Forms other than oral administrable forms are also possible. The inventive vaccine may be administered by any appropriate means, including but not limited to inhalation; injection (intravenous, intraperitoneal, intramuscular, subcutaneous); by absorption through epithelial or mucocutaneous linings (oral mucosa, rectal and vaginal epithelial linings, nasopharyngial mucosa, intestinal mucosa); orally, rectally, transdermally, topically, intradermally, intragastrically, intracutaneously, intravaginally, intravasally, intranasally, intrabuccally, percutaneously, sublingually, or any other means available within the pharmaceutical arts.

The vaccine of the present invention, containing a conjugate comprising the saccharide of general formula (I) conjugated to an immunogenic carrier, the saccharide of general formula (I) or pharmaceutically acceptable salts thereof as an active ingredient will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active ingredient may be combined with any oral nontoxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and colouring agents may also be incorporated in the mixture.

Suitable binders include starch, gelatin, natural sugars, corn sweeteners, natural and synthetic gums such as acacia, sodium alginate, carboxymethyl-cellulose, polyethylene glycol and waxes. Among the lubricants that may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the vaccine of the present invention may be formulated in sustained release form to provide the rate controlled release of any one or more of the components or active ingredients to optimize the therapeutic effects. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidifies.

Also included are solid form preparations that are intended to be converted, shortly before use, to liquid form preparations for either oral or parenteral administration. Such liquid forms include solutions, suspensions and emulsions.

The vaccine of the present invention may also be deliverable transdermally. The transdermal compositions may take the form of creams, lotions, aerosols and/or emulsions and can be included in a transdermal patch of the matrix or reservoir type as are conventional in the art for this purpose.

The term capsule refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet means compressed or molded solid dosage form containing the active ingredients with suitable diluents. The tablet can be prepared by compression of mixtures or granulations obtained by wet granulation, dry granulation or by compaction well known to a person skilled in the art.

Oral gels refer to the active ingredients dispersed or solubilized in a hydrophilic semi-solid matrix.

Powders for constitution refer to powder blends containing the active ingredients and suitable diluents which can be suspended in water or juices.

Suitable diluents are substances that usually make up the major portion of the composition or dosage form. Suitable diluents include sugars such as lactose, sucrose, mannitol and sorbitol, starches derived from wheat, corn rice and potato, and celluloses such as microcrystalline cellulose. The amount of diluents in the composition can range from about 5 to about 95% by weight of the total composition, preferably from about 25 to about 75%, more preferably from about 30 to about 60% by weight, and most preferably from about 40 to 50% by weight.

The term disintegrants refers to materials added to the composition to help it break apart (disintegrate) and release the medicaments. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses and cross-linked microcrystalline celluloses such as sodium croscarmellose, alginates such as alginic acid and sodium alginate, clays such as bentonites, and effervescent mixtures. The amount of disintegrant in the composition can range from about 1 to about 40% by weight of the composition, preferably 2 to about 30% by weight of the composition, more preferably from about 3 to 20% by weight of the composition, and most preferably from about 5 to about 10% by weight.

Binders characterize substances that bind or "glue" powders together and make them cohesive by forming granules, thus serving as the "adhesive" in the formulation. Binders add cohesive strength already available in the diluents or bulking agent. Suitable binders include sugars such as sucrose, starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropyl-methylcellulose; polyvinylpyrrolidone; and inorganics such as magnesium aluminum silicate. The amount of binder in the composition can range from about 1 to 30% by weight of the composition, preferably from about 2 to about 20% by weight of the composition, more preferably from about 3 to about 10% by weight, even more preferably from about 3 to about 6% by weight.

Lubricant refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and D, L-leucine. Lubricants are usually added at the very last step before compression, since they must be present on the surfaces of the granules and in between them and the parts of the tablet press. The amount of lubricant in the composition can range from about 0.05 to about 15% by weight of the composition, preferably 0.2 to about 5% by weight of the composition, more preferably from about 0.3 to about 3%, and most preferably from about 0.3 to about 1.5% by weight of the composition.

Glidents are materials that prevent caking and improve the flow characteristics of granulations, so that flow is smooth and uniform. Suitable glidents include silicon dioxide and talc. The amount of glident in the composition can range from about 0.01 to 10% by weight of the composition, preferably 0.1% to about 7% by weight of the total composition, more preferably from about 0.2 to 5% by weight, and most preferably from about 0.5 to about 2% by weight.

Colouring agents are excipients that provide coloration to the composition or the dosage form. Such excipients can include food grade dyes and food grade dyes adsorbed onto a suitable adsorbent such as clay or aluminium oxide. The amount of the colouring agent can vary from about 0.01 to 10% by weight of the composition, preferably from about 0.05 to 6% by weight, more preferably from about 0.1 to about 4% by weight of the composition, and most preferably from about 0.1 to about 1%.

Techniques for the formulation and administration of the vaccine of the present invention may be found in "Remington's Pharmaceutical Sciences" Mack Publishing Co., Easton Pa. A suitable vaccine composition comprising at least one conjugate of the present invention and/or pharmaceutically acceptable salts thereof may be a solution of one conjugate comprising a saccharide of general formula (I) conjugated to an immunogenic carrier in a suitable liquid pharmaceutical carrier or any other formulation such as tablets, pills, film tablets, coated tablets, dragees, capsules, powders and deposits, gels, syrups, slurries, suspensions, emulsions, and the like.

A therapeutically effective dosage of one conjugate according to the present invention or of one saccharide of general formula (I) refers to that amount of the compound that results in an at least a partial immunization against a disease. Toxicity and therapeutic efficacy of such compounds can be determined by standard pharmaceutical, pharmacological, and toxicological procedures in cell cultures or experimental animals. The dose ratio between toxic and therapeutic effect is the therapeutic index. The actual amount of the composition administered will be dependent on the subject being treated, on the subject's weight, the severity of the affliction, the manner of administration and the judgement of the prescribing physician.

Yet another aspect of the present invention refers to saccharide of general formula (I) for use as marker in immunological assays for detection of antibodies against bacteria containing N-acetyl-L-pneumosamine in their capsular polysaccharide.

Such assays comprise, for instance, microarray and ELISA useful for detection of antibodies against bacteria containing N-acetyl-L-pneumosamine in their capsular polysaccharide, such as *Streptococcus pneumoniae* serotype 5.

The saccharides of the present invention can be easily conjugated to solid supports for providing immunological assays useful for detection of antibodies against bacteria containing N-acetyl-L-pneumosamine in their capsular polysaccharide. Said solid supports present on their surface a functionality that is prone to react with the amino group of saccharides of general formula (I) or with the functional group Y of the interconnecting molecule to provide modified solid supports, presenting on their surface the functional group X of the interconnecting molecule that can further react with the amino group of saccharides of general formula (I). In an embodiment according to the present invention the solid supports are microarray slides, which present on their surface a functionality that is prone to react with the functional group Y of the interconnecting molecule to provide modified microarray slides, presenting of their surface the functional group X of the interconnecting molecule. Example of such microarray slides include, but are not restricted to Corning® epoxide coated slides or Corning® GAPS™ II coated slides.

In a preferred embodiment the solid supports are microarray slides presenting on their surface a functionality that is prone to react with the amino group of saccharides of general formula (I), and more preferably an N-hydroxysuccinimide (NHS) activated ester. Such microarray slides are for example CodeLink® NHS slides.

A glycan microarray prepared as described in Example 78 was used to identify the binding epitopes of commercial anti-SP5 specific typing sera generated in rabbits (see FIG. 4).

As shown by FIG. 4A, only three out of the eleven printed glycans were bound by specific anti-SP5 IgG, namely tetrasaccharide 33* (position 1), α-PneNAc-(1→2)-GlcA disaccharide 27* (position 8) and α-PneNAc monosaccharide 36* (position 10). All three recognized oligosaccharides contain the α-PneNAc residue, demonstrating that this motif is part of the recognized epitope. It was further observed that IgG bound tetrasaccharide 33* and disaccharide 27* in comparable levels, suggesting that α-PneNAc-(1→2)-GlcA is in fact the epitope recognized by IgG of specific SP5 typing sera. FIG. 4B shows a microarray sample where the typing serum was pre-incubated with a solution of the natural SP5 CPS. The anti-glycan IgG levels are significantly reduced compared to the sample of FIG. 4A. This means that antibodies bound to the natural CPS during pre-incubation are no longer available for binding to the synthetic glycans. Consequently, the binding epitopes of natural CPS and the synthetic glycans are identical.

In order to identify epitopes recognized by the human immune system, further screenings were carried out using pooled sera of humans who had received a pneumococcal CPS-based vaccine, containing the CPS of multiple different serotypes (see FIG. 5).

The IgG response of immunized humans towards the synthetic glycans is shown in FIG. 5A. Although the sera of immunized humans were not SP5 specific, they contained IgG predominantly against tetrasaccharide 33* (position 1). IgG binding to PneNAc-(1→2)-GlcA disaccharide 27* (position 8) and PneNAc 36* (position 10) were also observed, however at lower levels.

Additionally, low levels of anti-21* (position 5) and anti-51* (position 6) IgG and very low levels of anti-20* (position 4), anti-44* (position 7), anti-52* (position 9) and anti-37* (position 11) IgG were detected. Antibodies against D-FucNAc 15* (position 3) and the Sug-containing sample 14* (position 2) were not detected at all. Interestingly, higher levels of anti-disaccharide 21* antibodies were detected than for the sample containing L-FucNAc-(1→3)-β-Sug 20*. This would suggest that the presence of the ketone is indeed detrimental to antibody binding. Pre-incubation of the human sera with the natural SP5 CPS, shown in FIG. 5B, led to a significant reduction of anti-tetrasaccharide 33* IgG levels. This proves that the antibodies binding 33* are SP5 specific since they also bind the SP5 CPS.

Further microarray data indicated that the type sera recognized the several synthetic glycans along with CPS-5 polysaccharide (FIG. 8B). However the type sera also recognized the tetrasaccharide 33* and pentasaccharide 73* with high affinity and considered to be the B cell epitopes that has been presented to the MHCII molecules. Thus, suggesting that these oligosaccharides are critical for immunity.

It has been shown that substructure of the SP5 CPS such as reference structure 1 (Ref.1) and 2 (Ref.2) which do not contain the pneumosamine sugar are not recognized by the antibodies produced during immunization. Therefore, it is assumed that the pneumosamine is a very important part of the immunogenic epitope and is somehow required for effective and protective immune response and antibody production. So far it was not possible to trigger determinable antibody titer against SP5 CPS when using one of the above mentioned reference structure conjugated to $CRM_{197}$ for immunization in rabbits.

In conclusion, the microarray analyses revealed that the terminal PneNAc residue is part of the epitope recognized by anti-SP5 CPS antibodies and that α-PneNAc-(1→2)-GlcA is the predominant epitope recognized by SP5 typing sera. In the case of vaccinated humans, the SP5-specific epitope seems to be larger, resembling tetrasaccharide 33* and pentasaccharide 73*. The reducing end D-FucNAc or Sug residues do not seem to be important for the immunological response to SP5.

Glycan microarray with antibodies raised in rabbit against ST5 synthetic glycan conjugates also demonstrates (Example 81, FIGS. 9B and D). This result suggested that the tetrasaccharide 33* and pentasaccharide 73* are immunogenic in rabbit and induced cross-reactive antibodies.

As shown in Example 82 and FIG. 10, antibody responses analyzed by ELISA support that pentasaccharide 73* is more immunogenic compared to tetrasaccharide 33*.

Surface binding of anti-ST5 glycan conjugates sera indicates that antibodies against the anti-ST5 glycans localized the epitope on the surface of pneumococci (Example 83, FIG. 11) and considered to be a novel synthetic vaccine candidate.

Opsonophagocytic killing assay was performed to assess the functional relevance of the antibodies induced in response to immunization with ST5 (tetrasaccharide) conjugate 58*c. This data demonstrates that ST5 (tetrasaccharide) conjugate 58*c generates neutralizing antibodies and promote the killing of pneumococci by differentiated HL-60 cells.

Chemical Synthesis

Scheme 1: Retrosynthetic scheme.

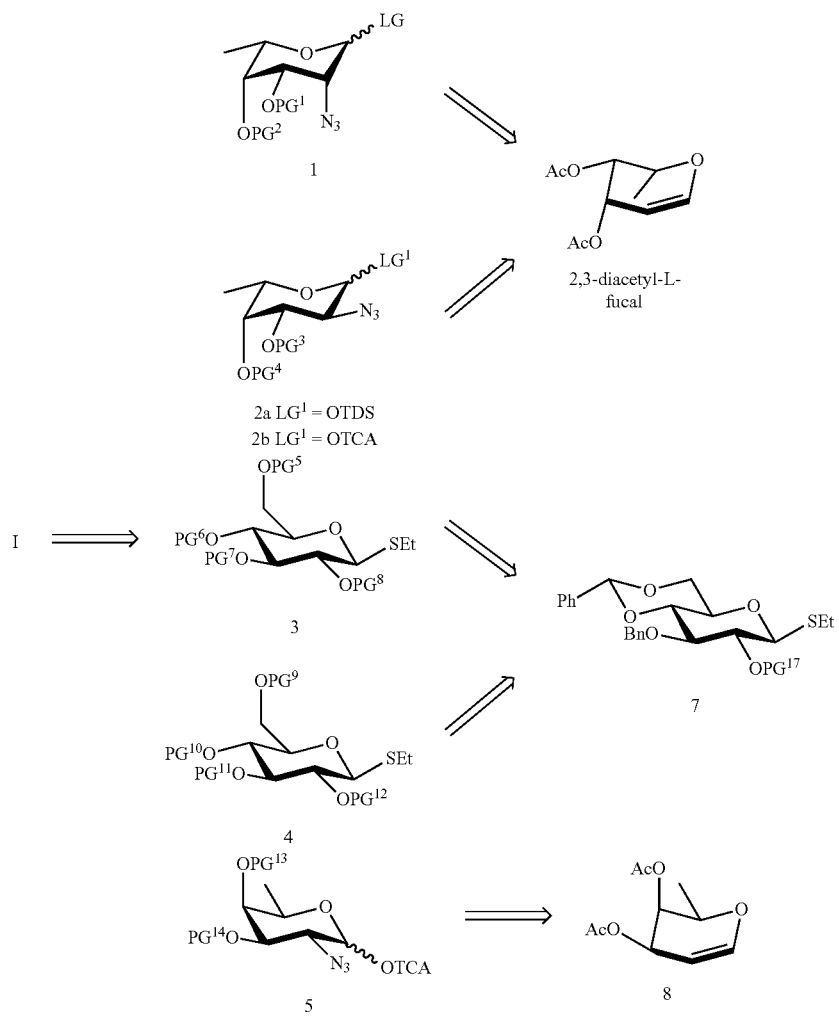

The saccharides of general formula I can be assembled starting from building blocks 1, 2, 3, 4, 5 and 6 (see Scheme 1). Building blocks 1 and 2 can be easily prepared via an azidoselenation reaction starting from known 3,4-diacetyl-L-fucal. Thioglucosides 3 and 4 can, for example, be accessed by regioselective opening of the benzylidene acetal installed at the positions 4 and 6 of the thioglucoside building block 7. D-Fucose building block 5 can be obtained via an azidoselenation reaction starting from known D-fucal 8.

LG represents a leaving group that is preferably selected from:

—F, —Cl, —Br, —I, —$SR^{28}$, —$SeR^{29}$, —$OPO_3R^{30}{}_2$,

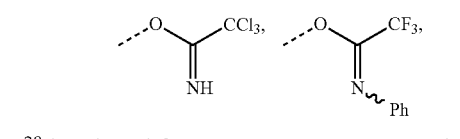

$R^{28}$ is selected from: —$CH_3$, —$CH_2CH_3$, -Ph, $R^{29}$ represents —Ph;
$R^{30}$ represents —$CH_2CH_2CH_2CH_3$.

$PG^1$, $PG^2$, $PG^3$, $PG^4$, $PG^5$, $PG^6$, $PG^7$, $PG^8$, $PG^9$, $PG^{10}$, $PG^{11}$, $PG^{12}$, $PG^{13}$, $PG^{14}$, $PG^{15}$, $PG^{16}$ and $PG^{17}$ represent protecting groups. The term "protecting group" as used herein refers to commonly used groups in organic synthesis, preferably used for protection of amines, hydroxyl groups, thiols, imines, carbonyls, carboxyls or other common functional groups, and particularly preferred for amines and hydroxyl groups.

The protecting groups can be differentiated in permanent protecting groups and temporary protecting groups. Permanent protecting groups are protecting groups that are stable during the entire synthesis and that can be efficiently removed at the late stage of the synthesis. In this case, permanent protecting groups include $PG^1$, $PG^2$, $PG^6$, $PG^7$, $PG^9$, $PG^{11}$, $PG^{15}$ and $PG^{16}$. $PG^1$, $PG^2$, $PG^6$, $PG^7$, $PG^9$ and $PG^{11}$ are masking the hydroxyl groups during the entire synthesis, while protecting groups $PG^{15}$ and $PG^{16}$ are masking the terminal amino group present on the linker L. Preferably, protecting groups $PG^1$, $PG^2$, $PG^6$, $PG^7$, $PG^9$, $PG^{10}$, $PG^{11}$ and $PG^{15}$ are benzyl groups and protecting group $PG^{16}$ is a benzyloxycarbonyl protecting group (Cbz).

The temporary protecting groups are generally orthogonal protecting groups that can be selectively removed at different levels of the synthesis to free hydroxyl groups for subsequent introduction of different substituents, including monosaccharides or other protecting groups. In this case, temporary protecting groups include $PG^3$, $PG^4$, $PG^5$, $PG^8$, $PG^{12}$, $PG^{13}$, $PG^{14}$ and $PG^{17}$.

The ingenious choice of protecting groups allows expedient access to a library of saccharides of general formula I functionalized with an amino group for subsequent conjugation to an immunogenic carrier or a solid support.

More specifically $PG^3$, $PG^4$, $PG^5$, $PG^8$, $PG^{12}$, $PG^{13}$, $PG^{14}$ and $PG^{17}$ are temporary protecting groups suitable for protection of hydroxyl groups i.e. being capable to be removed subsequently one after another by a suitable sequence of deprotection reactions. Preferably $PG^3$, $PG^4$, $PG^5$, $PG^8$, $PG^{12}$, $PG^{13}$, $PG^{14}$ and $PG^{17}$ are selected from the group consisting of or comprising: allyl, acetyl, benzoyl, p-methoxybenzyl, trityl, 2-naphthylmethyl, triisopropylsilyl, tert-butyldimethylsilyl, tert-butyldiphenylsilyl, tert-butylmethoxphenylsilyl, triethylsilyl, trimethylsilyl, 2-trimethylsilylethoxymethyl, 9-fluorenylmethoxycarbonyl and levulinoyl.

Preferably, $PG^3$ and $PG^4$ installed at C-3 and C-4 of building block 2 are participating protecting groups ensuring the formation of the α-glycosidic linkage, and more preferably they are acetyl groups.

Preferably, protecting groups $PG^8$ and $PG^{12}$ present at position 2 of the glucoside building blocks 3 and 4 are participating protecting groups favoring the formation of the β-glycosidic linkage that are selected from benzoyl and levulinoyl. Preferably protecting group $PG^{17}$ has the same meaning as protecting groups $PG^8$ and $PG^{12}$.

Orthogonal protecting group $PG^5$ was installed at the 6$^{th}$ position of the glucoside 3 in anticipation of the introduction of the carboxylic acid group at this position. Preferably, protecting group $PG^5$ represents allyl, 2-naphthylmethyl, benzoyl or p-methoxybenzyl. Alternatively, building block 3a could be used instead of building block 3 for the assembly of the saccharides of general formula (I).

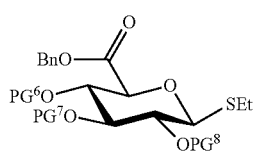

3a

Protecting groups $PG^{13}$ and $PG^{14}$ are non-participating protecting groups. Preferably, protecting group $PG^{14}$ can be removed in presence of $PG^{13}$ in anticipation of the chain elongation at the C-3 position. Such non-participating protecting groups are known to the person skilled in the art and include, but are not restricted to allyl ether, silyl ethers, 2-naphthylmethyl ether and p-methoxybenzyl ether. Preferably, $PG^{14}$ is p-methoxybenzyl and $PG^{13}$ is 2-naphthylmethyl.

Hence, the saccharides of general formula I with $R^1$ representing $R^4$ and $R^4$ representing $R^6$ (i.e. monosaccharides of general formula 10) can be synthesized according to the synthetic pathway described in Scheme 2. Synthesis of trichloroacetimidate L-pneumosamine 1 was accomplished via azidoselenation of known 3,4-diacetyl-L-fucal. The terminal amino linker was appended at the anomeric position by treatment of the builiding block 1 with the amino alcohol HO-L-NBnCbz in presence of TMSOTf at −30° C.

Protected monosaccharide 9 can be converted to saccharides of general formula (10) following deprotection procedures known to the skilled person. For example, hydrogenolysis using Pd/C as catalyst in a mixture of solvents EtOH/$H_2O$/AcOH provides saccharides of general formula 10 with $R^{23}$ being —H. Saccharides of general formula 10 with $R^{23}$ being —C(O)$CH_3$ can be accessed via a two-step deprotection procedure including conversion of the azido group to the acetamido group by treatment with thioacetic acid in pyridine, followed by hydrogenolysis using Pd/C as catalyst. Saccharides of general formula 10 with $R^{23}$ being —C(O)$CF_3$ or —C(O)$CCl_3$ can be prepared via a three step deprotection procedure including chemoselective reduction of the azido group to the amino group, followed by acylation and hydrogenolysis using Pd/C as catalyst. The chemoselective reduction can be carried out via Staudinger reaction ($PPh_3$ or $PMe_3$, THF/$H_2O$) or via hydrogenolysis on Pd/C in presence of ammonia, ammonium acetate, triphenylphosphine or pyridine. The acylation can be for example accomplished by treatment of the amine with the suitable acyl chloride or the suitable anhydride in presence of pyridine.

Scheme 2: Synthesis of monosaccharides of general formula 10:
a. HO—L—NBnCbz, TMSOTf, DCM, 4Å molecular sieves, −30° C. to −20° C.; b. general deprotection procedure.

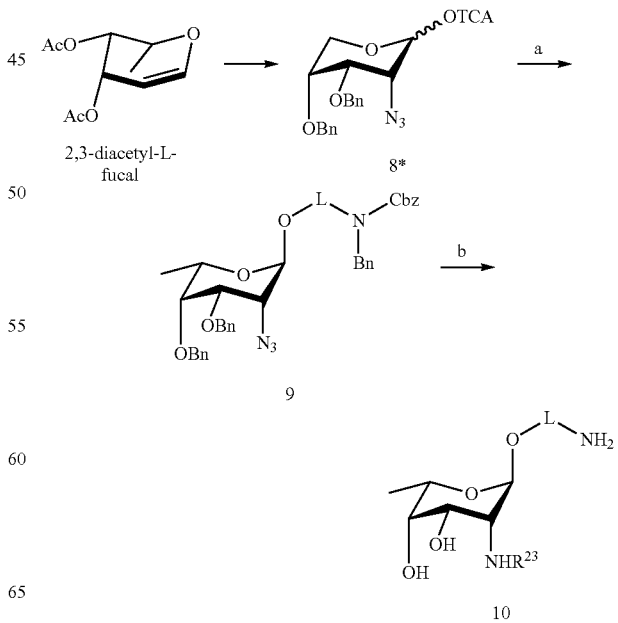

The saccharides of general formula I with $R^1$ representing $R^4$ and $R^4$ representing

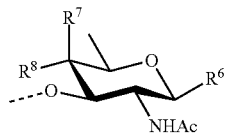

(i.e. disaccharides of general formula 11) can be, for example, prepared according to the synthetic pathway described in Scheme 3. Hence, starting from known D-fucal 8, trichloroacetimidate 4* was synthesized in 5 steps according to procedures described in the literature. At this level, the amino linker was appended at the anomeric position by reacting the trichloroacetimidate 4* with amino alcohol HO-L-NBnCbz in presence of TMSOTf at −15° C. to give monosaccharide 13. To access disaccharides of general formula 11, wherein $R^{23}$ is selected from —H, —C(O)CF$_3$ and —C(O)CCl$_3$, the azido group is converted at this level to the acetamido group by, treatment with thioacetic acid in pyridine to provide intermediate 14. Removal of the PMB protecting group on intermediates 13 and 14 provides alcohols 15 and 16 representing the glycosyl acceptor for the next glycosylation reaction. Alcohol 15 was then reacted with imidate 8* in presence of TMSOTf to provide disaccharide 17 corresponding to the precursors of disaccharides of general formula 11 with $R^{23}$ being —C(O)CH$_3$. The same reaction procedure applied to monosaccharide 16 results in the formation of the disaccharide 18, which is the precursor of the disaccharide of general formula 11 with $R^{23}$ being selected from —H, —C(O)CF$_3$ and —C(O)CCl$_3$. Step e including installation of the residues $R^7$ and $R^8$ and the final deprotection is in detail described for compound 17 in Scheme 4. The same pathway is performed for the compound 18.

Scheme 3: Synthesis of disaccharides of general formula 11:
a. HO—L—NBnCbz, TMSOTf, DCM, 4Å molecular sieves, -15° C.;
b. CAN, acetone/water; c. 1, TMSOTf, DCM, 4Å molecular sieves, -30° C. to -20° C.; d. 1) installation of the residues $R^7$ and $R^8$; 2) deprotection.

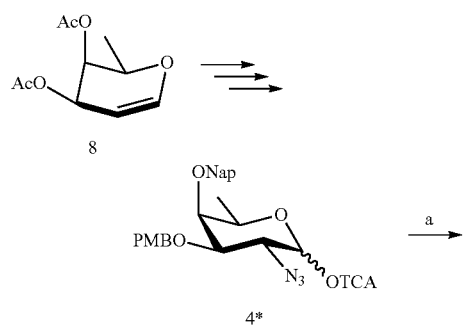

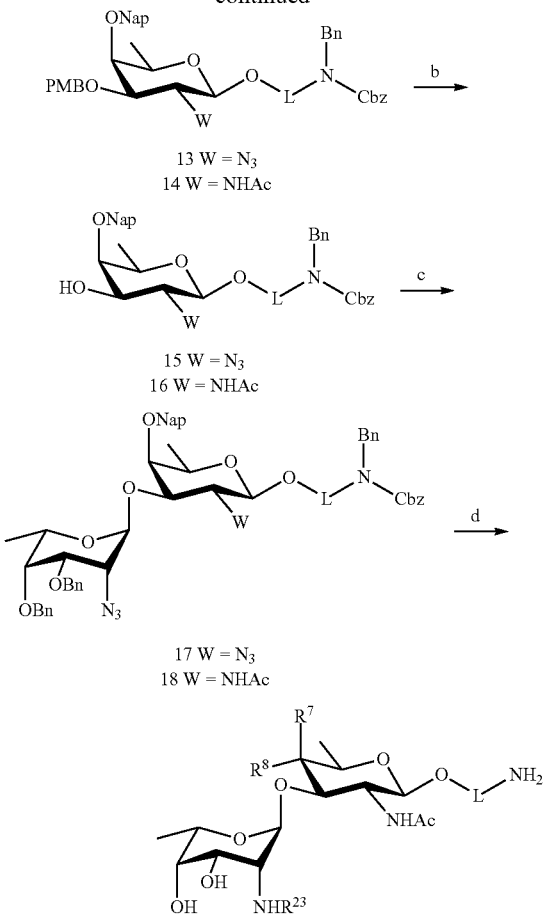

To access disaccharide 21 ($R^7$=—OH and $R^8$=—H) compound 17 is treated with thioacetic acid in pyridine so that the azido group is converted to the acetamido group, then the Nap protecting group is removed with DDQ and hydrogenolysis on Pd/C is performed. To Z provide disaccharide 25 ($R^7$ and $R^8$ represent —OH or they form together a =O residue), intermediate alcohol 20 is submitted to an oxidation reaction using Dess-Martin periodinane to provide ketone 22. Then, the permanent protecting groups on ketone 22 are removed to provide disaccharide 25 as a ketone ($R^7$ and $R^8$ form together a =O residue) or as a hydrated ketone ($R^7$ and $R^8$ represent —OH). When required, ketone 22 can be temporarily protected as a dithiane to avoid degradation.

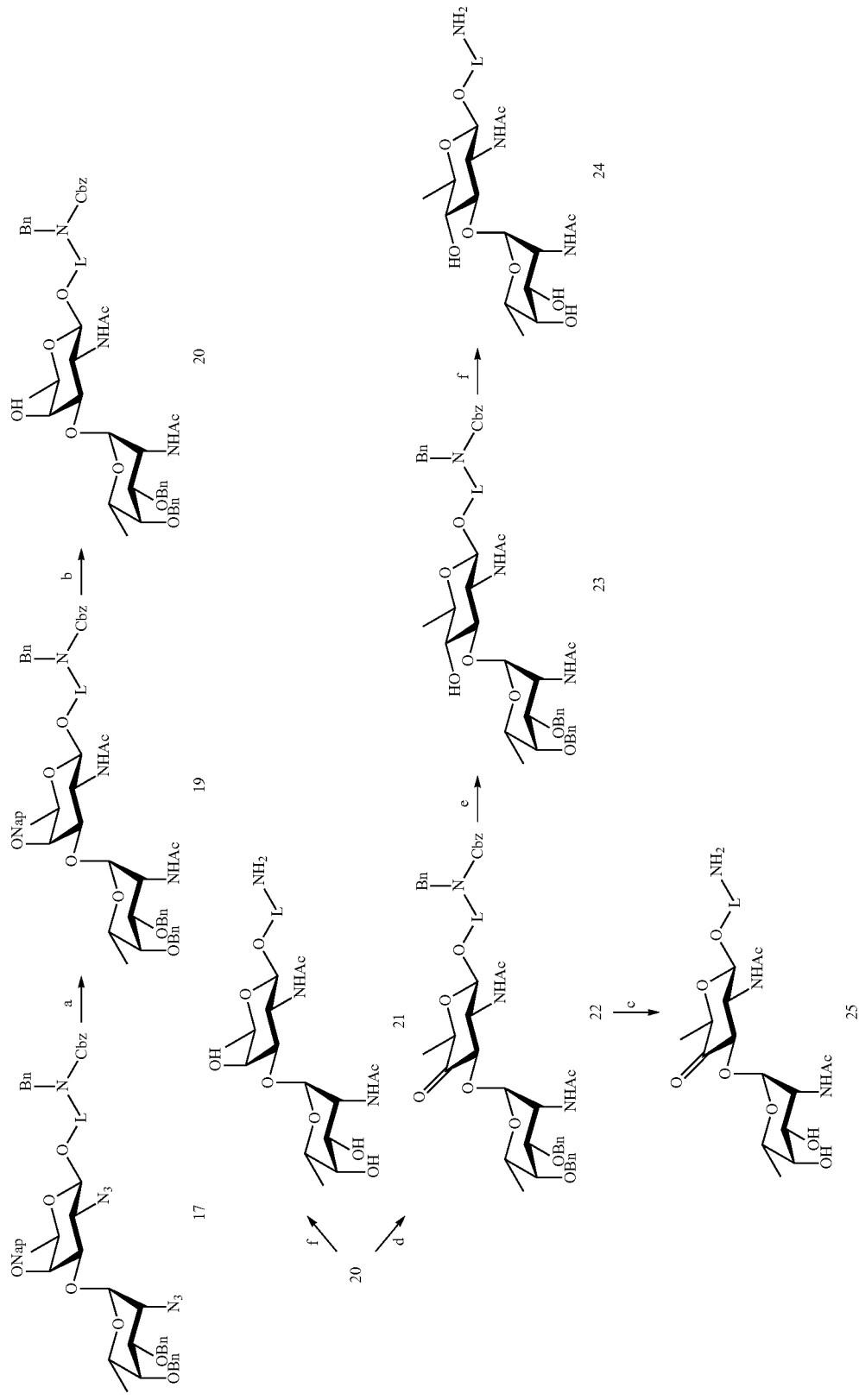

Starting from ketone intermediate 22, disaccharide 24 ($R^7$=—H and $R^8$=—OH) can be easily accessed via regioselective reduction of the ketone with L-selectride and subsequent hydrogenolysis using Pd/C as catalyst.

The saccharides of general formula I with $R^1$ representing

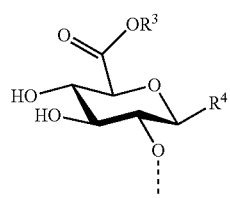

and $R^4$ representing $R^6$ (disaccharides of general formula 26) can be assembled following the synthetic route shown in Scheme 5.

Union of thioglycoside 10* with the linker by activation with NIS/TfOH provides monosaccharide 28. A thioglycoside 10*, which is protected at the $6^{th}$ position as a benzoyl ester instead of 2-naphthylmethyl ether is also suitable to be used as building block at this level. Removal of the levulinic ester gives alcohol 29 that is further subjected to glycosylation with 8*, resulting in disaccharide 30. At this level, residue B can be installed on the molecule applying one the reactions mentioned for Scheme 2. Subsequently, Nap protecting group is removed with DDQ to provide primary alcohol 31, which is further oxidized with TEMPO and iodobenzene diacetate to give the carboxylic acid. The carboxylic acid is further subjected to hydrogenolysis using Pd/C as catalyst to give the disaccharides of general formula 26. To access disaccharides with $R^3$ being different of —H i.e. $R^3$ being selected from —$CH_3$, —$C_2H_5$, —$C_3H_7$, —$C_4H_9$ and —$CF_3$, an esterification step should be inserted between step f and step g.

Scheme 5: Synthesis of disaccharides of general formula 26:

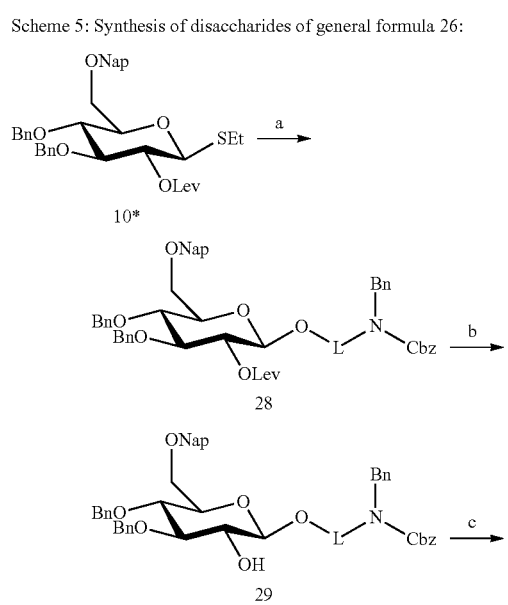

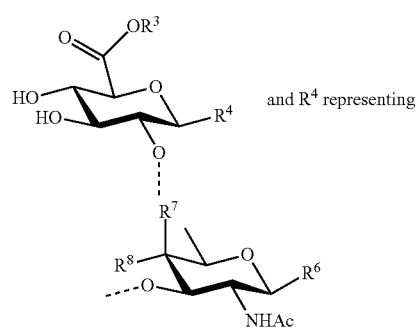

a. HO—L—NBnCbz, NIS/TfOH, DCM, 4 Å MS, -30° C. to -20° C.; b. $N_2H_4 \cdot H_2O$, AcOH/pyridine, DCM; c. 8*, TMSOTf, DCM, 4 Å MS, -30° C. to -20° C.; d. conversion —$N_3$ residue to —$NHR^{23}$ residue; e. DDQ, DCM, phosphate buffer, pH 7.2, 0° C. to rt; f. TEMPO, iodobenzene diacetate, DCM, $H_2O$, 0° C. to rt; g. $H_2$, Pd/C, EtOH/EtOAc/$H_2O$/AcOH.

The saccharides of general formula (I) with $R^1$ representing (trisaccharides of general formula 32) can be assembled following the synthetic route shown in Scheme 6.

Firstly, building blocks 15 and 16 obtained as previously described are reacted with thioglucoside 10* (see Scheme 5) in presence of an activator such as NIS/TfOH to provide disaccharides 33 and 34. Removal of the Lev protecting group furnishes secondary alcohols 36 and 37 that are further involved in a glycosidic coupling to give trisaccharides 38 and 39. Conversion of the —$N_3$ group to corresponding —$NHR^{23}$ residue according to one of the previously described procedure, followed by cleavage of the Nap ether furnishes the diol of general formula 40. Regioselective oxidation of the primary alcohol with TEMPO and iodobenzene diacetate gives carboxylic acid 41 that can be further converted using the appropriate reaction conditions for installation of the residues $R^7$ and $R^8$ (see Scheme 4) and hydrogenolysis to trisaccharides of general formula 32. Optionally, trisaccharides of general formula 32 with $R^{23}$ being —H could be easily accessed starting by subjecting trisaccharide 38 to steps e, f and g.

Scheme 6: Synthesis of trisaccharides of general formula 32: a. 10*, NIS/TfOH, DCM, 4 Å MS, -20° C. to -10° C.; b. $N_2H_4 \cdot H_2O$, AcOH/pyridine, DCM; c. 8*, TMSOTf, DCM, 4ÅMS, -30° C. to -20° C.; d. conversion —$N_3$ residue to —$NHR^{23}$ residue.; e. DDQ, DCM, phosphate buffer, pH 7.2, 0° C. to rt; f. TEMPO, iodobenzene diacetate, DCM, $H_2O$, 0° C. to rt; g. 1) installation of the residues $R^7$ and $R^8$; 2) $H_2$, Pd/C, EtOH/EtOAc/$H_2O$/AcOH.

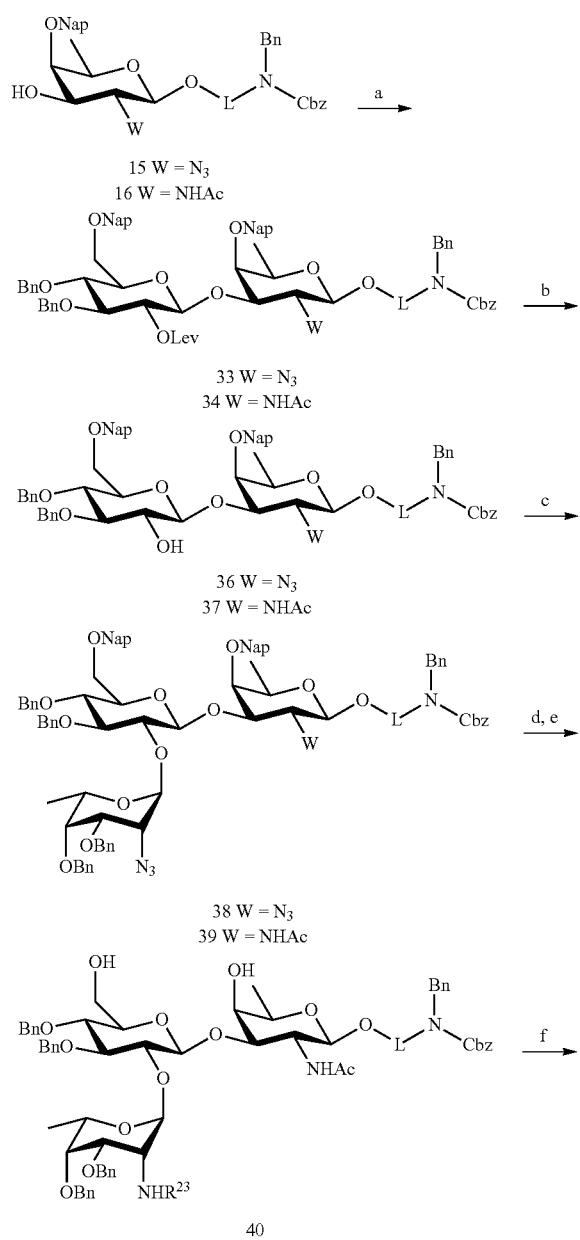

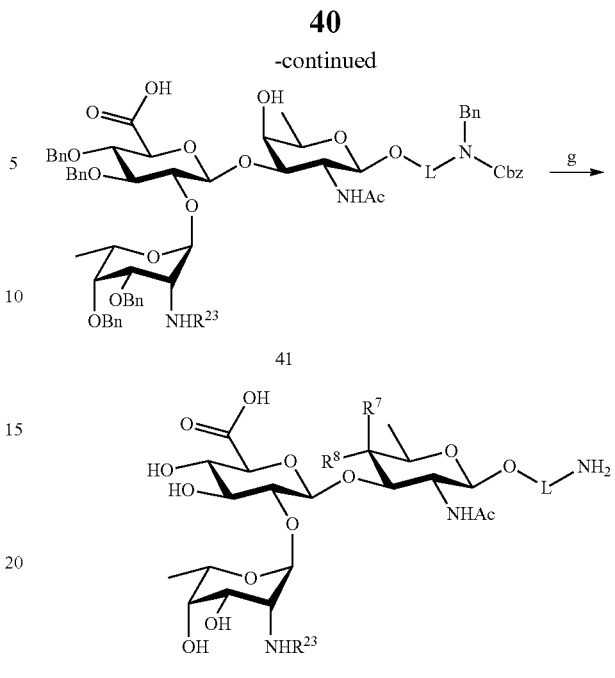

The saccharides of general formula (I), wherein $R^1$ represents

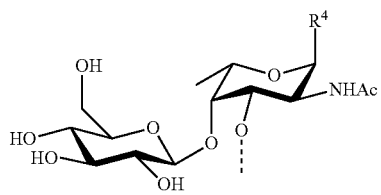

and $R^4$ represents $R^6$ i.e triasccharides of general formula 42 can be synthesized according to the synthetic route presented in Scheme 7. The synthesis commences with the installation of the β-D-glucose residue at the fourth position of the D-fucose. This step is achieved by treatment of the thioglucoside 60* with L-fucoside 38* in presence of NIS/TfOH. Following cleavage of the levulinoyl ester, the free alcohol at the second position of the glucoside is protected as benzyl ether, the thexydimethylsilyl protecting group is removed to provide an intermediate lactol that is further converted to the corresponding trichloroacetimidate 46. At this level the linker is appended on the molecule by reacting trichloroacetimidate 46 with alcohol 6 in presence of an activator such as TMSOTf. Subsequently, the azido group on intermediate 47 is converted to the corresponding acetamide by treatment with thioacetic acid and pyridine. Removal of the acetate group using Zémplen conditions frees the secondary alcohol at the second position of the L-fucose furnishing the nucleophile for the next glycosylation reaction. The last sugar moiety is appended by reacting alcohol 49 with trichloroacetimidate 1 in presence of TMSOTf. Conversion of the fully protected trisaccharide to the target trisaccharide 42 includes conversion of the —$N_3$ residue to the —$NHR^{23}$ residue and removal of permanent protective groups following the procedures previously described.

Scheme 7: Synthesis of trisaccharides of general formula 42:

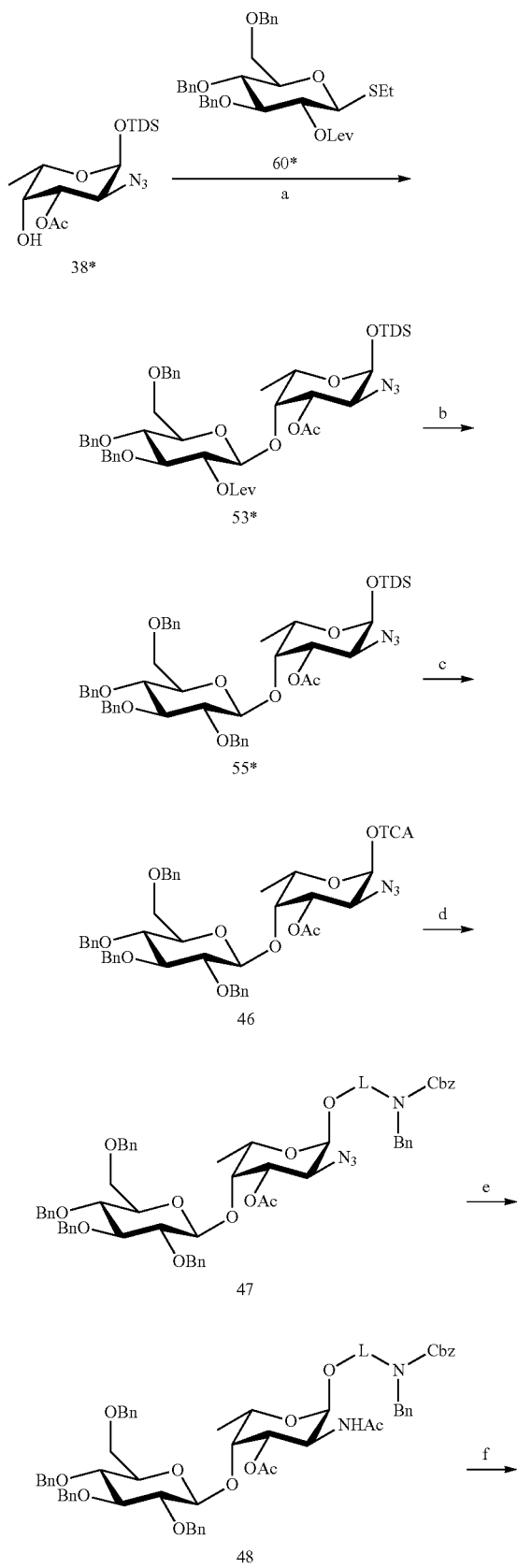
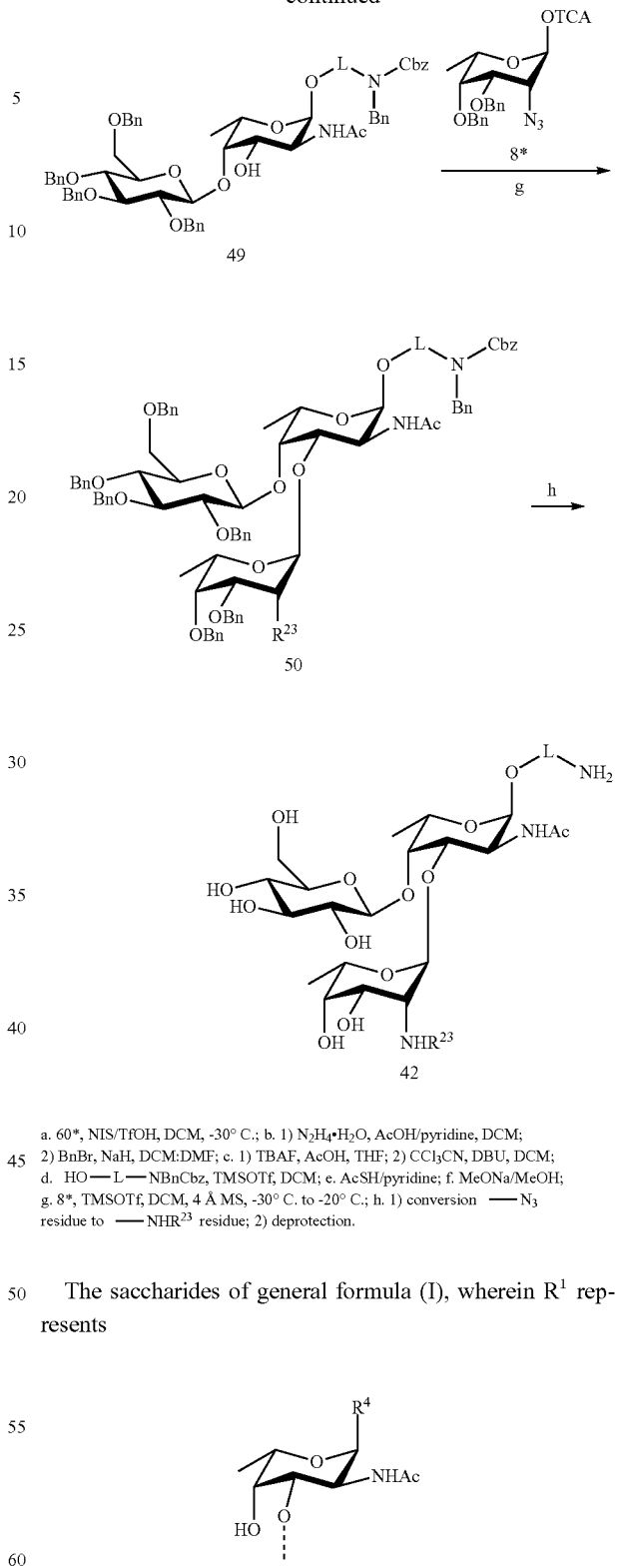

a. 60*, NIS/TfOH, DCM, -30° C.; b. 1) N$_2$H$_4$·H$_2$O, AcOH/pyridine, DCM; 2) BnBr, NaH, DCM:DMF; c. 1) TBAF, AcOH, THF; 2) CCl$_3$CN, DBU, DCM; d. HO—L—NBnCbz, TMSOTf, DCM; e. AcSH/pyridine; f. MeONa/MeOH; g. 8*, TMSOTf, DCM, 4 Å MS, -30° C. to -20° C.; h. 1) conversion —N$_3$ residue to —NHR$^{23}$ residue; 2) deprotection.

The saccharides of general formula (I), wherein R$^1$ represents and R$^4$ represents R$^6$ i.e. the disaccharides of general formula 57 can be synthesized according to the synthetic route presented in Scheme 8. The synthesis starts with the installation of the linker L on the L-fucose residue. This step is accomplished by treatment of imidate 52 with HO-L-

NBnCbz in presence of an activator such as TMSOTf. Subsequently, azide 53 is converted to the corresponding acetamide 54 by treatment with thioacetic acid and pyridine. Removal of the acetate groups using Zémplen conditions provides a diol intermediate that is further reacted with trimethyl orthoacetate and p-TsOH and subsequently treated with 80% AcOH to furnish alcohol 54. Alcohol 54 is further glycosylated with imidate 8* in presence of an activator to give disaccharide 55 that is further treated with MeONa/MeOH to provide alcohols 56, respectively. Starting from alcohol 56, the disaccharide of general formula 57 according to the present invention can be easily accessed following the procedures above described.

Scheme 8: Synthesis of disaccharide 57.

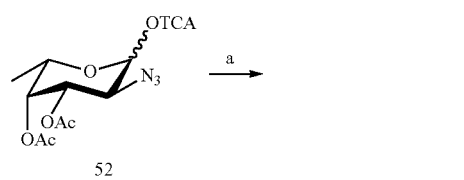

52

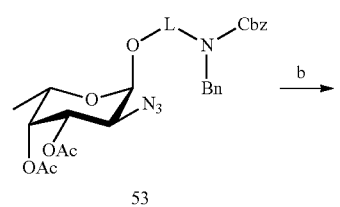

53

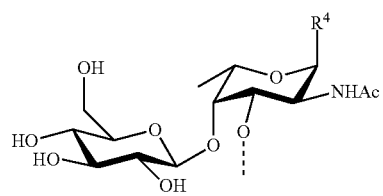

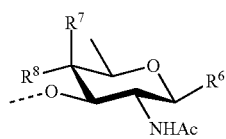

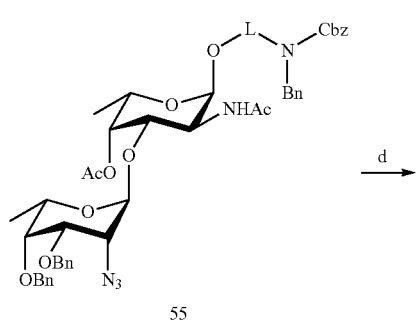

55

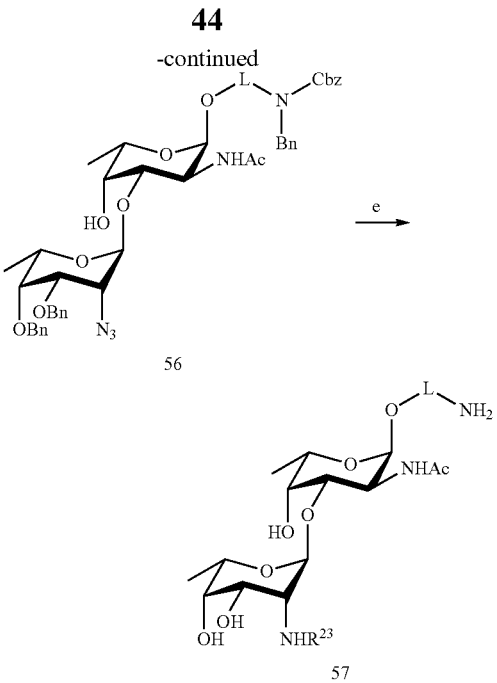

56

57 a. HO—L—NBnCbz, TMSOTf, DCM, 4 Å MS, -30° C. to -20° C.; b. 1) AcSH, pyridine; 2) MeONa, MeOH; 3) trimethyl orthoacetate, p-TsOH, DMF then 80% AcOH; c. 8*, TMSOTf, DCM, 4 Å MS, -30° C.; d. MeONa, MeOH; e. 1) conversion —N$_3$ residue to —NHR$^{23}$ residue; 2) deprotection.

A synthetic pathway for accessing the saccharides of general formula (I), wherein $R^1$ represents and $R^4$ represents i.e the tetrasaccharides of general formula 61 is shown in Scheme 9. The synthesis commences from disaccharide 55* on which the acetate ester was cleaved to provide alcohol 66. Glycosylation of alcohol 66 with 8* provides trisaccharide 58. Following removal of the thexydimethylsilyl protecting group, the intermediate lactol is converted to the corresponding trichloroacetimidate 59. The synthesis of fully protected tetrasaccharide is completed by appending the non-reducing end sugar moiety and transformation of the azido groups to the corresponding acetamido groups. Conversion of the protected tetrasaccharide 60 to target tetrasaccharide 61 follows the procedures described above.

Scheme 9: Synthesis of tetrasaccharide 61: a. MeONa/MeOH; b. 8*, TMSOTf, DCM; c. 1) TBAF, AcOH, THF; 2) CCl₃CN, DBU, DCM; d. 1) 15, TMSOTf, DCM; 2) AcSH, pyridine; e. 1) installation residues R⁷ and R⁸; 2) deprotection.

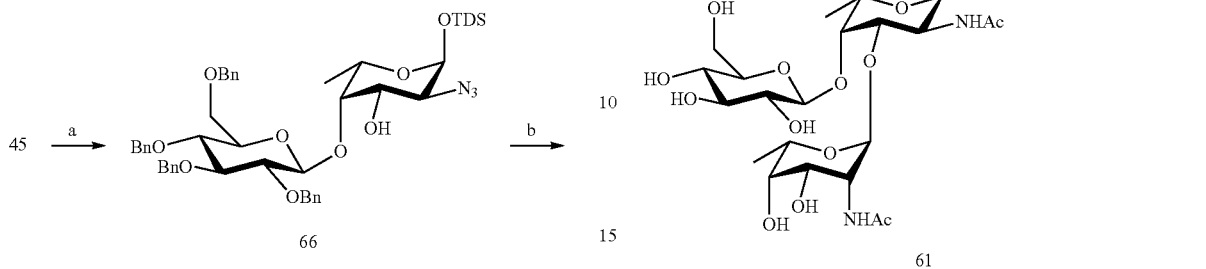

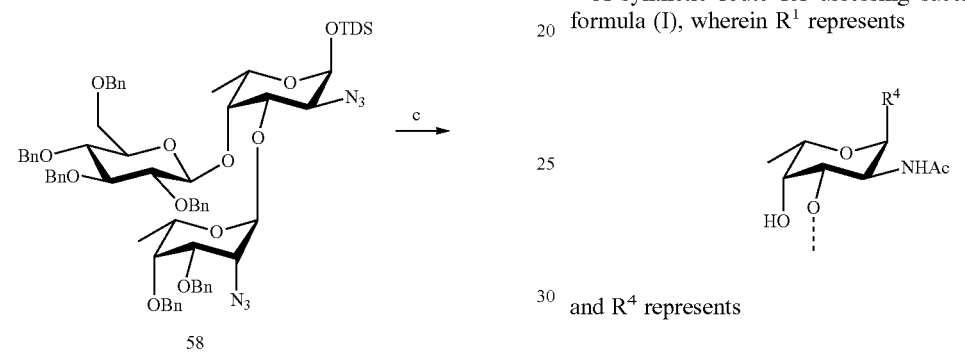

A synthetic route for assessing saccharides of general formula (I), wherein $R^1$ represents

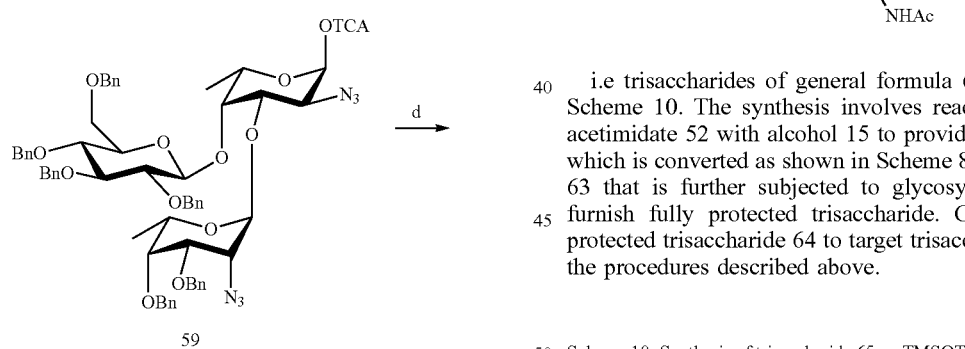

and $R^4$ represents

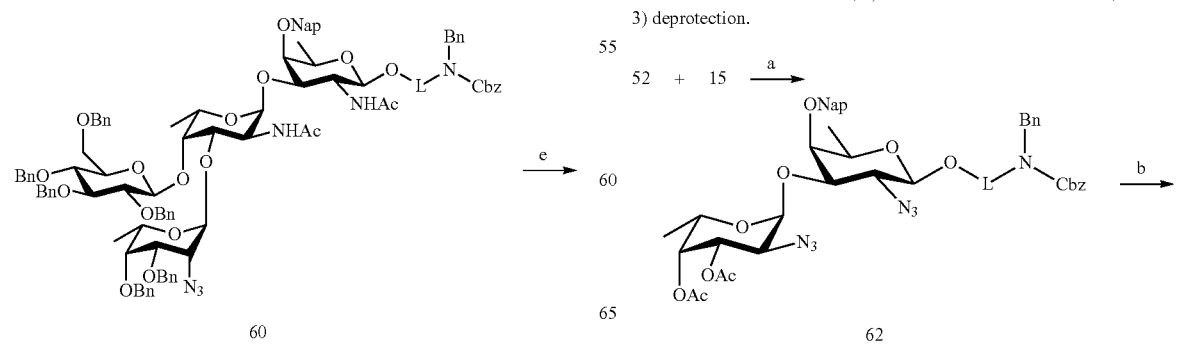

i.e trisaccharides of general formula 65 is displayed in Scheme 10. The synthesis involves reaction of trichloroacetimidate 52 with alcohol 15 to provide disaccharide 62, which is converted as shown in Scheme 8, step b to alcohol 63 that is further subjected to glycosylation reaction to furnish fully protected trisaccharide. Conversion of the protected trisaccharide 64 to target trisaccharide 65 follows the procedures described above.

Scheme 10: Synthesis of trisaccharide 65: a. TMSOTf, DCM; b. 1) AcSH, pyridine; 2) MeONa/MeOH; 3) trimethyl orthoacetate, p-TsOH, DMF then 80% AcOH; c. 1, TMSOTf, DCM; d. 1) conversion —N₃ residue to —NHR²³ residue; 2) installation residues R⁷ and R⁸; 3) deprotection.

-continued

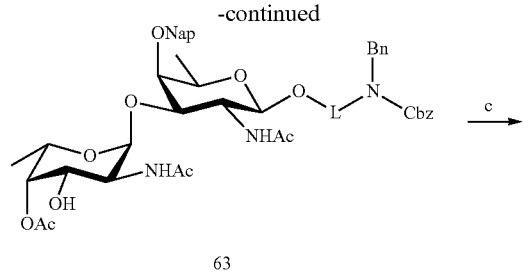

63

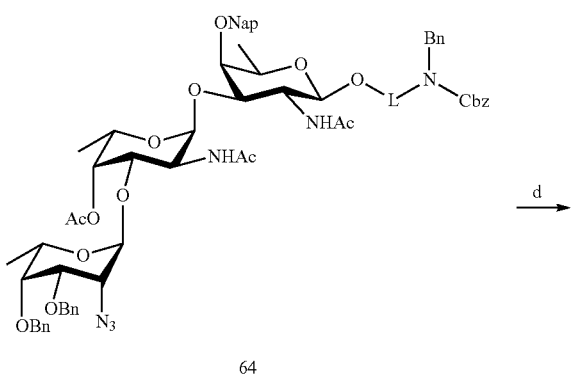

64

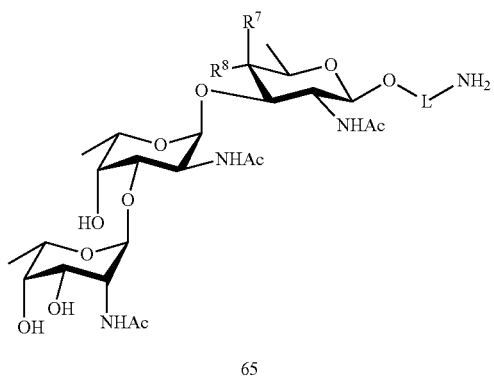

65

Finally, the saccharides of general formula (I), wherein $R^1$ represents

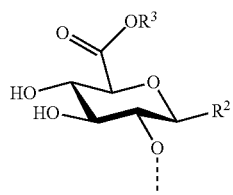

with $R^2$ being

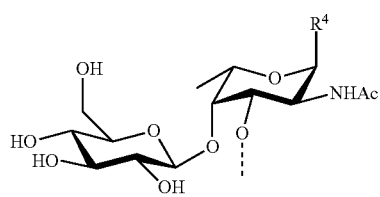

and $R^4$ representing

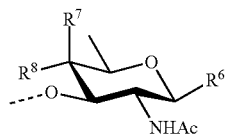

i.e. pentasaccharides of general formula 72 can be obtained according to the synthetic pathway presented in Scheme 11. The synthesis proceeds with the cleavage of the acetate on the L-fucose residue to provide alcohol 56* that is subjected to glycosylation reaction to give trisaccharide 57*. Treatment of trisaccharide 67 with TBAF/AcOH results in the removal of the thexydimethylsilyl protecting group furnishing an intermediate lactol that is further converted to the corresponding trichloroacetimidate 68. At this level, the reducing-end sugar moiety is appended on the molecule via glycosylation reaction and the levulinoyl ester on the glucose residue is cleaved to afford tetrasccharide 70. After installing the non-reducing end sugar moiety, fully protected target pentasaccharide 71 is achieved.

The conversion of the fully protected pentasaccharide 71 to the desired pentasaccharide 72 involves:

benzoyl removal followed by oxidation of the primary alcohol to the corresponding carboxylic acid;

conversion of the —$N_3$ residue to —$NHR^{23}$ residue;

installation of the residues $R^7$ and $R^8$; and deprotection.

Scheme 11: Synthesis of pentasaccharide 72:

45 $\xrightarrow{a}$

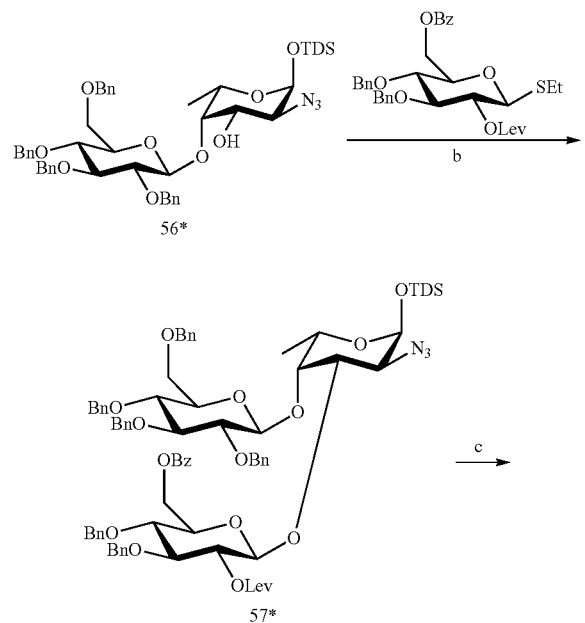

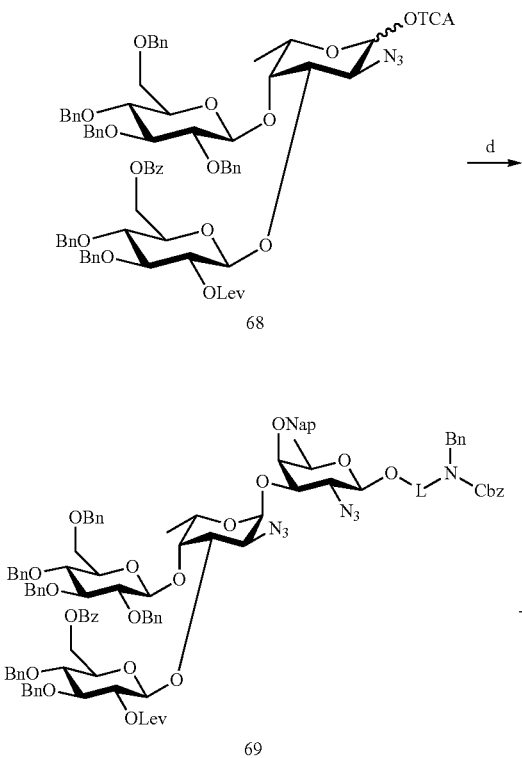

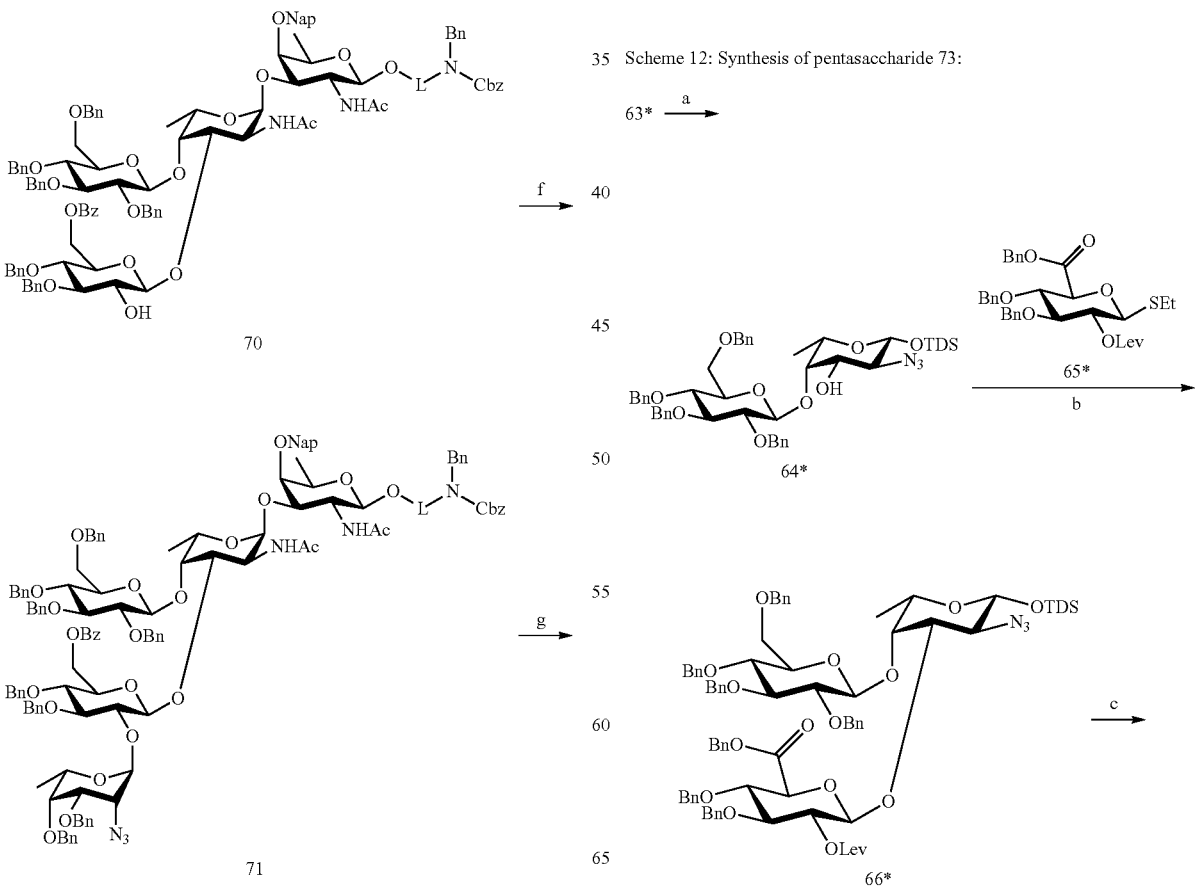

a. MeONa/MeOH; b. NIS/TfOH, DCM; c. 1) TBAF, AcOH, THF; 2) CCl₃CN, DBU, DCM; d. 15, TMSOTf, DCM; e. 1) AcSH, pyridine; 2) N₂H₄·H₂O, AcOH/pyridine, DCM; f. 1, TMSOTF, DCM; g. 1) MeONa/MeOH; 2) TEMPO, iodobenzene diacetate, DCM, H₂O; 3) conversion —N₃ residue to —NHR²³ residue; 4) installation residues R⁷ and R⁸; 5) deprotection.

Alternatively, pentasachharide 73 can be synthesized by the following synthetic route as shown in Scheme 12.

Scheme 12: Synthesis of pentasaccharide 73:

51
-continued

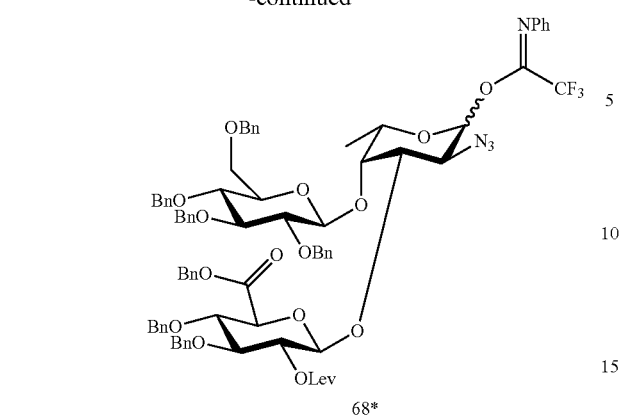
68*

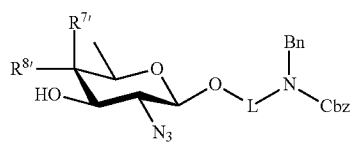

15 R⁷′ = ONap, R⁸′ = H; or
15a R⁷′ = H, R⁸′ = ONap

68* —d→

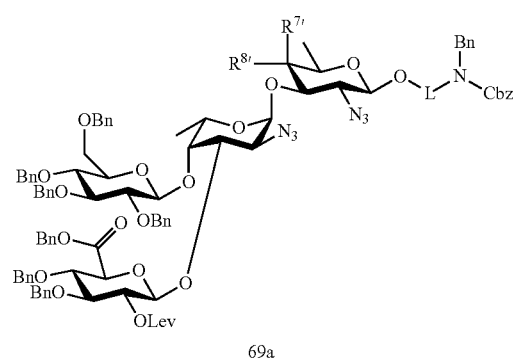
69a

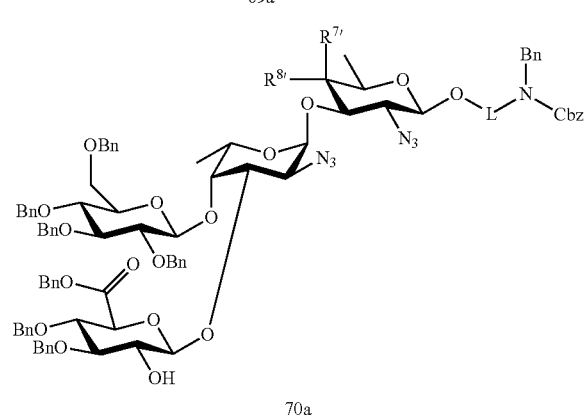
70a

70a —f→

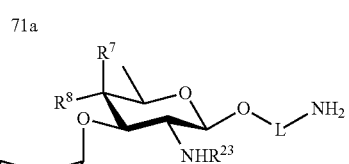
8a*

52
-continued

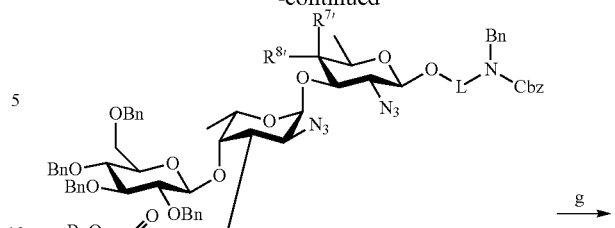
71a

—e→

$R^7 = OH, R^8 = H$; or
$R^7 = H, R^8 = OH$
73

—g→ a. DDQ, DCM/H₂O; b. NIS/TfOH, DCM/Tol; c. 1) HF·py, DCM/py; 2) CCl₃CNPhCl, Cs₂CO₃, DCM; d. TMSOTf, DCM; e. N₂H₄·H₂O, AcOH/pyridine/DCM;
f. 1, TMSOTF, Tol; g. conversion —N₃ residue to —NHR²³ residue.

DESCRIPTION OF THE FIGURES

FIG. 2 provides examples of commercially available interconnecting molecules according to the present invention.

A) Microarray slide printing pattern. (B) Microarray slide was incubated with rabbit type 5 sera (Statens Serum Institute, Denmark) at dilution 1 in 100. Microarray analysis suggested that type sera recognized synthetic structures along with native CPS-5 polysaccharide. (C) Structure description printed on the slide.

Figure 9:
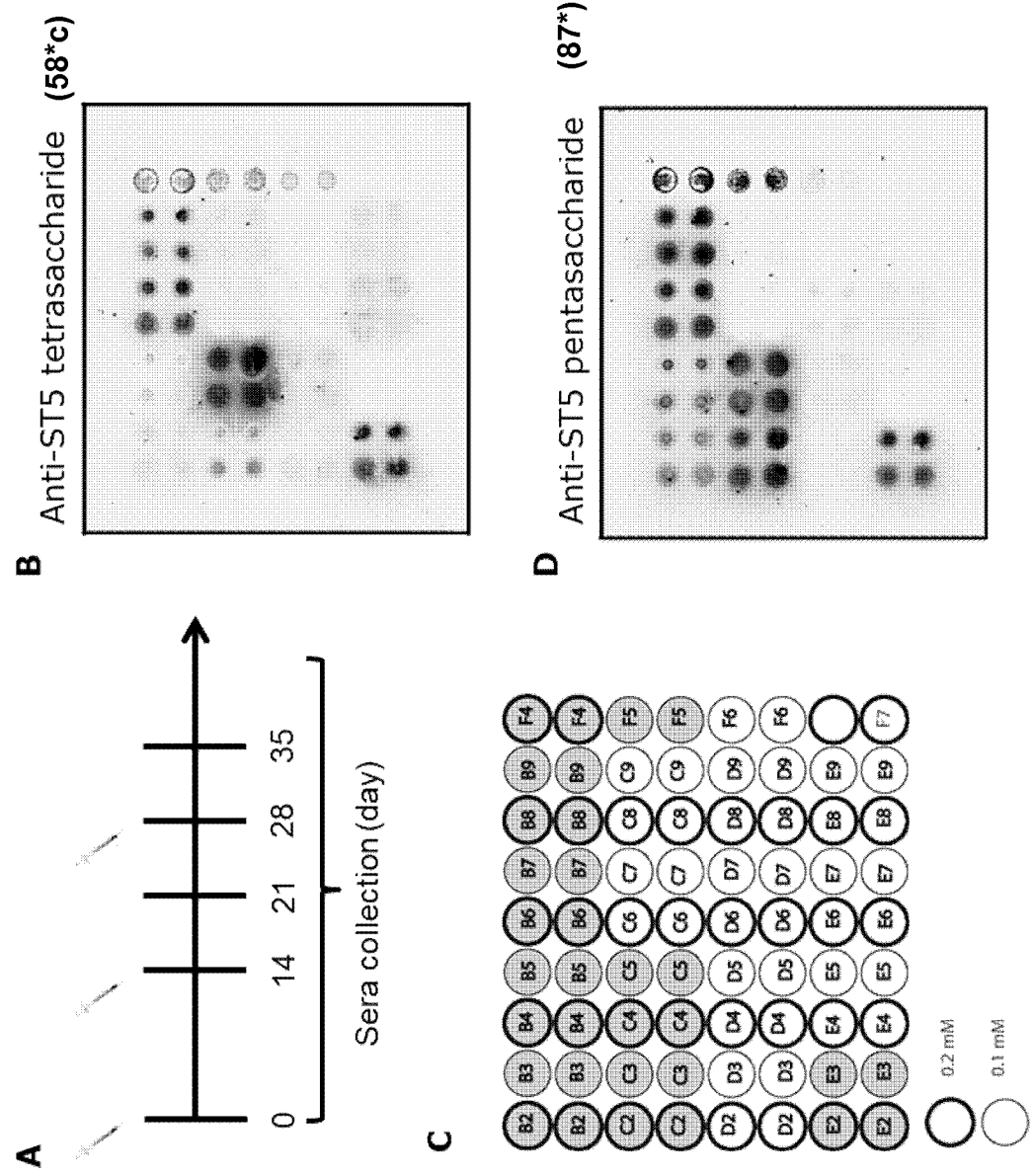

FIG. 9: Microarray with rabbit anti-ST5 synthetic conjugates serum (A) Immunization pattern and sera collection (printing pattern are the same in all studies). Rabbit were immunized as prime boost manner at day 0, 14 and 28. Preimmune (day 0) and hyperimmune serum (day 14, 21 and 35) was collected from individual rabbits. (B and D) Microarray slides were incubated with pooled rabbit sera (day 35) raised against tetrasaccharide and pentasaccharide conjugates to the slides. Both group of hyperimmune sera exhibited cross-reactivity with native polysaccharide. (C) Printing pattern of microarray slides.

Figure 10:
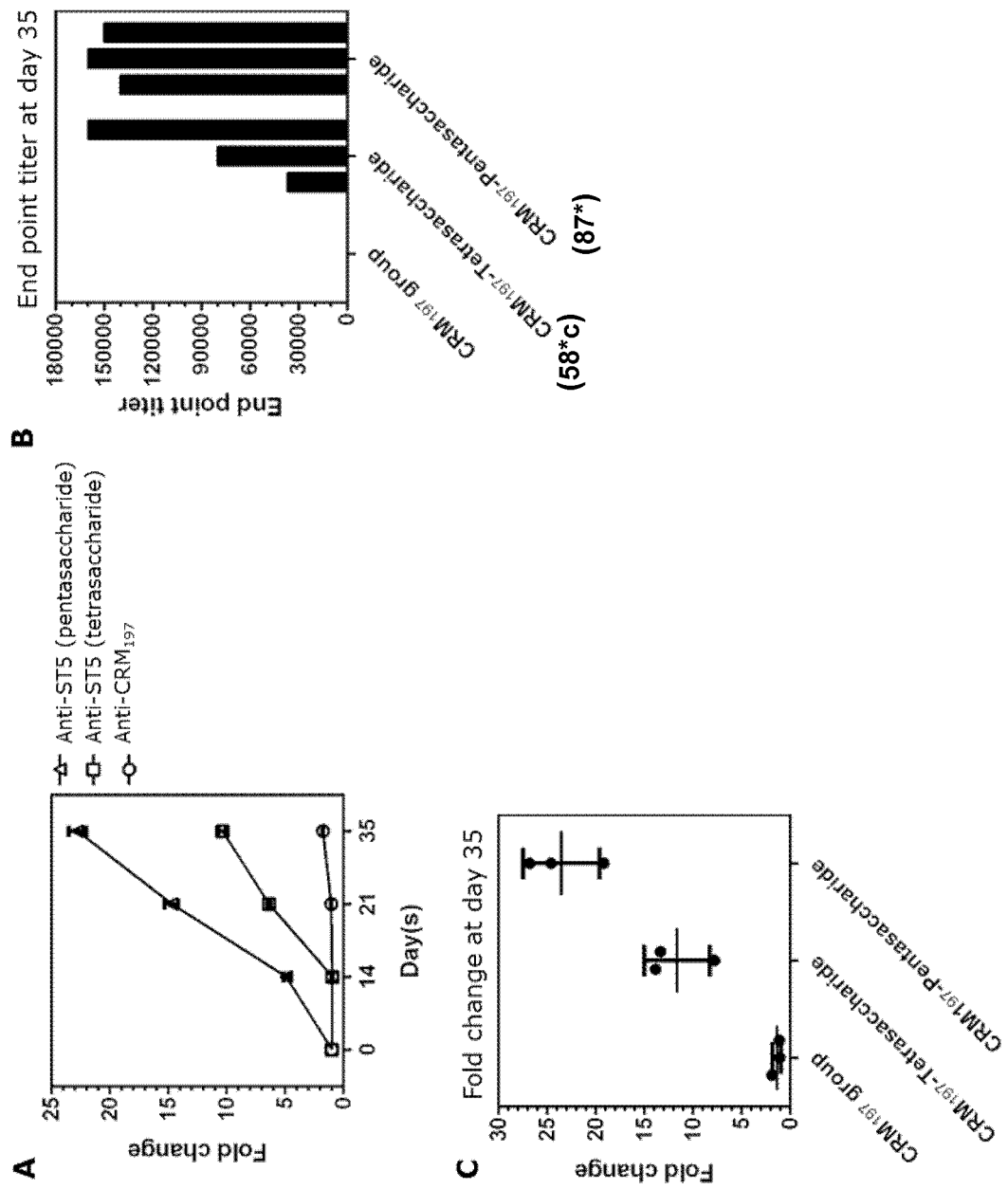

FIG. 10: End point titer analysis.

Immunization with ST5 glycan conjugates induces high antibody titers in rabbits. Three rabbits in each group (female ZIKA rabbits, 10-12 weeks, 2.5-3 kg) were immunized subcutaneously with 3 doses of 10 µg of tetrasaccharide and pentasaccharide conjugate (in alum) at day 0, 14 and 28. The immune response were analyzed and plotted in terms of fold change at every time point (A). The endpoint titer (total IgG) was determined in hyperimmune serum (day 35) from individual rabbit (B). Each bar represents the individual rabbit antibody titer. Antibody titers were plotted as the reciprocal of the highest dilution that gave a reading minus the absorbance value obtained with the preimmune sera (day 0; 1 in 100 dilutions). The antibody response between the groups were also analyzed (C).

Figure 11:
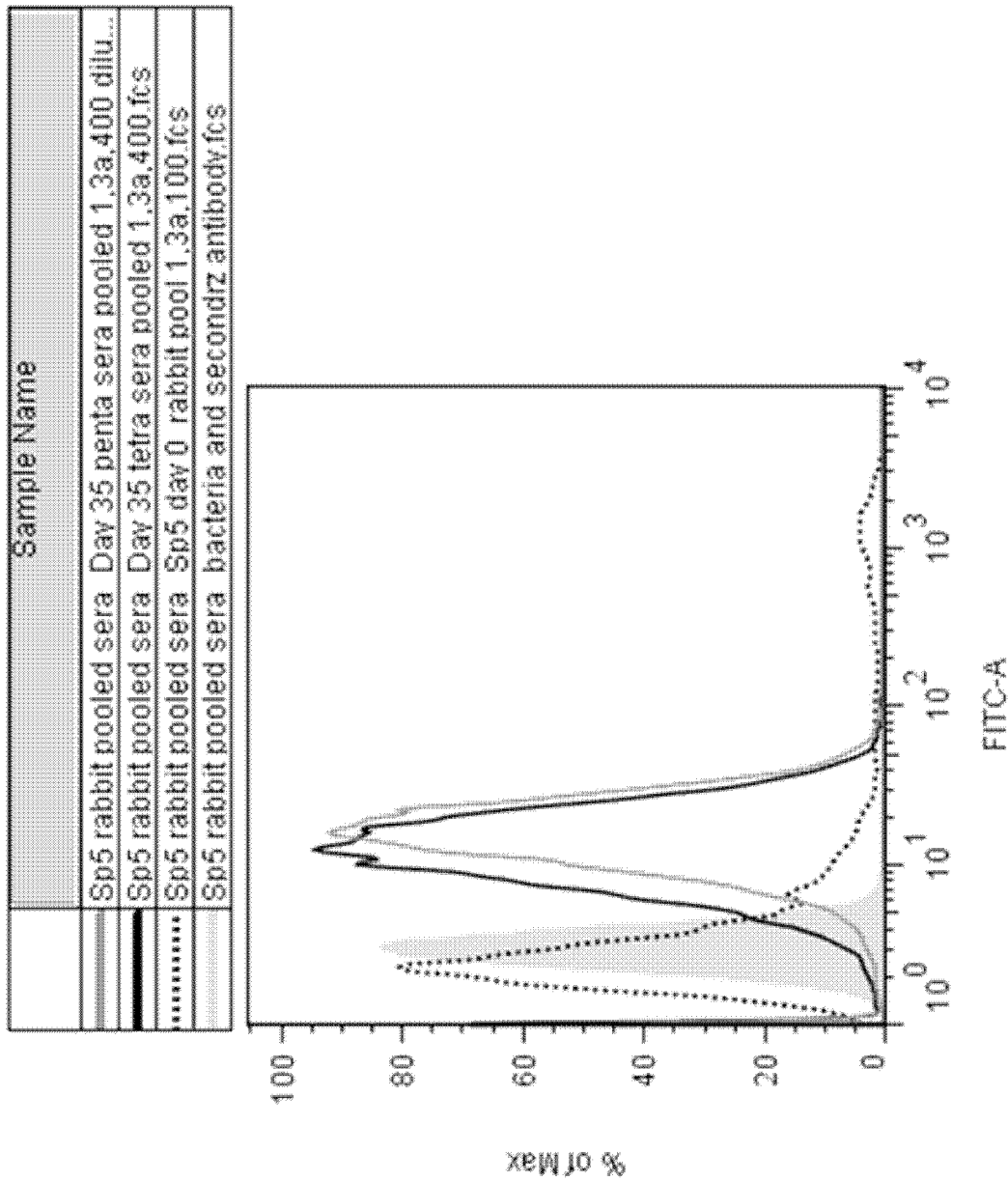

FIG. 11: Surface staining of anti-ST5 glycan conjugates with pneumococcal strain. Surface binding of anti-ST5 glycan conjugates sera with serotype 5 strain were analyzed by flow cytometry. The solid grey histogram represents the negative control (bacteria+secondary antibody), doted black represent the day 0. Black and gray histograms represent the tetrasaccharide and pentasaccharide respectively.

Figure 12:
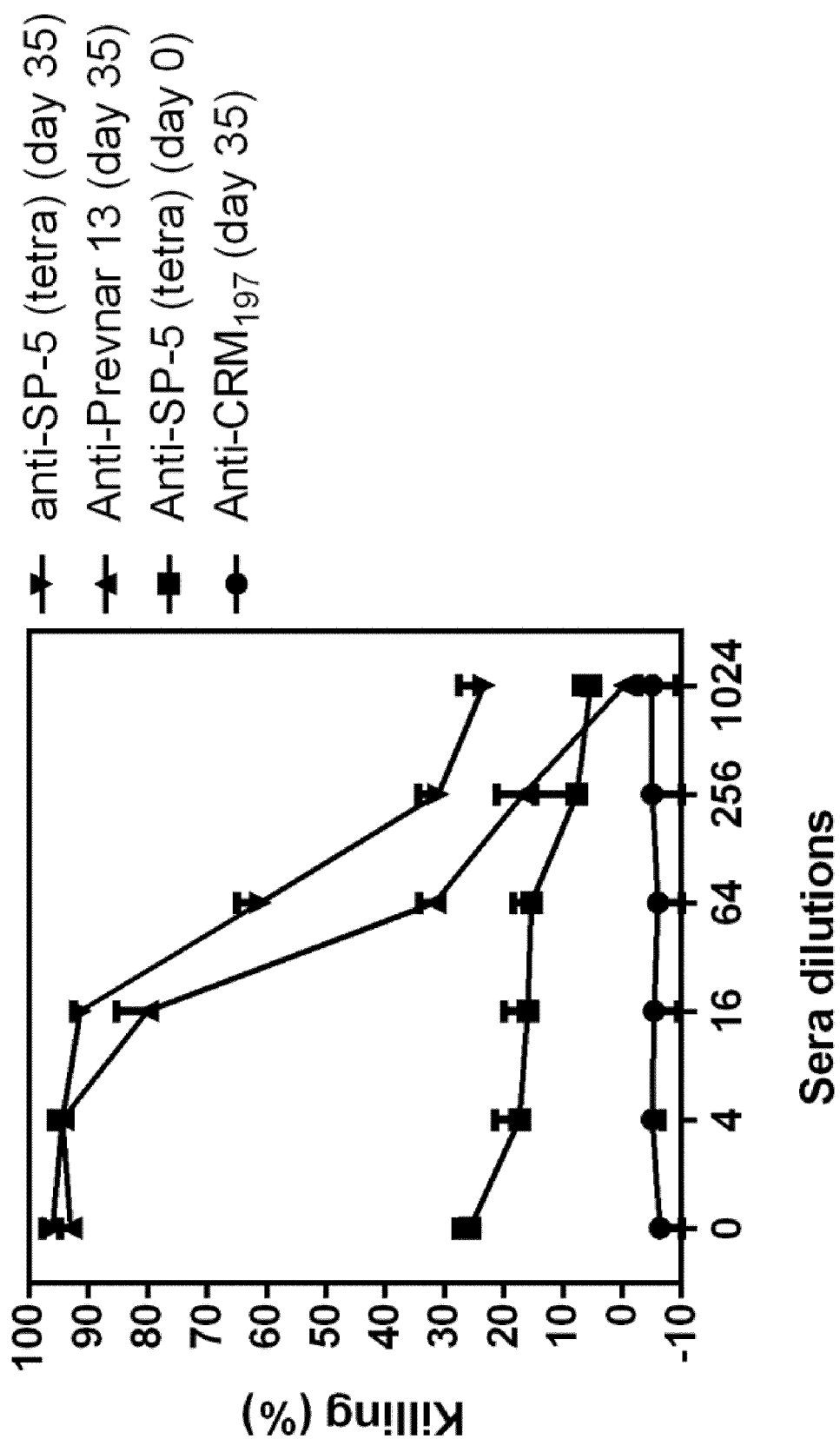

FIG. 12 Anti-ST5 (tetrasaccharide) antibodies promote the phagocytosis of pneumococci.

Differentiated HL-60 cells were incubated with serotype 5 bacteria pretreated with anti-ST5 (tetrasaccharide) or preimmune sera, and pneumococcal survival was assessed after 45 min. Percent killing of pneumococci was calculated based on viable pneumococcal colonies obtained relative to no sera control. This is the represent values one out of three independent experiments done in triplicates. Values represent mean±SE The following examples are included to demonstrate preferred embodiments of the invention. It should be appreciated by those skilled in the art that the techniques disclosed in the examples, which follow represent techniques discovered by the inventor to function well in the practice of the invention, and thus can be considered to constitute preferred modes for its practice. However, those skilled in the art should, in light of the present disclosure, appreciate that many changes can be made in the specific embodiments, which are disclosed and still obtain a like or similar result without departing from the spirit and scope of the invention.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

EXAMPLES

Chemical Synthesis

Abbreviations

NIS: N-iodosuccinimide;
TfOH: triflic acid;
h: hour;
DCM: dichloromethane;
TLC: thin layer chromatography;
rt: room temperature;
EtOAc: ethyl acetate;
MS: molecular sieves;
TMS: trimethylsilyl;
Tempo: 2,2,6,6-tetramethyl-1-piperidinyloxy, free radical;
BAIB: [bis(acetoxy)iodo]benzene;
TMSOTf: trimethylsilyl triflate;
TBAF: tetrabutylammonium fluoride;
TDS: dimethylthexylsilyl;
DDQ: 2,3-dichloro-5,6-dicyano-1,4-benzoquinone;
$Et_3N$: triethylamine;
DBU: 1,8-diazabicycloundec-7-ene;
Nap: 2-naphthylmethyl;
equiv: equivalents;
sat.: saturated;
aq.: aqueous;
Hex: hexanes;
$TMSN_3$: trimethylsilyl azide;
PMBCl: p-methoxybenzyl chloride;
THF: tetrahydrofuran;
DMAP: 4-dimethylaminopyridine;

TBAI: tetrabutylammonium iodide;
TBAB: tetrabutylammonium bromide;
$Bu_2SnO$: dibutyltin oxide;
CAN: cerium ammonium nitrate;
BnBr: benzylbromide;
$BH_3 \cdot THF$: borane tetrahydrofuran complex;
DMF: dimethylformamide;
UV: ultraviolet;
NMR: nuclear magnetic resonance;
MALDI-TOF: matrix-assisted laser desorption/ionization-time of flight spectrometry;
HRMS: high resolution mass spectroscopy;
ESI: electrospray ionization;
MeCN: acetonitrile;
IR: infrared;
EDC: 1-ethyl-3-(3-dimethylaminopropyl)carbodiimide;
$Et_2O$: diethyl ether;
NaOMe: sodium methoxide;
OTCA: trichloroacetimidate;

General Information for Chemical Synthesis

Commercial reagents were used without further purification except where noted. Solvents were dried and redistilled prior to use in the usual way. All reactions were performed in oven-dried glassware under an inert atmosphere unless noted otherwise. Analytical thin layer chromatography (TLC) was performed on Kieselgel 60 F254 aluminium plates precoated with a 0.25 mm thickness of silica gel. The TLC plates were visualized with UV light and by staining with Hanessian solution (ceric sulfate and ammonium molybdate in aqueous sulfuric acid) or sulfuric acid-ethanol solution. Column chromatography was performed on Fluka Kieselgel 60 (230-400 mesh). Optical rotations (OR) were measured with a Schmidt & Haensch UniPol L1000 polarimeter at a concentration (c) expressed in g/100 mL. $^1H$ and $^{13}C$ NMR spectra were measured with a Varian 400-MR or Varian 600 spectrometer with $Me_4Si$ as the internal standard. NMR chemical shifts ($\delta$) were recorded in ppm and coupling constants (J) were reported in Hz. High-resolution mass spectra (HRMS) were recorded with an Agilent 6210 ESI-TOF mass spectrometer at the Freie Universität Berlin, Mass Spectrometry Core Facility.

General Procedure (A) for Removal of the TDS Group at the Anomeric Position.

Anomeric TDS-protected starting material (1.0 equiv) was dissolved in THF (reaction concentration at 0.15 M) and cooled to 0° C. A solution of TBAF (1 M in THF, 10 equiv) and AcOH (12 equiv) was added, warmed to room temperature and stirred for 3 h. The reaction mixture was diluted with EtOAc, washed with 0.1 N HCl, sat. aq. $NaHCO_3$ and brine. The organic phases were dried over $MgSO_4$ and concentrated. Column chromatography on silica gel (hexanes/EtOAc) afforded the corresponding lactol as a mixture of α and β anomers.

General Procedure (B) for NIS/TfOH-Mediated Glycosylation of Thio- and Selenoglycosides.

The acceptor (1.0 to 2.0 equiv) and thio- or selenoglycoside (1.0 to 1.3 equiv) were co-evaporated with toluene three times and dried in vacuo. The residue was dissolved in DCM or MeCN (reaction concentration at 80 to 120 mM) together with freshly activated molecular sieves (4 Å) and NIS (1.2 equiv with regard to the thio- or selenoglycoside). The mixture was cooled and TfOH (0.1 equiv with regard to the thio- or selenoglycoside) was added. The reaction was stirred for 1 h, then quenched by the addition of $NEt_3$ and diluted with DCM. The organic layer was washed with sat. aq. $Na_2S_2O_3$ followed by sat. aq. $NaHCO_3$, dried over $MgSO_4$ and concentrated. Column chromatography (hexanes/EtOAc) afforded the pure product.

General Procedure (C) for Glycosyl-Trichloroacetimidate Synthesis with $K_2CO_3$.

To a solution of the lactol (1.0 equiv) in DCM (reaction concentration at 0.5 M) trichloroacetonitrile (10 equiv) and $K_2CO_3$ (1.7 equiv) were added and stirred for 3 h at room temperature. The crude product was concentrated and purified by column chromatography on silica gel (hexanes/EtOAc) to afford pure product.

General Procedure (D) for Glycosyl-Trichloroacetimidate Synthesis with DBU.

To a solution of the lactol (1.0 equiv) in DCM (reaction concentration at 0.5 M) at 0° C. trichloroacetonitrile (10 equiv) and DBU (1 drop) were added and stirred for 1 h at 0° C. The crude product was concentrated and purified by column chromatography on silica gel (hexanes/EtOAc) to afford pure product.

General Procedure (E) for TMSOTf-Mediated Glycosylation of Glycosyl-Imidates.

The acceptor (1.0 to 2.0 equiv) and glycosyl-trichloroacetimidate (1.0 to 1.3 equiv) were co-evaporated with toluene three times and dried in vacuo. The residue was dissolved in DCM (reaction concentration at 80 to 120 mM) and freshly activated molecular sieves (4 Å) were added. The mixture was cooled to −30° C. and TMSOTf (0.1 equiv) was added. The reaction was brought to −20° C., then quenched by the addition of $NEt_3$ and concentrated under reduced pressure. Column chromatography (hexanes/EtOAc) afforded the pure product.

General Procedure (F) for Thioacetic Acid Based Azide Reduction.

To a solution of azide starting material in pyridine (1 mL) thioacetic acid (0.5 mL) was added and stirred for 12 to 48 h. The reaction mixture was concentrated and purified by column chromatography on silica gel (hexanes/acetone) to afford the acetamide product.

General Procedure (G) for Removal of the Nap Protecting Group.

To a mixture of naphthylated starting material (1 equiv) in a mixture of DCM/phosphate-buffer (10:1 (v:v), 7 mM, pH 7.2, reaction concentration at 4 mM or $DCM/H_2O$ (10:1) at 0° C. DDQ (2-3 equiv) was added portionwise over 1.5 h. The reaction mixture was warmed to room temperature and stirred for further 1.5 to 5 h. The mixture was diluted with sat. aq. $NaHCO_3$ solution, extracted with DCM and the organic layer dried over $MgSO_4$ and concentrated. Column chromatography on silica gel (hexanes/EtOAc) afforded the pure product.

General Procedure (H) for TEMPO-Mediated Oxidation.

To a mixture of the primary alcohol (1.0 equiv) in $DCM/H_2O$ ((2.5:1, v:v), reaction concentration at 7 mM) at 0° C. was added TEMPO (0.2 equiv) and BAIB (5.0 equiv). The reaction mixture was warmed to room temperature, stirred for 2 h and then diluted with $H_2O$ and extracted with DCM. The organic phases were dried over $Na_2SO_4$ and concentrated. Size exclusion chromatography on Sephadex LH-20 ($CHCl_3/MeOH=1:1$) afforded the product.

General Procedure (I) for Hydrogenolysis.

A solution of starting material (reaction concentration at 4 to 8 mM) in a mixture of $EtOH/EtOAc/H_2O/AcOH$ was purged with Ar. After that 10% Pd/C was added and the solution purged with $H_2$ for 10 min, then stirred under an $H_2$ atmosphere for 12 h, filtered and concentrated. The crude product was dissolved in $H_2O$, subjected to reversed phase solid phase extraction (RP SPE) (Waters Sep-Pak®, C18) and lyophilized. When necessary, size exclusion chromatography on Sephadex LH-20 (MeOH) was performed.

Example 1: Synthesis of phenyl 2-azido-2-deoxy-1-seleno-α-D-fucopyranoside (1*)

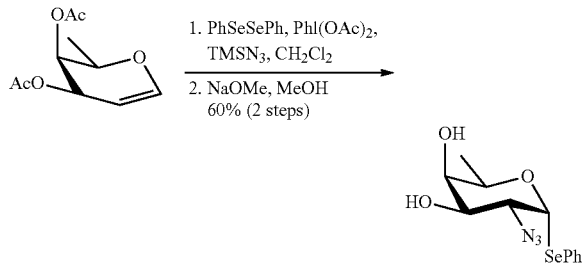

To a solution of the fucal (Bedini, E. et. al. *Synlett* 2006, 6, 825-830) (4.6 g, 21.6 mmol) and $Ph_2Se_2$ (6.75 g, 21.6 mmol) in DCM (70 mL) at −30° C. was added $PhI(OAc)_2$ (6.96 g, 21.6 mmol). Then, $TMSN_3$ (5.74 mL, 43.2 mmol) was added dropwise to the resulting solution. The reaction was warmed to −10° C. After 4 h at −10° C. the reaction was complete. The reaction was mixture was allowed to warm to room temperature and washed with $NaHCO_3$ saturated solution followed by brine. The solvent was evaporated and the impure was dissolved in MeOH (190 mL). NaOMe 0.5 M (4.75 mmol, 9.5 mL) solution was added dropwise to the mixture at room temperature. The reaction was stirred at room temperature for 1 h. Amberlite was added and let stir until the pH decreased to 5. The reaction mixture was filtered and the solvent evaporated. The residue was purified by silica-gel chromatography (DCM 100% to DCM:MeOH: Acetone 97:1.5:1.5). The yellow solid obtained was washed with hexanes to give diol 1* as a white solid (4.24 g, 12.9 mmol, 60% yield). $[\alpha]_D^{20}$=241.6° (c=1.00, $CHCl_3$); IR $\nu_{max}$ (film) 3321, 2925, 2105, 1578, 1475, 1438, 1093, 1059, 739 $cm^{-1}$; $^1$H NMR (400 MHz, $CD_3OD$) δ 7.71-7.47 (m, 2H), 7.35-7.09 (m, 3H), 5.90 (d, J=5.4 Hz, 1H), 4.28 (q, J=6.6 Hz, 1H), 4.00 (dd, J=9.9, 5.3 Hz, 1H), 3.70 (ddd, J=6.6, 4.5, 2.2 Hz, 2H), 1.13 (d, J=6.5 Hz, 3H). $^{13}$C NMR (101 MHz, $CD_3OD$) δ 134.5, 128.6, 127.3, 85.5, 71.5, 71.3, 69.2, 61.5, 15.0. HRMS (ESI+) Calcd for $C_{12}H_{15}O_3N_3SeNa^+$ $[M+Na]^+$ 352.0171, found 352.0179.

Example 2: Synthesis of phenyl 2-azido-2-deoxy-3-O-p-methoxybenzyl-1-seleno-α-D-fucopyranoside (2*)

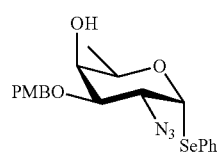

Diol 2* (2.5 g, 7.62 mmol) was co-evaporated with dry toluene twice and let dry under high vacuum for 30 min. Then, dry toluene (80 mL) was added, followed by $Bu_2SnO$ (2.84 g, 11.43 mmol) and 4 A MS. The reaction was stirred for 1 hour under reflux. The reaction was cooled to 40° C.; PMBCl (3.11 mL, 22.85 mmol) and TBAB (3.68 g, 11.43 mmol) were added and left stir overnight at rt. In the morning the reaction was complete. The reaction was filtered and the solvent evaporated. The residue was purified by silica-gel chromatography (EtOAC in Hex 10 to 20%). Alcohol 2* was obtained as a yellow oil (3.09 g, 6.89 mmol, 90%). $[\alpha]_D^{20}$=+177.4° (c=0.77, $CHCl_3$); IR $\nu_{max}$ (film) 3493, 2935, 2111, 1613, 1514, 1249, 1091, 740 $cm^{-1}$; $^1$H NMR (400 MHz, $CDCl_3$) δ 7.79-7.47 (m, 2H), 7.41-7.12 (m, 5H), 6.92 (d, J=8.7 Hz, 2H), 5.88 (d, J=5.4 Hz, 1H), 4.69 (d, J=11.0 Hz, 1H), 4.63 (d, J=11.0 Hz, 1H), 4.29 (q, J=6.5 Hz, 1H), 4.15 (dd, J=10.2, 5.3 Hz, 1H), 3.89-3.84 (m, 1H), 3.82 (s, 3H), 3.69 (dd, J=10.2, 3.1 Hz, 1H), 2.36 (s, 1H), 1.26 (d, J=6.6 Hz, 3H). $^{13}$C NMR (101 MHz, $CDCl_3$) δ 159.7, 134.4, 129.8, 129.1, 129.0, 128.5, 127.8, 114.1, 85.2, 78.9, 71.8, 68.6, 68.5, 60.1, 55.3, 16.1. HRMS (ESI+) Calcd for $C_{20}H_{23}O_4N_3SeNa^+$ $[M+Na]^+$ 472.0746, found 472.0755.

Example 3: Synthesis of phenyl 2-azido-2-deoxy-3-O-p-methoxybenzyl-4-O-(2-naphthalenylmethyl)-1-seleno-α-D-fucopyranoside-2-(bromomethyl)-naphthalene (3*)

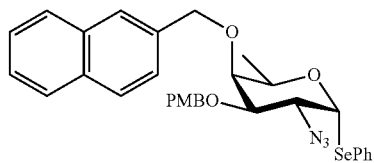

2-(bromomethyl)-naphthalene (2.8 g, 12.67 mmol) was added to a solution of alcohol 2* (2.84 g, 6.33 mmol) in DMF:THF (1:1, 64 mL). Then, the mixture was cooled to 0° C. and NaH 60% (304 mg, 7.60 mmol) was added. The reaction was warmed to room temperature and let stir for 1 h. The reaction was not completed. Then, it was cooled to 0° C. again and 100 mg of NaH were added. In 1 h the reaction was completed. The reaction mixture was cooled to 0° C., MeOH was added and the reaction warmed to room temperature. The reaction mixture was diluted with ether, washed with HCl, $NaHCO_3$ and brine. The solvent was evaporated and the residue purified by silica-gel chromatography (EtOAC in Hex 5 to 10%). Product 3* was obtained as a colorless oil (2.56 g, 4.35 mmol, 69%). $[\alpha]_D^{20}$=151.28 (c=2.00, $CHCl_3$); IR $\nu_{max}$ (film) 2896, 2109, 1612, 1513, 1249, 1101, 1065, 820, 740 $cm^{-1}$; $^1$H NMR (400 MHz, $CDCl_3$) δ 7.94-7.75 (m, 3H), 7.71 (s, 1H), 7.63-7.53 (m, 2H), 7.52-7.42 (m, 3H), 7.40-7.31 (m, 2H), 7.29-7.20 (m, 3H), 7.00-6.84 (m, 2H), 5.94 (d, J=5.2 Hz, 1H), 5.09 (d, J=11.7 Hz, 1H), 4.78 (d, J=11.7 Hz, 1H), 4.74 (d, J=11.1 Hz, 1H), 4.70 (d, J=11.1 Hz, 1H), 4.48-4.30 (m, 1H), 4.22 (q, J=6.5 Hz, 1H), 3.84 (s, 1H), 3.77-3.66 (m, 1H), 1.13 (d, J=6.5 Hz, 3H). $^{13}$C NMR (101 MHz, $CDCl_3$) δ 159.5, 135.6, 134.3, 133.1, 133.0, 129.6, 129.0, 128.7, 128.1, 127.9, 127.7, 127.6, 126.9, 126.3, 126.1, 125.9, 114.0, 85.6, 80.4, 75.7, 74.9, 72.4, 69.4, 60.9, 55.3, 16.6. HRMS (ESI+) Calcd for $C_{31}H_{31}O_4N_3SeNa^+$ $[M+Na]^+$ 612.1373, found 612.1371.

Example 4: Synthesis of 2-azido-2-deoxy-3-O-p-methoxybenzyl-4-O-(2-naphthalenylmethyl)-α,β-D-fucopyranosyl trichloroacetimidate (4*)

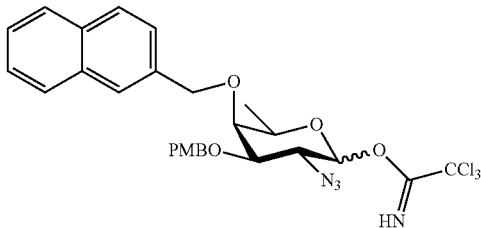

Selenide compound 3* (730 mg, 1.24 mmol) was dissolved in THF:H$_2$O (1.7:1, 38 mL) and NIS (558 mg, 2.48 mmol) added. The reaction was stirred at room temperature for 2 h and quenched with NaS$_2$O$_3$. Then, the reaction mixture was diluted with CH$_2$Cl$_2$ and washed with NaHCO$_3$ and brine. The solvent was evaporated and the residue purified by silica-gel chromatography (EtOAc in Hex 20%). A colorless oil was obtained in 94% yield (524 mg, 1.17 mmol). The product was dissolved in DCM (12 mL) and cooled to 0° C. Trichloroacetonitrile (1.16 mL, 11.57 mmol) and DBU (0.012 mmol, 2 µL) were added. After 1 h stirring at 0° C. the reaction was not complete. Then, trichloroacetonitrile (1 mL) was added. One hour later the reaction was complete. The solvent was evaporated and the residue purified by silica-gel chromatography (EtOAc in Hex 20%). Trichloroacetimidate 4* was obtained as mixture of alpha and beta anomers (α:β, 1:3) in quantitative yield (700 mg, 1.18 mmol). Characterization is given for the beta anomer. [α]$_D^{20}$=−8.69° (c=1.99, CHCl$_3$); IR ν$_{max}$ (film) 2934, 2113, 1675, 1513, 1059, 821, 796 cm$^{-1}$; $^1$H NMR (400 MHz, CDCl$_3$) δ 8.63 (s, 1H), 7.98-7.78 (m, 3H), 7.73 (s, 1H), 7.59-7.43 (m, 3H), 7.34 (d, J=8.7 Hz, 2H), 6.92 (d, J=8.7 Hz, 2H), 5.53 (d, J=8.5 Hz, 1H), 5.10 (d, J=11.8 Hz, 1H), 4.86 (d, J=11.8 Hz, 1H), 4.70 (s, 2H), 4.07 (dd, J=10.2, 8.6 Hz, 1H), 3.83 (s, 3H), 3.68-3.52 (m, 2H), 3.45 (dd, J=10.3, 2.7 Hz, 1H), 1.23 (d, J=6.4 Hz, 3H). $^{13}$C NMR (101 MHz, CDCl$_3$) δ 161.5, 159.5, 135.4, 133.1, 133.0, 129.6, 129.5, 128.1, 127.9, 127.7, 127.4, 126.6, 126.1, 126.0, 114.0, 97.2, 92.5, 80.7, 74.8, 74.5, 72.6, 71.9, 62.5, 55.3, 29.7, 16.9. HRMS (ESI+) Calcd for C$_{27}$H$_{27}$O$_4$N$_4$Cl$_3$Na$^+$ [M+Na]$^+$ 617.0912, found 617.0930.

Example 5: Synthesis of N-(benzyl)benzyloxycarbonyl-5-amino-pentanyl 2-azido-2-deoxy-3-O-p-methoxybenzyl-4-O-(2-naphthalenylmethyl)-β-D-fucopyranoside (5*)

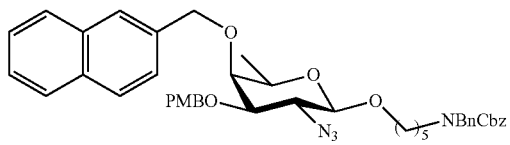

Imidate 4* (538 mg, 0.91 mmol) and the linker N-(benzyl)benzyloxycarbonyl-5-amino-1-pentanol (593 mg, 1.8 mmol) were co-evaporated with dry toluene and dried in high vacuum. The residue was dissolved in acetonitrile and cooled to −15° C. TMSOTf (16 µL, 0.09 mmol) was added and the reaction was stirred for 1 h. The reaction was quenched with triethylamine and the solvent evaporated. The residue was purified by silica-gel chromatography (EtOAc in Hex 15 to 20%) to give monosaccharide 5* as a colorless oil in 74% yield (510 mg, 0.672 mmol). [α]$_D^{20}$=−21.34° (c=2.10, CHCl$_3$); IR ν$_{max}$ (film) 2935, 2110, 1697, 1513, 1248, 1068, 819, 699 cm$^{-1}$; $^1$H NMR (400 MHz, CDCl$_3$) δ 7.90-7.77 (m, 3H), 7.72 (s, 1H), 7.58-7.43 (m, 3H), 7.38-7.14 (m, 12H), 6.91 (d, J=8.6 Hz, 2H), 5.18 (d, J=12.1 Hz, 1H), 5.07 (d, J=11.9 Hz, 1H), 4.84 (d, J=11.9 Hz, 1H), 4.73-4.60 (m, 1H), 4.50 (d, J=7.6 Hz, 1H), 4.14 (t, J=8.7 Hz, 1H), 3.93-3.71 (m, 2H), 3.53 (d, J=2.4 Hz, 1H), 3.44-3.35 (m, 1H), 3.32-3.15 (m, 1H), 1.66-1.47 (m, 1H), 1.41-1.26 (m, 1H), 1.19 (d, J=6.4 Hz, 1H). $^{13}$C NMR (101 MHz, CDCl$_3$) δ 137.9, 135.7, 133.1, 133.0, 129.8, 129.5, 128.5, 128.5, 128.0, 127.9, 127.8, 127.7, 127.2, 126.7, 126.0, 125.9, 113.9, 102.3, 80.7, 74.7, 74.6, 72.5, 70.5, 69.6, 67.1, 63.1, 55.3, 50.5, 50.2, 47.1, 46.2, 29.2, 27.9, 27.5, 23.2, 17.0. HRMS (ESI+) Calcd for C$_{45}$H$_{50}$O$_7$N$_4$Na$^+$ [M+Na]$^+$ 781.3577, found 781.3590.

Example 6: Synthesis of N-(benzyl)benzyloxycarbonyl-5-amino-pentanyl 2-azido-2-deoxy-4-O-(2-naphthalenylmethyl)-β-D-fucopyranoside (6*)

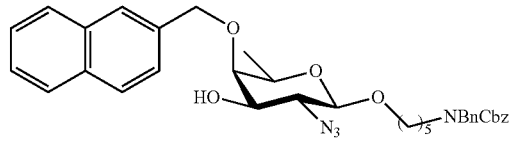

PMB protected compound 5* (510 mg) was dissolved in acetone (10 mL) and H$_2$O (1.1 mL), then 700 mg of CAN was added (solid). After that, a solution of CAN (700 mg) in acetone (1.7 mL) and H$_2$O (0.2 mL) was added over 70 min. After 10 min the reaction was poured in NaHCO$_3$ and extracted with CH$_2$Cl$_2$. The solvent was evaporated and the residue purified by silica-gel chromatography (EtOAc in Hex 20%). Alcohol 6* was obtained was a yellow oil in 73% yield (315 mg, 0.493 mmol). [α]$_D^{20}$=−1.73° (c=2.18, CHCl$_3$); IR ν$_{max}$ (film) 3440, 3031, 2935, 2109, 1694, 1068, 698 cm$^{-1}$; $^1$H NMR (400 MHz, CDCl$_3$) δ 7.89-7.74 (m, 4H), 7.62-7.43 (m, 3H), 7.41-7.21 (m, 9H), 7.17 (d, J=6.9 Hz, 1H), 5.18 (d, J=13.1 Hz, 2H), 4.97 (d, J=11.8 Hz, 1H), 4.90 (d, J=11.8 Hz, 1H), 4.50 (d, J=8.7 Hz, 2H), 4.18 (t, J=8.6 Hz, 1H), 3.95-3.80 (m, 1H), 3.64-3.37 (m, 5H), 3.23 (m, 2H), 2.31 (s, 1H), 1.69-1.46 (m, 4H), 1.43-1.18 (m, 2H), 1.31 (d, J=6.5 Hz, 3H). $^{13}$C NMR (101 MHz, CDCl$_3$) δ 137.9, 135.3, 133.2, 133.1, 128.5, 128.4, 128.0, 127.9, 127.8, 127.7, 127.2, 127.1, 126.2, 126.1, 126.1, 102.2, 78.2, 75.9, 73.0, 70.8, 69.7, 67.1, 64.7, 50.5, 50.2, 47.1, 46.2, 29.2, 27.9, 27.4, 23.2, 17.0. HRMS (ESI+) Calcd for C$_{37}$H$_{42}$O$_6$N$_4$Na$^+$ [M+Na]$^+$ 661.3002, found 661.3015.

Example 7: Synthesis of phenyl 2-azido-3,4-di-O-benzyl-2-deoxy-1-seleno-β-L-pneumopyranoside (7*)

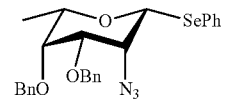

To a impure mixture containing approx. 25% of 2-azido-2-deoxy-1-seleno-β-L-pneumopyranoside (192 mg) in DMF (5 mL) at 0° C., BnBr (0.21 mL, 1.8 mmol) and NaH (31 mg, 1.3 mmol) were added. After 3 h the reaction was quenched with MeOH at 0° C. and diluted with Et₂O. The organic layer was washed with 0.1 M aq. HCl solution, sat. aq. NaHCO₃ and brine. The organic layers were dried over MgSO₄ and concentrated. Column chromatography on silica gel (hexanes/ethyl acetate) afforded 7* (66 mg, 0.13 mmol, 22%). $[α]_D^{20}$=−72.2° (c=1.6, CHCl₃); IR $ν_{max}$ (film) 3062, 3031, 2933, 2869, 2106, 1578, 1496, 1477, 1454, 1438, 1361, 1279, 1202, 1162, 1105, 1067 cm⁻¹; ¹H-NMR (400 MHz, CDCl₃) δ 7.58-7.23 (m, 15H), 5.80 (d, J=1.5, 1H), 5.02 (J=11.8, 1H), 4.81-4.64 (m, 3H), 4.24-4.10 (m, 2H), 3.99-3.90 (m, 1H), 3.71-3.66 (m, 1H), 1.24 (d, J=6.5, 3H); ¹³C-NMR (100 MHz, CDCl₃) δ 138.4, 137.4, 133.9, 129.4, 129.1, 128.8, 128.6, 128.3, 128.2, 128.0, 127.8, 127.7, 83.9, 77.5, 75.4, 75.0, 71.4, 70.6, 60.0, 16.7; HRMS (ESI): Calcd for $C_{26}H_{27}N_3O_3SeNa^+$ [M+Na]⁺ 532.1115, found 532.1112.

Example 8: Synthesis of 2-azido-3,4-di-O-benzyl-2-deoxy-α-L-pneumopyranosyl trichloroacetimidate (8*)

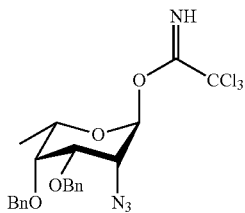

To a solution of 7* (30 mg, 59 μmol) in THF (1.25 mL) and H₂O (0.75 mL) was added NIS (27 mg, 180 μmol) and stirred for 2 h. The reaction was diluted with DCM and the organic layer washed with sat. aq. Na₂S₂O₃ followed by sat. aq. NaHCO₃, dried over MgSO₄ and concentrated. Column chromatography (hexanes/EtOAc) afforded the free lactol (20 mg, 54 μmol, 92%) as a mixture of α and β anomers. IR $ν_{max}$ (film) 3413, 3031, 2872, 2110, 1496, 1454, 1360, 1306, 1176, 1109, 1053, 1027 cm⁻¹; ¹H-NMR (400 MHz, CDCl₃) δ 7.59-7.20 (m, 10H), 5.20 (d, J=1.6 Hz, 0.5H), 4.99 (d, J=11.7 Hz, 1H), 4.81-4.64 (m, 3H), 4.56 (d, J=1.8 Hz, 0.5H), 4.02 (t, J=3.4 Hz, 1H), 3.67 (t, J=3.4 Hz, 0.5H), 3.65-3.63 (m, 0.5H), 3.60-3.55 (m, 0.5H), 3.44 (qd, J=6.3, 1.1 Hz, 0.5H), 1.26 (d, J=6.4 Hz, 1.5H), 1.23 (d, J=6.6 Hz, 1.5H); ¹³C-NMR (100 MHz, CDCl₃) δ 138.4, 138.1, 137.8, 137.3, 129.0, 128.8 (2C), 128.6, 128.4, 128.3, 128.2, 127.9, 127.7, 127.5, 127.4, 93.6, 93.2, 79.7, 76.7, 75.4, 74.9, 73.8, 71.8, 71.4, 71.2, 67.3, 60.4, 58.3, 17.0, 16.9; HRMS (ESI): Calcd for $C_{20}H_{23}N_3O_4Na^+$ [M+Na]⁺ 392.1586, found 392.1583. According to general procedure (C), the lactol (75 mg, 0.20 mmol) was reacted with trichloroacetonitrile (0.20 mL, 2.0 mmol) and K₂CO₃ (48 mg, 0.35 mmol) in DCM (2 mL) to afford compound 8* (65 mg, 0.13 mmol, 62%). $[α]_D^{20}$=−32.3° (c=1.5, CHCl₃); IR $ν_{max}$ (film) 3336, 2910, 2113, 1672, 1454, 1356, 1273, 1157, 1063 cm⁻¹; ¹H-NMR (400 MHz, CDCl₃) δ 8.65-8.49 (m, 1H), 7.43-7.22 (m, 10H), 6.19 (d, J=1.5 Hz, 1H), 5.03 (d, J=11.7 Hz, 1H), 4.78 (d, J=11.8 Hz, 1H), 4.70 (d, J=3.7 Hz, 2H), 4.09-3.98 (m, 3H), 3.69 (dd, J=1.6, 1.2 Hz, 1H), 1.23 (d, J=6.5 Hz, 3H); ¹³C-NMR (100 MHz, CDCl₃) δ 159.9, 138.2, 137.2, 128.9, 128.8 (2C), 128.7, 128.4, 128.3, 128.2, 128.0, 127.9 (2C), 97.0, 91.0, 76.0, 75.1, 74.5, 71.2, 70.3, 56.2, 16.9; HRMS (MALDI-TOF): Calcd for $C_{22}H_{23}Cl_3N_4O_4Na^+$ [M+Na]⁺ 535.0677, found 535.0660.

Example 9: Synthesis of ethyl 2-O-benzoyl-3,4-di-O-benzyl-6-O-(2-naphthalenylmethyl)-1-thio-β-D-glucopyranoside (9*)

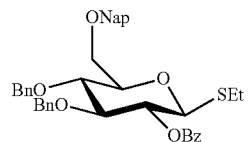

To a solution of 2-O-benzoyl-3-O-benzyl-4,6-O-benzylidene-1-thio-β-D-glucopyranoside (584 mg, 1.15 mmol) in DCM (10 mL), BH₃-THF (1 M in THF, 6.9 mL, 6.9 mmol) and TMSOTf (0.1 mL, 0.6 mmol) were added dropwise at 0° C. The reaction was warmed to room temperature over 2 h, cooled to 0° C. again and quenched by drop wise addition of sat. aq. NaHCO₃ solution. The emulsion was diluted with DCM and washed with a sat. aq. NaHCO₃ solution. The organic phase was then dried over MgSO₄, filtered and concentrated to give the crude alcohol. To a solution of crude alcohol in THF/DMF (9:1, 10 mL) at 0° C., naphtyl bromide (509 mg, 2.30 mmol) and NaH (33 mg, 1.38 mmol) were added. The reaction was warmed to room temperature and stirred for 30 min, cooled to 0° C. and quenched by the addition of water. After dilution with Et₂O the organic phase was washed with 0.1 M HCl and sat. aq. NaHCO₃ solutions. The organic phase was then dried over MgSO₄, filtered and concentrated. Column chromatography on silica gel (hexanes/ethyl acetate) afforded 9* (626 mg, 0.97 mmol, 84%). $[α]_D^{20}$=+29.5° (c=3.1, CHCl₃), IR $ν_{max}$ (film) 3061, 3030, 2867, 1722, 1602, 1496, 1452, 1359, 1315, 1264, 1087, 1067, 1026 cm⁻¹; ¹H-NMR (400 MHz, CDCl₃) δ 8.06-8.01 (m, 2H), 7.86-7.79 (m, 4H), 7.60-7.42 (m, 6H), 7.26-7.04 (m, 10H), 5.34 (dd, J=10.0, 8.9 Hz, 1H), 4.84-4.54 (m, 7H), 3.88-3.74 (m, 4H), 3.60 (ddd, J=9.5, 4.5, 2.0 Hz, 1H), 2.81-2.68 (m, 2H), 1.26 (t, J=7.5 Hz, 3H); ¹³C-NMR (100 MHz, CDCl₃) δ 165.4, 138.0, 137.9, 135.8, 133.4, 133.3, 133.2, 130.1, 130.0, 128.5 (2C), 128.4, 128.3, 128.1 (3C), 127.9, 127.8 (2C), 126.6, 126.2, 126.0, 125.9, 84.5, 83.4, 79.7, 78.1, 75.4, 75.2, 73.7, 72.6, 69.1, 24.1, 15.1; HRMS (MALDI-TOF): Calcd for $C_{40}H_{40}O_6SNa^+$ [M+Na]⁺ 671.2438, found 671.2478.

Example 10: Synthesis of ethyl 3,4-di-O-benzyl-2-O-levulinoyl-6-O-(2-naphthalenylmethyl)-1-thio-β-D-glucopyranoside (10*)

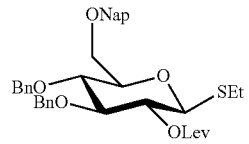

To a solution of 9* (367 mg, 0.57 mmol) in DCM (5.0 mL) was added 0.5 M NaOMe in MeOH (5.0 mL) and stirred for 16 h. The mixture was neutralized with Amberlite® IR 120 (H⁺) ion exchange resin, filtered and concentrated. The residue was dissolved in DCM (5.0 mL) together with DMAP (7 mg, 0.06 mmol), levulinic acid (81 μL, 0.79 mmol) and EDC (120 μL, 0.68 mmol). The reaction mixture was stirred for 4 h, concentrated and redissolved in EtOAc. The organic layer was washed with sat. aq. NH₄Cl, sat. aq. NaHCO₃ and brine, then dried over MgSO₄ and concentrated. Column chromatography on silica gel (hexanes/ethyl acetate) afforded 10* (271 mg, 0.42 mmol, 75%). $[\alpha]_D^{20}=-1.0°$ (c=1.5, CHCl$_3$), IR $v_{max}$ (film) 3061, 3031, 2926, 2869, 1746, 1718, 1497, 1454, 1404, 1361, 1203, 1158, 1081, 1062 cm$^{-1}$; $^1$H-NMR (400 MHz, CDCl$_3$) δ 7.89-7.73 (m, 4H), 7.55-7.42 (m, 3H), 7.41-6.97 (m, 10H), 5.11-5.02 (m, 1H), 4.82-4.69 (m, 5H), 4.56 (d, J=10.8 Hz, 1H), 4.39 (d, J=10.0 Hz, 1H), 3.82-3.68 (m, 4H), 3.53 (ddd, J=9.2, 4.6, 2.1 Hz, 1H), 2.80-2.64 (m, 4H), 2.60-2.46 (m, 2H), 2.16 (s, 3H), 1.28 (t, J=7.5 Hz, 3H); $^{13}$C-NMR (100 MHz, CDCl$_3$) δ 206.2, 171.6, 138.3, 137.9, 135.7, 133.3, 133.1, 128.4 (2C), 128.3, 128.2, 128.0 (2C), 127.9 (3C), 127.8 (2C), 126.5, 126.2, 125.9, 125.8, 84.4, 83.5, 79.5, 77.9, 75.2, 75.1, 73.6, 72.3, 68.9, 38.0, 29.9, 28.2, 24.0, 15.0; HRMS (MALDI-TOF): Calcd for $C_{38}H_{42}O_7SNa^+$ [M+Na]$^+$ 665.2543, found 665.2558.

Example 11: Synthesis of N-(benzyl)benzyloxycarbonyl-5-amino-pentanyl 2-azido-3-O-benzyl-2-deoxy-4-O-(2-naphthalenylmethyl)-β-D-fucopyranoside (11*)

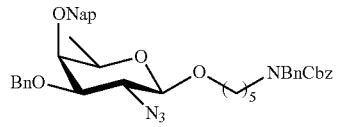

To a solution of 6* (50 mg, 78 μmol) in DMF (4 ml) at 0° C., BnBr (28 μL, 240 μmol), TBAI (3 mg, 8 μmol) and NaH (3 mg, 125 mmol) were added. After 3 h the reaction was quenched with MeOH at 0° C. and diluted with Et$_2$O. The organic layer was washed with 0.1 M aq. HCl solution, sat. aq. NaHCO$_3$ and brine. The organic layers were dried over MgSO$_4$ and concentrated. Column chromatography on silica gel (hexanes/ethyl acetate) afforded 11* (32 mg, 44 μmol, 56%). $[\alpha]_D^{20}=-24.2°$ (c=1.6, CHCl$_3$); IR $v_{max}$ (film) 3031, 2935, 2110, 1697, 1496, 1454, 1421, 1362, 1230, 1172, 1111, 1068 cm$^{-1}$; $^1$H-NMR (400 MHz, CDCl$_3$) δ 7.42 (s, 22H), 5.19 (d, J=12.8 Hz, 2H), 5.09 (d, J=11.9 Hz, 1H), 4.86 (d, J=11.9 Hz, 1H), 4.79-4.68 (m, 2H), 4.51 (d, J=8.8 Hz, 2H), 4.22-4.11 (m, 1H), 3.96-3.80 (m, 2H), 3.58 (d, J=2.5 Hz, 1H), 3.51-3.36 (m, 2H), 3.34-3.17 (m, 3H), 1.67-1.47 (m, 4H), 1.46-1.28 (m, 2H), 1.21 (d, J=6.4 Hz, 3H); $^{13}$C-NMR (100 MHz, CDCl$_3$) δ 138.0, 137.9, 135.8, 133.2, 133.1, 128.6 (2C), 128.6, 128.1 (2C), 128.0, 127.9, 127.8, 127.3, 126.8, 126.1, 126.0, 102.4, 81.1, 74.8, 74.7, 72.9, 70.6, 69.8, 67.2, 63.3, 50.6, 50.3, 47.2, 46.3, 29.3, 28.0, 27.6, 23.3, 17.1; HRMS (MALDI-TOF): Calcd for $C_{44}H_{48}N_4O_6Na^+$ [M+Na]$^+$ 751.3466, found 751.3417.

Example 12: Synthesis of N-(benzyl)benzyloxycarbonyl-5-amino-pentanyl 2-N-acetyl-3-O-benzyl-2-deoxy-4-O-(2-naphthalenylmethyl)-β-D-fucosaminopyranoside (12*)

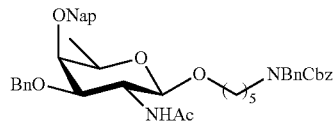

According to general procedure (F), azido-monosaccharide 11* (32 mg, 44 μmol) was reacted with thioacetic acid for 24 h to give 12* (26 mg, 35 μmol, 80%). $[\alpha]_D^{20}=+8.8°$ (c=1.4, CHCl$_3$); IR $v_{max}$ (film) 3288, 3062, 2933, 1698, 1654, 1555, 1496, 1454, 1422, 1366, 1308, 1231, 1173, 1113, 1068 cm$^{-1}$; $^1$H-NMR (400 MHz, CDCl$_3$) δ 7.93-7.08 (m, 22H), 5.17 (d, J=15.1 Hz, 2H), 5.06 (d, J=11.9 Hz, 1H), 4.95 (d, J=8.3 Hz, 1H), 4.84 (d, J=12.0 Hz, 1H), 4.72-4.63 (m, 1H), 4.60-4.32 (m, 4H), 3.92-3.72 (m, 1H), 3.65 (d, J=2.2 Hz, 1H), 3.57 (q, J=6.3 Hz, 1H), 3.53-3.32 (m, 2H), 3.32-3.09 (m, 2H), 1.98-1.79 (m, 3H), 1.63-1.41 (m, 4H), 1.33-1.16 (m, 5H); $^{13}$C-NMR (100 MHz, CDCl$_3$) δ 171.1, 138.0, 133.2, 133.0, 128.6, 128.1, 128.0 (2C), 127.9, 127.8, 127.3, 127.0, 126.7, 126.1, 125.9, 99.4, 78.2, 75.5, 74.7, 72.6, 70.4, 69.5, 67.2, 55.5, 50.3, 47.3, 29.1, 27.5, 23.8, 23.5, 17.3; HRMS (MALDI-TOF): Calcd for $C_{46}H_{52}N_2O_7Na^+$ [M+Na]$^+$ 767.3667, found 767.3575.

Example 13: Synthesis of N-(benzyl)benzyloxycarbonyl-5-amino-pentanyl 2-N-acetyl-3-O-benzyl-2-deoxy-β-D-fucosaminopyranoside (13*)

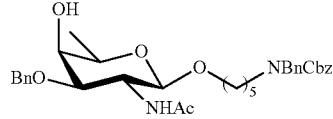

According to general procedure (G), monosaccharide 12* (20 mg, 27 μmol) was reacted with DDQ (12 mg, 53 μmol) in DCM/H$_2$O to give alcohol 13* (12 mg, 20 μmol, 74%). $[\alpha]_D^{20}=+13.9°$ (c=1.2, CHCl$_3$); IR $v_{max}$ (film) 3298, 3032, 2934, 1697, 1657, 1554, 1497, 1454, 1423, 1369, 1303, 1229, 1173, 1069 cm$^{-1}$; $^1$H-NMR (400 MHz, CDCl$_3$) δ 7.53-7.07 (m, 15H), 5.16 (d, J=18.4 Hz, 2H), 4.85 (d, J=8.4 Hz, 1H), 4.67 (d, J=11.7 Hz, 1H), 4.59-4.42 (m, 3H), 4.31-4.15 (m, 1H), 3.92-3.72 (m, 2H), 3.61 (q, J=6.4 Hz, 1H), 3.45-3.10 (m, 4H), 2.34 (s, 1H), 1.99-1.80 (m, 3H), 1.64-1.43 (m, 4H), 1.36-1.20 (m, 5H); $^{13}$C-NMR (100 MHz, CDCl$_3$) δ 170.9, 138.0, 128.7, 128.6, 128.1 (2C), 127.9, 127.4, 127.3, 99.4, 77.4, 76.7, 71.9, 70.0, 69.5, 68.7, 67.3, 54.6, 50.5, 50.3, 47.4, 29.3, 29.0, 27.5, 23.8, 23.6, 16.7; HRMS (MALDI-TOF): Calcd for $C_{35}H_{77}N_2O_7Na^+$ [M+Na]$^+$ 627.3041, found 627.2969.

Example 14: Synthesis of 5-amino-pentanyl 2-acetamido-2,5-dideoxy-β-D-xylo-hexos-4-uloside (14*)

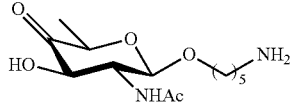

To a solution of alcohol 13* (12 mg, 20 μmol) in DCM (2 mL) Dess Martin periodinane (17 mg, 40 μmol) was added and stirred for 12 h. The reaction mixture was loaded onto a silica gel column and purified by column chromatography (hexanes/acetone) to give the crude protected ketone. According to general procedure (I), the crude protected ketone was subjected to hydrogenolysis to give 14* as a minor component in a mixture of compounds. HRMS (ESI): Calcd for $C_{13}H_{26}N_2O_6Na^+$ [M+H$_2$O+Na]$^+$ 329.1689, found 329.1479.

Example 15: Synthesis of 5-amino-pentanyl 2-N-acetyl-2-deoxy-β-D-fucosaminopyranoside (15*)

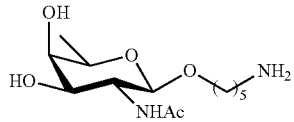

According to general procedure (I), D-fucosaminoside 12* (7 mg, 9 μmol) was subjected to hydrogenolysis to give 15* (2.5 mg, 8.6 μmol, 92%). $^1$H-NMR (600 MHz, D$_2$O) δ 4.43 (d, J=8.5 Hz, 1H), 3.94-3.81 (m, 2H), 3.80-3.68 (m, 3H), 3.64-3.56 (m, 1H), 3.06-2.96 (m, 2H), 2.05 (s, 3H), 1.69 (dt, J=15.2, 7.6 Hz, 2H), 1.63-1.57 (m, 2H), 1.45-1.37 (m, 2H), 1.28 (d, J=6.3 Hz, 3H); $^{13}$C-NMR (150 MHz, D$_2$O) δ 177.2, 104.1, 73.8, 73.5, 73.1, 72.6, 54.8, 41.9, 30.8, 29.0, 24.8, 24.7, 18.1; HRMS (ESI): Calcd for C$_{13}$H$_{27}$N$_2$O$_5^+$ [M+H]$^+$ 291.1920, found 291.1925.

Example 16: Synthesis of N-(benzyl)benzyloxycarbonyl-5-amino-pentanyl 2-azido-2-deoxy-α-L-fucopyranosyl-(1→3)-2-azido-2-deoxy-4-O-(2-naphthalenylmethyl)-β-D-fucopyranoside (16*)

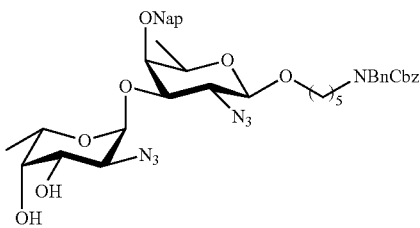

According to general procedure (E), 2-azido-3,4-di-O-benzyl-2-deoxy-α-L-fucopyranosyl trichloroacetimidate (140 mg, 335 μmol) and 6* (100 mg, 157 μmol) were reacted in DCM (2 mL) at −20° C. to −15° C. over 30 min to give the crude disaccharide. To a solution of the crude disaccharide in DCM/MeOH (1:1, 2 mL) was added 0.5 M NaOMe in MeOH (0.1 mL) and stirred for 16 h. The mixture was neutralized with Amberlite® IR 120 (H$^+$) ion exchange resin, filtered and concentrated. Column chromatography (DCM/MeOH/acetone) afforded disaccharide 16* (110 mg, 136 μmol, 87%). [α]$_D^{20}$=−41.6° (c=1.5, CHCl$_3$); IR v$_{max}$ (film) 3328, 2936, 2119, 1697, 1422, 1255, 1095, 1070, 1028 cm$^{-1}$; $^1$H-NMR (400 MHz, CDCl$_3$) δ 7.94-7.72 (m, 4H), 7.59-7.44 (m, 3H), 7.41-7.03 (m, 10H), 5.24 (d, J=3.6 Hz, 1H), 5.17 (d, J=12.9 Hz, 2H), 4.99 (d, J=12.2 Hz, 1H), 4.80 (d, J=12.2 Hz, 1H), 4.49 (d, J=6.9 Hz, 2H), 4.21 (t, J=9.3 Hz, 1H), 3.99-3.84 (m, 2H), 3.59-3.39 (m, 6H), 3.31-3.12 (m, 4H), 2.30 (s, 2H), 1.69-1.47 (m, 4H), 1.43-1.27 (m, 5H), 1.10 (d, J=6.6 Hz, 3H); $^{13}$C-NMR (100 MHz, CDCl$_3$) δ 136.0, 133.2, 133.1, 128.6, 128.3, 128.0, 127.9, 127.8, 127.4, 126.8, 126.6, 126.5, 126.3, 102.8, 99.9, 79.1, 78.2, 75.6, 71.4, 71.0, 69.9, 67.9, 67.3, 66.3, 63.8, 59.7, 50.6, 50.3, 47.2, 46.3, 29.3, 23.3, 17.3, 16.2; HRMS (MALDI-TOF): Calcd for C$_{43}$H$_{51}$N$_7$O$_9$Na$^+$ [M+Na]$^+$ 832.3640, found 832.3676.

Example 17: Synthesis of N-(benzyl)benzyloxycarbonyl-5-amino-pentanyl 3,4-di-O-benzyl-2-azido-2-deoxy-α-L-fucopyranosyl-(1→3)-2-azido-2-deoxy-4-O-(2-naphthalenylmethyl)-β-D-fucopyranoside (17*)

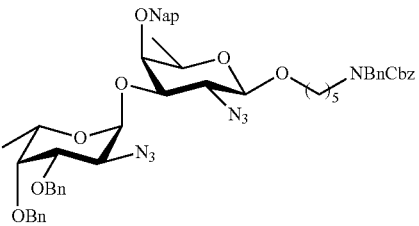

To a solution of diol 16* (87 mg, 107 μmol) in DMF (5 mL) at 0° C., BnBr (77 μL, 645 μmol), TBAI (4 mg, 11 μmol) and NaH (8 mg, 333 mmol) were added. After 3 h the reaction was quenched with MeOH at 0° C. and diluted with Et$_2$O. The organic layer was washed with 0.1 M aq. HCl solution, sat. aq. NaHCO$_3$ and brine. The organic layers were dried over MgSO$_4$ and concentrated. Column chromatography on silica gel (hexanes/ethyl acetate) afforded 17* (88 mg, 89 μmol, 83%). [α]$_D^{20}$=−50.2° (c=1.4, CHCl$_3$); IR v$_{max}$ (film) 2937, 2114, 1697, 1496, 1454, 1421, 1360, 1233, 1171, 1103, 1068, 1038 cm$^{-1}$; $^1$H-NMR (400 MHz, CDCl$_3$) δ 7.92-7.72 (m, 4H), 7.63-7.07 (m, 23H), 5.22 (d, J=3.7 Hz, 1H), 5.18 (d, J=13.1 Hz, 2H), 4.95 (d, J=12.1 Hz, 1H), 4.83 (dd, J=12.5 Hz, 2H), 4.57-4.36 (m, 5H), 4.21 (dd, J=11.6, 8.1 Hz, 1H), 4.02-3.84 (m, 2H), 3.75 (dd, J=10.8, 3.5 Hz, 1H), 3.64-3.40 (m, 6H), 3.33-3.15 (m, 3H), 1.70-1.49 (m, 4H), 1.43-1.26 (m, 5H), 1.00 (d, J=6.5 Hz, 3H); $^{13}$C-NMR (100 MHz, CDCl$_3$) δ 138.1, 137.6, 136.0, 133.2, 133.0, 128.6, 128.5, 128.4, 128.3, 128.0, 127.9 (2C), 127.8, 127.3, 126.5, 126.4, 126.2, 102.7, 100.4, 79.4, 78.9, 75.8, 75.7, 74.9, 72.2, 70.9, 70.0, 67.2, 63.9, 59.4, 50.6, 50.3, 47.2, 46.3, 29.3, 28.0, 27.5, 23.3, 17.3, 16.8; HRMS (MALDI-TOF): Calcd for C$_{57}$H$_{63}$N$_7$O$_9$Na$^+$ [M+Na]$^+$ 1012.4579, found 1012.4502.

Example 18: Synthesis of N-(benzyl)benzyloxycarbonyl-5-amino-pentanyl 2-N-acetyl-3,4-di-O-benzyl-α-L-fucosaminopyranosyl-(1→3)-2-N-acetyl-4-O-(2-naphthalenylmethyl)-β-D-fucosaminopyranoside (18*)

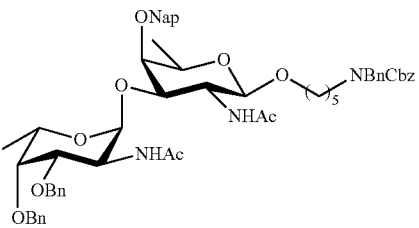

According to general procedure (F), azido-disaccharide 17* (88 mg, 89 μmol) was reacted with thioacetic acid for 24 h to give 18* (82 mg, 80 μmol, 90%). [α]$_D^{20}$=−21.0° (c=1.2, CHCl$_3$); IR v$_{max}$ (film) 3314, 2933, 1682, 1497, 1454, 1366, 1304, 1233, 1172, 1104, 1063, 1029 cm$^{-1}$; $^1$H-NMR (400 MHz, CDCl$_3$) δ 7.91-7.71 (m, 4H), 7.55-7.04 (m, 23H), 5.21-5.08 (m, 2H), 5.00-4.62 (m, 5H), 4.60-4.40 (m, 4H), 4.35-4.00 (m, 3H), 3.90-3.66 (m, 3H), 3.57-3.09

(m, 7H), 2.07-1.84 (m, 6H), 1.65-1.40 (m, 4H), 1.36-1.15 (m, 5H), 1.05 (d, J=6.5 Hz, 3H); $^{13}$C-NMR (100 MHz, CDCl$_3$) δ 171.4, 170.8, 133.2, 132.9, 128.6, 128.5, 128.4 (2C), 128.3, 128.2, 128.0, 127.9, 127.8, 127.6, 127.5, 127.4, 127.3, 126.4, 126.1, 126.0, 125.5, 101.4, 100.5, 78.5, 75.5, 74.3, 72.2, 70.7, 68.5, 67.6, 67.2, 52.0, 50.5, 48.1, 47.6, 29.2, 28.7, 23.6, 23.5, 17.4, 17.0; HRMS (MALDI-TOF): Calcd for C$_{61}$H$_{71}$N$_3$O$_{11}$Na$^+$ [M+Na]$^+$ 1044.4981, found 1044.4917.

Example 19: Synthesis of N-(benzyl)benzyloxycarbonyl-5-amino-pentanyl 2-N-acetyl-3,4-di-O-benzyl-α-L-fucosaminopyranosyl-(1→3)-2-N-acetyl-β-D-fucosaminopyranoside (19*)

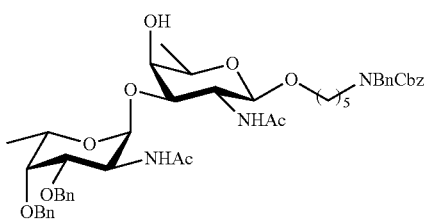

According to general procedure (G), disaccharide 18* (46 mg, 45 μmol) was reacted with DDQ (30 mg, 132 μmol) in DCM/H$_2$O to give alcohol 19* (30 mg, 34 μmol, 76%). [α]$_D^{20}$=−35.7° (c=1.0, CHCl$_3$); IR v$_{max}$ (film) 3290, 3088, 2932, 1702, 1646, 1548, 1497, 1454, 1422, 1372, 1304, 1227, 1101, 1063, 1024 cm$^{-1}$; $^1$H-NMR (400 MHz, CDCl$_3$) δ 7.41-7.14 (m, 20H), 5.22-5.07 (m, 2H), 5.01-4.85 (m, 2H), 4.84-4.31 (m, 6H), 4.29-4.18 (m, 1H), 4.11-3.89 (m, 2H), 3.87-3.38 (m, 6H), 3.36-3.04 (m, 3H), 2.00 (s, 3H), 1.91 (s, 3H), 1.63-1.38 (m, 4H), 1.27 (d, J=6.4 Hz, 5H), 1.17 (d, J=6.5 Hz, 3H); $^{13}$C-NMR (100 MHz, CDCl$_3$) δ 170.8, 128.7, 128.6, 128.5, 128.4 (2C), 128.0, 127.6, 127.5, 127.4, 101.5, 101.1, 80.4, 78.4, 75.8, 74.8, 72.0, 71.5, 70.1, 68.8, 67.4, 67.3, 51.3, 50.6, 48.8, 47.6, 28.7, 27.0, 23.6, 23.5, 17.2, 16.5; HRMS (MALDI-TOF): Calcd for C$_{50}$H$_{63}$N$_3$O$_{11}$Na$^+$ [M+Na]$^+$ 904.4355, found 904.4344.

Example 20: Synthesis of 5-amino-pentanyl 2-N-acetyl-α-L-fucosaminopyranosyl-(1→3)-2-acetamido-2,5-dideoxy-β-D-xylo-hexos-4-uloside (20*)

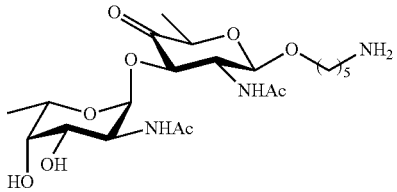

To a solution of 19* (9 mg, 10 μmol) in DCM (2 mL) Dess Martin periodinane (9 mg, 9 μmol) was added and stirred for 12 h. The reaction mixture was loaded onto a silica gel column and purified by column chromatography (hexanes/acetone) to give the crude protected ketone. According to general procedure (I), the crude protected ketone was subjected to hydrogenolysis to give 20* as a mixture of compounds (approx. 2 mg, approx. 4 μmol, approx. 39%). $^1$H-NMR (600 MHz, D$_2$O) δ 5.02 (d, J=4.0 Hz, 1H), 4.49 (q, J=6.5 Hz, 1H), 4.45 (d, J=8.8 Hz, 1H), 4.15 (dd, J=11.2, 4.1 Hz, 1H), 3.99 (dd, J=11.2, 3.2 Hz, 1H), 3.92-3.83 (m, 3H), 3.66-3.54 (m, 3H), 3.01-2.97 (m, 2H), 2.06 (s, 3H), 1.98 (s, 3H), 1.70-1.64 (m, 2H), 1.61-1.55 (m, 2H), 1.42-1.36 (m, 2H), 1.29 (d, J=6.4 Hz, 3H), 1.20 (d, J=6.6 Hz, 3H); $^{13}$C-NMR (150 MHz, D$_2$O) δ 177.0, 176.4, 104.0, 100.9, 95.4, 81.4, 75.9, 73.7, 72.8, 70.2, 69.9, 52.1, 42.0, 30.8, 29.1, 24.9, 24.8, 24.7, 17.9, 13.8; HRMS (ESI): Calcd for C$_{21}$H$_{40}$N$_3$O$_{10}^+$ [M+H$_2$O+H]$^+$ 494.2714, found 494.2740.

Example 21: Synthesis of 5-amino-pentanyl 2-N-acetyl-α-L-fucosaminopyranosyl-(1→3)-2-N-acetyl-β-D-fucosaminopyranoside (21*)

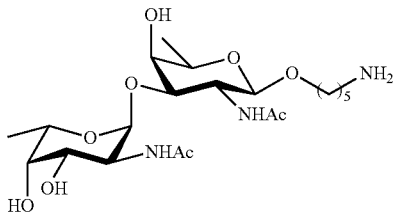

According to general procedure (I), disaccharide 20* (7 mg, 7 μmol) was subjected to hydrogenolysis to give 21* (2.73 mg, 5.7 μmol, 83%). $^1$H-NMR (600 MHz, D$_2$O) δ 5.00 (d, J=4.0 Hz, 1H), 4.41 (d, J=8.5 Hz, 1H), 4.15-4.09 (m, 2H), 4.01-3.94 (m, 2H), 3.89 (dt, J=10.2, 6.0 Hz, 1H), 3.85 (d, J=3.0 Hz, 1H), 3.82-3.74 (m, 3H), 3.58 (dt, J=10.1, 6.4 Hz, 1H), 3.04-2.96 (m, 2H), 2.05 (s, 3H), 2.00 (s, 3H), 1.72-1.64 (m, 2H), 1.63-1.55 (m, 2H), 1.44-1.36 (m, 2H), 1.28 (d, J=6.5 Hz, 3H), 1.24 (d, J=6.6 Hz, 3H); $^{13}$C-NMR (150 MHz, D$_2$O) δ 176.8, 176.7, 104.2, 101.6, 79.4, 73.6, 73.3, 73.1, 72.7, 70.1, 69.7, 54.0, 52.1, 41.9, 30.8, 29.1, 24.8 (2C), 24.7, 18.0 (2C); HRMS (ESI): Calcd for C$_{21}$H$_{40}$N$_3$O$_9^+$ [M+H]$^+$ 478.2765, found 478.2775.

Example 22: Synthesis of N-(benzyl)benzyloxycarbonyl-5-amino-pentanyl 3,4-di-O-benzyl-2-O-levulinoyl-6-O-(2-naphthalenylmethyl)-β-D-glucopyranoside (22*)

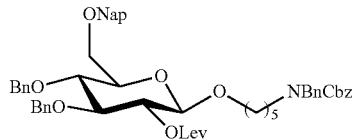

According to general procedure (B), thioglucoside 10* (30 mg, 47 μmol) was reacted with N-(benzyl)benzyloxycarbonyl-5-amino-pentanol (31 mg, 93 μmol), NIS (13 mg, 56 μmol) and TfOH (0.8 μL, 9 μmol) in DCM (1 mL) at −30° C. to −20° C. over 1 h. After work-up column chromatography (hexanes/EtOAc) afforded 22* (26 mg, 29 μmol, 61%). [α]$_D^{20}$=+3.7° (c=0.9, CHCl$_3$); IR v$_{max}$ (film) 2924, 1747, 1698, 1454, 1421, 1362, 1210, 1153, 1071 cm$^{-1}$; $^1$H-NMR (400 MHz, CDCl$_3$) δ 7.84-7.76 (m, 4H), 7.26 (s, 22H), 7.09-7.05 (m, 2H), 5.21-5.13 (m, 3H), 4.98 (t, J=8.6 Hz, 1H), 4.77 (d, J=10.9 Hz, 3H), 4.70 (d, J=11.6 Hz, 2H), 4.53-4.44 (m, 4H), 4.37-4.27 (m, 1H), 3.85-3.59 (m, 5H), 3.53-3.11 (m, 3H), 2.82-2.39 (m, 4H), 2.17-2.03 (m, 2H), 1.62-1.43 (m, 8H), 1.37-1.17 (m, 3H); $^{13}$C-NMR (100 MHz, CDCl$_3$) δ 171.5, 138.4, 133.4, 133.1, 128.7, 128.5, 128.3, 128.1 (2C), 128.0, 127.9, 127.8 (2C), 126.7, 126.2, 126.0, 101.1, 83.0, 78.1, 75.2 (2C), 75.1, 73.7 (2C), 69.6, 68.8, 67.3, 50.3, 47.2, 37.9, 30.0, 29.3, 28.1, 23.3; HRMS (MALDI-TOF): Calcd for C$_{56}$H$_{61}$NO$_{10}$Na$^+$ [M+Na]$^+$ 930.4188, found 930.4190.

Example 23: Synthesis of N-(benzyl)benzyloxycarbonyl-5-amino-pentanyl 3,4-di-O-benzyl-6-O-(2-naphthalenymethyl)-β-D-glucopyranoside (23*)

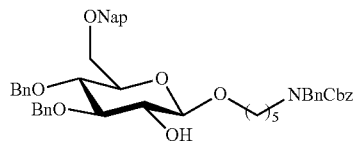

To a solution of 22* (13 mg, 14 μmol) in DCM (1 mL) hydrazine hydrate (2.8 μL, 57 μmol) dissolved in AcOH (40 μL) and pyridine (60 μL) was added and the solution stirred for 1 h. The reaction was then quenched by the addition of acetone and concentrated. Column chromatography on silica gel (hexanes/ethyl acetate) afforded 23* (10 mg, 12 μmol, 86%). [α]$_D^{20}$=+4.9° (c=1.0, CHCl$_3$); IR v$_{max}$ (film) 2926, 1698, 1454, 1230, 1063 cm$^{-1}$; $^1$H-NMR (400 MHz, CDCl$_3$) δ 7.84-7.01 (m, 27H), 5.16 (d, J=9.8 Hz, 2H), 4.93 (t, J=11.1 Hz, 1H), 4.81 (dd, J=11.0, 6.1 Hz, 2H), 4.75 (d, J=12.4 Hz, 1H), 4.67 (d, J=12.4 Hz, 1H), 4.51-4.43 (m, 3H), 4.26-4.17 (m, 1H), 4.02-3.79 (m, 2H), 3.78-3.67 (m, 2H), 3.60-3.44 (m, 4H), 3.30-3.12 (m, 2H), 1.66-1.43 (m, 4H), 1.38-1.19 (m, 2H); $^{13}$C-NMR (100 MHz, CDCl$_3$) δ 138.0, 135.7, 133.4, 133.1, 128.7, 128.6, 128.5, 128.3, 128.1, 128.0 (2C), 127.8, 127.3, 126.8, 126.2, 126.0, 103.1, 84.7, 77.7, 75.3, 75.2, 74.8, 73.7, 70.1, 69.9, 69.0, 67.3, 50.3, 47.2, 46.2, 32.4, 29.3, 27.5, 23.5; HRMS (MALDI-TOF): Calcd for C$_{51}$H$_{55}$NO$_8$Na$^+$ [M+Na]$^+$ 832.3820, found 832.3870.

Example 24: Synthesis of N-(benzyl)benzyloxycarbonyl-5-amino-pentanyl 2-azido-3,4-di-O-benzyl-2-deoxy-α-L-pneumopyranosyl-(1→2)-3,4-di-O-benzyl-6-O-(2-naphthalenylmethyl)-β-D-glucopyranoside (24*)

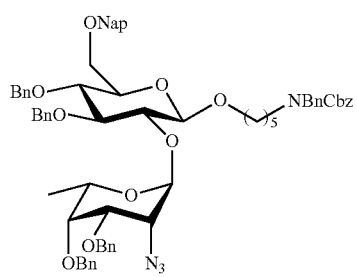

According to general procedure (E), pneumosyl-imidate 8* (12 mg, 23 μmol) and 23* (10 mg, 12 μmol) were reacted in DCM (1 mL) at −30° C. to −20° C. over 30 min to give 24* (13 mg, 11 μmol, 91%). [α]$_D^{20}$=−0.7° (c=0.7, CHCl$_3$); IR v$_{max}$ (film) 2929, 2868, 2112, 1697, 1496, 1454, 1421, 1361, 1229, 1126, 1057 cm$^{-1}$; $^1$H-NMR (400 MHz, CDCl$_3$) δ 7.86-7.72 (m, 4H), 7.50-7.43 (m, 3H), 7.41-7.02 (m, 30H), 5.24-5.08 (m, 3H), 4.93 (dd, J=30.9, 11.5 Hz, 2H), 4.77-4.44 (m, 10H), 4.26-4.08 (m, 2H), 3.85-3.67 (m, 4H), 3.66-3.51 (m, 5H), 3.47-3.29 (m, 2H), 3.25-3.09 (m, 2H), 1.61-1.38 (m, 4H), 1.32-1.03 (m, 5H); $^{13}$C-NMR (100 MHz, CDCl$_3$) δ 137.9, 133.4, 133.1, 128.8, 128.7 (2C), 128.6 (2C), 128.4, 128.2, 128.1, 128.0, 127.9, 127.8, 127.2, 126.8, 126.3, 126.0 (2C), 101.8, 99.2, 78.7, 77.4, 75.7, 75.1 (2C), 73.8 (2C), 70.9, 68.9, 67.3, 66.9, 29.5, 23.4, 17.0; HRMS (MALDI-TOF): Calcd for C$_{71}$H$_{76}$N$_4$O$_{11}$Na$^+$ [M+Na]$^+$ 1183.5403, found 1183.5391.

Example 25: Synthesis of N-(benzyl)benzyloxycarbonyl-5-amino-pentanyl 2-N-acetyl-3,4-di-O-benzyl-α-L-pneumosaminopyranosyl-(1→2)-3,4-di-O-benzyl-6-O-(2-naphthalenylmethyl)-β-D-glucopyranoside (25*)

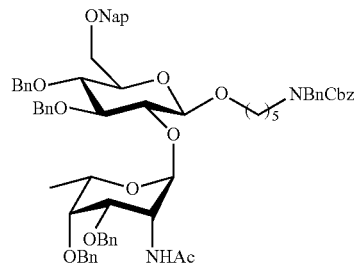

According to general procedure (F), azido-disaccharide 24* (13 mg, 11 μmol) was reacted with thioacetic acid for 24 h to give 25* (10 mg, 8 μmol, 76%). [α]$_D^{20}$=−31.1° (c=1.0, CHCl$_3$); IR v$_{max}$ (film) 2930, 1698, 1497, 1454, 1363, 1229, 1056 cm$^{-1}$; $^1$H-NMR (400 MHz, CDCl$_3$) δ 7.85-7.73 (m, 4H), 7.49-7.43 (m, 3H), 7.35-7.12 (m, 28H), 7.08-7.02 (m, 2H), 7.01-6.94 (m, 1H), 5.28 (s, 1H), 5.21-5.13 (m, 2H), 4.90-4.81 (m, 3H), 4.77-4.67 (m, 5H), 4.60-4.54 (m, 1H), 4.51-4.30 (m, 5H), 4.28-4.20 (m, 1H), 3.90-3.78 (m, 2H), 3.76-3.57 (m, 6H), 3.49-3.43 (m, 1H), 3.38 (s, 1H), 3.28-3.14 (m, 2H), 1.65 (s, 3H), 1.58-1.45 (m, 4H), 1.30-1.16 (m, 5H); $^{13}$C-NMR (100 MHz, CDCl$_3$) δ 169.8, 138.5, 138.3, 137.9, 135.7, 133.4, 133.2, 128.7 (2C), 128.5 (3C), 128.3 (2C), 128.2, 128.1, 128.0 (3C), 127.9, 127.7, 127.6, 126.8, 126.3, 126.0, 102.0, 100.3, 86.0, 79.0, 78.5, 77.4, 75.6 (2C), 75.1, 75.0, 73.8, 73.3, 70.0, 69.0, 67.3, 66.6, 50.7, 50.4, 47.6, 29.6, 27.7, 23.5, 23.3, 16.8; HRMS (MALDI-TOF): Calcd for C$_{73}$H$_{80}$N$_2$O$_{12}$Na$^+$ [M+Na]$^+$ 1199.5603, found 1199.5599.

Example 26: Synthesis of N-(benzyl)benzyloxycarbonyl-5-amino-pentanyl 2-N-acetyl-3,4-di-O-benzyl-α-L-pneumosaminopyranosyl-(1→2)-3,4-di-O-benzyl-β-D-glucopyranoside (26*)

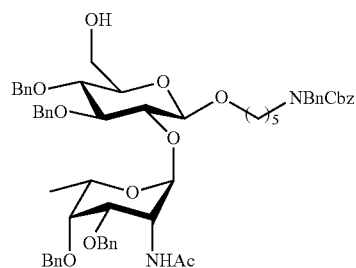

According to general procedure (G), disaccharide 25* (10 mg, 8 µmol) was reacted with DDQ (6 mg, 25 µmol) for 4 h to give primary alcohol 26* (7 mg, 7 µmol, 79%). $[\alpha]_D^{20}=-34.5°$ (c=0.7, CHCl$_3$); IR v$_{max}$ (film) 3404, 2925, 1697, 1497, 1454, 1421, 1362 1260, 1027 cm$^{-1}$; $^1$H-NMR (400 MHz, CDCl$_3$) δ 7.39-7.16 (m, 30H), 7.04-6.93 (m, 1H), 5.28 (s, 1H), 5.23-5.14 (m, 2H), 4.92-4.83 (m, 3H), 4.80 (d, J=11.0 Hz, 1H), 4.72 (d, J=12.2 Hz, 2H), 4.63-4.55 (m, 2H), 4.53-4.47 (m, 2H), 4.45-4.37 (m, 1H), 4.35-4.23 (m, 2H), 3.90-3.72 (m, 3H), 3.72-3.53 (m, 5H), 3.47-3.30 (m, 2H), 3.29-3.14 (m, 2H), 1.66 (s, 3H), 1.58-1.45 (m, 4H), 1.30-1.16 (m, 5H); $^{13}$C-NMR (100 MHz, CDCl$_3$) δ 169.8, 138.5, 138.2, 138.0, 128.7 (3C), 128.5 (2C), 128.3, 128.2 (2C), 128.1, 128.0, 127.7, 127.6, 102.0, 100.4, 85.7, 78.9, 78.1, 77.4, 75.8, 75.6, 75.1, 73.2, 70.0, 67.4, 66.7, 62.1, 50.5, 47.6, 47.2, 29.4, 28.1, 27.4, 23.3, 16.7; HRMS (MALDI-TOF): Calcd for $C_{62}H_{72}N_2O_{12}Na^+$ [M+Na]$^+$ 1059.4977, found 1059.4938.

Example 27: Synthesis of 5-amino-pentanyl 2-N-acetyl-α-L-pneumosaminopyranosyl-(1→2)-β-D-glucopyranosyluronate (27*)

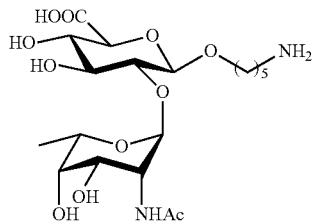

According to general procedure (H), alcohol 26* (6 mg, 6 µmol) was reacted with TEMPO (0.2 mg, 2 µmol) and BAIB (9 mg, 30 µmol) to give the protected uronate disaccharide. According to general procedure (I), the uronate disaccharide was subjected to hydrogenolysis to give 27* (1.6 mg, 3.4 µmol, 59%). $^1$H-NMR (600 MHz, D$_2$O) δ 5.15 (s, 1H), 4.55 (d, J=7.9 Hz, 1H), 4.33 (q, J=6.7 Hz, 1H), 4.23 (d, J=4.8 Hz, 1H), 4.09 (dd, J=4.8, 3.2 Hz, 1H), 3.92 (dt, J=10.0, 6.9 Hz, 1H), 3.85-3.81 (m, 1H), 3.74-3.65 (m, 3H), 3.55-3.50 (m, 1H), 3.43 (dd, J=9.0, 8.0 Hz, 1H), 3.00 (t, J=7.6 Hz, 2H), 2.06 (s, 3H), 1.73-1.66 (m, 4H), 1.49-1.42 (m, 2H), 1.26 (d, J=6.6 Hz, 3H); $^{13}$C-NMR (150 MHz, D$_2$O) δ 178.4, 176.74, 103.6, 102.6, 80.8, 78.8, 78.7, 74.3, 73.6, 72.7, 69.9, 66.5, 53.8, 42.0, 30.9, 28.9, 25.0, 24.7, 18.1; HRMS (ESI): Calcd for $C_{19}H_{34}N_2O_{11}Na^+$ [M+Na]$^+$ 489.2060, found 489.2060.

Compounds 27*a-27*e constitute further examples according to the present invention that can be obtained following the procedure described for compound 27:

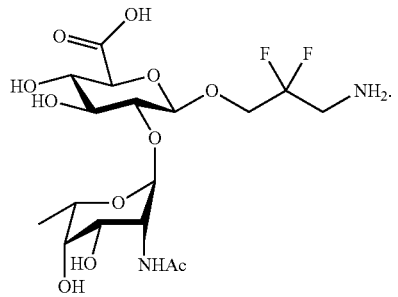

2-(2-aminoethoxy)ethyl 2-N-acetyl-α-L-pneumosaminopyranosyl-(1 → 2)-β-D-glucopyranosyluronate
Chemical formula: $C_{18}H_{32}N_2O_{12}$, Exact mass: 468.1955

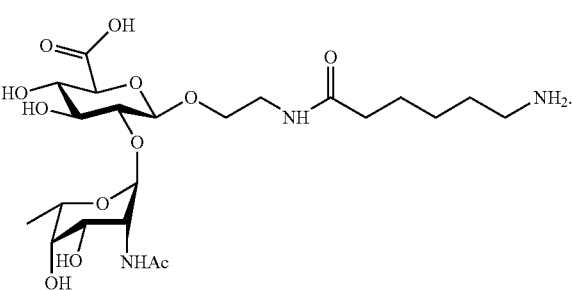

3-amino-2,2-difluoropropyl 2-N-acetyl-α-L-pneumosaminopyranosyl-(1 → 2)-β-D-glucopyranosyluronate
Chemical formula: $C_{17}H_{28}F_2N_2O_{11}$; Exact mass: 474.1661

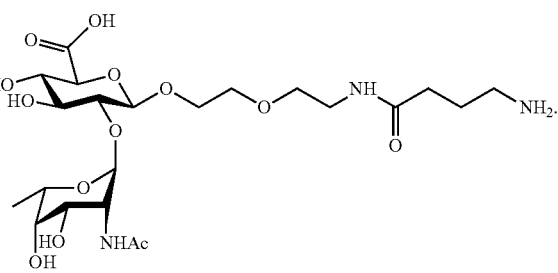

N-(2-N-acetyl-α-L-pneumosaminopyranosyl-(1 → 2)-β-D-glucopyranosyluronate ethyl)-6-amino-hexanamide
Chemical formula: $C_{22}H_{39}N_3O_{12}$, Exact mass: 537.2534

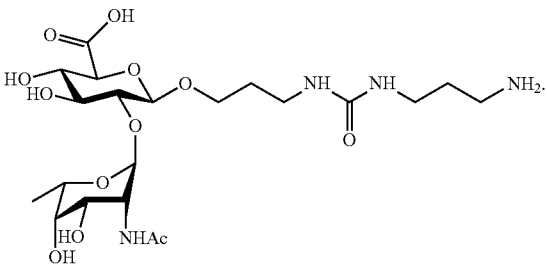

N-(2-N-acetyl-α-L-pneumosaminopyranosyl-(1 → 2)-β-D-glucopyranosyluronyl 2-ethoxyethyl)-3-aminopropanamide
Chemical formula: $C_{22}H_{39}N_3O_{12}$; Exact mass: 537.2534

3-(3-aminopropyl)ureido-propyl 2-N-acetyl-α-L-pneumosaminopyranosyl-(1 → 2)-β-D-glucopyranosyluronate
Chemical formula: $C_{21}H_{38}N_4O_{12}$; Exact mass: 538.2486

Example 28: Synthesis of N-(benzyl)benzyloxycarbonyl-5-amino-pentanyl 4-O-acetyl-2-azido-2-deoxy-α-L-fucopyranosyl-(1→3)-2-azido-2-deoxy-4-O-(2-naphthalenylmethyl)-β-D-fucopyranoside (28*)

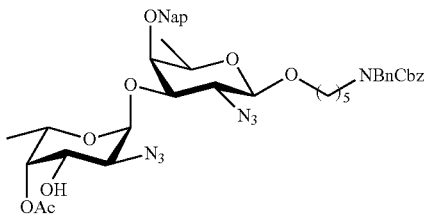

To a solution of the disaccharide 16* (110 mg, 136 μmol) in DMF (1 mL) was added trimethyl orthoacetate (104 μL, 815 μmol) and p-TSA (4 mg, 21 μmol) and the reaction mixture stirred for 30 min. Triethylamine (2 drops) was added and the solvent removed under vacuum using toluene as an azeotrope. The crude residue was taken up in 80% acetic acid (3 mL) and the reaction mixture stirred for 1 h. The solvent was removed under vacuum and azeotroped with toluene. Column chromatography on silica gel (hexanes/EtOAc) afforded 28* (92 mg, 108 μmol, 80%). $[\alpha]_D^{20}$=−50.9° (c=1.3, CHCl$_3$); IR v$_{max}$ (film) 3436, 2937, 2114, 1743, 1696, 1423, 1363, 1232, 1165, 1125, 1093, 1070, 1036 cm$^{-1}$; $^1$H-NMR (400 MHz, CDCl$_3$) δ 7.95-7.74 (m, 4H), 7.59-7.47 (m, 3H), 7.41-7.10 (m, 10H), 5.24 (d, J=3.6 Hz, 1H), 5.17 (d, J=13.3 Hz, 2H), 5.05 (d, J=12.4 Hz, 1H), 4.74 (d, J=12.4 Hz, 1H), 4.49 (d, J=7.6 Hz, 2H), 4.41 (d, J=2.2 Hz, 1H), 4.21 (dd, J=11.2, 8.3 Hz, 1H), 4.01-3.84 (m, 2H), 3.60-3.37 (m, 6H), 3.31-3.16 (m, 3H), 2.09 (s, 3H), 1.67-1.48 (m, 4H), 1.44-1.27 (m, 5H), 0.94 (d, J=6.6 Hz, 3H); $^{13}$C-NMR (100 MHz, CDCl$_3$) δ 171.3, 138.0, 136.0, 133.1 (2C), 128.6, 128.4, 127.9, 127.8, 127.3, 126.9, 126.8, 126.7, 126.5, 102.7, 99.8, 79.2, 78.1, 75.8, 72.7, 71.0, 70.0, 67.2, 66.5, 65.4, 63.9, 59.6, 50.6, 50.3, 47.2, 46.3, 29.3, 28.0, 27.5, 23.3, 20.8, 17.3, 16.1; HRMS (MALDI-TOF): Calcd for C$_{45}$H$_{53}$N$_7$O$_{10}$Na$^+$ [M+Na]$^+$ 874.3746, found 874.3737.

Example 29: Synthesis of N-(benzyl)benzyloxycarbonyl-5-amino-pentanyl 3,4-di-O-benzyl-6-O-(2-naphthalenylmethyl)-β-D-glucopyranosyl-(1→3)-4-O-acetyl-2-azido-2-deoxy-α-L-fucopyranosyl-(1→3)-2-azido-2-deoxy-4-O-(2-naphthalenylmethyl)-β-D-fucopyranoside (29*)

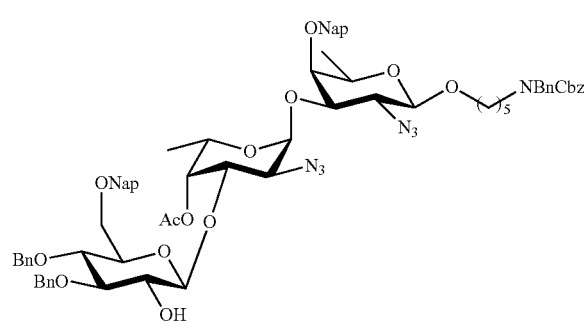

According to general procedure (B), thioglucoside 10* (75 mg, 117 μmol) was reacted with disaccharide 28* (50 mg, 59 μmol), NIS (29 mg, 129 μmol) and TfOH (1 μL, 12 μmol) in DCM (2 mL) at −20° C. to −10° C. over 1 h to give the crude trisaccharide. To a solution of the crude trisaccharide in DCM (3 mL) hydrazine hydrate (11 μL, μmol) dissolved in AcOH (40 μL) and pyridine (60 μL) was added and the solution stirred for 1 h. The reaction was then quenched by the addition of acetone and concentrated. Column chromatography on silica gel (hexanes/ethyl acetate) afforded alcohol 29* (72 mg, 54 μmol, 91%). $[\alpha]_D^{20}$=−19.2° (c=1.0, CHCl$_3$); IR v$_{max}$ (film) 2936, 2115, 1697, 1454, 1360, 1235, 1069 cm$^{-1}$; $^1$H-NMR (400 MHz, CDCl$_3$) δ 7.87-7.72 (m, 8H), 7.50-7.17 (m, 24H), 7.10-7.03 (m, 2H), 5.33 (d, J=3.6 Hz, 1H), 5.19 (d, J=12.8 Hz, 2H), 5.05 (d, J=11.3 Hz, 1H), 4.98 (d, J=12.3 Hz, 1H), 4.88-4.70 (m, 6H), 4.60-4.46 (m, 4H), 4.32-4.19 (m, 1H), 4.09 (d, J=7.0 Hz, 1H), 4.01-3.86 (m, 3H), 3.74-3.66 (m, 3H), 3.63-3.42 (m, 7H), 3.40 (d, J=2.1 Hz, 1H), 3.33-3.18 (m, 3H), 2.13 (s, 3H), 1.71-1.50 (m, 4H), 1.47-1.21 (m, 5H), 0.90 (d, J=6.5 Hz, 3H); $^{13}$C-NMR (100 MHz, CDCl$_3$) δ 174.1, 138.4, 138.2, 138.0, 137.9, 135.6, 133.2, 133.0, 132.9, 128.5, 128.4, 128.3, 128.1 (2C), 128.0, 127.9, 127.8, 127.7 (2C), 127.6 (2C), 127.5, 127.3, 127.2, 126.7, 126.5, 126.4, 126.3, 126.1, 126.0, 125.7, 102.7, 100.3, 100.2, 85.1, 82.0, 77.9, 77.4, 77.0, 76.7, 75.5, 75.5, 75.0, 74.9, 74.5, 74.2, 73.4, 70.8, 69.8, 68.5, 67.1, 63.8, 58.1, 29.2, 27.9, 23.2, 17.1, 16.6; HRMS (MALDI-TOF): Calcd for C$_{76}$H$_{83}$N$_7$O$_{15}$Na$^+$ [M+Na]$^+$ 1356.5839, found 1356.5896.

Example 30: Synthesis of N-(benzyl)benzyloxycarbonyl-5-amino-pentanyl 2-azido-3,4-di-O-benzyl-2-deoxy-α-L-pneumopyranosyl-(1→2)-3,4-di-O-benzyl-6-O-(2-naphthalenylmethyl)-β-D-glucopyranosyl-(1→3)-4-O-acetyl-2-azido-2-deoxy-α-L-fucopyranosyl-(1→3)-2-azido-2-deoxy-4-O-(2-naphthalenyl methyl)-β-D-fucopyranoside (30*)

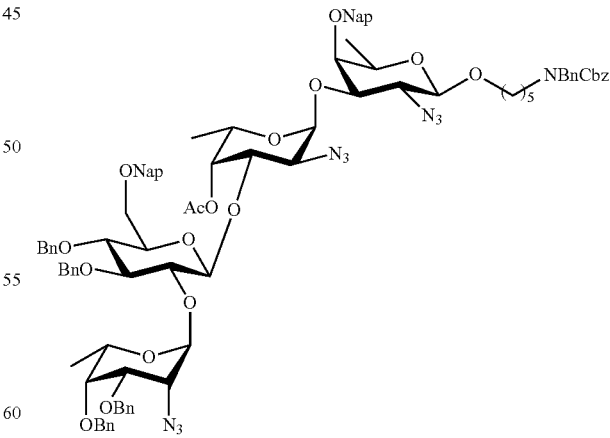

According to general procedure (E), pneumosyl-imidate 8* (100 mg, 196 μmol) and trisaccharide 29* (58 mg, 43 μmol) were reacted in DCM (2 mL) at −30° C. to −20° C. over 30 min to give tetrasaccharide 30* (40 mg, 24 μmol, 55%). $[\alpha]_D^{20}$=−38.3° (c=1.2, CHCl$_3$); IR v$_{max}$ (film) 2936, 2114, 1744, 1697, 1496, 1454, 1361, 1231, 1065 cm⁻¹; ¹H-NMR (400 MHz, CDCl₃) δ 7.85-6.94 (m, 44H), 5.34 (d, J=3.7 Hz, 1H), 5.23 (s, 1H), 5.21-5.10 (m, 3H), 4.96 (dd, J=11.8, 3.2 Hz, 2H), 4.88 (d, J=11.3 Hz, 1H), 4.77-4.36 (m, 12H), 4.27-4.14 (m, 2H), 4.08-3.99 (m, 1H), 3.95-3.85 (m, 2H), 3.81-3.76 (m, 1H), 3.74-3.60 (m, 5H), 3.58-3.37 (m, 8H), 3.33-3.16 (m, 3H), 1.90 (s, 3H), 1.64-1.46 (m, 4H), 1.42-1.22 (m, 5H), 1.19 (d, J=6.5 Hz, 3H), 0.83 (d, J=6.4 Hz, 3H); ¹³C-NMR (100 MHz, CDCl₃) δ 170.3, 138.4, 138.0, 137.9, 137.7, 135.6, 133.2, 133.1, 133.0, 128.9, 128.7, 128.6 (2C), 128.5, 128.4, 128.3, 128.2, 128.1, 128.0 (2C), 127.9, 127.8, 127.7, 127.4, 127.2, 126.8, 126.5, 126.4, 126.1, 125.9, 125.8, 102.8, 100.1, 98.6, 96.7, 84.8, 78.7, 78.5, 77.4, 76.0, 75.3, 75.1, 75.0, 74.7, 73.3, 71.0, 70.9, 69.9, 68.9, 68.7, 67.3, 65.7, 63.9, 57.4, 57.0, 29.3, 27.6, 23.3, 20.9, 17.6, 16.8, 16.3; HRMS (MALDI-TOF): Calcd for C₉₆H₁₀₄N₁₀O₁₈Na⁺ [M+Na]⁺ 1707.7422, found 1707.7445.

Example 31: Synthesis of N-(benzyl)benzyloxycarbonyl-5-amino-pentanyl 2-N-acetyl-3,4-di-O-benzyl-α-L-pneumosaminopyranosyl-(1→2)-3,4-di-O-benzyl-6-O-(2-naphthalenylmethyl)-β-D-glucopyranosyl-(1→3)-4-O-acetyl-2-N-acetyl-α-L-fucosaminopyranosyl-(1→3)-2-N-acetyl-4-O-(2-naphthalenylmethyl)-β-D-fucosaminopyranoside (31*)

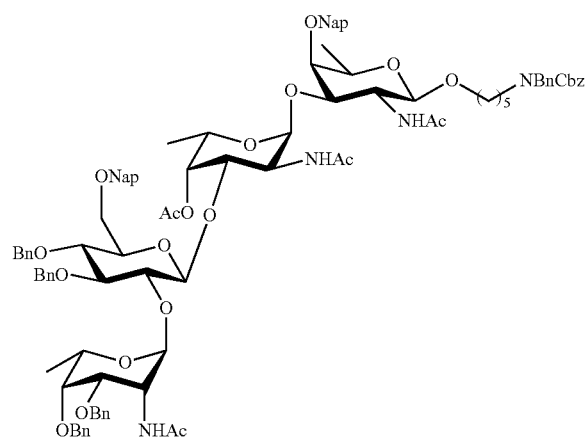

According to general procedure (F), azido-tetrasaccharide 30* (40 mg, 24 µmol) was reacted with thioacetic acid for 48 h to give 31* (31 mg, 18 µmol, 75%). [α]$_D^{20}$=−58.3° (c=1.2, CHCl₃); IR v$_{max}$ (film) 2963, 1740, 1674, 1519, 1454, 1365, 1260, 1234, 1025 cm⁻¹; ¹H-NMR (400 MHz, CDCl₃) δ 7.89-6.61 (m, 44H), 5.40-5.04 (m, 6H), 4.95-4.80 (m, 2H), 4.79-4.11 (m, 16H), 4.10-3.92 (m, 2H), 3.91-3.73 (m, 4H), 3.74-3.54 (m, 4H), 3.54-3.31 (m, 4H), 3.30-3.02 (m, 4H), 2.00 (s, 3H), 1.90-1.85 (m, 3H), 1.68 (s, 3H), 1.58-1.38 (m, 4H), 1.38-1.23 (m, 5H), 1.20 (d, J=6.4 Hz, 3H), 1.10-1.00 (m, 3H); ¹³C-NMR (100 MHz, CDCl₃) δ 171.2, 170.7 (2C), 170.0, 138.5, 138.1, 137.9, 137.7, 136.2, 133.4, 133.1 (2C), 133.0, 128.8, 128.7, 128.5 (2C), 128.4, 128.2, 128.0, 127.9, 127.7 (2C), 127.6, 127.5, 127.4, 127.3, 126.7, 126.3, 125.9, 125.5, 100.7, 98.7, 98.6, 97.1, 84.1, 79.1, 78.4, 77.4, 75.6, 75.0, 74.5, 74.0, 73.8, 73.5, 73.3, 73.1, 70.7, 70.1, 69.7, 69.3, 68.1, 67.3, 66.9, 66.0, 50.4, 48.6, 47.6, 47.4, 29.0, 27.2, 23.8, 23.4, 23.1, 21.0, 17.3, 16.9, 16.7; HRMS (MALDI-TOF): Calcd for C₁₀₂H₁₁₆N₄O₂₁Na⁺ [M+Na]⁺ 1755.8024, found 1755.8089.

Example 32: Synthesis of N-(Benzyl)benzyloxycarbonyl-5-amino-pentanyl 2-N-acetyl-3,4-di-O-benzyl-α-L-pneumosaminopyranosyl-(1→2)-3,4-di-O-benzyl-β-D-glucopyranosyl-(1→3)-2-N-acetyl-α-L-fucosaminopyranosyl-(1→3)-2-N-acetyl-β-D-fucosaminopyranoside (32*)

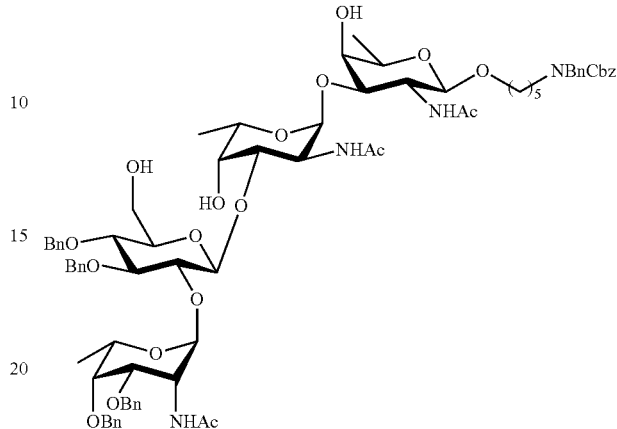

To a solution of 31* (19 mg, 11 µmol) in DCM/MeOH (1:1, 1 mL) was added 0.5 M NaOMe in MeOH (0.5 mL) and stirred for 16 h. The mixture was neutralized with Amberlite® IR 120 (H⁺) ion exchange resin, filtered and concentrated. According to general procedure (G), the crude material was reacted with DDQ (9 mg, 40 µmol) in DCM/H₂O to give triol 32* (10 mg, 7 µmol, 64%). [α]$_D^{20}$=−69.7° (c=1.0, CHCl₃); IR v$_{max}$ (film) 3400, 3030, 2933, 1656, 1524, 1497, 1454, 1421, 1366, 1305, 1232, 1055 cm⁻¹; ¹H-NMR (400 MHz, CDCl₃) δ 7.53-6.98 (m, 30H), 5.25-5.01 (m, 4H), 4.94-4.70 (m, 4H), 4.67-4.34 (m, 7H), 4.28-4.10 (m, 4H), 4.00-3.10 (m, 19H), 2.06 (s, 3H), 1.99-1.94 (m, 3H), 1.70 (s, 3H), 1.63-1.37 (m, 4H), 1.37-1.07 (m, 11H); ¹³C-NMR (100 MHz, CDCl₃) δ 171.6, 170.9, 170.1, 138.3, 128.7, 128.6 (2C), 128.5, 128.4, 128.3, 128.2, 128.1, 127.7, 127.5, 127.3, 127.2, 126.8, 101.7, 101.4, 101.2, 100.6, 99.5, 84.2, 80.8, 78.5, 77.5, 77.4, 77.2, 76.8, 75.7, 75.5, 75.2, 72.7, 72.5, 71.8, 71.3, 70.2, 69.7, 68.7, 68.6, 68.2, 67.3, 66.9, 61.9, 51.4, 50.6, 49.5, 48.5, 47.9, 23.9, 23.8, 23.5, 21.2, 16.6; HRMS (MALDI-TOF): Calcd for C₇₈H₉₈N₄O₂₀Na⁺ [M+Na]⁺ 1433.6666, found 1433.6640.

Example 33: Synthesis of 5-amino-pentanyl 2-N-acetyl-α-L-pneumosaminopyranosyl-(1→2)-β-D-glucopyranosyl-(1→3)-2-N-acetyl-α-L-fucosaminopyranosyl-(1→3)-2-N-acetyl-β-D-fucosaminopyranoside (3*)

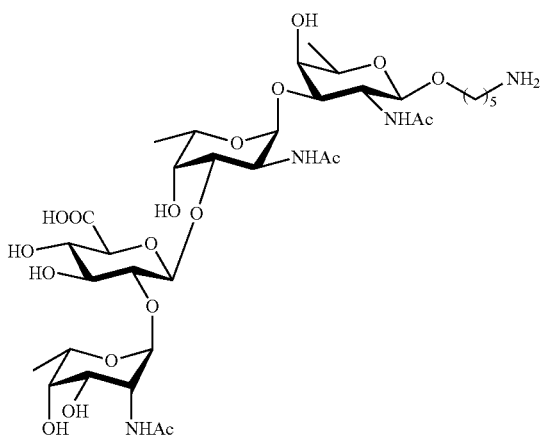

According to general procedure (H), triol 32* (10 mg, 7 µmol) was reacted with TEMPO (0.3 mg, 2 µmol) and BAIB (6 mg, 19 µmol) to give the protected uronate tetrasaccharide. According to general procedure (I), the uronate tetrasaccharide was subjected to hydrogenolysis to give carboxylic acid 33* (4.9 mg, 5.8 µmol, 83%). $^1$H-NMR (600 MHz, D$_2$O) δ 5.18 (s, 1H), 5.07 (d, J=3.9 Hz, 1H), 4.69 (d, J=7.8 Hz, 1H), 4.65 (q, J=6.7 Hz, 1H), 4.41 (d, J=8.6 Hz, 1H), 4.37 (dd, J=11.6, 3.0 Hz, 1H), 4.18 (d, J=4.8 Hz, 1H), 4.12 (dd, J=4.7, 3.2 Hz, 1H), 4.10-4.06 (m, 2H), 4.03 (dd, J=11.6, 3.9 Hz, 1H), 3.94 (t, J=9.6 Hz, 1H), 3.88 (dt, J=10.1, 6.0 Hz, 1H), 3.82-3.74 (m, 4H), 3.73-3.68 (m, 2H), 3.61-3.52 (m, 2H), 3.51 (dd, J=9.2, 7.9 Hz, 1H), 3.02-2.98 (m, 2H), 2.05 (s, 3H), 2.04 (s, 3H), 2.00 (s, 3H), 1.71-1.65 (m, 2H), 1.61-1.56 (m, 2H), 1.44-1.37 (m, 2H), 1.28 (d, J=6.5 Hz, 3H), 1.24 (d, J=6.6 Hz, 3H), 1.15 (d, J=6.6 Hz, 3H); $^{13}$C-NMR (150 MHz, D$_2$O) δ 178.4, 176.8, 176.5, 176.3, 104.2, 102.1, 101.0, 98.2, 79.1, 78.8, 78.1, 74.3, 73.7, 73.5, 73.2, 73.1, 72.6, 69.8, 69.6, 68.9, 66.4, 54.0, 53.7, 51.0, 41.9, 30.8, 29.0, 25.0, 24.9, 24.8, 24.7, 18.1, 18.0, 17.9; HRMS (ESI): Calcd for C$_{35}$H$_{60}$N$_4$O$_{19}$Na$^+$ [M+Na]$^+$ 863.3744, found 864.3774.

Compounds 33*a-33*e constitute further examples according to the present invention that can be obtained following the procedure described for compound 33*:

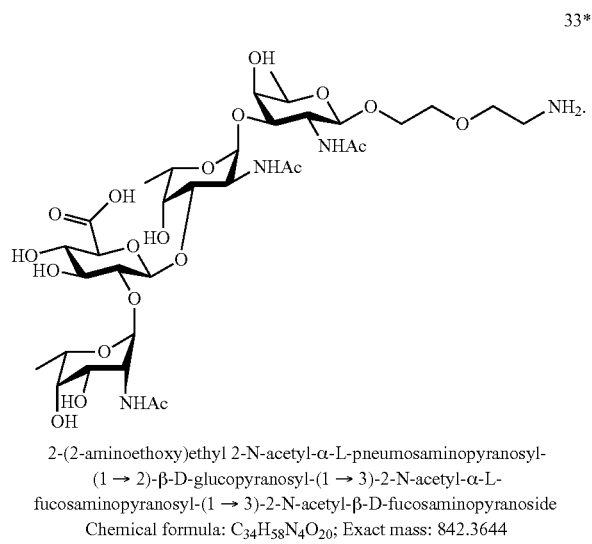

33*a 2-(2-aminoethoxy)ethyl 2-N-acetyl-α-L-pneumosaminopyranosyl-(1 → 2)-β-D-glucopyranosyl-(1 → 3)-2-N-acetyl-α-L-fucosaminopyranosyl-(1 → 3)-2-N-acetyl-β-D-fucosaminopyranoside
Chemical formula: C$_{34}$H$_{58}$N$_4$O$_{20}$; Exact mass: 842.3644

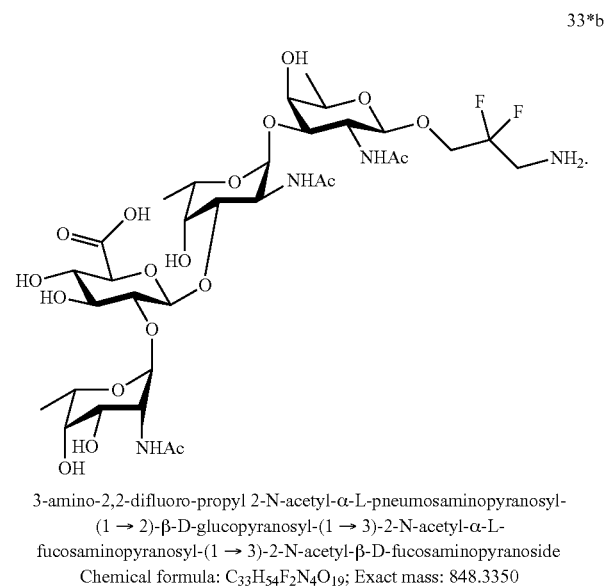

33*b 3-amino-2,2-difluoro-propyl 2-N-acetyl-α-L-pneumosaminopyranosyl-(1 → 2)-β-D-glucopyranosyl-(1 → 3)-2-N-acetyl-α-L-fucosaminopyranosyl-(1 → 3)-2-N-acetyl-β-D-fucosaminopyranoside
Chemical formula: C$_{33}$H$_{54}$F$_2$N$_4$O$_{19}$; Exact mass: 848.3350

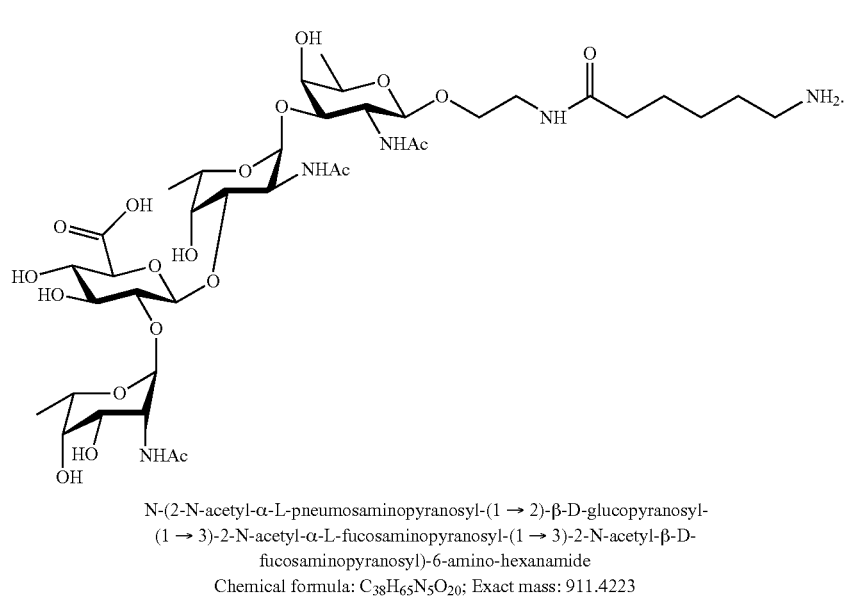

33*c

N-(2-N-acetyl-α-L-pneumosaminopyranosyl-(1 → 2)-β-D-glucopyranosyl-(1 → 3)-2-N-acetyl-α-L-fucosaminopyranosyl-(1 → 3)-2-N-acetyl-β-D-fucosaminopyranosyl)-6-amino-hexanamide
Chemical formula: C$_{38}$H$_{65}$N$_5$O$_{20}$; Exact mass: 911.4223

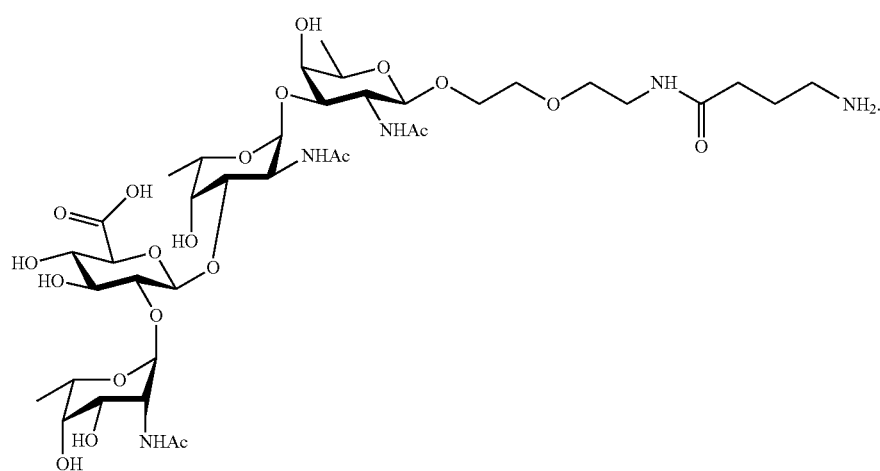

33*d

N-(2-N-acetyl-α-L-pneumosaminopyranosyl-(1 → 2)-β-D-glucopyranosyl-
(1 → 3)-2-N-acetyl-α-L-fucosaminopyranosyl-(1 → 3)-2-N-acetyl-β-D-
fucosaminopyranosyl 2-ethoxyethyl)-3-aminopropanamide
Chemical formula: $C_{38}H_{65}N_5O_{21}$; Exact mass: 927.4172

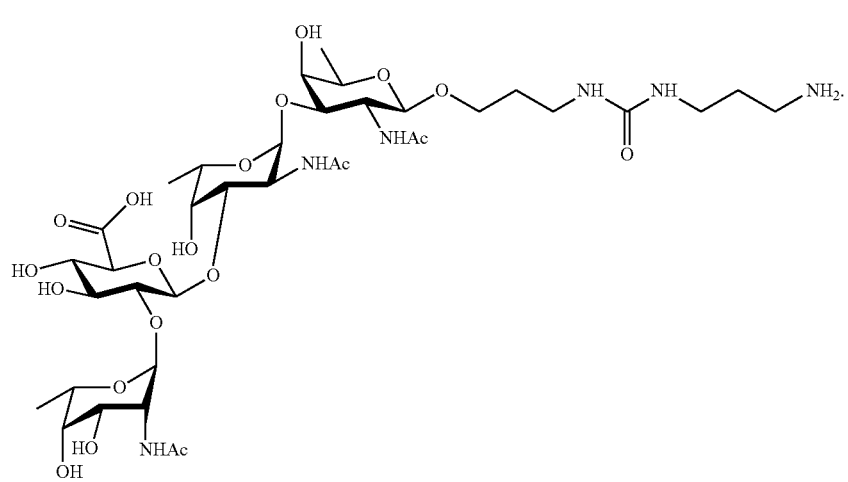

33*e 3-(3-aminopropyl)ureido-propyl 2-N-acetyl-α-L-pneumosaminopyranosyl-
(1 → 2)-β-D-glucopyranosyl-(1 → 3)-2-N-acetyl-α-L-fucosaminopyranosyl-
(1 → 3)-2-N-acetyl-β-D-fucosaminopyranoside
Chemical formula: $C_{37}H_{64}N_6O_{20}$; Exact mass: 912.4175

Example 34: Synthesis of N-(Benzyl)benzyloxycar-
bonyl-5-amino-pentanyl 2-azido-3,4-di-O-benzyl-2-
deoxy-L-pneumopyranosides (34*α and 34*β)

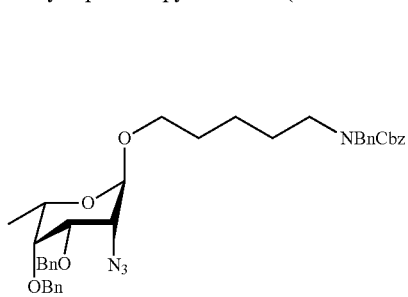

34*α

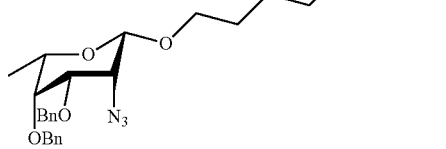

34*β

According to general procedure (E), pneumosyl-imidate 8* (30 mg, 58 μmol) and N-(benzyl)benzyloxycarbonyl-5-amino-pentanol (38 mg, 117 μmol) were reacted in DCM (1 mL) at −30° C. to −20° C. over 30 min to give α and β anomers 34*α (28 mg, 41 μmol, 71%) and 34*β (10 mg, 15

μmol, 25%). 34*α: $[α]_D^{20}$=−18.0° (c=1.3, CHCl$_3$); IR $ν_{max}$ (film) 2934, 2111, 1697, 1496, 1454, 1422, 1360, 1229, 1061 cm$^{-1}$; $^1$H-NMR (400 MHz, CDCl$_3$) δ 7.60-7.06 (m, 20H), 5.18 (d, J=13.0 Hz, 2H), 4.99 (d, J=11.7 Hz, 1H), 4.79-4.69 (m, 3H), 4.64 (d, J=11.8 Hz, 1H), 4.50 (d, J=6.9 Hz, 2H), 3.98-3.85 (m, 2H), 3.83-3.73 (m, 1H), 3.62 (s, 1H), 3.58-3.45 (m, 1H), 3.37-3.15 (m, 3H), 1.58-1.41 (m, 4H), 1.31-1.16 (m, 5H); $^{13}$C-NMR (100 MHz, CDCl$_3$) δ 138.4, 137.8, 128.8, 128.7, 128.6, 128.3, 128.1, 127.9 (2C), 127.7, 127.4, 98.6, 77.2, 75.2, 74.9, 71.2, 67.7, 67.3, 66.9, 58.1, 50.6, 50.3, 47.2, 46.2, 29.1, 23.5, 16.9. 34*β: $[α]_D^{20}$=+59.2° (c=0.9, CHCl$_3$); IR $ν_{max}$ (film) 2928, 2110, 1697, 1496, 1454, 1421, 1359, 1229, 1119, 1070 cm$^{-1}$; $^1$H-NMR (400 MHz, CDCl$_3$) δ 7.55-7.09 (m, 20H), 5.17 (d, J=12.4 Hz, 2H), 5.02 (d, J=11.9 Hz, 1H), 4.77-4.70 (m, 2H), 4.62 (d, J=12.2 Hz, 1H), 4.53-4.44 (m, 2H), 4.31 (d, J=14.7 Hz, 1H), 3.96-3.78 (m, 2H), 3.52 (s, 2H), 3.44-3.14 (m, 4H), 1.62-1.45 (m, 4H), 1.38-1.20 (m, 5H); $^{13}$C-NMR (100 MHz, CDCl$_3$) δ 138.6, 138.1, 137.6, 128.7, 128.6, 128.2, 128.1, 128.0, 127.9, 127.6 (2C), 127.4, 100.1, 78.8, 77.5, 77.2, 76.8, 74.8, 74.1, 71.8, 70.8, 69.3, 67.2, 58.8, 29.3, 23.4, 16.9; HRMS (MALDI-TOF): Calcd for C$_{40}$H$_{46}$N$_4$O$_6$Na$^+$ [M+Na]$^+$ 701.3310, found 701.3337.

Example 35: Synthesis of N-(benzyl)benzyloxycarbonyl-5-amino-pentanyl 2-N-acetyl-3,4-di-O-benzyl-L-pneumosaminopyranosides (35*α and 35*β)

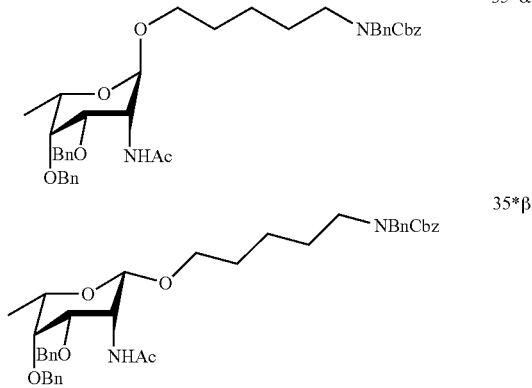

According to general procedure (F), azido-pneumosides 34*α (28 mg, 41 μmol) and 34*β (10 mg, 15 μmol) were individually reacted with thioacetic acid for 12 h to give 35*α (19 mg, 27 μmol, 66%) and 35*β (7 mg, 10 μmol, 68%). 35*α: $[α]_D^{20}$=−47.4° (c=1.9, CHCl$_3$); IR $ν_{max}$ (film) 3404, 2935, 1698, 1675, 1515, 1497, 1454, 1421, 1361, 1305, 1228, 1120, 1055, 1040 cm$^{-1}$; $^1$H-NMR (400 MHz, CDCl$_3$) δ 7.43-7.12 (m, 20H), 5.18 (d, J=14.2 Hz, 2H), 4.90 (d, J=10.3 Hz, 1H), 4.75-4.68 (m, 1H), 4.60 (d, J=10.3 Hz, 1H), 4.56-4.40 (m, 4H), 3.92-3.79 (m, 2H), 3.67-3.60 (m, 1H), 3.59-3.15 (m, 5H), 1.74 (s, 3H), 1.61-1.40 (m, 4H), 1.35-1.15 (m, 5H); $^{13}$C-NMR (100 MHz, CDCl$_3$) δ 170.4, 138.3, 138.2, 138.0, 128.7, 128.6, 128.5 (2C), 128.2, 128.1, 127.9, 127.7 (2C), 127.4, 127.3, 100.1, 78.7, 75.7, 72.8, 69.9, 67.7, 67.3, 66.3, 50.6, 50.3, 48.0, 47.2, 46.2, 29.3, 28.1, 27.7, 23.5, 16.8. 35*β: $[α]_D^{20}$=+18.3° (c=0.7, CHCl$_3$); IR $ν_{max}$ (film) 3420, 2929, 2865, 1698, 1677, 1521, 1454, 1421, 1367, 1312, 1230, 1113, 1058 cm$^{-1}$; $^1$H-NMR (400 MHz, CDCl$_3$) δ 7.42-7.13 (m, 20H), 6.79 (d, J=9.8 Hz, 1H), 5.16 (d, J=11.6 Hz, 2H), 4.91 (d, J=10.2 Hz, 1H), 4.84-4.73 (m, 2H), 4.58 (d, J=10.2 Hz, 1H), 4.52-4.42 (m, 3H), 4.28 (d, J=13.1 Hz, 1H), 3.80-3.65 (m, 1H), 3.59-3.51 (m, 2H), 3.50-3.35 (m, 2H), 3.27-3.10 (m, 2H), 1.76 (s, 3H), 1.59-1.43 (m, 4H), 1.34-1.17 (m, 5H); $^{13}$C-NMR (100 MHz, CDCl$_3$) δ 170.7, 138.2, 138.1, 128.8, 128.6 (2C), 128.5, 128.1, 128.0, 127.9 (2C), 127.8, 127.3, 100.5, 77.7, 76.2, 75.7, 71.4, 69.8, 67.2, 47.9, 29.3, 23.6, 23.3, 16.8; HRMS (MALDI-TOF): Calcd for C$_{42}$H$_{50}$N$_2$O$_7$Na$^+$ [M+Na]$^+$ 717.3510, found 717.3543.

Example 36: Synthesis of 5-amino-pentanyl 2-N-acetyl-L-pneumosaminopyranosides (36* and 37*)

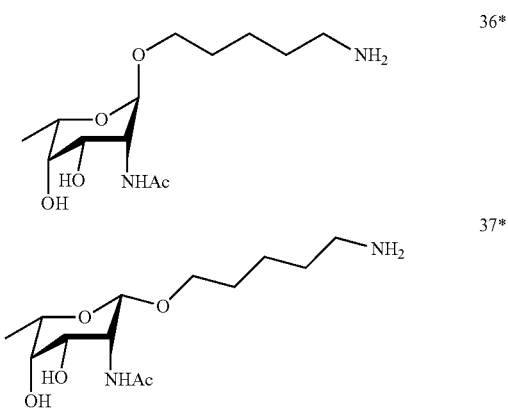

According to general procedure (I), pneumosaminosides 35*α (19 mg, 27 μmol) and 35*β (7 mg, 10 μmol) were individually submitted to hydrogenolysis to give 36* (7 mg, 24 μmol, 88%) and 37* (2 mg, 7 μmol, 68%), respectively. 36*: $^1$H-NMR (400 MHz, D$_2$O) δ 4.75 (s, 1H), 4.13-3.93 (m, 3H), 3.78 (s, 1H), 3.71-3.61 (m, 1H), 3.55-3.44 (m, 1H), 3.03-2.91 (m, 2H), 2.01 (s, 3H), 1.74-1.57 (m, 4H), 1.49-1.35 (m, 2H), 1.22 (d, J=6.6 Hz, 3H); $^{13}$C-NMR (150 MHz, D$_2$O) δ 176.8, 101.6, 73.5, 70.2, 69.5, 66.6, 53.9, 42.0, 30.5, 29.2, 25.0, 18.1. 37*: $^1$H-NMR (400 MHz, D$_2$O) δ 4.61 (d, J=1.7 Hz, 1H), 4.29 (d, J=5.0 Hz, 1H), 3.88 (dd, J=4.5, 3.4 Hz, 1H), 3.81 (dt, J=9.9, 6.3 Hz, 1H), 3.71-3.58 (m, 3H), 3.00-2.93 (m, 2H), 2.02 (s, 3H), 1.68-1.54 (m, 4H), 1.42-1.33 (m, 2H), 1.25 (d, J=6.5 Hz, 3H); $^{13}$C-NMR (150 MHz, D$_2$O) δ 177.2, 102.4, 74.2, 72.9, 72.0, 70.1, 54.5, 42.0, 30.8, 29.3, 25.9, 25.2, 24.8, 18.0; HRMS (ESI): Calcd for C$_{13}$H$_{26}$N$_2$O$_5$Na$^+$ [M+Na]$^+$ 313.1739, found 313.1750.

Example 37: Synthesis of thexyldimethylsilyl 3-O-acetyl-2-azido-2-deoxy-α-L-fucopyranoside (38*) and thexyldimethylsilyl 4-O-acetyl-2-azido-2-deoxy-α-L-fucopyranoside (39*)

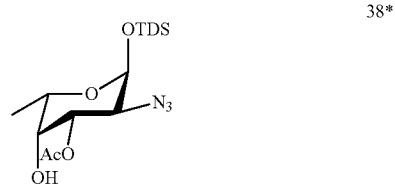

83

-continued

39*

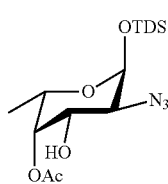

To a solution of 2-azido-2-deoxy-α-L-fucopyranoside (200 mg, 0.60 mmol) in DCM/pyridine (4:1 (v/v), 10 mL), a solution of AcCl (51 μL, 0.72 mmol) in DCM (1 mL) was added drop-wise at 0° C. and stirred for 6 h at the same temperature. The mixture was diluted with DCM and washed with sat. aq. NaHCO$_3$. The combined organic layers were dried over MgSO$_4$, filtered and concentrated. Column chromatography on silica gel (DCM/MeOH/acetone) afforded 38* (163 mg, 0.44 mmol, 72%). $[\alpha]_D^{20}$=+4.4° (c=1.0, CHCl$_3$); IR $v_{max}$ (film) 3483, 2958, 2868, 2111, 1747, 1726, 1465, 1370, 1251, 1171, 1145, 1069, 1039 cm$^{-1}$; $^1$H-NMR (400 MHz, CDCl$_3$) δ 4.66 (dd, J=10.8, 3.1 Hz, 1H), 4.50 (d, J=7.6 Hz, 1H), 3.77 (d, J=2.6 Hz, 1H), 3.61 (qd, J=6.4, 0.8 Hz, 1H), 3.55 (dd, J=10.8, 7.6 Hz, 1H), 2.16 (s, 3H), 1.66 (dt, J=13.7, 6.9 Hz, 1H), 1.28 (d, J=6.5 Hz, 3H), 0.89 (d, J=1.0 Hz, 3H), 0.88 (s, 9H), 0.19 (s, 6H); $^{13}$C-NMR (100 MHz, CDCl$_3$) δ 170.3, 97.3, 74.0, 70.4, 69.5, 63.5, 34.0, 25.0, 21.2, 20.1, 20.0, 18.6, 18.5, 16.4, −1.9, −3.2; HRMS (MALDI-TOF): Calcd for C$_{16}$H$_{31}$N$_3$O$_5$SiNa$^+$ [M+Na]$^+$ 396.1925, found 396.1911. Thexyldimethylsilyl 4-O-acetyl-2-azido-2-deoxy-α-l-fucopyranoside (39*) (22 mg, 0.06 mmol, 10%) was obtained as a byproduct. $[\alpha]_D^{20}$=+5.3° (c=1.3, CHCl$_3$); IR $v_{max}$ (film) 3462, 2959, 2869, 2112, 1744, 1465, 1443, 1380, 1252, 1185, 1114, 1073 cm$^{-1}$; $^1$H-NMR (400 MHz, CDCl$_3$) δ 5.09 (dd, J=3.5, 1.1 Hz, 1H), 4.48 (d, J=7.6 Hz, 1H), 3.65 (qd, J=6.4, 1.2 Hz, 1H), 3.57 (dd, J=10.4, 3.6 Hz, 1H), 3.40 (dd, J=10.4, 7.6 Hz, 1H), 2.19 (s, 3H), 1.68 (dt, J=13.7, 6.9 Hz, 1H), 1.17 (d, J=6.5 Hz, 3H), 0.93-0.86 (m, 12H), 0.19 (d, J=1.6 Hz, 6H); $^{13}$C-NMR (100 MHz, CDCl$_3$) δ 171.7, 97.2, 71.9, 71.1, 69.4, 66.5, 34.0, 25.0, 21.0, 20.1, 20.0, 18.6, 18.3, 16.5, −1.9, −3.0; HRMS (MALDI-TOF): Calcd for C$_{16}$H$_{31}$N$_3$O$_5$SiNa$^+$ [M+Na]$^+$ 396.1925, found 396.1954.

Example 38: Synthesis of thexyldimethylsilyl 2-O-benzoyl-3,4,6-tri-O-benzyl-β-D-glucopyranosyl-(1→3)-4-O-acetyl-2-azido-2-deoxy-α-L-fucopyranoside 40*)

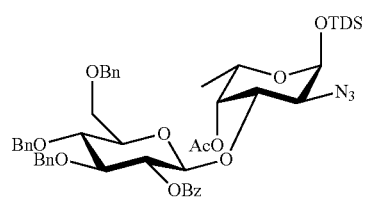

According to general procedure (B), 2-O-benzoyl-3,4,6-tri-O-benzyl-1-thio-β-D-glucopyranoside (109 mg, 0.18 mmol) was reacted with fucoside 39* (62 mg, 0.17 mmol),

84

NIS (45 mg, 0.20 mmol) and TfOH (1.8 μL, 20 μmol) in DCM (1 mL) at −25° C. to −20° C. over 1 h. After workup column chromatography (hexanes/EtOAc) afforded 40* (139 mg, 0.15 mmol, 92%). $[\alpha]_D^{20}$=−13.9° (c=1.9, CHCl$_3$); IR $v_{max}$ (film) 2958, 2867, 2113, 1744, 1496, 1453, 1364, 1267, 1234, 1179, 1095, 1071 cm$^{-1}$; $^1$H-NMR (400 MHz, CDCl$_3$) δ 8.10-8.03 (m, 2H), 7.60-7.54 (m, 1H), 7.50-7.42 (m, 2H), 7.41-7.21 (m, 10H), 7.16-7.02 (m, 5H), 5.32 (dd, J=9.1, 7.7 Hz, 1H), 5.12 (d, J=2.8 Hz, 1H), 4.82 (d, J=11.0 Hz, 1H), 4.76-4.66 (m, 4H), 4.63 (dd, J=11.0, 6.5 Hz, 2H), 4.36 (d, J=7.7 Hz, 1H), 3.89 (dd, J=10.4, 3.5 Hz, 1H), 3.86-3.80 (m, 2H), 3.79-3.72 (m, 2H), 3.62 (ddd, J=9.4, 5.3, 1.9 Hz, 1H), 3.50-3.41 (m, 2H), 1.73-1.62 (m, 1H), 1.49 (s, 3H), 1.07 (d, J=6.4 Hz, 3H), 0.92-0.87 (m, 12H), 0.17 (d, J=4.6 Hz, 6H); $^{13}$C-NMR (100 MHz, CDCl$_3$) δ 170.6, 164.9, 138.6, 138.0, 137.8, 133.3, 130.2, 129.8, 128.6, 128.5, 128.4, 128.3, 128.2, 128.1, 128.0, 127.7, 127.6 (2C), 97.1, 96.8, 83.0, 78.1, 75.7, 75.3, 75.1, 74.6, 73.7, 73.5, 69.0, 68.9, 67.8, 63.9, 34.0, 25.0, 20.2, 20.1 (2C), 18.6 (2C), 16.5, −1.8, −3.0; HRMS (MALDI-TOF): Calcd for C$_{50}$H$_{63}$N$_3$O$_{11}$SiNa$^+$ [M+Na]$^+$ 932.4124, found 932.4125.

Example 39: Synthesis of 2-O-benzoyl-3,4,6-tri-O-benzyl-β-d-glucopyranosyl-(1→3)-4-O-acetyl-2-azido-2-deoxy-α-l-fucopyranosyl trichloroacetimidate (41*)

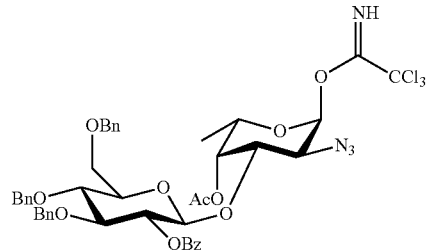

According to general procedure (A), disaccharide 40* (55 mg, 60 μmol) was reacted with TBAF (1 m in THF, 600 μL, 600 μmol) and AcOH (42 μL, 725 μmol) in THF (2 mL) to give the crude lactol. According to general procedure (D), the crude lactol was reacted with trichloroacetonitrile (60 μL, 600 μmol) and DBU in DCM (2 mL) at 0° C. to afford 41* (44 mg, 48 mmol, 81%). $[\alpha]_D^{20}$=−64.8° (c=1.8, CHCl$_3$) IR $v_{max}$ (film) 2871, 2115, 1743, 1673, 1496, 1453, 1361, 1267, 1229, 1093, 1070, 1027 cm$^{-1}$; $^1$H-NMR (400 MHz, CDCl$_3$) δ 8.67 (s, 1H), 8.11-8.03 (m, 2H), 7.60-7.56 (m, 1H), 7.50-7.43 (m, 2H), 7.42-7.26 (m, 8H), 7.24-7.18 (m, 2H), 7.16-7.03 (m, 5H), 6.35 (d, J=3.6 Hz, 1H), 5.38-5.30 (m, 2H), 4.84-4.78 (m, 2H), 4.73 (d, J=11.0 Hz, 1H), 4.67-4.54 (m, 5H), 4.21 (q, J=6.4 Hz, 1H), 3.88-3.71 (m, 5H), 3.61 (ddd, J=9.5, 4.7, 1.8 Hz, 1H), 1.44 (s, 3H), 1.08 (d, J=6.5 Hz, 3H); $^{13}$C-NMR (100 MHz, CDCl$_3$) δ 170.3, 165.0, 160.9, 138.3, 137.9, 137.8, 133.4, 130.3, 129.7, 128.6, 128.5 (2C), 128.4, 128.2, 128.1, 128.0, 127.8, 127.7, 96.8, 95.4, 91.1, 82.9, 78.1, 75.8, 75.4, 75.2, 73.9, 73.7, 70.8, 69.0, 68.2, 68.0, 57.2, 19.9, 16.3; HRMS (ESI): Calcd for C$_{44}$H$_{45}$Cl$_3$N$_4$O$_{11}$Na$^+$ [M+Na]$^+$ 933.2048, found 933.2051.

Example 40: Synthesis of N-(benzyl)benzyloxycarbonyl-5-amino-pentanyl 2-O-benzoyl-3,4,6-tri-O-benzyl-β-D-glucopyranosyl-(1→3)-4-O-acetyl-2-azido-2-deoxy-L-fucopyranoside (42*)

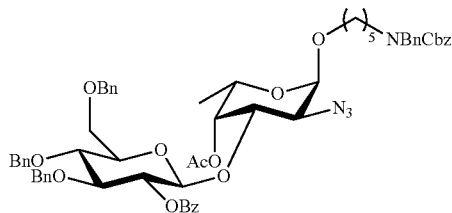

According to general procedure (E), disaccharide-imidate 41* (44 mg, 48 μmol) and N-(benzyl)benzyloxycarbonyl-5-amino-pentanol (32 mg, 96 μmol) were reacted in DCM (2 mL) at −30° C. to −20° C. over 30 min to give the α and β anomers of 42* (45 mg, 42 μmol, 87%) in a ratio α/β=1:6. Analytical data is given for the α anomer. $[α]_D^{20}$=−68.5° (c=0.5, CHCl$_3$); IR $v_{max}$ (film) 2927, 2111, 1743, 1698, 1454, 1267, 1091 cm$^{-1}$; $^1$H-NMR (400 MHz, CDCl$_3$) δ 8.06 (d, J=7.9 Hz, 2H), 7.57 (t, J=7.4 Hz, 1H), 7.44 (d, J=7.6 Hz, 2H), 7.39-7.27 (m, 15H), 7.23-7.01 (m, 10H), 5.31 (t, J=8.4 Hz, 1H), 5.25 (s, 1H), 5.16 (d, J=7.8 Hz, 2H), 4.85-4.78 (m, 2H), 4.74-4.69 (m, 2H), 4.63-4.52 (m, 4H), 4.45 (s, 3H), 4.01-3.90 (m, 1H), 3.85-3.69 (m, 4H), 3.59 (dd, J=8.6, 4.1 Hz, 2H), 3.41 (dd, J=10.8, 3.6 Hz, 2H), 3.18 (d, J=20.7 Hz, 2H), 1.56-1.43 (m, 4H), 1.42 (s, 3H), 1.35-1.18 (m, 3H), 1.02 (d, J=6.4 Hz, 3H); $^{13}$C-NMR (100 MHz, CDCl$_3$) δ 170.5, 165.0, 138.4, 138.0, 137.8, 133.3, 130.3, 129.8, 128.7, 128.6, 128.5, 128.4, 128.3, 128.2, 128.1, 128.0, 127.9, 127.7 (2C), 98.6, 97.4, 83.1, 78.1, 77.4, 75.7, 75.4, 75.2, 73.7, 73.6, 70.9, 69.1, 68.9, 68.5, 67.3, 65.0, 57.8, 50.6, 47.2, 46.2, 29.2, 23.4, 20.0, 16.3; HRMS (ESI): Calcd for $C_{62}H_{68}N_4O_{13}Na^+$ $[M+Na]^+$ 1099.4681, found 1099.4679.

Example 41: Synthesis of N-(benzyl)benzyloxycarbonyl-5-amino-pentanyl 2-O-benzoyl-3,4,6-tri-O-benzyl-α-D-glucopyranosyl-(1→3)-2-N-acetyl-4-O-acetyl-α-L-fucosaminopyranoside (43*)

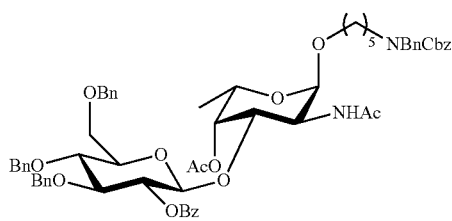

According to general procedure (F), azido-disaccharide 42* (10 mg, 9 μmol) was reacted with thioacetic acid for 48 h to give 43* (8 mg, 7 μmol, 79%). $[α]_D^{20}$=−5.5° (c=1.0, CHCl$_3$); IR $v_{max}$ (film) 2928, 1743, 1697, 1454, 1365, 1266, 1232, 1091 cm$^{-1}$; $^1$H-NMR (400 MHz, CDCl$_3$) δ 8.06-8.01 (m, 2H), 7.61-7.55 (m, 1H), 7.47-7.42 (m, 2H), 7.38-7.26 (m, 15H), 7.26-7.20 (m, 2H), 7.18-7.06 (m, 8H), 6.50-6.27 (m, 1H), 5.22-5.12 (m, 5H), 4.80 (d, J=10.9 Hz, 1H), 4.69 (d, J=10.9 Hz, 1H), 4.66-4.60 (m, 2H), 4.50 (dd, J=22.3, 11.3 Hz, 5H), 4.08 (s, 2H), 3.98-3.86 (m, 1H), 3.82-3.49 (m, 6H), 3.43-3.28 (m, 1H), 3.28-3.06 (m, 2H), 1.83 (s, 3H), 1.64 (s, 3H), 1.55-1.42 (m, 4H), 1.29-1.16 (m, 2H), 1.01 (d, J=6.5 Hz, 3H); $^{13}$C-NMR (100 MHz, CDCl$_3$) δ 170.7, 165.1, 138.0, 137.8, 137.6, 133.3, 130.1, 129.8, 128.7 (2C), 128.6, 128.4 (2C), 128. (2C), 127.9, 127.8, 98.9, 97.1, 82.9, 77.8, 77.4, 75.2 (2C), 74.5, 73.5, 73.3, 72.6, 69.9, 68.9, 68.3, 67.3, 64.8, 49.7, 29.2, 23.4, 23.1, 20.2, 16.3; HRMS (MALDI-TOF): Calcd for $C_{64}H_{72}N_2O_{14}Na^+$ $[M+Na]^+$ 1115.4876, found 1115.4890.

Example 42: Synthesis of 5-amino-pentanyl β-D-glucopyranosyl-(1→3)-2-N-acetyl-α-L-fucosaminopyranoside (44*)

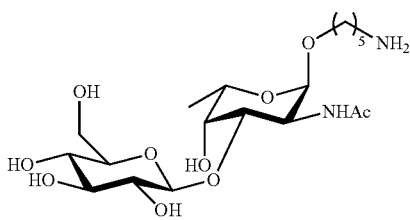

To a solution of 43* (8 mg, 7 μmol) in MeOH (1 mL) was added 0.5 m NaOMe in MeOH (0.2 mL) and stirred for 16 h. The mixture was neutralized with Amberlite® IR 120 (H$^+$) ion exchange resin and the resulting diol was filtered and concentrated. According to general procedure (I), the crude diol was submitted to hydrogenolysis to give 44* (3.4 mg, 7.5 μmol, 89%). $^1$H-NMR (600 MHz, D$_2$O) δ 4.95 (d, J=3.7 Hz, 1H), 4.55 (d, J=7.9 Hz, 1H), 4.19 (dd, J=11.3, 3.7 Hz, 1H), 4.13 (dd, J=11.3, 2.9 Hz, 1H), 4.09 (q, J=6.6 Hz, 1H), 4.03 (d, J=2.5 Hz, 1H), 3.98 (dd, J=12.2, 2.1 Hz, 1H), 3.75-3.68 (m, 2H), 3.54-3.45 (m, 3H), 3.38 (t, J=9.5 Hz, 1H), 3.31 (dd, J=9.4, 8.0 Hz, 1H), 3.03-2.98 (m, 2H), 2.05 (s, 3H), 1.73-1.62 (m, 4H), 1.49-1.41 (m, 2H), 1.27 (d, J=6.6 Hz, 3H); $^{13}$C-NMR (150 MHz, D$_2$O) δ 177.1, 103.0, 99.3, 78.7, 78.1, 77.8, 75.4, 72.3, 71.3, 70.4, 69.0, 63.6, 50.9, 42.0, 30.5, 29.0, 24.8, 24.6, 18.1; HRMS (ESI): Calcd for $C_{19}H_{36}N_2O_{10}Na^+$ $[M+Na]^+$ 475.2268, found 475.2273.

Example 43: Synthesis of thexyldimethylsilyl 3,4-di-O-benzyl-2-O-levulinoyl-6-O-(2-naphthalenylmethyl)-β-d-glucopyranosyl-(1→4)-3-O-acetyl-2-azido-2-deoxy-α-L-fucopyranoside (45*)

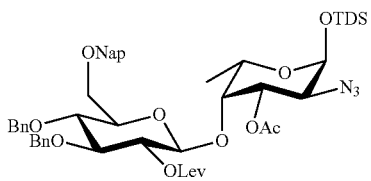

According to general procedure (B), thioglucoside 10* (140 mg, 218 μmol) was reacted with fucoside 38* (50 mg, 134 µmol), NIS (54 mg, 240 µmol) and TfOH (2.4 µL, 27 µmol) in DCM (1 mL) at −30° C. to −20° C. over 1 h. After work-up, column chromatography (hexanes/EtOAc) afforded 45* (114 mg, 119 µmol, 89%). [α]$_D^{20}$=−13.0° (c=1.8, CHCl$_3$); IR v$_{max}$ (film) 2958, 2867, 2112, 1748, 1721, 1603, 1509, 1455, 1364, 1240, 1147, 1072 cm$^{-1}$; $^1$H-NMR (400 MHz, CDCl$_3$) δ 7.87-7.76 (m, 4H), 7.52-7.43 (m, 3H), 7.35-7.25 (m, 5H), 7.23-7.12 (m, 3H), 7.04-6.98 (m, 2H), 5.16 (dd, J=9.6, 8.1 Hz, 1H), 4.80-4.75 (m, 3H), 4.70 (d, J=12.1 Hz, 1H), 4.60 (d, J=12.2 Hz, 1H), 4.49-4.39 (m, 3H), 4.30 (d, J=8.1 Hz, 1H), 3.94 (d, J=3.4 Hz, 1H), 3.85-3.79 (m, 1H), 3.76-3.65 (m, 3H), 3.58 (dd, J=11.0, 7.6 Hz, 1H), 3.52 (q, J=6.5 Hz, 1H), 3.39 (ddd, J=9.8, 3.5, 2.0 Hz, 1H), 2.93-2.81 (m, 1H), 2.68-2.63 (m, 1H), 2.62-2.58 (m, 1H), 2.54-2.45 (m, 1H), 2.16 (s, 3H), 2.11 (s, 3H), 1.67 (dt, J=13.7, 6.9 Hz, 1H), 1.25 (d, J=6.5 Hz, 3H), 0.92 (s, 3H), 0.90 (s, 3H), 0.89 (s, 6H), 0.18 (s, 3H), 0.15 (s, 3H); $^{13}$C-NMR (100 MHz, CDCl$_3$) δ 206.4, 171.4, 171.2, 138.3, 137.9, 135.1, 133.3, 133.1, 128.4 (3C), 128.1, 128.0, 127.9, 127.8 (3C), 126.6, 126.3, 126.1, 125.8, 101.9, 97.2, 82.9, 77.5, 75.1, 75.0 (2C), 74.3, 73.8, 73.4, 72.8, 70.0, 68.7, 62.8, 38.1, 34.0, 29.9, 28.0, 24.9, 21.0, 20.0 (2C), 18.6, 18.5, 16.4, −2.0, −3.1; HRMS (MALDI-TOF): Calcd for C$_{52}$H$_{67}$N$_3$O$_{12}$SiNa$^+$ [M+Na]$^+$ 976.4386, found 976.4333.

Example 44: Synthesis of 3,4-di-O-benzyl-2-O-levulinoyl-6-O-(2-naphthalenylmethyl)-β-D-glucopyranosyl-(1→4)-3-O-acetyl-2-azido-2-deoxy-L-fucopyranoside (46*)

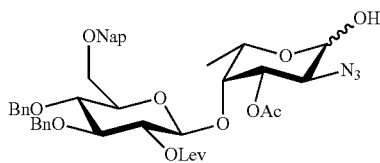

According to general procedure (A), disaccharide 45* (105 mg, 0.11 mmol) was reacted with TBAF (1.0 mL, 1.00 mmol) and AcOH (70 µL, 1.22 mmol) in THF (2 mL) to give lactol 46* (81 mg, 0.10 mmol, 95%) as a mixture of α and β anomers. IR v$_{max}$(film) 3424, 2869, 2111, 1742, 1717, 1454, 1363, 1237, 1151, 1059 cm$^{-1}$; $^1$H-NMR (400 MHz, CDCl$_3$) δ 7.87-7.75 (m, 4H), 7.53-7.41 (m, 3H), 7.34-7.25 (m, 5H), 7.22-7.10 (m, 3H), 7.03-6.95 (m, 2H), 5.37-5.28 (m, 0.5H) 5.25 (d, J=3.5 Hz, 0.5H), 5.16-5.02 (m, 1.5H), 4.80-4.65 (m, 4H), 4.60 (d, J=12.1 Hz, 1H), 4.50-4.43 (m, 2H), 4.35 (d, J=8.0 Hz, 0.5H), 4.31 (d, J=8.1 Hz, 0.5H), 4.19 (q, J=6.6 Hz, 0.5H), 4.07 (dd, J=11.1, 3.1 Hz, 1H), 3.88-3.56 (m, 6H), 3.41-3.35 (m, 1H), 2.92-2.62 (m, 2H), 2.55-2.44 (m, 1H), 2.24 (s, 1.5H), 2.15 (s, 1.5H), 2.12 (s, 1.5H), 2.09 (s, 1.5H), 1.29 (d, J=6.5 Hz, 1.5H), 1.19 (d, J=6.6 Hz, 1.5H); $^{13}$C-NMR (100 MHz, CDCl$_3$) δ 208.9, 206.4, 171.9, 171.7, 171.2, 171.1, 138.5, 138.4, 137.9, 135.1 (2C), 133.3, 133.1, 128.5 (2C), 128.4 (2C), 128.1, 127.9 (4C), 127.8 (3C), 127.7, 126.8, 126.6, 126.4, 126.1, 125.9, 125.8, 101.7, 100.9, 96.8, 92.2, 83.0, 82.9, 77.8, 77.6, 75.4, 75.2, 75.1, 75.0 (2C), 73.9 (2C), 73.6, 73.3, 72.8, 70.7, 70.4, 68.8, 68.6, 65.8, 62.8, 57.9, 38.1, 37.6, 30.5, 30.0, 28.1 (2C), 21.1, 21.0, 17.0, 16.3; HRMS (MALDI-TOF): Calcd for C$_{44}$H$_{49}$N$_3$O$_{12}$Na$^+$ [M+Na]$^+$ 834.3208, found 834.3222.

Example 45: Synthesis of 3,4-di-O-benzyl-2-O-levulinoyl-6-O-(2-naphthalenylmethyl)-β-D-glucopyranosyl-(1→4)-3-O-acetyl-2-azido-2-deoxy-L-fucopyranosyl trichloroacetimidate (47*)

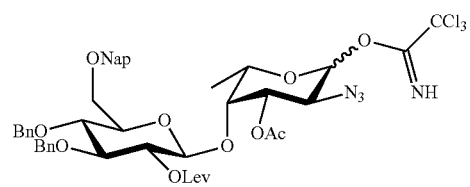

According to general procedure (D), lactol 46* (81 mg, 100 µmol) was reacted with trichloroacetonitrile (100 µL, 998 µmol) and DBU in DCM (2 mL) at 0° C. to afford 47* (82 mg, 86 mmol, 86%) as a mixture of α and β anomers. Analytical data is given for the α anomer. [α]$_D^{20}$=−88.7° (c=1.5, CHCl$_3$); IR v$_{max}$ (film) 3336, 3060, 3030, 2906, 2868, 2113, 1746, 1718, 1673, 1363, 1273, 1243, 1144, 1063, 1028 cm$^{-1}$; $^1$H-NMR (400 MHz, CDCl$_3$) δ 8.67 (s, 1H), 7.90-7.75 (m, 4H), 7.52-7.42 (m, 3H), 7.35-7.25 (m, 5H), 7.23-7.10 (m, 3H), 7.05-6.96 (m, 2H), 6.36 (d, J=3.6 Hz, 1H), 5.14 (dd, J=9.6, 8.1 Hz, 1H), 5.08 (dd, J=11.1, 3.1 Hz, 1H), 4.80-4.69 (m, 4H), 4.60 (d, J=12.1 Hz, 1H), 4.47 (d, J=10.8 Hz, 1H), 4.34 (d, J=8.0 Hz, 1H), 4.22-4.13 (m, 2H), 4.10 (dd, J=11.1, 3.6 Hz, 1H), 3.87-3.72 (m, 3H), 3.71-3.64 (m, 1H), 3.40 (ddd, J=9.8, 3.5, 2.0 Hz, 1H), 2.84-2.64 (m, 2H), 2.61-2.46 (m, 2H), 2.17 (s, 3H), 2.13 (s, 3H), 1.24 (d, J=6.6 Hz, 3H); $^{13}$C-NMR (100 MHz, CDCl$_3$) δ 206.3, 171.7, 171.0, 161.1, 138.3, 137.9, 135.0, 133.3, 133.2, 128.5, 128.4, 128.1, 128.0, 127.9, 127.8 (2C), 126.7, 126.4, 126.1, 125.9, 101.7, 95.2, 91.1, 82.9, 77.5, 75.1, 74.5, 73.9, 73.5, 70.7, 68.7, 68.5, 56.6, 38.1, 30.0, 28.1, 21.0, 16.3; HRMS (ESI): Calcd for C$_{46}$H$_{49}$Cl$_3$N$_4$O$_{12}$Na$^+$ [M+Na]$^+$ 977.2310, found 977.2312.

Example 46: Synthesis of N-(benzyl)benzyloxycarbonyl-5-amino-pentanyl 3,4-di-O-benzyl-2-O-levulinoyl-6-O-(2-naphthalenylmethyl)-β-d-glucopyranosyl-(1→4)-3-O-acetyl-2-azido-2-deoxy-L-fucopyranoside (48*)

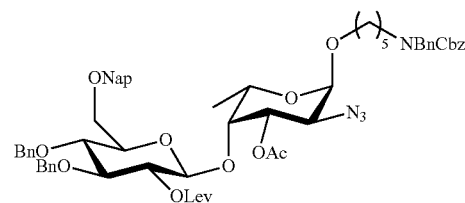

According to general procedure (E), disaccharide-imidate 47* (17 mg, 18 µmol) and N-(benzyl)benzyloxycarbonyl-5-amino-pentanol (12 mg, 36 µmol) were reacted in DCM (1 mL) at −30° C. to −20° C. over 30 min to give the α and β anomers of 48* (18 mg, 16 µmol, 90%) in a ratio α/β=1:3. Analytical data is given for the α anomer. [α]$_D^{20}$=−70.3° (c=0.3, CHCl$_3$); IR v$_{max}$ (film) 2936, 2110, 1746, 1699, 1497, 1454, 1421, 1362, 1244, 1131, 1054 cm$^{-1}$; $^1$H-NMR (400 MHz, CDCl$_3$) δ 7.84-7.73 (m, 4H), 7.49-7.40 (m, 3H), 7.34-7.21 (m, 14H), 7.19-7.09 (m, 4H), 7.00-6.95 (m, 2H), 5.18-5.07 (m, 3H), 5.00 (dd, J=11.1, 2.6 Hz, 1H), 4.78-4.65

(m, 5H), 4.57 (d, J=12.0 Hz, 1H), 4.51-4.42 (m, 3H), 4.28 (d, J=7.9 Hz, 1H), 4.04 (s, 1H), 3.92-3.86 (m, 1H), 3.77 (d, J=9.4 Hz, 1H), 3.72-3.57 (m, 4H), 3.36 (d, J=9.6 Hz, 2H), 3.26-3.15 (m, 2H), 2.82-2.57 (m, 3H), 2.50 (t, J=7.0 Hz, 2H), 2.13 (s, 3H), 2.08 (s, 3H), 1.54-1.46 (m, 4H), 1.33-1.25 (m, 2H), 1.15 (d, J=6.4 Hz, 3H); $^{13}$C-NMR (100 MHz, CDCl$_3$) δ 206.4, 171.7, 171.2, 138.4, 137.9, 135.1, 133.4, 133.2, 128.7, 128.5 (2C), 128.1, 128.0, 127.9 (3C), 127.8, 127.4, 126.7, 126.4, 126.1, 125.9, 101.7, 98.0, 83.0, 77.6, 77.4, 75.4, 75.1 (2C), 75.0, 73.9, 73.5, 70.3, 68.7, 68.3, 67.3, 65.6, 57.1, 38.2, 30.0, 29.3, 28.1, 23.5, 21.1, 16.3; HRMS (MALDI-TOF): Calcd for $C_{64}H_{72}N_4O_{14}Na^+$ [M+Na]$^+$ 1143.4937, found 1143.4974.

Example 47: Synthesis of N-(benzyl)benzyloxycarbonyl-5-amino-pentanyl 3,4-di-O-benzyl-2-O-levulinoyl-6-O-(2-naphthalenylmethyl)-β-D-glucopyranosyl-(1→4)-2-N-acetyl-3-O-acetyl-α-L-fucosaminopyranoside (49*)

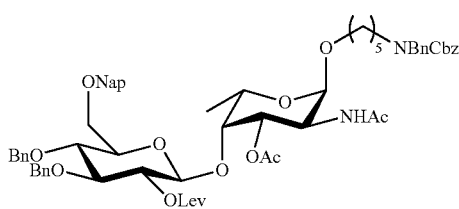

According to general procedure (F), azido-disaccharide 48* (28 mg, 25 μmol) was reacted with thioacetic acid for 24 h to give 49* (20 mg, 18 μmol, 70%). $[α]_D^{20}$=−53.6° (c=1.0, CHCl$_3$); IR v$_{max}$ (film) 2926, 1694, 1454, 1364, 1247, 1053 cm$^{-1}$; $^1$H-NMR (400 MHz, CDCl$_3$) δ 7.92-7.72 (m, 4H), 7.60-7.08 (m, 21H), 7.06-6.90 (m, 2H), 5.90-5.30 (m, 1H), 5.27-5.02 (m, 3H), 4.84 (d, J=11.4 Hz, 1H), 4.80-4.67 (m, 5H), 4.64-4.57 (m, 1H), 4.56-4.39 (m, 4H), 4.34 (d, J=8.0 Hz, 1H), 3.99-3.46 (m, 7H), 3.39 (d, J=9.7 Hz, 1H), 3.36-3.10 (m, 3H), 2.89-2.62 (m, 2H), 2.62-2.44 (m, 2H), 2.15 (s, 3H), 2.04 (s, 3H), 1.92 (s, 3H), 1.66-1.41 (m, 4H), 1.39-1.22 (m, 2H), 1.19 (d, J=5.6 Hz, 3H); $^{13}$C-NMR (100 MHz, CDCl$_3$) δ 206.8, 171.9, 171.3, 171.1, 138.4, 137.9, 135.3, 133.4, 133.1, 128.7, 128.6, 128.5 (2C), 128.4, 128.3, 128.1, 128.0 (2C), 127.8 (2C), 127.7, 126.5, 126.3, 126.0, 125.9, 101.8, 97.5, 83.2, 77.7, 77.4, 75.5, 75.1, 74.9, 73.9, 73.5, 70.3, 69.0, 67.3, 65.6, 50.3, 47.5, 47.2, 38.2, 38.0, 30.0, 29.3, 28.1, 27.5, 23.9, 23.5, 21.2, 16.4; HRMS (MALDI-TOF): Calcd for $C_{66}H_{76}N_2O_{15}Na^+$ [M+Na]$^+$ 1159.5138, found 1159.5148.

Example 48: Synthesis of N-(benzyl)benzyloxycarbonyl-5-amino-pentanyl 3,4-di-O-benzyl-β-D-glucopyranosyl-(1→4)-2-N-acetyl-α-L-fucosaminopyranoside (50*)

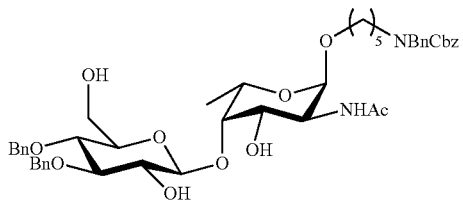

According to general procedure (G), disaccharide 49* (20 mg, 18 μmol) was reacted with DDQ (12 mg, 53 μmol) for 1.5 h to give the crude primary alcohol. To a solution of crude primary alcohol in MeOH (1 mL) was added 0.5 m NaOMe in MeOH (0.3 mL) and stirred for 16 h. The mixture was neutralized with Amberlite® IR 120 (H$^+$) ion exchange resin, filtered and concentrated. Column chromatography (DCM/MeOH/acetone) afforded 50* (9 mg, 11 μmol, 60%). $[α]_D^{20}$=−45.2° (c=0.7, CHCl$_3$); IR v$_{max}$ (film) 3354, 2925, 1695, 1542, 1497, 1454, 1422, 1361, 1231, 1049 cm$^{-1}$; $^1$H-NMR (400 MHz, CDCl$_3$) δ 7.68-6.84 (m, 20H), 6.07-5.61 (m, 1H), 5.18 (d, J=11.9 Hz, 2H), 5.01-4.76 (m, 3H), 4.76-4.58 (m, 2H), 4.57-4.33 (m, 4H), 4.02-3.80 (m, 2H), 3.80-3.42 (m, 8H), 3.39-3.14 (m, 3H), 2.53 (s, 1H), 2.01 (s, 3H), 1.91-1.63 (m, 2H), 1.63-1.45 (m, 4H), 1.36-1.26 (m, 5H); $^{13}$C-NMR (100 MHz, CDCl$_3$) δ 172.0, 138.6, 137.9, 128.7, 128.6 (2C), 128.3, 128.1, 128.0, 127.9 (2C), 103.4, 98.1, 84.3, 83.3, 77.7, 77.4, 76.3, 75.4, 75.2, 74.9, 70.5, 67.4, 67.2, 61.9, 50.3, 47.0, 46.2, 29.3, 27.5, 23.7, 16.8; HRMS (MALDI-TOF): Calcd for $C_{48}H_{60}N_2O_{12}Na^+$ [M+Na]$^+$ 879.4038, found 879.4004.

Example 50: Synthesis of 5-amino-pentanyl β-D-glucopyranosyluronate-(1→4)-2-N-acetyl-α-L-fucosaminopyranoside (51*)

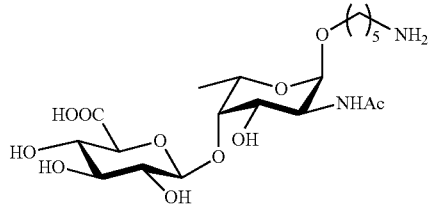

According to general procedure (H), triol 50* (8 mg, 9 μmol) was reacted with TEMPO (0.3 mg, 2 μmol) and BAIB (15 mg, 47 μmol) to give the protected uronate disaccharide. According to general procedure (I), the uronate disaccharide was subjected to hydrogenolysis to give carboxylic acid 51* (2.6 mg, 5.3 μmol, 57%). $^1$H-NMR (600 MHz, D$_2$O) δ 4.89 (d, J=3.7 Hz, 1H), 4.53 (d, J=7.3 Hz, 1H), 4.20-4.12 (m, 2H), 4.05 (d, J=2.9 Hz, 1H), 3.93 (dd, J=11.2, 3.0 Hz, 1H), 3.77-3.72 (m, 1H), 3.70 (dt, J=8.1, 5.6 Hz, 1H), 3.59-3.45 (m, 4H), 3.06-2.97 (m, 2H), 2.05 (s, 3H), 1.73-1.63 (m, 4H), 1.49-1.42 (m, 2H), 1.34 (d, J=6.6 Hz, 3H); $^{13}$C-NMR (150 MHz, D$_2$O) δ 178.1, 177.1, 105.5, 99.6, 82.5, 78.8, 77.9, 75.8, 74.4, 70.5, 69.6, 69.5, 53.2, 42.0, 30.6, 29.1, 24.9, 24.5, 17.9; HRMS (ESI): Calcd for $C_{19}H_{34}N_2O_{11}Na^+$ [M+Na]$^+$ 489.2060, found 489.2063.

Example 51: Synthesis of 5-amino-pentanyl 2-N-acetyl-L-fucosaminopyranoside (52*)

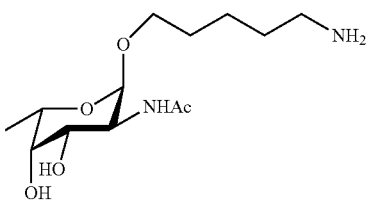

The fucosamine derivative 52* was obtained according to the synthetic procedure described for the synthesis of pneumosamine derivative 36* (3.26 mg, 11 μmol, 83% yield) ¹H-NMR (400 MHz, D₂O) δ 4.81 (d, J=3.8 Hz, 1H), 4.11-4.02 (m, 2H), 3.88 (dd, J=11.1, 3.3 Hz, 1H), 3.77 (d, J=3.1 Hz, 1H), 3.65 (dt, J=10.1, 6.6 Hz, 1H), 3.44 (dt, J=10.1, 6.3 Hz, 1H), 3.01-2.92 (m, 2H), 2.01 (s, 3H), 1.70-1.57 (m, 4H), 1.47-1.35 (m, 2H), 1.20 (d, J=6.6 Hz, 3H); ¹³C-NMR (100 MHz, D₂O) δ 174.4, 96.8, 71.0, 67.7, 67.7, 66.5, 49.6, 39.2, 27.9, 26.4, 22.2, 21.8, 15.3; HRMS (ESI): Calcd for $C_{13}H_{26}N_2O_5Na^+$ [M+Na]⁺ 313.1739, found 313.1750.

Example 52: Synthesis of thexyldimethylsilyl 3,4,6-tri-O-benzyl-2-O-levulinoyl-β-D-glucopyranosyl-(1→4)-3-O-acetyl-2-azido-2-deoxy-α-L-fucopyranoside (53*)

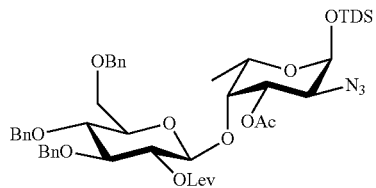

Alcohol 38* (100 mg, 0.268 mmol, 1.0 equiv) and 2-O-levulinoyl-3,4,6-tri-O-benzyl-1-thio-β-D-glucopyranoside (190 mg, 0.321 mmol, 1.2 equiv) were co-evaporated with toluene two times and dried in vacuo. The residue was dissolved in dry dichloromethane. Molecular sieves (4 Å) were added and the reaction mixture cooled to −30° C. NIS (73 mg, 0.321 mmol, 1.2 equiv) and TfOH (3 μL, 0.032 mmol, 0.12 equiv) were added and the reaction let warm to −20° C. over one hour. The reaction was quenched with triethylamine and diluted with dichloromethane. The organic phase was washed with saturated aqueous $Na_2S_2O_3$, $NaHCO_3$ and brine. The organic layer was dried over $Na_2SO_4$ and concentrated. Column chromatography on silica gel (hexanes/ethyl acetate) afforded disaccharide 53* (182 mg, 0.201 mmol, 75%). ¹H NMR (400 MHz, CDCl₃) δ 7.40-7.25 (m, 13H), 7.15-7.12 (m, 2H), 5.14 (dd, J=9.5, 8.2 Hz, 1H), 4.79 (d, J=10.8 Hz, 1H), 4.76 (s, 2H), 4.59-4.35 (m, 5H), 4.30 (d, J=8.1 Hz, 1H), 3.93 (d, J=3.3 Hz, 1H), 3.81 (t, J=9.3 Hz, 1H), 3.75-3.64 (m, 3H), 3.57 (dd, J=10.9, 7.7 Hz, 1H), 3.52 (dd, J=12.9, 6.4 Hz, 1H), 3.40-3.34 (m, 1H), 2.93-2.42 (m, 4H), 2.16 (s, 3H), 2.09 (s, 3H), 1.73-1.59 (m, 1H), 1.26 (d, J=6.5 Hz, 3H), 0.93-0.85 (m, 12H), 0.17 (s, 3H), 0.15 (m, 3H).

Example 53: Synthesis of thexyldimethylsilyl 3,4,6-tri-O-benzyl-β-D-glucopyranosyl-(1→4)-3-O-acetyl-2-azido-2-deoxy-α-L-fucopyranoside (54*)

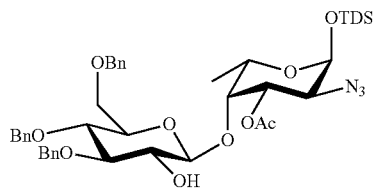

To a solution of disaccharide 53* (180 mg, 0.199 mmol, 1 equiv) in DCM (11 mL) hydrazine hydrate (40 μL, 0.796 mmol, 4 equiv) dissolved in AcOH (0.22 mL) and pyridine (0.33 mL) was added and the solution stirred for 1 h. The reaction was then quenched by the addition of acetone and concentrated. Column chromatography on silica gel (hexanes/ethyl acetate) afforded disaccharide 54* (150 mg, 0.186 mmol, 93%). ¹H NMR (400 MHz, CDCl₃) δ 7.38-7.21 (m, 13H), 7.15-7.10 (m, 2H), 5.02 (d, J=11.2 Hz, 1H), 4.83 (d, J=11.0 Hz, 1H), 4.81 (d, J=11.4 Hz, 1H), 4.57-4.32 (m, 5H), 4.20 (d, J=7.7 Hz, 1H), 4.00 (d, J=3.3 Hz, 1H), 3.80-3.50 (m, 7H), 3.44-3.30 (m, 1H), 3.21 (s, 1H), 2.11 (s, 3H), 1.74-1.63 (m, 1H), 1.33 (d, J=6.5 Hz, 3H), 0.94-0.85 (m, 12H), 0.2 (s, 6H).

Example 54: Synthesis of thexyldimethylsilyl 3,4,6-tri-O-benzyl-β-D-glucopyranosyl-(1→4)-3-O-acetyl-2-azido-2-deoxy-α-L-fucopyranoside (55*)

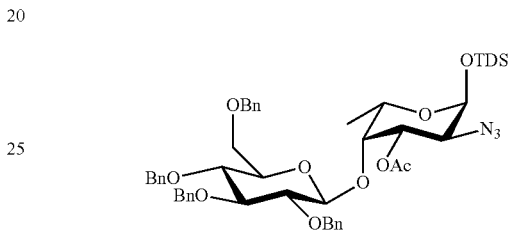

Benzyl bromide (0.074 mL, 0.620 mmol, 10 equiv) was added to a solution of alcohol 55* (50 mg, 0.062 mmol, 1 equiv) in DCM (0.5 mL). Then, the mixture was cooled to 0° C. and NaH 60% in mineral oil (304 mg, 7.60 mmol) was added. After 10 min, DMF was added (17 μL). The reaction was warmed to room temperature and let stir for 30 min. The reaction mixture was cooled to 0° C. and quenched with AcOH (0.1 mL). The reaction mixture was warmed to room temperature and the solvent evaporated. Column chromatography on silica gel (hexanes/ethyl acetate) afforded disaccharide 55* (55 mg, 0.061 mmol, 99%). ¹H NMR (400 MHz, CDCl₃) δ 7.45-7.03 (m, 20H), 5.19 (dd, J=9.6, 8.1 Hz, 1H), 4.89 (d, J=12.6 Hz, 1H), 4.82-4.75 (m, 2H), 4.70 (d, J=11.4 Hz, 1H), 4.56-4.44 (m, 3H), 4.40 (d, J=12.0 Hz, 1H), 4.35 (d, J=12.0 Hz, 1H), 4.31 (d, J=7.7 Hz, 1H), 3.87 (d, J=3.0 Hz, 1H), 3.73-3.43 (m, 6H), 3.34 (q, J=6.5 Hz, 1H), 3.10 (dd, J=10.5, 3.1 Hz, 1H), 1.99 (s, 3H), 1.72-1.59 (m, 1H), 1.28 (d, J=6.6 Hz, 3H), 0.96-0.77 (m, 12H), 0.13 (m, 6H).

Example 55: Synthesis of thexyldimethylsilyl 2,3,4,6-tetra-O-benzyl-β-D-glucopyranosyl-(1→4)-2-azido-2-deoxy-α-L-fucopyranoside (56*)

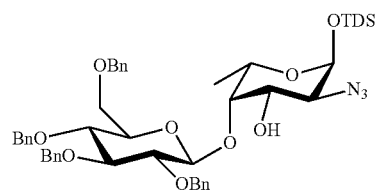

To a solution of disaccharide 55* (55 mg, 61 μmol) in MeOH (1 mL) was added 0.5 M NaOMe in MeOH (0.12 mL) and stirred for 16 h. The mixture was neutralized with Amberlite® IR 120 (H⁺) ion exchange resin and the resulting alcohol was filtered and concentrated. Column chromatography on silica gel (hexanes/ethyl acetate) afforded disaccharide 56* (43 mg, 50 μmol, 82%). $^1$H NMR (400 MHz, CDCl$_3$) δ 7.42-7.20 (m, 18H), 7.18-7.12 (m, 2H), 5.00 (d, J=11.3 Hz, 1H), 4.85 (d, J=11.4 Hz, 2H), 4.76 (d, J=11.3 Hz, 1H), 4.63 (d, J=12.2 Hz, 1H), 4.51 (d, J=10.9 Hz, 1H), 4.48-4.32 (m, 4H), 3.93 (d, J=2.9 Hz, 1H), 3.76-3.46 (m, 7H), 3.40 (q, J=6.6 Hz, 1H), 3.18 (dd, J=10.5, 3.1 Hz, 1H), 1.73-1.63 (m, 1H), 1.32 (d, J=6.5 Hz, 3H), 0.92-0.83 (m, 12H), 0.16 (d, J=2.4 Hz, 6H).

Example 56: Synthesis of thexyldimethylsilyl [2,3,4,6-tetra-O-benzyl-β-D-glucopyranosyl-(1→4)]-3,4-di-O-benzyl-6-O-benzoyl-2-levulinoyl-β-D-glucopyranosyl-(1→3)-2-azido-2-deoxy-α-L-fucopyranoside (57*)

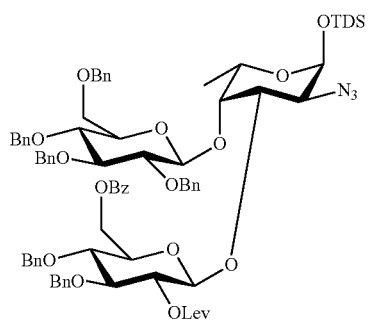

Acceptor 56* (40 mg, 0.047 mmol, 1.0 equiv) and 6-O-benzoyl-3,4-di-O-benzyl-2-O-levulinoyl-1-thio-β-D-glucopyranoside (43 mg, 0.070 mmol, 1.5 equiv) were coevaporated with toluene two times and dried in vacuo. The residue was dissolved in a mixture of toluene (2 mL) and dichloromethane (1 mL). Molecular sieves (4 Å) were added and the reaction mixture cooled to −45° C. NIS (21 mg, 0.094 mmol, 2 equiv) and TfOH (0.5 μL, 5.6 μmol, 0.12 equiv) were added and the reaction let warm to −30° C. over two hours. The reaction was quenched with triethylamine and diluted with dichloromethane. The organic phase was washed with saturated aqueous Na$_2$S$_2$O$_3$, NaHCO$_3$ and brine. The organic layer was dried over Na$_2$SO$_4$ and concentrated. Column chromatography on silica gel (hexanes/ethyl acetate) afforded trisaccharide 57* (52 mg, 0.037 mmol, 79%). $^1$H NMR (400 MHz, CDCl$_3$) δ 8.10-7.98 (m, 2H), 7.57-7.50 (m, 1H), 7.47-7.09 (m, 30H), 7.07-7.00 (m, 2H), 5.23 (d, J=8.1 Hz, 1H), 5.14-5.05 (m, 1H), 4.91 (d, J=5.1 Hz, 1H), 4.88 (d, J=6.4 Hz, 1H), 4.84-4.76 (m, 2H), 4.73-4.31 (m, 11H), 4.28 (d, J=7.8 Hz, 1H), 3.99 (d, J=2.9 Hz, 1H), 3.96-3.87 (m, 2H), 3.85-3.82 (m, 1H), 3.71-3.34 (m, 8H), 3.18 (dd, J=10.4, 3.1 Hz, 1H), 2.66-2.14 (m, 4H), 2.03 (s, 1H), 1.60-1.48 (m, 1H), 1.44 (d, J=6.5 Hz, 3H), 0.83 (dd, J=7.6, 2.4 Hz, 12H), 0.12 (d, J=10.5 Hz, 6H).

Example 57: Synthesis of thexyldimethylsilyl 3-O-p-methoxybenzyl-2-azido-2-deoxy-β-L-fucopyranoside (59*)

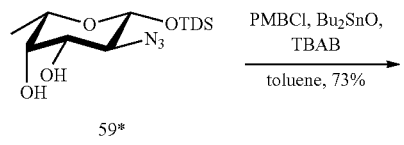

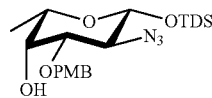

Diol 59* (1.02 g, 3.07 mmol, 1.0 equiv) was co-evaporated with dry toluene twice and let dry in vacuo for 30 min. Then, dry toluene (30 mL) was added, followed by Bu$_2$SnO (1.14 g, 4.60 mmol, 1.5 equiv) and 4 Å MS. The reaction was stirred for 1 hour under reflux. The reaction was cooled to 40° C.; PMBCl (1.25 mL, 9.20 mmol, 3 equiv) and TBAB (1.48 g, 4.60 mmol, 1.5 equiv) were added and left stir overnight at rt. The reaction mixture was filtered and the solvent evaporated. Column chromatography on silica gel (hexanes/ethyl acetate) afforded building block 59a* (1.01 g, 2.23 mmol, 73%).). [α]$_D^{20}$=25.6 (c=2.00, CHCl$_3$); IR ν$_{max}$ (film) 3494, 2960, 2870, 2112, 1515, 1251, 1073, 829 cm$^{-1}$; $^1$H NMR (400 MHz, CDCl$_3$) δ 7.36-7.28 (m, 2H), 6.97-6.84 (m, 2H), 4.63 (s, 2H), 4.39 (d, J=7.7 Hz, 1H), 3.81 (s, 3H), 3.71-3.63 (m, 1H), 3.53-3.39 (m, 2H), 3.24 (dd, J=10.1, 3.3 Hz, 1H), 2.41-2.26 (m, 1H), 1.67 (hept, J=6.8 Hz, 1H), 1.31 (d, J=6.5 Hz, 3H), 0.89 (d, J=7.0 Hz, 12H), 0.17 (d, J=3.5 Hz, 6H). $^{13}$C NMR (101 MHz, CDCl$_3$) δ 159.6, 129.7, 129.5, 114.1, 97.0, 79.0, 71.8, 70.2, 68.4, 65.2, 55.4, 34.0, 24.9, 20.1, 20.0, 18.6, 18.5, 16.5, −1.8, −3.2. LRMS (ESI+) Calcd for C$_{22}$H$_{37}$N$_3$O$_5$SiNa$^+$ [M+Na]$^+$ 474.2400, found 474.2.

Example 58: Synthesis of thexyldimethylsilyl 3,4,6-tri-O-benzyl-2-O-levulinoyl-β-D-glucopyranosyl-(1→4)-3-O-p-methoxybenzyl-2-azido-2-deoxy-β-L-fucopyranoside (61*)

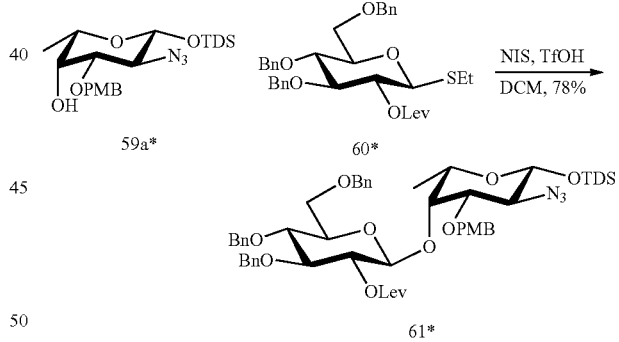

L-fucosyl acceptor 59a* (200 mg, 0.443 mmol, 1.0 equiv) and thioglucoside 60* (354 mg, 0.70 mmol, 1.35 equiv) were coevaporated with toluene two times and dried in vacuo. The residue was dissolved in DCM (15 mL). Molecular sieves acid washed (4 Å) were added and the reaction mixture cooled to −40° C. NIS (149 mg, 0.66 mmol, 1.5 equiv) and TfOH (2 μL, 0.02 mmol, 0.05 equiv) were added and let stir for one hour at −40° C. The reaction was quenched with triethylamine and diluted with DCM. The organic phase was washed with saturated aqueous Na$_2$S$_2$O$_3$, NaHCO$_3$ and brine, dried over Na$_2$SO$_4$, filtered and concentrated. Column chromatography on silica gel (hexanes/ethyl acetate) afforded disaccharide 61* (338 mg, 0.34 mmol, 78%). [α]$_D^{20}$=−2.5 (c=1.00, CHCl$_3$); IR ν$_{max}$ (film) 2959, 2868, 2112, 1750, 1721, 1515, 1250, 1075, 832 cm$^{-1}$, $^1$H NMR (600 MHz, CDCl$_3$) δ 7.41-7.19 (m, 15H), 7.18-7.11 (m, 2H), 6.82 (d, J=8.4 Hz, 2H), 5.19 (t, J=8.8 Hz, 1H), 4.83-4.74 (m, 4H), 4.53-4.43 (m, 3H), 4.39 (d, J=5.3 Hz, 2H), 4.26 (d, J=7.7 Hz, 1H), 3.85-3.82 (m, 1H), 3.77 (s, 3H), 3.73-3.63 (m, 2H), 3.60-3.43 (m, 4H), 3.33 (q, J=6.6 Hz, 1H), 3.08 (dd, J=10.5, 3.0 Hz, 1H), 2.90-2.79 (m, 1H), 2.65-2.55 (m, 2H), 2.53-2.45 (m, 1H), 2.14 (s, 3H), 1.64 (h, J=6.8 Hz, 1H), 1.27 (d, J=6.6 Hz, 3H), 0.91-0.81 (m, 12H), 0.11 (d, J=12.5 Hz, 6H). $^{13}$C NMR (151 MHz, CDCl$_3$) δ 206.6, 171.3, 159.2, 138.4, 137.9, 130.2, 129.6, 128.6, 128.5, 128.5, 128.3, 128.2, 128.0, 128.0, 127.8, 127.8, 113.8, 101.7, 97.2, 83.2, 78.0, 75.3, 75.2, 75.0, 74.0, 73.9, 73.6, 70.3, 70.0, 69.7, 64.7, 55.4, 38.2, 34.1, 30.0, 28.0, 24.9, 20.1, 20.1, 18.63, 18.58, 17.0, -1.8, -3.1. HRMS (ESI+) Calcd for C$_{54}$H$_{71}$N$_3$O$_{12}$SiNa$^+$ [M+Na]$^+$ 1004.4705, found 1004.4709.

Example 59: Synthesis of thexyldimethylsilyl 3,4,6-tri-O-benzyl-β-D-glucopyranosyl-(1→4)-3-O-p-methoxybenzyl-2-azido-2-deoxy-β-L-fucopyranoside (62*)

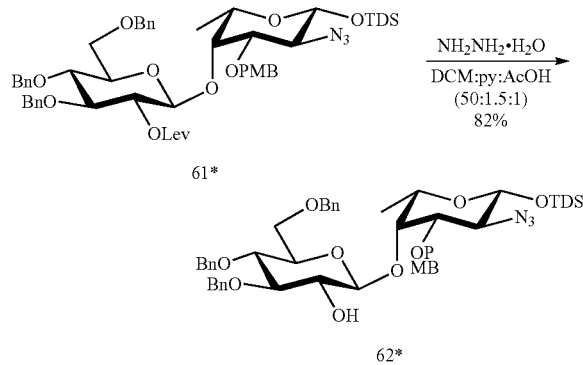

To a solution of disaccharide 61* (970 mg, 0.99 mmol, 1 equiv) in DCM (11 mL), a solution of hydrazine hydrate (190 µL, 3.95 mmol, 4 equiv) dissolved in AcOH (1.1 mL) and pyridine (1.7 mL) was added. The resulting reaction mixture was stirred at rt for 1 to 2 h. The reaction was quenched by the addition of acetone and the solvent evaporated. Column chromatography on silica gel (hexanes/ethyl acetate) afforded disaccharide 62* (720 mg, 0.81 mmol, 82%). [α]$_D^{20}$=28.5 (c=0.10, CHCl$_3$); IR ν$_{max}$(film) 3470, 2930, 2870, 2113, 1515, 1252, 1115, 1069, 832 cm$^{-1}$, $^1$H NMR (600 MHz, CDCl$_3$) δ 7.40-7.36 (m, 2H), 7.35-7.21 (m, 13H), 7.20-7.12 (m, 2H), 6.80 (d, J=8.3 Hz, 2H), 5.00 (d, J=11.4 Hz, 1H), 4.86 (d, J=10.9 Hz, 1H), 4.80-4.72 (m, 2H), 4.60 (d, J=11.6 Hz, 1H), 4.53 (d, J=10.8 Hz, 1H), 4.50-4.40 (m, 3H), 4.36 (d, J=7.7 Hz, 1H), 3.90 (d, J=3.0 Hz, 1H), 3.74 (s, 3H), 3.69-3.44 (m, 8H), 3.39 (q, J=6.4 Hz, 1H), 3.18 (dd, J=10.5, 3.1 Hz, 1H), 1.66 (h, J=6.8 Hz, 1H), 1.29 (d, J=6.5 Hz, 3H), 0.94-0.81 (m, 12H), 0.17 (d, J=4.3 Hz, 6H). $^{13}$C NMR (151 MHz, CDCl$_3$) δ 159.6, 139.2, 138.3, 138.1, 130.3, 129.3, 128.51, 128.50, 128.46, 128.2, 127.94, 127.89, 127.8, 127.6, 114.0, 102.5, 97.2, 84.6, 78.0, 77.0, 75.4, 75.2, 75.1, 73.8, 73.6, 72.2, 72.1, 70.7, 69.6, 65.7, 55.4, 34.1, 25.0, 20.2, 20.1, 18.7, 18.6, 17.5, -1.7, -3.0. HRMS (ESI+) Calcd for C$_{49}$H$_{65}$N$_3$O$_{10}$SiNa$^+$ [M+Na]$^+$ 906.4337, found 906.4371.

Example 60: Synthesis of thexyldimethylsilyl 2,3,4,6-tetra-O-benzyl-β-D-glucopyranosyl-(1→4)-3-O-p-methoxybenzyl-2-azido-2-deoxy-β-L-fucopyranoside (63*)

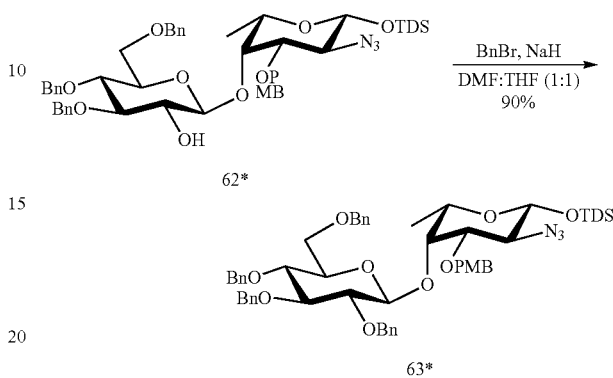

Benzyl bromide (194 µL, 1.63 mmol, 2 equiv) was added to a solution of alcohol 62* (720 mg, 0.81 mmol, 1 equiv) in THF:DMF (1:1, 17 mL). Then, the mixture was cooled to 0° C. and NaH 60% in mineral oil (65 mg, 1.63 mmol, 2 equiv) was added. The reaction mixture was warmed to room temperature and let stir for 3 h. Then, it was diluted with DCM and quenched with NaHCO$_3$. The aqueous layer was extracted with DCM (3×). The organic phase was washed with brine, dried over Na$_2$SO$_4$, filtered and the solvent evaporated. Column chromatography on silica gel (hexanes/ethyl acetate) afforded disaccharide 63* (715 mg, 0.73 mmol, 90%). [α]$_D^{20}$=-5.4 (c=2.44, CHCl$_3$); IR ν$_{max}$ (film) 3066, 3033, 2957, 2867, 2112, 1514, 1249, 1068, 831, 698 cm$^{-1}$, $^1$H NMR (400 MHz, CDCl$_3$) δ 7.47-7.07 (m, 22H), 6.83 (d, J=8.2 Hz, 2H), 5.17 (d, J=10.4 Hz, 1H), 5.04 (d, J=11.1 Hz, 1H), 4.90-4.69 (m, J=25.2, 21.0, 11.5 Hz, 5H), 4.54-4.32 (m, 6H), 3.97 (d, J=3.2 Hz, 1H), 3.78 (s, 3H), 3.73-3.36 (m, 9H), 3.15 (dd, J=10.5, 3.1 Hz, 1H), 1.68-1.56 (h, J=6.8 Hz, 1H), 1.38 (d, J=6.5 Hz, 3H), 0.92-0.78 (m, 12H), 0.15 (s, 6H). $^{13}$C NMR (101 MHz, CDCl$_3$) δ 159.2, 138.9, 138.2, 137.9, 137.8, 130.1, 129.8, 129.3, 128.52, 128.49, 128.47, 128.34, 128.32, 128.03, 127.97, 127.8, 127.7, 113.7, 104.5, 97.1, 85.0, 81.8, 77.9, 76.6, 75.8, 75.1, 75.0, 74.9, 73.7, 73.5, 70.5, 70.0, 69.6, 65.2, 55.3, 34.0, 24.9, 20.2, 20.0, 18.6, 18.5, 17.3, -1.9, -3.2. HRMS (ESI+) Calcd for C$_{56}$H$_{71}$N$_3$O$_{10}$SiNa$^+$ [M+Na]$^+$ 1004.4806, found 996.4809.

Example 61: Synthesis of thexyldimethylsilyl 2,3,4,6-tetra-O-benzyl-β-D-glucopyranosyl-(1→4)-2-azido-2-deoxy-β-L-fucopyranoside (64*)

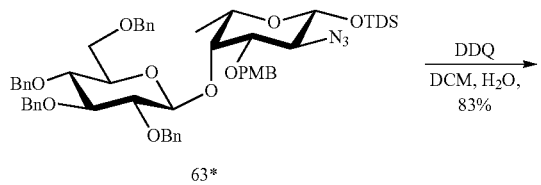

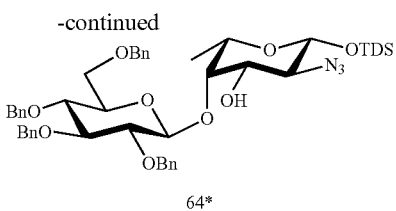

64*

To a solution of disaccharide 63* (630 mg, 0.65 mmol, 1 equiv) in DCM:H$_2$O (18:1, 5.3 mL) was added 2,3-dichloro-5,6-dicyano-1,4-benzoquinone (DDQ) (161 mg, 0.71 mmol, 1.1 equiv) at 0° C. The reaction was warmed to rt and let stir for 2.5 h. The reaction was not complete, then 10 mg DDQ were added. After 30 minutes, the reaction was diluted with DCM and NaHCO$_3$ added. The organic phase was washed (3×) with NaHCO$_3$ until the solution was colorless. Then, the organic phase was washed with brine, dried over Na$_2$SO$_4$, filtered and the solvent evaporated. Column chromatography on silica gel (hexanes/ethyl acetate) afforded disaccharide 64* (460 mg, 0.54 mmol, 83%). $[\alpha]_D^{20}$=1.9 (c=1.36, CHCl$_3$); IR $\nu_{max}$ (film) 3484, 3034, 2959, 2869, 2112, 1254, 1069, 833, 629 cm$^{-1}$, $^1$H NMR (400 MHz, CDCl$_3$) δ 7.43-7.19 (m, 18H), 7.16-7.08 (m, 2H), 5.08-4.97 (m, 2H), 4.87-4.75 (m, 3H), 4.59-4.44 (m, 4H), 4.37 (d, J=7.7 Hz, 1H), 3.73-3.34 (m, 10H), 1.66 (h, J=7.0 Hz, 1H), 1.30 (d, J=6.4 Hz, 3H), 0.93-0.78 (m, 12H), 0.20 (s, 6H). $^{13}$C NMR (101 MHz, CDCl$_3$) δ 138.6, 137.9, 137.85, 137.81, 128.8, 128.6, 128.5, 128.4, 128.2, 128.1, 128.0, 127.9, 127.9, 127.8, 104.0, 97.3, 84.6, 81.5, 80.6, 77.6, 77.4, 75.9, 75.3, 75.0, 73.8, 71.4, 70.3, 68.8, 67.7, 34.1, 24.9, 20.2, 20.0, 18.6, 18.5, 16.7, -1.9, -3.0. HRMS (ESI+) Calcd for C$_{48}$H$_{63}$N$_3$O$_9$SiNa$^+$ [M+Na]$^+$ 876.4231, found 876.4234.

Example 62: Synthesis of thexyldimethylsilyl [2,3,4,6-tetra-O-benzyl-β-D-glucopyranosyl-(1→4)]-benzyl-3,4-di-O-benzyl-6-O-benzoyl-2-levulinoyl-β-D-glucopyranosyluronate-(1→3)-2-azido-2-deoxy-β-L-fucopyranoside (66*)

Acceptor 64* (91 mg, 0.11 mmol, 1.0 equiv) and thioglucoside 65* (129 mg, 0.21 mmol, 2 equiv) were coevaporated with toluene two times and dried in vacuo. The residue was dissolved in a mixture of toluene (4 mL) and DCM (2 mL). Molecular sieves acid washed (4 Å) were added and the reaction mixture cooled to -30° C. NIS (53 mg, 0.23 mmol, 2.2 equiv) and TfOH (0.5 µL, 5.3 µmol, 0.05 equiv) were added and the reaction let warm to -15° C. over two hours. The reaction was quenched with triethylamine and diluted with DCM. The organic phase was washed with saturated aqueous Na$_2$S$_2$O$_3$, NaHCO$_3$ and brine, dried over Na$_2$SO$_4$, filtered and concentrated. Column chromatography on silica gel (hexanes/ethyl acetate) afforded trisaccharide 66* (114 mg, 0.08 mmol, 76%). $[\alpha]_D^{20}$=-26.6 (c=0.87, CHCl$_3$); IR $\nu_{max}$ (film) 3034, 2929, 2870, 2116, 1751, 1720, 1072, 832, 698 cm$^{-1}$, $^1$H NMR (400 MHz, CDCl$_3$) δ 7.56-6.90 (m, 35H), 5.21-5.06 (m, 5H), 5.02-4.94 (m, 2H), 4.83-4.61 (m, 6H), 4.53-4.32 (m, 6H), 4.06-3.88 (m, 3H), 3.83-3.73 (m, 2H), 3.65-3.33 (m, 8H), 3.21 (t, J=9.2 Hz, 1H), 2.78-2.57 (m, 2H), 2.50-2.37 (m, 2H), 2.11 (s, 3H), 1.68-1.53 (m, 1H), 1.35 (d, J=6.5 Hz, 3H), 0.94-0.73 (m, 12H), 0.15 (d, J=8.8 Hz, 6H). $^{13}$C NMR (101 MHz, CDCl$_3$) δ 206.3, 171.3, 168.6, 138.8, 138.4, 138.3, 138.2, 138.0, 137.9, 135.3, 129.2, 128.7, 128.65, 128.60, 128.56, 128.55, 128.53, 128.4, 128.20, 128.18, 128.1, 128.0, 127.9, 127.8, 127.73, 127.70, 127.67, 104.0, 96.8, 95.5, 84.9, 82.0, 81.4, 79.5, 78.3, 75.9, 75.2, 74.9, 74.8, 74.4, 74.3, 74.1, 73.4, 73.4, 73.0, 72.4, 70.5, 69.2, 67.3, 64.6, 37.9, 34.1, 30.1, 28.2, 24.9, 20.2, 20.0, 18.7, 18.5, 17.5, -1.9, -3.2. HRMS (ESI+) Calcd for C$_{80}$H$_{95}$N$_3$O$_{17}$SiNa$^+$ [M+Na]$^+$ 1420.6328, found 1420.6322.

Example 63: Synthesis of [2,3,4,6-Tetra-O-benzyl-β-D-glucopyranosyl-(1→4)]-benzyl-3,4-di-O-benzyl-6-O-benzoyl-2-levulinoyl-β-D-glucopyranosyluronate-(1→3)-2-azido-2-deoxy-α,β-L-fucopyranoside (67*)

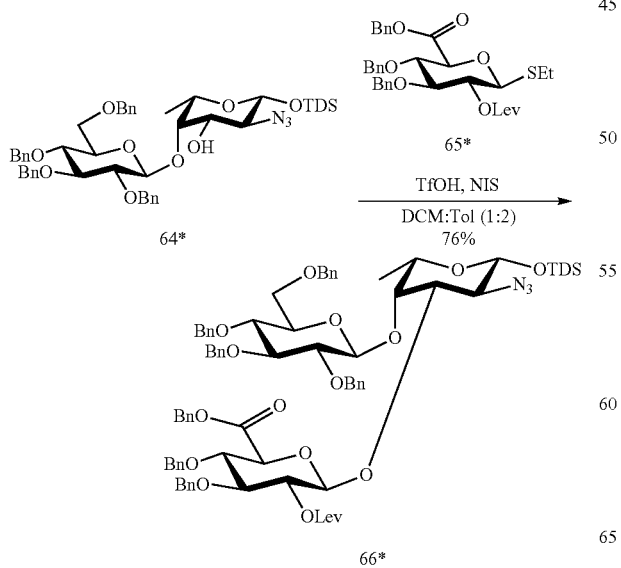

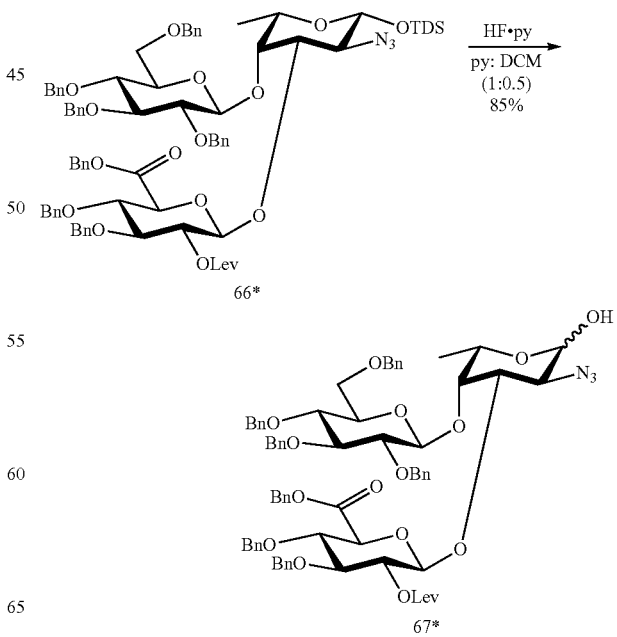

Trisaccharide 66* (235 mg, 0.17 mmol, 1.0 equiv) was dissolved in a mixture of pyridine (1 mL) and DCM (0.5 mL) in a plastic falcon tube. HF.py (0.15 mL, 1.70 mmol, 10 equiv) was added dropwise and the reaction let stir at rt for 48-72 h. The reaction was diluted with DCM and quenched with NaHCO$_3$. The phases were separated and the organic phase washed with brine, dried over Na$_2$SO$_4$, filtered and concentrated. Column chromatography on silica gel (hexanes/ethyl acetate) afforded trisaccharide lactol 67*

Example 64: Synthesis of N-(Benzyl)benzyloxycarbonyl-5-amino-pentanyl [2,3,4,6-tetra-O-benzyl-β-D-glucopyranosyl-(1→4)]-benzyl-3,4-di-O-benzyl-6-O-benzoyl-2-levulinoyl-β-D-glucopyranosyluronate-(1→3)-2-azido-2-deoxy-α-L-fucopyranosyl-(1→3)-2-azido-2-deoxy-4-O-(2-naphthalenylmethyl)-β-D-fucopyranoside (69*)

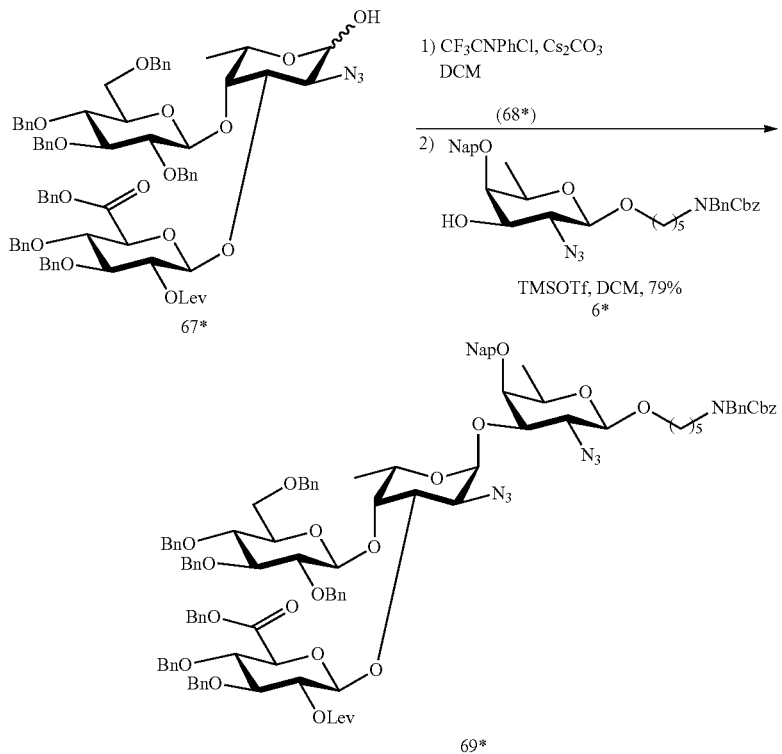

(180 mg, 0.14 mmol, 85%). α:β (1.4:1) mixture: clear oil. $[\alpha]_D^{20}$=−36.8 (c=1.12, CHCl$_3$); IR ν$_{max}$ (film) 3480, 3033, 2912, 2870, 2115, 1750, 1720, 1071, 740, 698 cm$^{-1}$, $^1$H NMR (600 MHz, CDCl$_3$) δ 7.48-7.03 (m, 60H), 5.29 (d, J=3.5 Hz, 1H), 5.21-5.05 (m, 9H), 5.00-4.94 (m, 2H), 4.82-4.76 (m, 4H), 4.74-4.63 (m, 7H), 4.53-4.43 (m, 9H), 4.35 (dd, J=10.2, 3.0 Hz, 1H), 4.16 (q, J=6.7 Hz, 1H), 4.07 (d, J=2.9 Hz, 1H), 4.03-3.95 (m, 4H), 3.90 (dd, J=10.2, 3.5 Hz, 1H), 3.87 (dd, J=10.4, 3.1 Hz, 1H), 3.84-3.77 (m, 2H), 3.67-3.59 (m, 4H), 3.57-3.48 (m, 3H), 3.47-3.38 (m, 3H), 3.31-3.25 (m, 2H), 2.70-2.65 (m, 3H), 2.56-2.47 (m, 2H), 2.45-2.36 (m, 2H), 2.13 (s, 2H), 2.11 (s, 3H), 1.39 (d, J=6.6 Hz, 2H), 1.36 (d, J=6.7 Hz, 3H). $^{13}$C NMR (151 MHz, CDCl$_3$) δ 206.4, 206.1, 171.3, 168.5, 168.4, 138.7, 138.40, 138.38, 138.3, 138.1, 138.00, 137.98, 135.3, 135.2, 129.0, 128.9, 128.73, 128.72, 128.67, 128.64, 128.61, 128.58, 128.54, 128.53, 128.50, 128.47, 128.39, 128.37, 128.19, 128.16, 128.1, 128.05, 127.98, 127.93, 127.92, 127.88, 127.86, 127.84, 127.77, 127.75, 127.71, 103.8, 103.7, 96.14, 96.09, 96.0, 91.9, 84.9, 82.6, 82.4, 81.44, 81.40, 79.7, 79.5, 78.3, 75.9, 75.2, 75.14, 75.13, 75.06, 74.96, 74.94, 74.6, 74.5, 74.43, 74.40, 74.3, 74.2, 73.6, 73.4, 73.3, 73.0, 72.3, 71.7, 71.0, 69.2, 69.1, 67.4, 67.1, 63.6, 59.9, 37.8, 30.10, 30.07, 28.3, 17.5, 17.2. HRMS (ESI+) Calcd for C$_{72}$H$_{77}$N$_3$O$_{17}$Na$^+$ [M+Na]$^+$ 1278.5151, found 1278.5177.

To a solution of the trisaccharide lactol 67* (80 mg, 0.06 mmol, 1.0 equiv) in DCM (3 mL) were added Cs$_2$CO$_3$ (42 mg, 0.12 mmol, 2.0 equiv) and 2,2,2-trifluoro-N-phenylacetimidoyl chloride (30 μL, 0.19 mmol, 3.0 equiv) at 0° C. After 2 h at rt, the product (68*) was filtered and the solvent evaporated. The crude mixture was passed through a small plug of silica and used in the next reaction without further purification. Acceptor 6* (81 mg, 0.13 mmol, 2.0 equiv) and trisaccharide imidate 68* (90 mg, 0.06 mmol, 1.0 equiv) were coevaporated with toluene two times and dried in vacuo. The residue was dissolved in DCM (3 mL). Molecular sieves acid washed (4 Å) were added and the reaction mixture cooled to −35° C. TMSOTf (1 μL, 6 μmol, 0.1 equiv) was added and the reaction let warm to −20° C. over 1 h. The reaction was quenched with triethylamine, filtered and the solvent evaporated. Column chromatography on silica gel (hexanes/ethyl acetate) afforded tetrasaccharide 69* (94 mg, 0.05 mmol, 79%). $[\alpha]_D^{20}$=−52.6 (c=0.54, CHCl$_3$); IR ν$_{max}$ (film) 3033, 2929, 2870, 2116, 1751, 1699, 1361, 1071, 737, 698 cm$^{-1}$, $^1$H NMR (600 MHz, CDCl$_3$) δ 7.81-7.75 (m, 3H), 7.72 (s, 1H), 7.51-7.48 (m, 1H), 7.45-7.40 (m, 2H), 7.39-7.07 (m, 43H), 7.04 (d, J=7.5 Hz, 2H), 5.26 (d, J=3.6 Hz, 1H), 5.20-5.14 (m, 2H), 5.12-5.05 (m, 2H), 4.99-4.94 (m, 2H), 4.91 (d, J=11.0 Hz, 1H), 4.86 (d, J=12.2 Hz, 1H), 4.83-4.71 (m, 4H), 4.69-4.59 (m, 4H), 4.54-4.40 (m, 6H), 4.35 (d, J=7.9 Hz, 1H), 4.30 (dd, J=10.3, 3.0 Hz, 1H), 4.22-4.12 (m, 1H), 4.03 (d, J=9.9 Hz, 1H), 3.95 (t, J=9.3 Hz, 1H), 3.88-3.82 (m, 3H), 3.79-3.73 (m, 1H), 3.73-3.65 (m, 2H), 3.63-3.54 (m, 2H), 3.53-3.35 (m, 7H), 3.32 (t, J=9.4 Hz, 1H), 3.29-3.23 (m, 1H), 3.22-3.16 (m, 1H), 2.63 (t, J=6.6 Hz, 2H), 2.44 (dt, J=17.4, 6.5 Hz, 1H), 2.36 (dt, J=17.4, 6.7 Hz, 1H), 2.08 (s, 3H), 1.68-1.46 (m, 4H), 1.43-1.27 (m, 2H), 1.31 (d, J=6.4 Hz, 3H), 1.00 (d, J=6.5 Hz, 3H). $^{13}$C NMR (151 MHz, CDCl$_3$) δ 206.2, 171.3, 168.1, 138.7, 138.4, 138.2, 138.0, 135.8, 135.1, 133.2, 133.1, 128.7, 128.62, 128.59, 128.56, 128.55, 128.52, 128.51, 128.46, 128.4, 128.3, 128.21, 128.20, 128.1, 128.03, 127.99, 127.97, 127.9, 127.82, 127.75, 127.7, 127.5, 127.4, 127.1, 126.3, 126.2, 103.7, 102.74, 99.1, 97.0, 85.0, 82.4, 81.4, 79.7, 79.0, 78.3, 75.8, 75.2, 74.9, 74.8, 74.72, 74.68, 74.4, 73.7, 73.2, 71.0, 69.2, 67.3, 67.2, 64.0, 59.0, 50.7, 50.4, 47.3, 46.4, 37.8, 30.1, 29.4, 28.2, 23.4, 17.4, 16.8. HRMS (ESI+) Calcd for C$_{109}$H$_{117}$N$_7$O$_{22}$Na$^+$ [M+Na]$^+$ 1900.1187, found 1900.184.

Example 65: Synthesis of N-(Benzyl)benzyloxycarbonyl-5-amino-pentanyl [2,3,4,6-tetra-O-benzyl-β-D-glucopyranosyl-(1→4)]-benzyl-3,4-di-O-benzyl-6-O-benzoyl-β-D-glucopyranosyluronate-(1→3)-2-azido-2-deoxy-α-L-fucopyranosyl-(1→3)-2-azido-2-deoxy-4-O-(2-naphthalenylmethyl)-β-D-fucopyranoside (70*)

To a solution of tetrasaccharide 69* (40 mg, 0.021 mmol, 1 equiv) in DCM (2 mL), a solution of hydrazine hydrate (13 µL, 0.26 mmol, 12 equiv) dissolved in AcOH (0.08 mL) and pyridine (0.12 mL) was added. The resulting reaction mixture was stirred at rt for 1 to 2 h. The reaction was quenched by the addition of acetone and the solvent evaporated. Column chromatography on silica gel (hexanes/ethyl acetate) afforded tetrasaccharide 70* (34 mg, 0.019 mmol, 90%). [α]$_D$20=−66.6 (c=1.00, CHCl$_3$); IR ν$_{max}$ (film) 3501, 3033, 2928, 2870, 2116, 1749, 1698, 1070, 735, 698 cm$^{-1}$, $^1$H NMR (400 MHz, CDCl$_3$) δ 7.87-7.74 (m, 3H), 7.17 (s, 1H), 7.58-6.92 (m, 48H), 5.29 (d, J=3.7 Hz, 1H), 5.21-5.13 (m, 3H), 5.08-4.71 (m, 10H), 4.59-4.38 (m, 6H), 4.37-4.29 (m, 2H), 4.27-4.18 (m, 2H), 4.00-3.86 (m, 5H), 3.78-3.17 (m, 17H), 1.72-1.47 (m, 4H), 1.39 (d, J=6.4 Hz, 3H), 1.43-1.27 (m, 2H), 1.04 (d, J=6.6 Hz, 3H). $^{13}$C NMR (101 MHz, CDCl$_3$) δ 168.0, 156.8, 156.3, 138.7, 138.7, 138.2, 138.1, 138.0, 137.83, 137.78, 135.6, 135.3, 133.1, 133.0, 128.9, 128.7, 128.62, 128.61, 128.51, 128.49, 128.47, 128.44, 128.40, 128.35, 128.26, 128.2, 128.1, 127.92, 127.89, 127.86, 127.8, 127.7, 127.6, 127.3, 127.0, 126.7, 126.5, 126.3, 104.1, 103.4, 102.8, 100.7, 84.6, 83.9, 82.3, 79.0, 78.8, 78.2, 77.6, 75.8, 75.7, 75.3, 75.23, 75.20, 75.1, 75.0, 74.2, 73.2, 71.0, 70.0, 69.9, 68.2, 67.4, 67.2, 66.8, 63.8, 58.0, 50.6, 50.3, 47.2, 46.3, 29.3, 28.0, 27.5, 23.3, 17.5, 16.8. HRMS (ESI+) Calcd for C$_{104}$H$_{111}$N$_7$O$_{20}$Na$^+$ [M+Na]$^+$ 1801.7815, found 1801.7992.

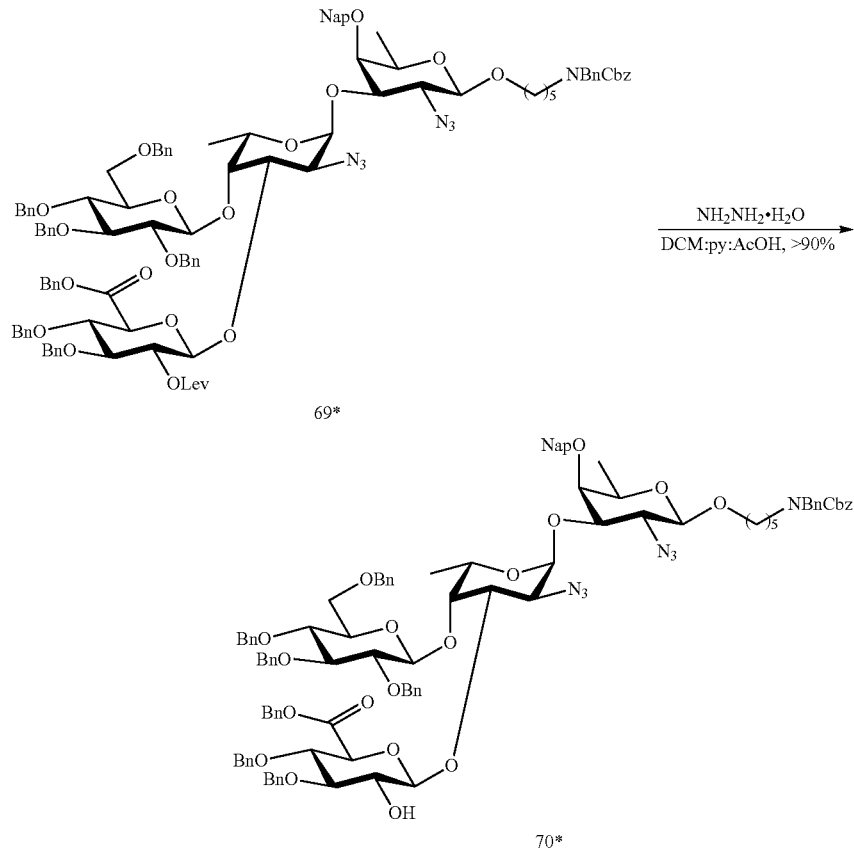

Example 66: Synthesis of N-(Benzyl)benzyloxycarbonyl-5-amino-pentanyl 2-azido-3,4-di-O-benzyl-2-deoxy-α-L-pneumopyranosyl-(1→2)-[2,3,4,6-tetra-O-benzyl-β-D-glucopyranosyl-(1→4)]-benzyl-3,4-di-O-benzyl-6-O-benzoyl-β-D-glucopyranosyluronate-(1→3)-2-azido-2-deoxy-α-L-fucopyranosyl-(1→3)-2-azido-2-deoxy-4-O-(2-naphthalenylmethyl)-β-D-fucopyranoside (71*)

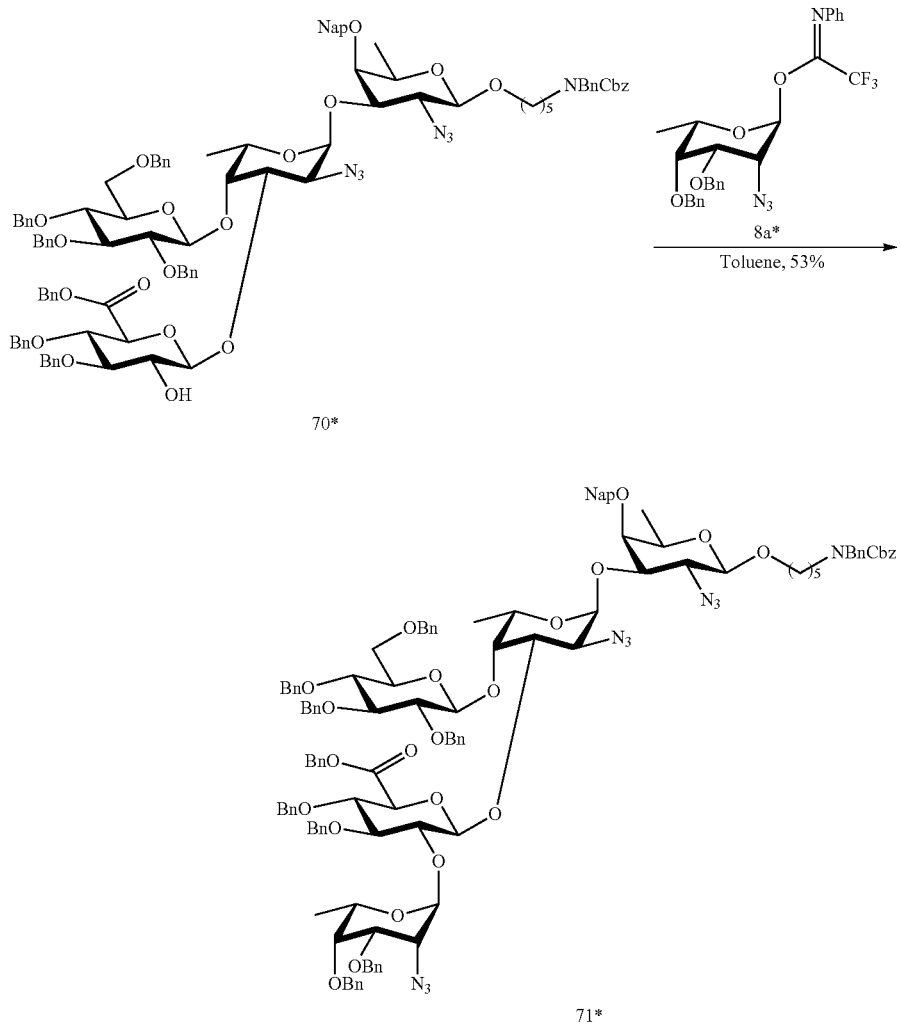

Acceptor 70* (25 mg, 0.014 mmol, 1.0 equiv) and imidate 8a* (23 mg, 0.042 mmol, 3.0 equiv) were coevaporated with toluene two times and dried in vacuo. The residue was dissolved in toluene (2 mL). The reaction mixture cooled to −35° C. TMSOTf (0.25 μL, 1.4 μmol, 0.1 equiv) was added and the reaction let warm to −20° C. over 2 h. The reaction was quenched with triethylamine, filtered and the solvent evaporated. Column chromatography on silica gel (hexanes/ethyl acetate) afforded pentasaccharide 71* (16 mg, 0.07 mmol, 53%). $[α]_D^{20}$=−39.5 (c=0.30, CHCl$_3$); IR $v_{max}$ (film) 3034, 2931, 2870, 2115, 1750, 1698, 1455, 1070, 736, 698 cm$^{-1}$, $^1$H NMR (600 MHz, CDCl$_3$) δ 7.87-7.73 (m, 3H), 7.68 (s, 1H), 7.62-7.02 (m, 55H), 7.02-6.86 (m, 3H), 5.32 (d, J=3.9 Hz, 1H), 5.28-5.22 (m, 2H), 5.21-5.13 (m, 2H), 5.03-4.39 (m, 22H), 4.33 (d, J=7.9 Hz, 1H), 4.26 (d, J=10.9 Hz, 1H), 4.24-4.16 (m, 2H), 4.06 (d, J=9.7 Hz, 1H), 4.01-3.86 (m, 4H), 3.85-3.79 (m, 2H), 3.73 (t, J=8.3 Hz, 1H), 3.67-3.54 (m, 4H), 3.54-3.32 (m, 8H), 3.31-3.12 (m, 4H), 1.74-1.46 (m, 4H), 1.46-1.18 (m, 8H), 0.97 (d, J=6.7 Hz, 3H). $^{13}$C NMR (151 MHz, CDCl$_3$) δ 168.1, 138.7, 138.4, 137.7, 137.60, 135.58, 134.9, 133.2, 128.73, 128.65, 128.62, 128.57, 128.5, 128.44, 128.42, 128.37, 128.35, 128.23, 128.20, 128.1, 128.03, 127.97, 127.91, 127.87, 127.8, 127.7, 127.6, 127.5, 127.4, 127.2, 127.1, 126.7, 126.4, 126.2, 103.9, 102.9, 100.3, 99.2, 95.4, 85.2, 84.1, 81.2, 80.4, 78.8, 78.2, 77.5, 76.8, 76.5, 75.6, 75.1, 74.9, 74.84, 74.77, 74.5, 74.2, 73.2, 72.5, 71.1, 70.5, 70.0, 69.92, 69.87, 69.3, 68.0, 67.3, 67.0, 66.9, 66.5, 64.0, 57.9, 57.3, 50.7, 50.4, 47.3, 47.3, 46.3, 32.1, 29.8, 29.5, 29.4, 28.0, 27.60, 23.4, 23.3, 22.8, 17.5, 17.1, 17.0, 14.7, 14.3. HRMS (ESI+) Calcd for $C_{124}H_{132}N_{10}O_{23}Na^+$ [M+Na]$^+$ 2152.9398, found 2152.9582.

Example 67: Synthesis of N-(Benzyl)benzyloxycarbonyl-5-N-acetyl-amino-pentanyl 2-N-acetyl-3,4-di-O-benzyl-α-L-pneumopyranosyl-(1→2)-[2,3,4,6-tetra-O-benzyl-β-D-glucopyranosyl-(1→4)]-benzyl-3,4-di-O-benzyl-6-O-benzoyl-β-D-glucopyranosyluronate-(1→3)-2-N-acetyl-α-L-fucopyranosyl-(1→3)-2-N-acetyl-4-O-(2-naphthalenylmethyl)-β-D-fucopyranoside (72*)

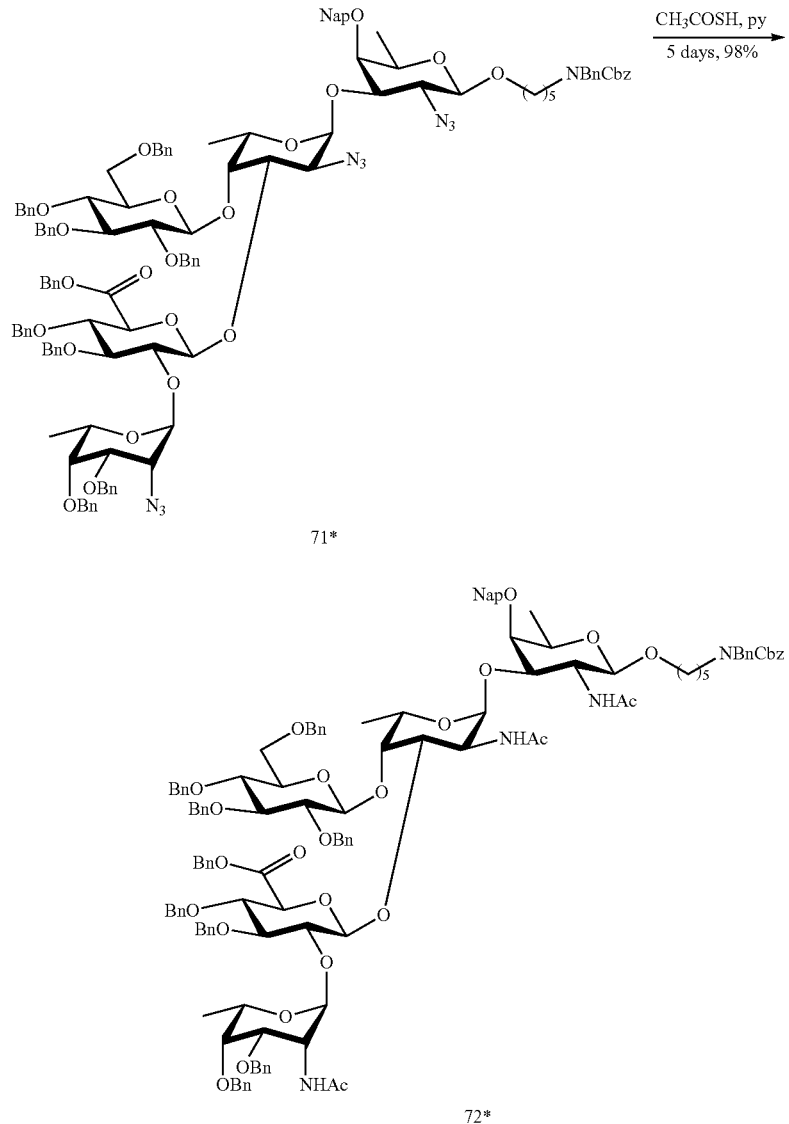

To a solution of azido pentasaccharide 71* (32 mg, 0.015 mmol, 1 equiv) in pyridine (2 mL), thioacetic acid (0.5 mL) was added and stirred for 5 days at rt. The reaction mixture was concentrated and purified by column chromatography on silica gel (hexanes/acetone) to afford the acetamide pentasaccharide 72* (32 mg, 0.015 mmol, 98%). $[\alpha]_D^{20}$=−26.6 (c=0.87, CHCl$_3$); IR $\nu_{max}$ (film) 3420, 3330, 3030, 2935, 2870, 1677, 1455, 1364, 1070, 7, 698 cm$^{-1}$, $^1$H NMR (400 MHz, CDCl$_3$) δ 7.92-7.67 (m, 5H), 7.63-6.87 (m, 55H), 6.80 (d, J=7.5 Hz, 2H), 6.09 (bs, 1H), 5.76 (bs, 1H), 5.51 (bs, 1H), 5.46-5.36 (m, 2H), 5.28 (s, 1H), 5.22-5.12 (m, 2H), 5.07-4.96 (m, 3H), 4.93-4.33 (m, 22H), 4.29-4.08 (m, 5H), 3.96-3.58 (m, 11H), 3.56-3.30 (m, 6H), 3.28-3.16 (m, 3H), 2.03-1.85 (m, 6H), 1.65-1.45 (m, 7H), 1.36-1.08 (m, 11H). $^{13}$C NMR (151 MHz, CDCl$_3$) δ 171.6, 170.7, 169.7, 169.4, 138.6, 138.3, 138.2, 138.02, 137.98, 137.8, 137.7, 137.6, 136.3, 134.5, 133.2, 133.1, 128.9, 128.7, 128.65, 128.62, 128.58, 128.48, 128.43, 128.36, 128.33, 128.29, 128.2, 128.1, 128.02, 127.97, 127.94, 127.89, 127.69, 127.67, 127.64, 127.56, 127.44, 127.39, 126.9, 126.53, 126.49, 126.2, 103.8, 100.5, 99.7, 97.0, 95.0, 85.3, 84.5, 80.9, 80.6, 78.8, 78.3, 77.8, 76.2, 75.8, 75.3, 75.1, 74.4, 74.22, 73.4, 73.2, 71.7, 70.7, 69.8, 69.5, 68.3, 67.4, 67.3, 66.6, 66.5, 55.2, 50.6, 50.4, 49.6, 48.0, 47.4, 46.2, 29.3, 27.99, 27.5, 24.0, 23.6, 23.3, 17.6, 17.5, 16.5. HRMS (ESI+) Calcd for $C_{130}H_{144}N_4O_{26}Na^+$ [M+Na]$^+$ 2201.0000, found 2201.0086.

Example 68: Synthesis of 5-amino-pentanyl 2-N-acetyl-α-L-pneumopyranosyl-(1→2)-[β-D-glucopyranosyl-(1→4)]-β-D-glucopyranosyluronate-(1→3)-2-N-acetyl-α-L-fucopyranosyl-(1→3)-2-N-acetyl-β-D-fucopyranoside (73*)

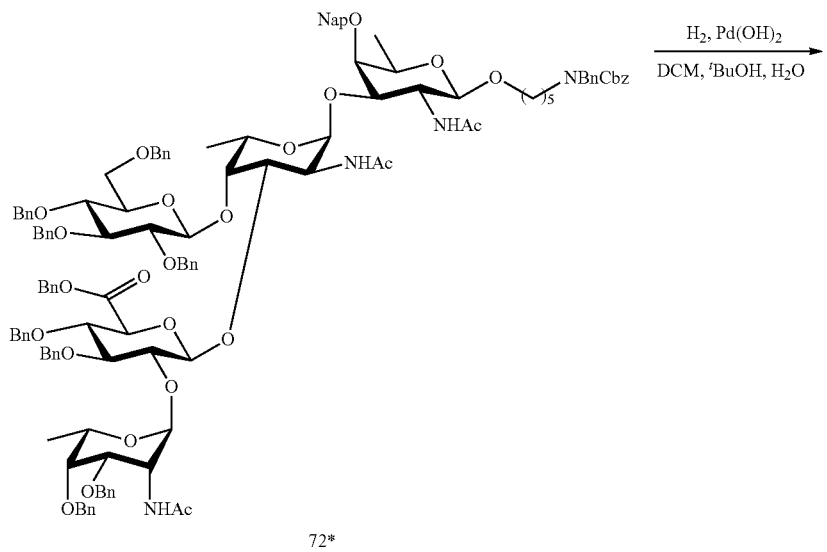

72*

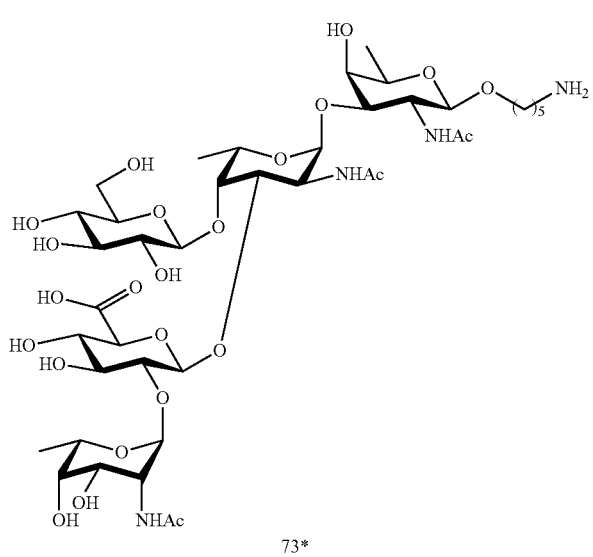

73*

The pentasaccharide 72* was dissolved in $CH_2Cl_2$/tBuOH/water (1.5:16:8, 1 mL, purged with argon and treated with a suspension of $Pd(OH)_2$ on carbon (20% (w/w) loading, 10 mg) in the same solvent mixture (1 mL). The suspension was purged with hydrogen, stirred under hydrogen atmosphere at rt. After 24 h, a freshly prepared suspension of $Pd(OH)_2$ (5 mg, 1 mL) was added and the reaction was stirred for 24 h more, filtered and concentrated. The residue was purified by solid phase extraction (Chromabond C18, Macherey-Nagel) and size exclusion chromatography on Sephadex LH-20 (MeOH:$H_2O$) and lyophilized to give pentasaccharide 73* (3 mg, 2.99 μmol, 50%) as a white solid.

$^1$H NMR (400 MHz, $D_2O$) δ 5.16 (d, J=4.0 Hz, 1H), 5.07 (s, 1H), 5.00 (d, J=7.6 Hz, 1H), 4.58-4.47 (m, 2H), 4.44-4.28 (m, 3H), 4.17-4.05 (m, 3H), 4.00-3.61 (m, 12H), 3.56-3.27 (m, 7H), 3.11 (dd, J=9.3, 7.9 Hz, 1H), 2.99-2.88 (m, 2H), 2.00 (s, 3H), 1.96 (s, 3H), 1.95 (s, 3H), 1.69-1.46 (m, 4H), 1.41-1.26 (m, 5H), 1.22 (d, J=6.4 Hz, 3H), 1.05 (d, J=6.5 Hz, 3H). $^{13}$C NMR (101 MHz, $D_2O$) δ 176.0, 174.01, 173.97, 173.3, 102.8, 101.6, 99.7, 97.3, 93.7, 77.8, 76.0, 75.8, 75.2, 73.8, 71.9, 71.7, 71.0, 70.9, 70.6, 70.3, 69.9, 69.8, 67.0, 66.9, 63.8, 60.6, 51.4, 50.8, 49.0, 39.2, 28.1, 26.3, 22.3, 22.1, 21.9, 15.9, 15.3, 15.2. HRMS (ESI+) Calcd for $C_{141}H_{70}N_4O_{24}Na^+$ [M+Na]$^+$ 1026.4311, found 1026.4397.

Example 69: N-(Benzyl)-benzyloxycarbonyl-5-amino-pentanyl 2-azido-2-deoxy-4-O-(2-naphthalenylmethyl)-3-O-allyl-β-D-fucopyranoside (74*)

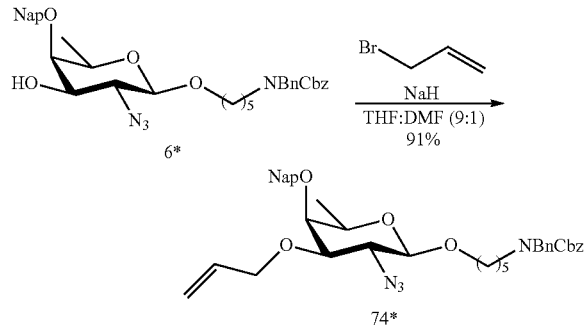

Allyl bromide (30 μL, 0.35 mmol, 1.5 equiv) was added to a solution of alcohol 6* (150 mg, 0.24 mmol, 1 equiv) in THF:DMF (9:1, 2.0 mL). Then, the mixture was cooled to 0° C. and NaH 60% in mineral oil (19 mg, 0.47 mmol, 2 equiv) was added. The reaction was warmed to room temperature and let stir overnight. The reaction mixture was diluted with DCM and quenched with NaHCO$_3$. The organic phase was washed with brine, dried over Na$_2$SO$_4$, filtered and the solvent evaporated. Column chromatography on silica gel (hexanes/ethyl acetate) afforded the allyl fucopyranoside 74* (145 mg, 0.21 mmol, 91%). $^1$H NMR (600 MHz, CDCl$_3$) δ 7.41-7.19 (m, 15H), 7.18-7.11 (m, 2H), 6.82 (d, J=8.4 Hz, 2H), 5.19 (t, J=8.8 Hz, 1H), 4.83-4.74 (m, 4H), 4.53-4.43 (m, 3H), 4.39 (d, J=5.3 Hz, 2H), 4.26 (d, J=7.7 Hz, 1H), 3.85-3.82 (m, 1H), 3.77 (s, 3H), 3.73-3.63 (m, 2H), 3.60-3.43 (m, 4H), 3.33 (q, J=6.6 Hz, 1H), 3.08 (dd, J=10.5, 3.0 Hz, 1H), 2.90-2.79 (m, 1H), 2.65-2.55 (m, 2H), 2.53-2.45 (m, 1H), 2.14 (s, 3H), 1.64 (h, J=6.8 Hz, 1H), 1.27 (d, J=6.6 Hz, 3H), 0.91-0.81 (m, 12H), 0.11 (d, J=12.5 Hz, 6H). $^{13}$C NMR (151 MHz, CDCl$_3$) δ 156.8, 156.3, 138.0, 137.0, 136.9, 135.8, 134.5, 133.2, 133.1, 128.6, 128.5, 128.1, 128.0, 127.9, 127.8, 127.3, 127.2, 126.7, 126.1, 126.0, 117.6, 102.3, 81.0, 74.7, 71.6, 70.6, 69.7, 69.6, 67.2, 63.0, 50.6, 50.3, 47.2, 46.3, 29.3, 28.0, 27.5, 23.3, 17.1. HRMS (ESI+) Calcd for C$_{40}$H$_{46}$N$_4$O$_6$Na$^+$ [M+Na]$^+$ 701.3315, found 701.3336.

Example 70: N-(Benzyl)-benzyloxycarbonyl-5-amino-pentanyl 2-azido-2-deoxy-4-O-acetyl-3-O-allyl-β-D-quinovopyranoside (77*)

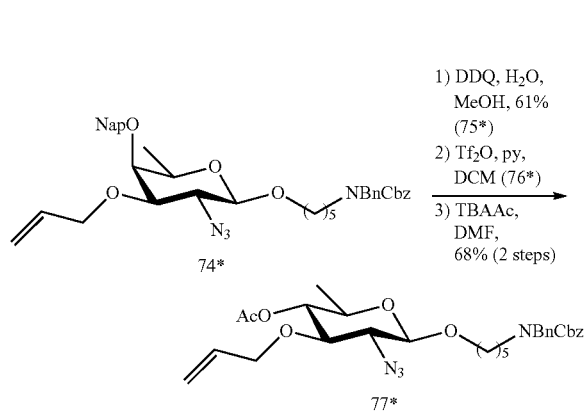

To a solution of fucopyranoside 74* (145 mg, 0.21 mmol, 1 equiv) in DCM:H$_2$O (18:1, 2 mL) was added 2,3-dichloro-5,6-dicyano-1,4-benzoquinone (58 mg, 0.26 mmol, 1.2 equiv) at 0° C. The reaction was warmed to rt and let stir for 2.5 h. The reaction was diluted with DCM and NaHCO$_3$ was added. The organic phase was washed (3×) with NaHCO$_3$ until the solution was colorless. Then, the organic phase was washed with brine, dried over Na$_2$SO$_4$ and the solvent evaporated. Column chromatography on silica gel (hexanes/ethyl acetate) afforded fucopyranoside 75* (70 mg, 0.13 mmol, 61%). To a solution of fucopyranoside 75* (35 mg, 0.065 mmol, 1 equiv) in DCM (1 mL) was added pyridine (32 μL, 0.390 mmol, 6 equiv) and triflic anhydride(22 μL, 0.130 mmol, 2 equiv) at 0° C. The resulting deep purple colored reaction mixture was let stir at 00° C. for 30 min. Then, the reaction was diluted with DCM and quenched with NaHCO$_3$. The phases were separated and the organic layer was washed with brine, dried over Na$_2$SO$_4$, filtered and the solvent evaporated. The resulting oil was co-evaporated with toluene, dissolved in DMF (1 mL) and used in the next step without further purification. Tetrabutylammonium acetate was added to the solution of the triflate (76*) in DMF and let stir overnight at rt. The solvent was evaporated. Column chromatography on silica gel (hexanes/ethyl acetate) afforded the quinovopyranoside 77* (26 mg, 0.044 mmol, 68%). [α]$_D^{20}$=−19.6 (c=0.56, CHCl$_3$); IR ν$_{max}$ (film) 2939, 2868, 2111, 1747, 1698, 1423, 1230, 1066, 699 cm$^{-1}$; $^1$H NMR (400 MHz, CDCl$_3$) δ 7.45-7.08 (m, 10H), 5.86 (ddt, J=17.2, 10.4, 5.7 Hz, 1H), 5.30-5.10 (m, 4H), 4.74 (t, J=9.5 Hz, 1H), 4.56-4.41 (m, 2H), 4.32-4.15 (m, 2H), 4.12-4.05 (m, 1H), 3.94-3.76 (m, 1H), 3.56-3.32 (m, 3H), 3.30-3.16 (m, 3H), 2.09 (s, 3H), 1.69-1.46 (m, 4H), 1.42-1.26 (m, 2H), 1.19 (d, J=6.2 Hz, 3H). $^{13}$C NMR (151 MHz, CDCl$_3$) δ 169.8, 138.1, 134.6, 128.7, 128.6, 128.04, 127.97, 127.4, 117.3, 102.0, 80.1, 74.9, 73.7, 70.2, 67.3, 66.2, 50.7, 50.4, 47.2, 46.3, 29.3, 28.0, 27.6, 23.3, 21.1, 17.5. HRMS (ESI+) Calcd for C$_{31}$H$_{40}$N$_4$O$_7$Na$^+$ [M+Na]$^+$ 603.2795, found 603.2809.

Example 71: N-(Benzyl)-benzyloxycarbonyl-5-amino-pentanyl 2-azido-2-deoxy-4-O-(2-naphthalenylmethyl)-3-O-allyl-β-D-quinovopyranoside (79*)

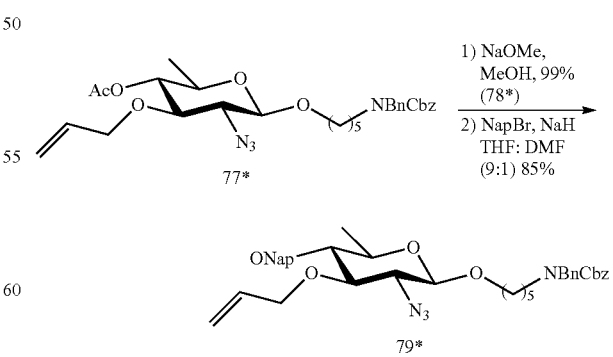

To a solution of quinovopyranoside 77* (35 mg, 0.060 mmol, 1 equiv) in MeOH (0.5 mL) was added 0.5 M NaOMe in MeOH (0.362 mL, 0.181 mmol, 3 equiv) and stirred overnight. The mixture was neutralized with Amberlite® IR 120 (H⁺) ion exchange resin, filtered and concentrated in vacuo. Column chromatography on silica gel (hexanes/ethyl acetate) afforded alcohol (78*) (32 mg, 0.059 mmol, 99%). 2-naphthalenylmethyl bromide (20 mg, 0.091 mmol, 1.5 equiv) was added to a solution of alcohol (78*) (32.5 mg, 0.060 mmol, 1 equiv) in THF: DMF (9:1, 1.0 mL). Then, the mixture was cooled to 0° C. and NaH 60% in mineral oil (3 mg, 0.121 mmol, 2 equiv) was added. The reaction was warmed to room temperature. After 1.5 h, 2 equiv of NaH were added and the reaction let stir for further 1 h. The reaction mixture was diluted with DCM and quenched with NaHCO₃. Then, the organic phase was washed with brine, dried over Na₂SO₄, filtered and the solvent evaporated. Column chromatography on silica gel (hexanes/ethyl acetate) afforded the quinovopyranoside 79* (35 mg, 0.052 mmol, 82%). ¹H NMR (400 MHz, CDCl₃) δ 7.78-7.71 (m, 3H), 7.70 (bs, 1H), 7.45-7.33 (m, 3H), 7.33-7.04 (m, 10H), 5.92 (ddt, J=16.4, 10.3, 5.8 Hz, 1H), 5.24 (dd, J=16.0, 1.6 Hz, 1H), 5.18-5.03 (m, 3H), 4.83 (ABq, J=11.0 Hz, 2H), 4.42 (d, J=7.7 Hz, 2H), 4.27 (qdt, J=12.2, 5.9, 1.5 Hz, 2H), 4.11 (t, J=8.7 Hz, 1H), 3.83-3.69 (tt, J=15.6, 6.3 Hz, 1H), 3.47-3.03 (m, 7H), 1.62-1.37 (m, 4H), 1.35-1.16 (m, 2H), 1.22 (d, J=6.1 Hz, 3H). ¹³C NMR (101 MHz, CDCl₃) δ 156.8, 156.3, 138.0, 137.0, 136.9, 135.5, 134.8, 133.4, 133.1, 128.63, 128.57, 128.4, 128.0, 127.9, 127.8, 127.4, 127.3, 126.9, 126.3, 126.2, 126.1, 101.9, 83.3, 82.7, 75.5, 74.4, 71.4, 70.0, 69.9, 67.2, 66.5, 50.6, 50.3, 47.2, 46.3, 29.3, 28.0, 27.5, 23.3, 18.0. HRMS (ESI+) Calcd for C₄₀H₄₆N₄O₆Na⁺ [M+Na]⁺ 701.3315, found 701.3348.

Example 72: N-(Benzyl)-benzyloxycarbonyl-5-amino-pentanyl 2-azido-2-deoxy-4-O-(2-naphthalenylmethyl)-β-D-quinovopyranoside (80*)

Iridium complex (0.71 mg, 0.884 µmol, 0.02 equiv) was taken in dry THF (2 mL) and bubbled with nitrogen for 2 minutes at rt. The red colored catalyst dissolved in THF. Then, the solution was purged with hydrogen for about 2 more minutes. The reaction mixture color changed from red to colorless and the solution was let stir for 15 minutes under hydrogen pressure. The solution of the active catalyst was added to the of solution of allyl quinovopyranoside 79* (30 mg, 0.044 mmol, 1 equiv) in dry THF (1 mL) under argon via syringe and let stir for 2 hours at rt. The reaction mixture was quenched with NaHCO₃ solution and extracted with DCM. Combined organic layers were washed with brine, dried over Na₂SO₄, filtered and evaporated to get the isomerized compound (isomerization confirmed by ¹H NMR). The substrate was taken in THF-water (2:1, 1.5 mL) and iodine (22 mg, 0.088 mmol, 2 equiv) was added at rt. The brown colored solution was stirred for 2 hours before quenched with 10% solution of Na₂S₂O₃ solution. Then, the aqueous phase was extracted with ethyl acetate (3×). Combined organic layers were dried over Na₂SO₄, filtered and the solvent evaporated to get brown liquid. Column chromatography on silica gel (hexanes/ethyl acetate) afforded the quinovopyranoside 80* (30 mg, 0.053 mmol, quant.). [α]$_D^{20}$=−8.4 (c=1.7, CHCl₃); IR ν$_{max}$ (film) 3429, 3032, 2937, 2868, 2110, 1698, 1455, 1424, 1093, 698 cm⁻¹; ¹H NMR (600 MHz, CDCl₃) δ 7.87-7.80 (m, 3H), 7.79 (s, 1H), 7.51-7.45 (m, 3H), 7.42-7.13 (m, 10H), 5.18 (d, J=18.8 Hz, 2H), 4.94 (ABq, J=11.4 Hz, 2H), 4.50 (d, J=12.8 Hz, 2H), 4.31-4.18 (m, 1H), 3.92-3.78 (m, 1H), 3.54-3.34 (m, 3H), 3.34-3.12 (m, 4H), 2.49 (d, J=2.8 Hz, 1H), 1.60 (q, J=13.9, 7.5 Hz, 4H), 1.43-1.27 (m, 2H), 1.36 (d, J=6.2 Hz, 3H). ¹³C NMR (151 MHz, CDCl₃) δ 156.9, 156.3, 138.1, 135.5, 133.4, 133.2, 128.7, 128.6, 128.1, 128.03, 127.96, 127.9, 127.3, 127.0, 126.4, 126.2, 126.0, 101.9, 83.2, 75.3, 71.4, 70.0, 67.3, 66.7, 50.7, 50.3, 47.2, 46.3, 29.4, 28.0, 27.6, 23.3, 18.1. HRMS (ESI+) Calcd for C₃₇H₄₂N₄O₆Na⁺ [M+Na]⁺ 661.3002, found 661.3019.

Example 73: Synthesis of N-(Benzyl)benzyloxycarbonyl-5-amino-pentanyl [2,3,4,6-tetra-O-benzyl-β-D-glucopyranosyl-(1→4)]-benzyl-3,4-di-O-benzyl-6-O-benzoyl-β-D-glucopyranosyluronate-(1→3)-2-azido-2-deoxy-α-L-fucopyranosyl-(1→3)-2-azido-2-deoxy-4-O-(2-naphthalenylmethyl)-β-D-quinovopyranoside (82*)

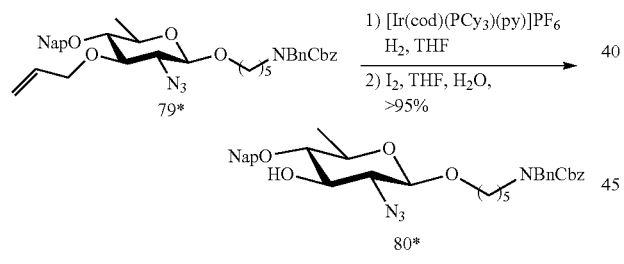

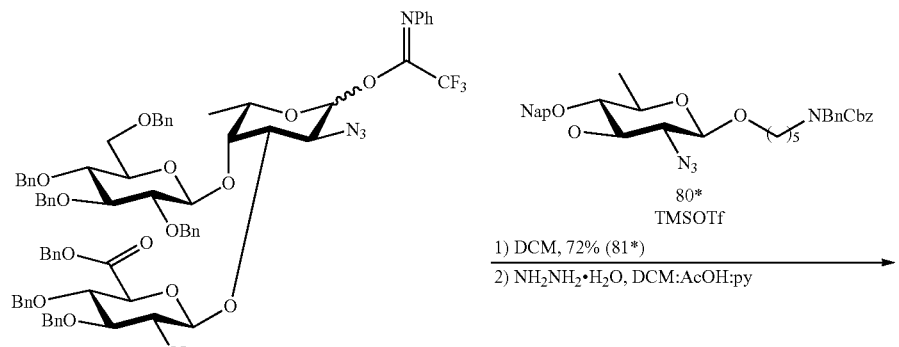

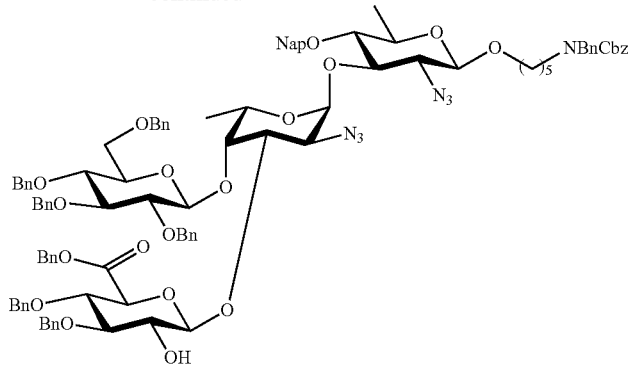

82*

Acceptor 80* (17 mg, 0.027 mmol, 1.9 equiv) and trisaccharide imidate 68* (20 mg, 0.014 mmol, 1.0 equiv) were coevaporated with toluene two times and dried in vacuo. The residue was dissolved in DCM (1 mL). Molecular sieves acid washed (4 Å) were added and the reaction mixture cooled to −35° C. TMSOTf (1 µL, 5.5 µmol, 0.4 equiv) was added and the reaction let warm to −20° C. over 1 h. The reaction was quenched with triethylamine, filtered and the solvent evaporated. Column chromatography on silica gel (hexanes/ethyl acetate) afforded tetrasaccharide (81*) (19.3 mg, 10.3 µmol, 73%). HRMS (ESI+) Calcd for $C_{109}H_{117}N_7O_{22}Na^+$ [M+Na]$^+$ 1899.8183, found 1899.8203. To a solution of tetrasaccharide (81*) (17 mg, 0.009 mmol, 1 equiv) in DCM (1 mL), a solution of hydrazine hydrate (6 µL, 0.12 mmol, 13 equiv) dissolved in AcOH (0.04 mL) and pyridine (0.06 mL) was added. The resulting reaction mixture was stirred at rt for 1 to 2 h. The reaction was quenched by the addition of acetone and the solvent evaporated. Column chromatography on silica gel (hexanes/ethyl acetate) afforded tetrasaccharide 82* (14 mg, 7.87 µmol, 87%). $^1$H NMR (400 MHz, CDCl$_3$) δ 7.72 (m, 3H), 7.66 (bs, 1H), 7.41-7.35 (m, 2H), 7.31-7.12 (m, 41H), 7.09-7.04 (m, 3H), 6.98-6.90 (m, 2H), 5.59 (d, J=3.7 Hz, 1H), 5.15-5.04 (m, 4H), 4.97-4.87 (m, 2H), 4.82-4.57 (m, 8H), 4.47-4.40 (m, 5H), 4.35-4.28 (m, 3H), 4.27-4.18 (m, 1H), 4.13 (d, J=7.1 Hz, 1H), 3.99-3.80 (m, 5H), 3.68-3.31 (m, 16H), 3.25-3.10 (m, 4H), 1.65-1.40 (m, 4H), 1.37-1.22 (m, 2H), 1.31 (d, J=6.1 Hz, 3H), 0.75 (d, J=6.6 Hz, 3H). HRMS (ESI+) Calcd for $C_{104}H_{111}N_7O_{20}Na^+$ [M+Na]$^+$ 1801.7815, found 1801.7781.

Example 74: Synthesis of N-(Benzyl)benzyloxycarbonyl-5-amino-pentanyl 2-azido-3,4-di-O-benzyl-2-deoxy-α-L-pneumopyranosyl-(1→2)-[2,3,4,6-tetra-O-benzyl-β-D-glucopyranosyl-(1→4)]-benzyl-3,4-di-O-benzyl-6-O-benzoyl-β-D-glucopyranosyluronate-(1→3)-2-azido-2-deoxy-α-L-fucopyranosyl-(1→3)-2-azido-2-deoxy-4-O-(2-naphthalenylmethyl)-β-D-quinovopyranoside (83*)

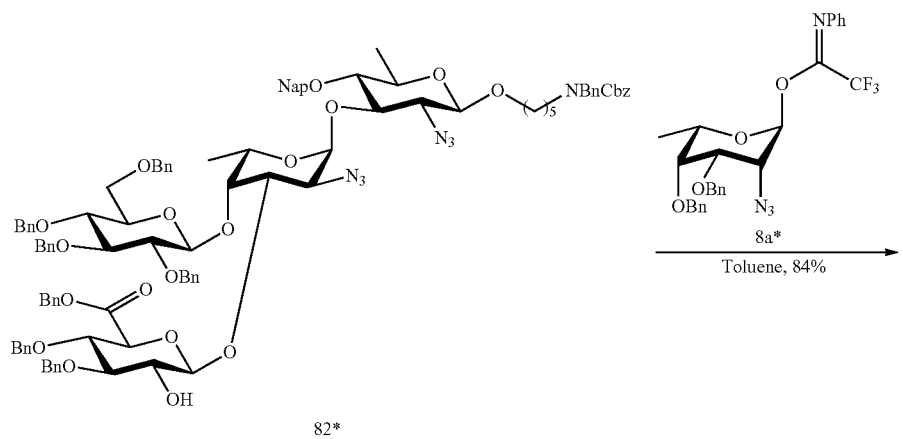

82*

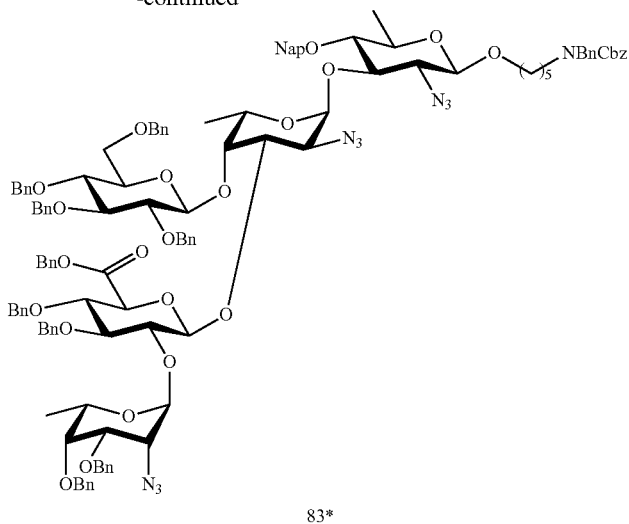

83*

Acceptor 82* (13.5 mg, 7.6 µmol, 1.0 equiv) and imidate 8a* (10 mg, 0.019 mmol, 2.4 equiv) were coevaporated with toluene two times and dried in vacuo. The residue was dissolved in toluene (1 mL). The reaction mixture cooled to −35° C. TMSOTf (0.25 µL, 1.4 µmol, 0.1 equiv) was added and the reaction let warm to −20° C. over 2 h. The reaction was quenched with triethylamine, filtered and the solvent evaporated. Column chromatography on silica gel (hexanes/ethyl acetate) afforded pentasaccharide 83* (13.5 mg, 6.34 µmol, 84%). HRMS (ESI+) Calcd for $C_{124}H_{132}N_{10}O_{23}Na^+$ [M+Na]$^+$ 2152.9398, found 2152.9406.

Example 75: Synthesis of 5-amino-pentanyl 2-N-acetyl-α-L-pneumopyranosyl-(1→2)-[β-D-glucopyranosyl-(1→4)]-β-D-glucopyranosyluronate-(1→3)-2-N-acetyl-α-L-fucopyranosyl-(1→3)-2-N-acetyl-β-D-quinovopyranoside (85*)

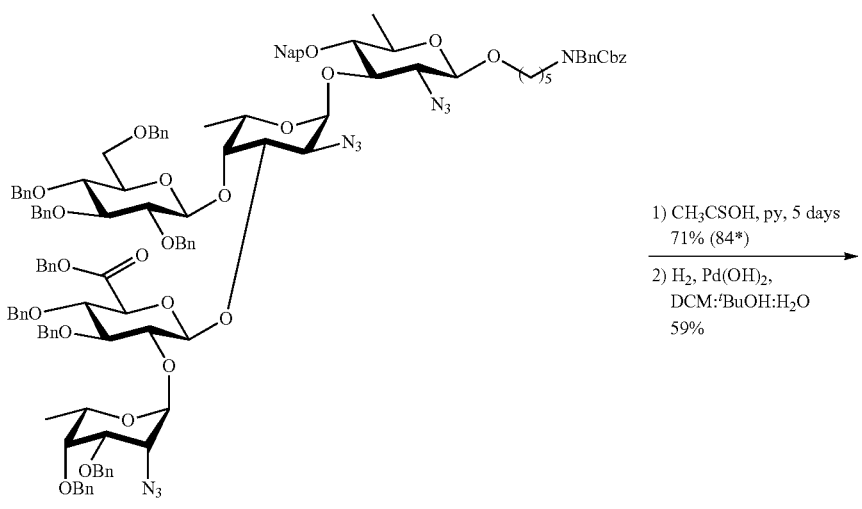

83*

1) CH$_3$CSOH, py, 5 days
   71% (84*)

2) H$_2$, Pd(OH)$_2$,
   DCM:$^t$BuOH:H$_2$O
   59%

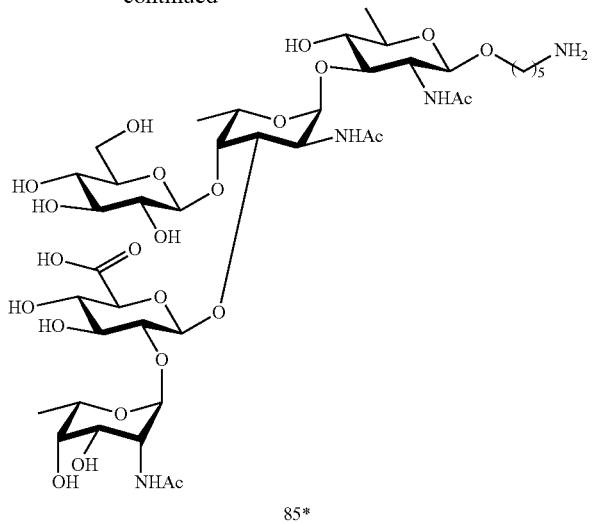

85*

To a solution of azido pentasaccharide 83* (13 mg, 6.1 μmol, 1 equiv) in pyridine (1 mL), thioacetic acid (0.25 mL) was added and stirred for 5 days at rt. The reaction mixture was concentrated and purified by column chromatography on silica gel (hexanes/acetone) to afford the acetamide pentasaccharide (84*) (9.4 mg, 4.31 μmol, 71%). HRMS (ESI+) Calcd for $C_{130}H_{144}N_4O_{26}Na^+$ [M+Na]$^+$ 2201.0000, found 2201.0027. The pentasaccharide (84*) (5.5 mg, 2.52 μmol, 1 equiv) was dissolved in $CH_2Cl_2$/tBuOH/water (1.5: 16:8, 1 mL), purged with argon and treated with a suspension of Pd(OH)$_2$ on carbon (20% (w/w) loading, 10 mg) in the same solvent mixture (1 mL). The suspension was purged with hydrogen and stirred under hydrogen atmosphere at rt. After 24 h, a freshly prepared suspension of Pd(OH)$_2$ (5 mg, 1 mL) was added and the reaction was stirred for 24 h more, filtered and concentrated. The residue was purified by solid phase extraction (Chromabond C18, Macherey-Nagel) and size exclusion chromatography on Sephadex LH-20 (MeOH:H$_2$O) and lyophilized to give pentasaccharide 85* (1.5 mg, 1.49 μmol, 59%) as a white solid. $^1$H NMR (400 MHz, D$_2$O) δ 5.20 (d, J=4.0 Hz, 1H), 5.09 (s, 1H), 5.01 (d, J=7.6 Hz, 1H), 4.52 (d, J=7.9 Hz, 1H), 4.51-4.29 (m, 5H), 4.18-4.13 (m, 1H), 4.13-4.07 (m, 1H), 4.02-3.90 (m, 2H), 3.86-3.62 (m, 6H), 3.58 (t, J=9.4 Hz, 1H), 3.54-3.30 (m, 9H), 3.25 (t, J=9.2 Hz, 1H), 3.13 (dd, J=9.3, 7.9 Hz, 1H), 2.97-2.92 (m, 2H), 2.01 (s, 3H), 1.97 (s, 3H), 1.96 (s, 3H), 1.68-1.49 (m, 4H), 1.40-1.31 (m, 2H), 1.31-1.23 (m, 6H), 1.07 (d, J=6.6 Hz, 3H). $^{13}$C NMR (151 MHz, D$_2$O) δ 175.8, 173.9, 173.6, 173.2, 102.6, 101.3, 99.5, 96.0, 93.6, 77.6, 77.1, 76.3, 75.8, 75.7, 75.3, 73.7, 73.4, 71.8, 71.5, 71.1, 70.7, 69.9, 69.7, 66.9, 66.8, 66.6, 63.7, 60.5, 55.5, 50.6, 48.7, 39.2, 28.0, 26.6, 22.2, 22.1, 22.0, 21.8, 16.6, 15.6, 15.2. HRMS (ESI+) Calcd for $C_{141}H_{70}N_4O_{24}Na^+$ [M+Na]$^+$ 1025. 4278, found 1025.4309.

Example 76: 5-amino-pentanyl [β-D-glucopyranosyl-(1→4)]-β-D-glucopyranosyluronate-(1→3)-2-N-acetyl-α-L-fucopyranoside (Ref. 1)

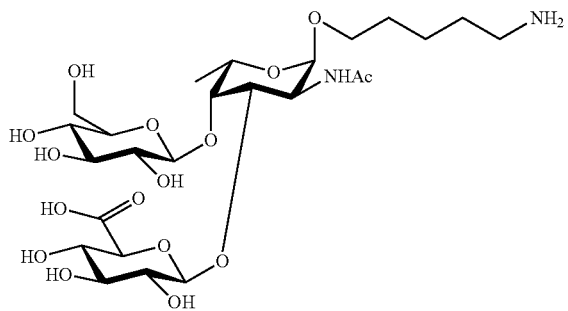

$^1$H NMR (400 MHz, D$_2$O) δ 4.93 (d, J=3.5 Hz, 1H), 4.67-4.56 (m, 2H), 4.30-4.27 (m, 1H), 4.26-4.03 (m, 3H), 3.92-3.84 (m, 1H), 3.76-3.60 (m, 3H), 3.54-3.25 (m, 8H), 2.94 (t, J=7.6 Hz, 2H), 1.97 (s, 3H), 1.68-1.52 (m, J=20.7, 7.0, 6.4 Hz, 4H), 1.44-1.34 (m, J=7.6 Hz, 1H), 1.31 (d, J=6.7 Hz, 3H), 1.27-1.18 (m, 1H). HRMS (ESI+) Calcd for $C_{25}H_{44}N_2O_6Na^+$ [M+Na]$^+$ 651.2589, found 651.2598.

Example 77: 5-amino-pentanyl [β-D-glucopyranosyl-(1→4)]-β-D-glucopyranosyluronate-(1→3)-2-N-acetyl-α-L-fucopyranosyl-(1→3)-2-N-acetyl-β-D-fucopyranoside (Ref. 2)

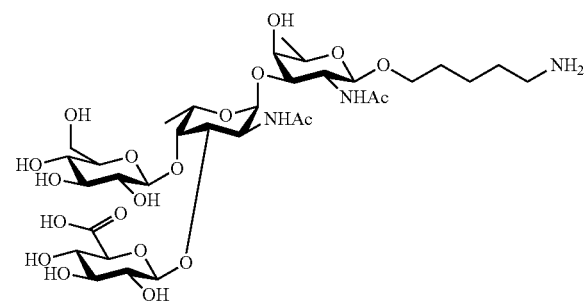

$^1$H NMR (400 MHz, D$_2$O) δ 5.04 (d, J=3.9 Hz, 1H), 4.65-4.60 (m, 2H), 4.38 (d, J=8.5 Hz, 1H), 4.34-4.06 (m,

4H), 3.95-3.24 (m, 16H), 2.98-2.90 (m, 2H), 1.98 (s, 3H), 1.96 (s, 3H), 1.68-1.49 (m, 4H), 1.41-1.17 (m, 2H), 1.31 (d, J=6.8 Hz, 3H), 1.23 (d, J=6.5 Hz, 3H). HRMS (ESI+) Calcd for $C_{33}H_{57}N_3O_{20}Na^+$ [M+Na]$^+$ 833. 3433, found 833.3441.

Example 78: Glycan Microarray Preparation and Screening—I 64 well glycan arrays were printed using a Scienion S3 microarray printer on CodeLink® NHS activated glass slides (Surmodics). All compounds (proteins and glycans containing an aminolinker) were dissolved in printing buffer (50 mM sodium phosphate, pH 8.5). The printed slides were stored overnight in a humidity saturated chamber for complete reaction, dried by centrifugation at 1200 g and stored at 4° C. afterwards. Prior to use, slides were washed with water, quenched with quenching solution (50 mM sodium phosphate, 100 mM ethanolamine, pH 7.4) at room temperature for 2 h, washed with water and blocked for 1 h at room temperature with 1% BSA in PBS. After washing with PBS, the slides were dried by centrifugation. A 64 well gasket was applied to the slides and primary antibody incubation (serum dilutions in 1% BSA-PBS) was carried out at room temperature for 1 h. The wells were washed three times for 10 min with PBS containing 0.1% Tween-20. Secondary antibody dilutions were pipetted into the wells. After 1 h incubation at room temperature in the dark, the slides were washed three times for 10 min with PBS containing 0.1% Tween-20 and once shortly with water. The gasket was removed and the slides were dried by centrifugation. Fluorescence was read out using a GenePix 4300A microarray scanner (Bucher Biotec, Basel, Switzerland) with a 488 nm laser for FITC excitation and a 594 nm laser for AlexaFluor 594. GenePix Pro 7 (Bucher Biotec) was used for analysis.

Figure 1:
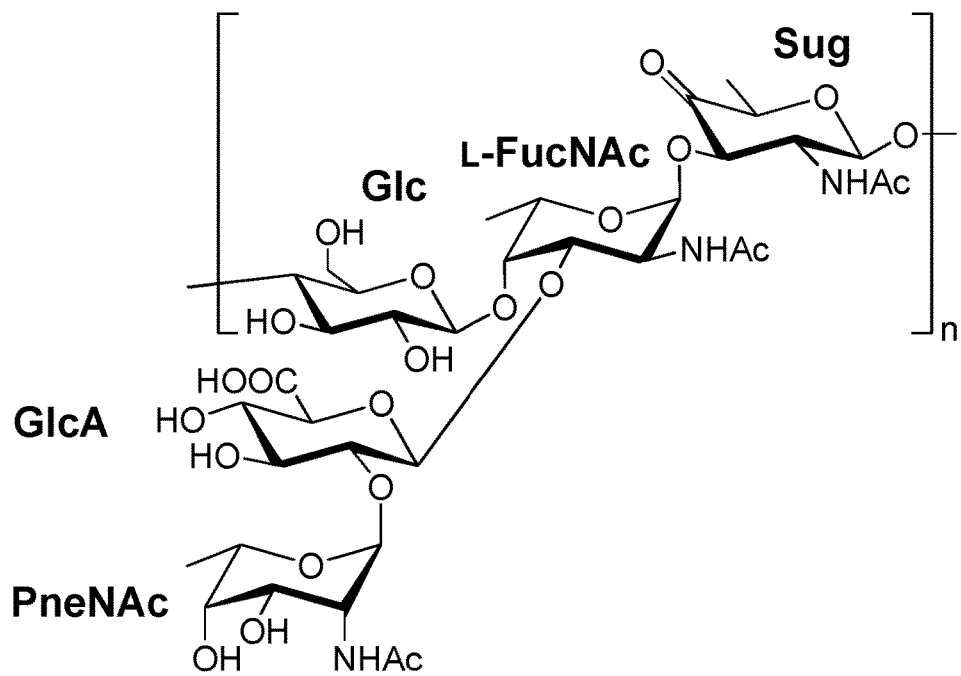
FIG. 1 shows the chemical structure of the *S. pneumoniae* serotype 5 repeating unit.
Figure 3:
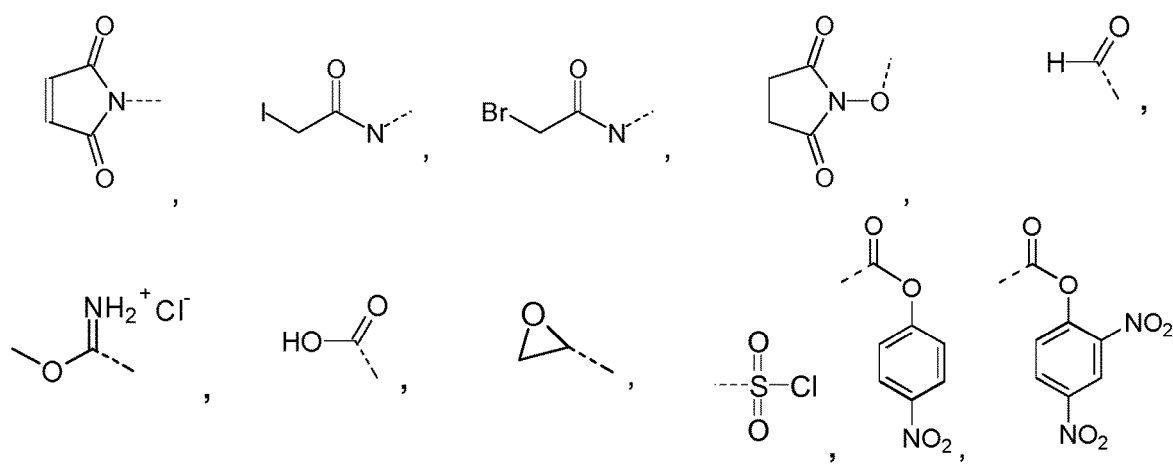
FIG. 3 provides examples of functional group X of the interconnecting molecule according to the present invention.
Figure 4:
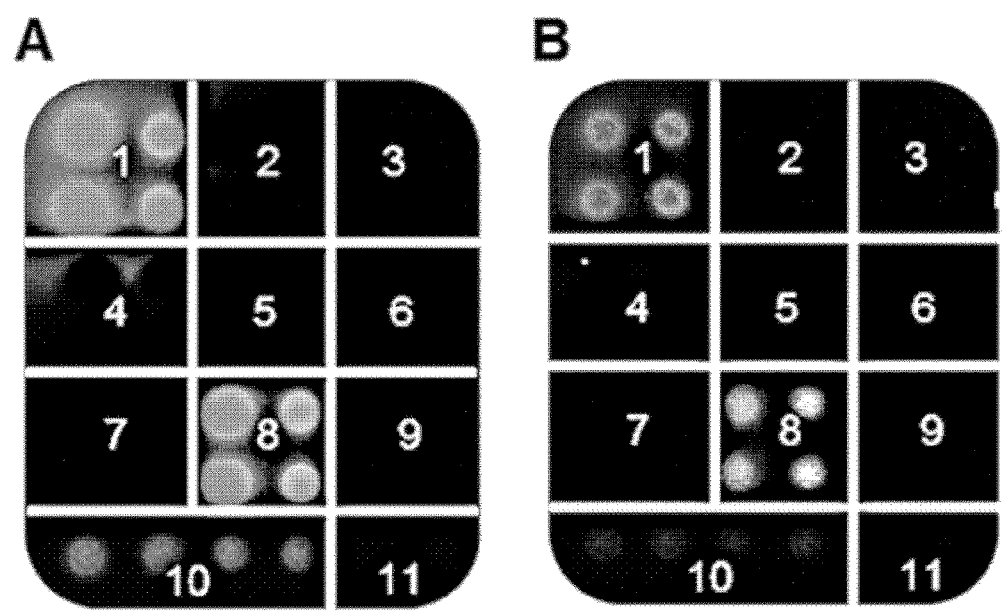
FIG. 4 shows the results of the glycan array screening of *S. pneumoniae* serotype 5 rabbit typing serum. A) Representative well of rabbit typing serum (dilution 1:1000); B) Representative well of rabbit typing serum (dilution 1:1000) pre-incubated with SP5 CPS (5 μg/mL); C) Table listing the positions 1-11 of respective glycans. Samples 14* and 20* were impure.

A glycan microarray prepared as above described containing eleven SP5 CPS substructures was used to identify the binding epitopes of commercial anti-SP5 specific typing sera generated in rabbits (see FIG. 4).

As shown by FIG. 4A, only three out of eleven glycans were bound by specific anti-SP5 IgG, namely tetrasaccharide 33* (position 1), α-PneNAc-(1→2)-GlcA disaccharide 27* (position 8) and α-PneNAc monosaccharide 36* (position 10). All three recognized oligosaccharides contain the α-PneNAc residue, demonstrating that this motif is part of the recognized epitope. It was further observed that IgG bound tetrasaccharide 33* and disaccharide 27* in comparable levels, suggesting that α-PneNAc-(1→2)-GlcA is in fact the epitope recognized by IgG of specific SP5 typing sera. FIG. 4B shows a microarray sample where the typing serum was pre-incubated with a solution of the natural SP5 CPS. The anti-glycan IgG levels are significantly reduced compared to the sample of FIG. 4A. This means that antibodies bound to the natural CPS during pre-incubation are no longer available for binding to the synthetic glycans. Consequently, the binding epitopes of natural CPS and the synthetic glycans are identical.

Figure 5:
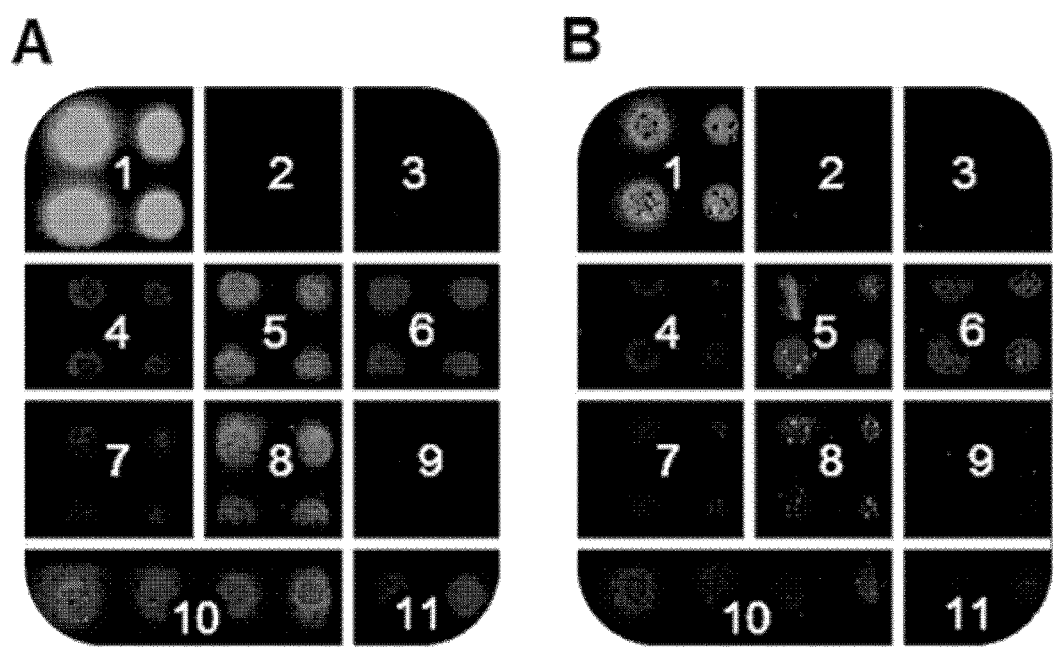
FIG. 5 shows the results of the glycan array screening of human pneumococcal CPS vaccine recipients' pooled serum. A) Representative well of human pneumococcal serum (dilution 1:100); B) Representative well of human pneumococcal serum (dilution 1:100) pre-incubated with SP5 CPS (5 µg/mL); C) Table listing the positions 1-11 of respective glycans. Samples 14* and 20* were impure.

In order to identify epitopes recognized by the human immune system, further screenings were carried out using pooled sera of humans who had received a pneumococcal CPS-based vaccine, containing the CPS of multiple different serotypes (see FIG. 5).

The IgG response of immunized humans towards the synthetic glycans is shown in FIG. 5A. Although the sera of immunized humans were not SP5 specific, they contained IgG predominantly against tetrasaccharide 33* (position 1). IgG binding to PneNAc-(1→2)-GlcA disaccharide 27* (position 8) and PneNAc 36* (position 10) were also observed, however at lower levels.

Additionally, low levels of anti-21* (position 5) and anti-51* (position 6) IgG and very low levels of anti-20* (position 4), anti-44* (position 7), anti-52* (position 9) and anti-37* (position 11) IgG were detected. Antibodies against D-FucNAc 15* (position 3) and the Sug-containing sample 14* (position 2) were not detected at all. Interestingly, higher levels of anti-disaccharide 21* antibodies were detected than for the sample containing L-FucNAc-(1→3)-β-Sug 20*. This would suggest that the presence of the ketone is indeed detrimental to antibody binding. Pre-incubation of the human sera with the natural SP5 CPS, shown in FIG. 5B, led to a significant reduction of anti-tetrasaccharide 33* IgG levels. This proves that the antibodies binding 33* are SP5 specific since they also bind the SP5 CPS.

In conclusion, the microarray analyses revealed that the terminal PneNAc residue is part of the epitope recognized by anti-SP5 CPS antibodies and that α-PneNAc-(1→2)-GlcA is the predominant epitope recognized by SP5 typing sera. In the case of vaccinated humans, the SP5-specific epitope seems to be larger, resembling tetrasaccharide 33*. The reducing end D-FucNAc or Sug residues do not seem to be important for the immunological response to SP5.

Example 79: Conjugation of Tetrasaccharide 33* to $CRM_{197}$: Synthesis of Conjugate 58*a, 58*b and 58*c Conjugates were prepared using a two-step procedure as described here in details.

Step 1: Formation of the p-Nitro Phenyl (PNP) Amide

To the tetrasaccharide 33* (0.5 mg, 0.6 μmol, 1 equivalent) and diphenyl adipate (1.6 mg, 4.2 μmol, 7 equivalents) in a glass vial were added a mixture of pyridine and DMSO (1:1, 0.24 mL) and the mixture let stir for 5 minutes for complete solubilization. Then, triethylamine (0.83 μL, 6 μmol, 10 equivalents) was added and let stir for 20 minutes. TLC indicated complete consumption of the starting material. The solvent was removed in vacuum. The residue was washed with dichloromethane (3×1 mL) to remove PNP ester excess and the white solid obtained was dried in vacuum.

Step 2: Conjugation with $CRM_{197}$

The compound obtained at step 1 (40 equivalents) was dissolved in DMSO (10 μL), $CRM_{197}$ (1 equivalent) was added in sodium phosphate buffer (0.1 NaPi, pH ~8.0) and the mixture let stir for 18 h. Then, the reaction mixture was washed twice with 400 μL of buffer (pH ~8.0), followed by washing with 400 μL of autoclaved water three times using amicon filter (10000 KDa). The material was transferred to Eppendorf vial using PBS buffer and stored at −20° C. (400 μL).

The same procedure was repeated with buffer pH ~8.5.

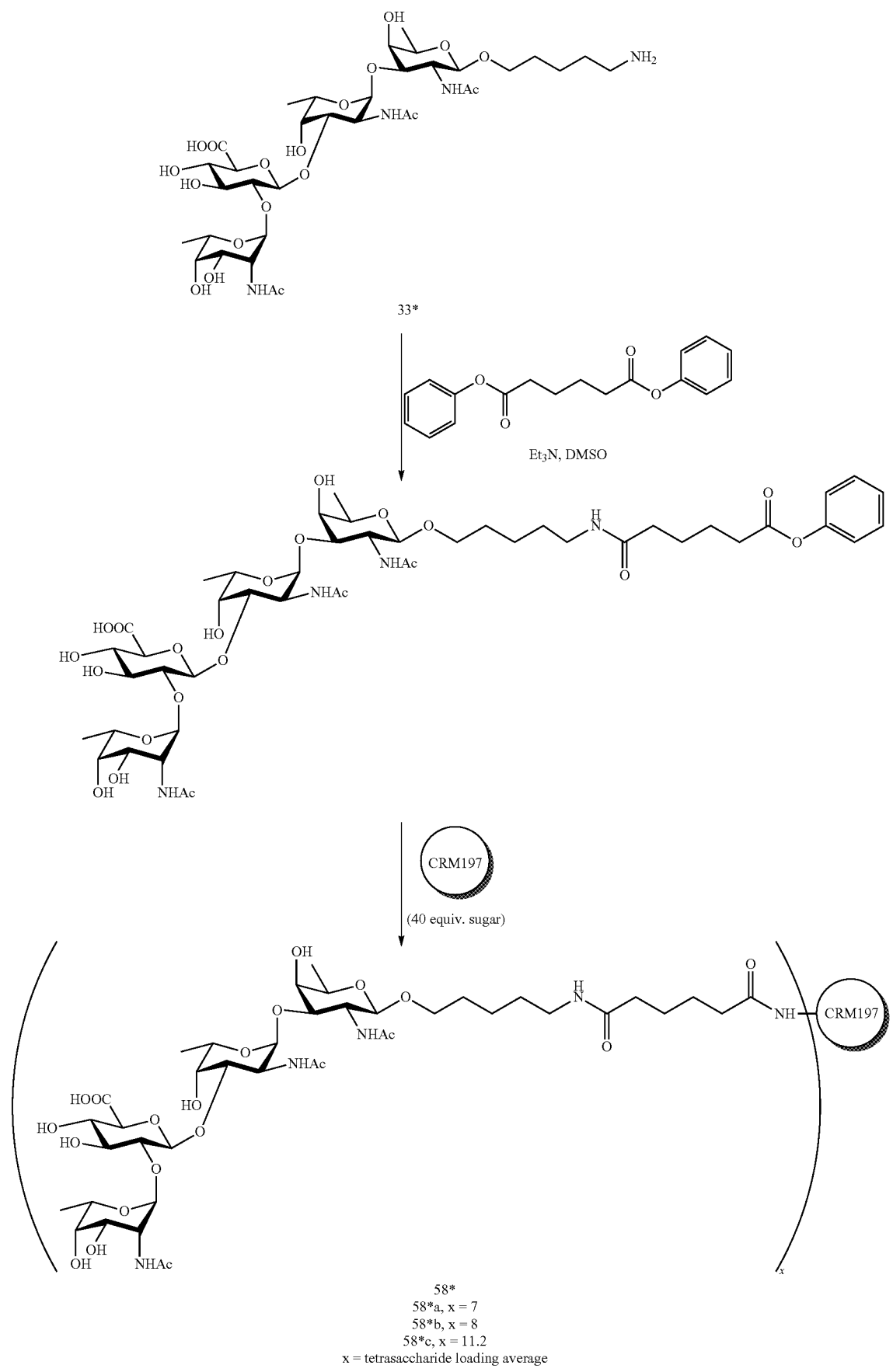

Pentasaccharide conjugate 87* was obtained by conjugation of pentasaccharide 73* to $CRM_{197}$.

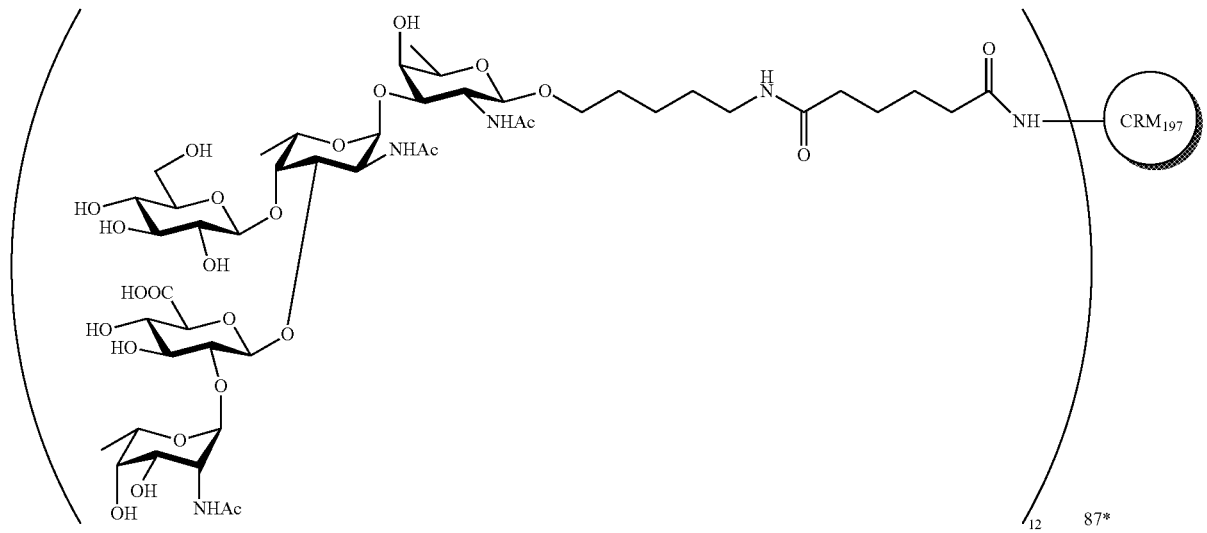

Figure 6:
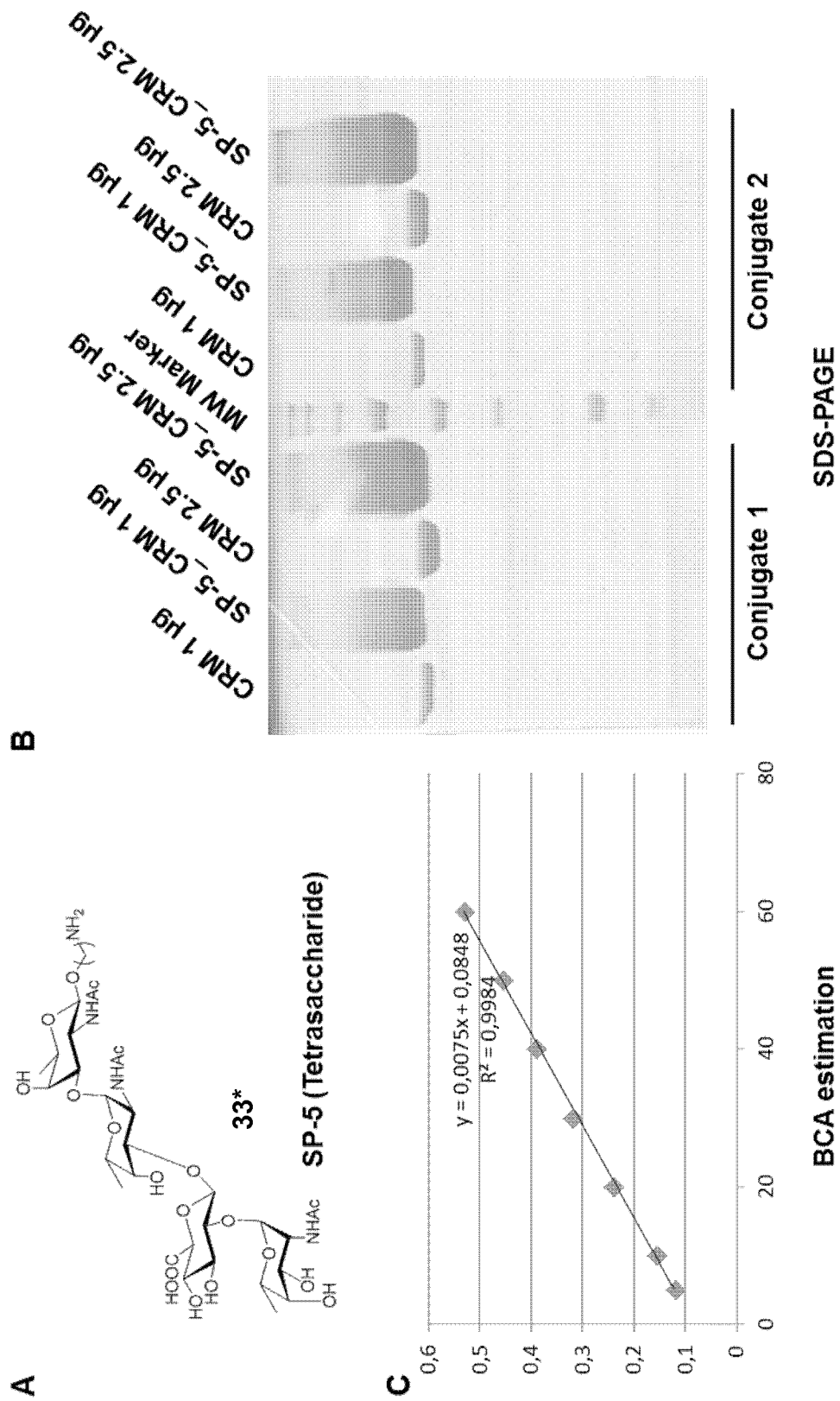
FIG. 6: A) Chemical structure of synthetic SP-5 tetrasaccharide 33*; B) Tetrasaccharide 33* was conjugated with $CRM_{197}$ by PNP based chemistry and resolved on 10% SDS-PAGE along with recombinant $CRM_{197}$ and stained with Coomassie brilliant blue R250. The molecular weight marker is shown in the middle of SDS-PAGE; C) The protein amount was estimated using the standard curve plotted with known concentration of BSA (BCA: Bicinchoninic Acid).
Figure 7:
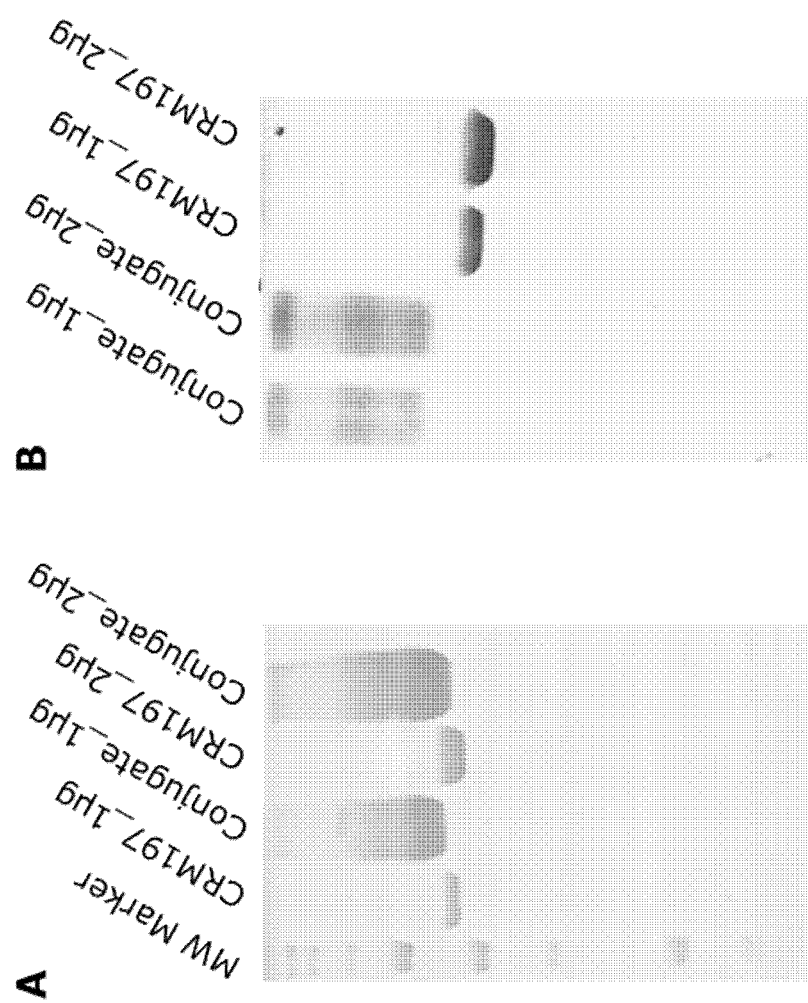
FIGS. 7: A and B: The tetrasaccharide 33* and pentasaccharide 73* of ST5 were conjugated with $CRM_{197}$ by PNP based chemistry and resolved on 10% SDS-PAGE along with recombinant $CRM_{197}$ and stained with Coomassie brilliant blue R250 respectively. The molecular weight marker is shown in the extreme left of SDS-PAGE; C and D: Matrix-assisted laser desorption/ionization (MALDI) analysis was carried out to measure the average molecular size of ST5 tetrasaccharide 33* and pentasaccharide 73* conjugates at pH 8.0 respectively. The recombinant $CRM_{197}$ was used as standard.

Maldi analysis:
1) Conjugate 58*α (conjugate 1 in FIG. 6 B): pH 8.0, 0.9 mg $CRM_{197}$, tetrasaccharide loading average=7
2) Conjugate 58*b (conjugate 2 in FIG. 6 B): pH 8.5, 0.6 mg $CRM_{197}$, tetrasaccharide loading average=8
3) Conjugate 58*c (conjugate 2 in FIG. 7 A): tetrasaccharide loading average=11.2
4) Conjugate 87* (conjugate in FIG. 7 B): at pH 8.0, pentasaccharide loading average=12

Characterization of Conjugates

Maldi Analysis:

The average molecular size of conjugates 58*a and 58*b was determined by Matrix-assisted laser desorption/ionization (MALDI) analysis using $CRM_{197}$ as standard and calculate the average number of tetrasaccharide attached per $CRM_{197}$ molecule.

SDS-PAGE:

The conjugates were resolved by SDS-PAGE (10%) in denaturing condition. The samples were prepared in 6×SDS-PAGE sample loading dye. The electrophoresis was carried out at 120 V and 25 mA for 1 hr 30 min in electrode buffer and gel was stained with Coomassie brilliant blue R250.

Protein Estimation

The protein concentration was estimated using Micro BCA Protein Assay Kit (Thermo-scientific, USA) following the manufacturer's instructions. The sample was prepared in PBS and mixed with equal volume of reagent mixture (B:C:A::24:1:25). The plate was incubated at 37° C. and the absorbance was measured at 560 nm. The standard curve was plotted with known concentration of BSA provided with the kit.

Mice Immunization and Generation of Polyclonal Sera

Ten to twelve week old female ZIKA rabbits (n=3) were immunized subcutaneously with the conjugates in alum (10 μg conjugate in alum (aluminum hydroxide)) formulation at day 0, 14 and 28. Preimmune and hyperimmune sera were collected at day 0, 14, 21 and 35. Control group received only $CRM_{197}$ in alum formulation. The immune responses were analyzed by glycan microarray and ELISA.

Example 80: Glycan Microarray Preparation and Screening—II

Preparation of Microarrays Slides:

Oligosaccharides, polysaccharides, $CRM_{197}$ and spacer bearing glass slides were prepared, quenched, blocked with 1% BSA-PBS and stored at 4° C. until use.

The CodeLink NHS activated glass slides (Surmodics) were spotted with synthetic glycans and native polysaccharides at two different concentrations (100 μM and 200 μM) in printing buffer (50 mM sodium phosphate, pH 8.5) by using a S3 piezoelectric microarray printer (Scienion) equipped with a type 4 coated nozzle. The relative humidity of spotted chamber was constantly maintained at 65%. The spotted slides were incubated over night at room temperature in a humidifying chamber. The unreactive groups on the slides were blocked with 50 mM sodium phosphate, 100 mM ethanolamine pH 9.0 at room temperature for one hour. Slides were subsequently washed three times for 5 min with water, dried by centrifugation at 300 g for 5 min (CombiSlide system, Eppendorf) and stored at 4° C. until use.

Microarray Binding Assays:

A FlexWell 64 (Grace Bio-Labs, Bend, Oreg., USA) grid was applied to microarray slides (The grid was applied on the printed slides as mentioned above). Slides were incubated with polyclonal sera raised in rabbits against SP-5 tetrasaccharide and pentasaccharide conjugates at different dilutions, diluted in 1% BSA-PBS (w/v) in a humid chamber for 1 h at room temperature, washed three times with 0.1% Tween-20 in PBS (v/v) and dried by centrifugation (300×g, 5 min). Slides were incubated with a fluorescence-labeled secondary antibody, goat anti-mouse IgG 635 nm (red; 1 in 400 dilution), goat anti mouse IgM 594 nm (yellow; 1 in 200 dilution) and goat anti-rabbit FITC488 (1 in 200 dilutions) (Life Technologies, USA) diluted in 1% BSA in PBS (w/v) in a humid chamber for 1 h at room temperature, washed three times with 0.1% Tween-20 in PBS (v/v), rinsed once with deionized water and dried by centrifugation (300×g, 5 min) prior to scanning with a GenePix 4300A microarray scanner (Molecular Devices, Sunnyvale, Calif., USA). Image analysis was carried out with the GenePix Pro 7 software (Molecular Devices). The photomultiplier tube (PMT) voltage was adjusted such that scans were free of saturation signals (FIG. 8).

Figure 8:
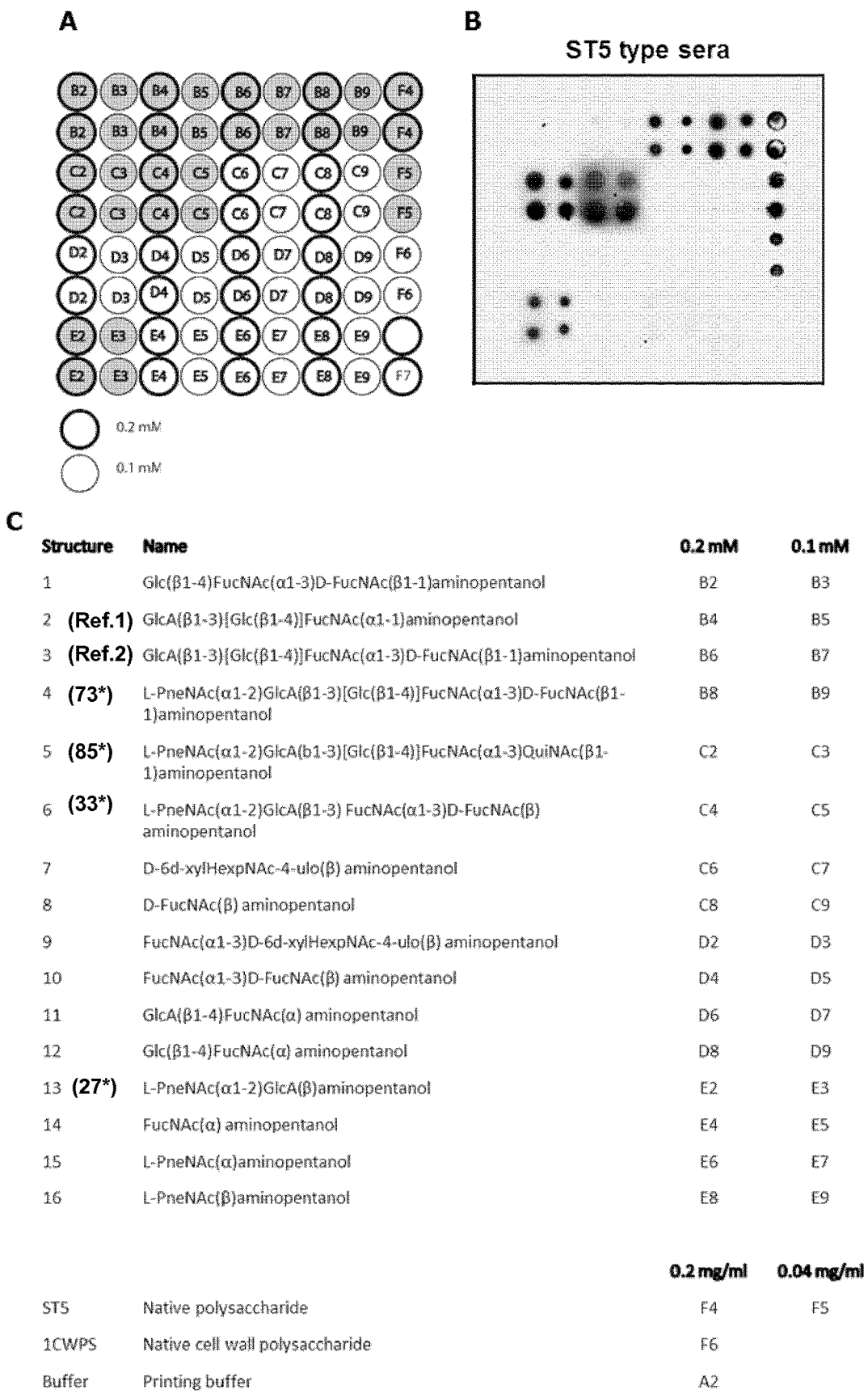
FIG. 8: Microarray with ST5 type sera

Further microarray was preparte to identify the smallest glycan structure of CPS-5 polysaccharide, we incubated the microarray slides with ST5 type sera raised in rabbit (FIG. 8). The reactivity pattern of type sera against printed glycan's and polysaccharide was analyzed by glycan microarray. The microarray data indicated that the type sera recognized the several synthetic glycans along with CPS-5 polysaccharide (FIG. 8B). However the type sera also recognized the tetrasaccharide 33* and pentasaccharide 73*/85* with high affinity which are considered to be the B cell epitopes that has been presented by the MHCII molecules. Thus, the following results suggest that these oligosaccharides are critical for immunity.

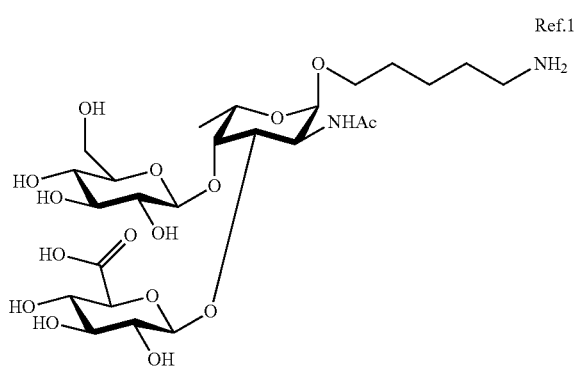

Ref.1

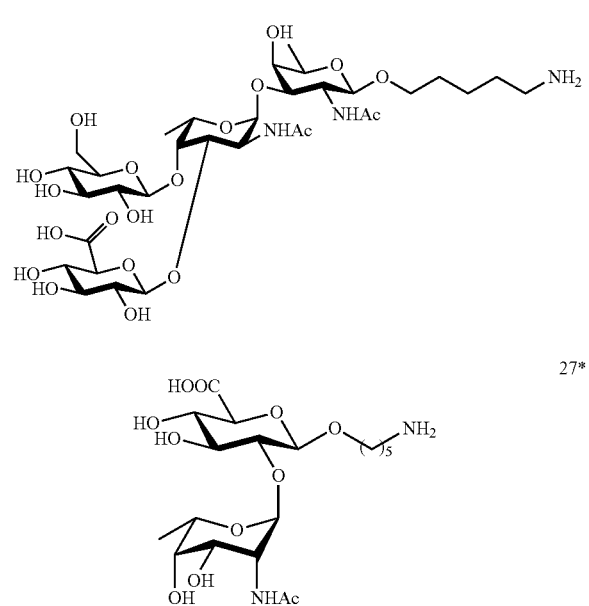

Ref.2

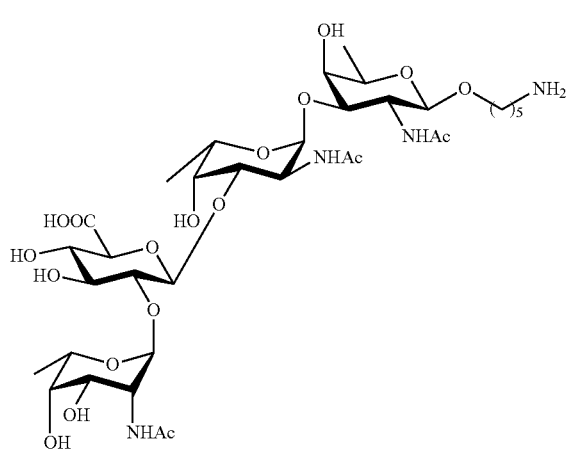

27*

33*

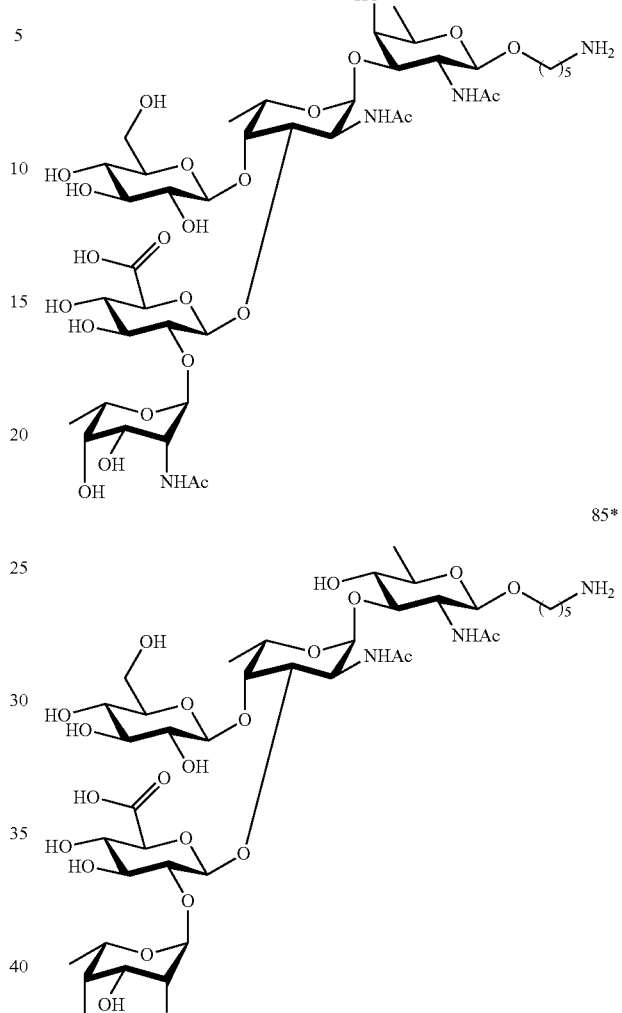

73*

85*

Example 81: Glycan Microarray with Antibodies Raised in Rabbit Against ST5 Synthetic Glycan Conjugates To analyze the ST5 synthetic glycans specific immune response, we subjected hyperimmune sera raised in rabbit (n=3) immunized with ST5 tetrasaccharide (58*c) and pentasaccharide conjugates (87*) to microarray slides. The microarray data suggested that the synthetic glycans specific antibodies were cross-reactive with the structures printed on slides and native polysaccharide (FIGS. 9B and D). This result suggested that the tetrasaccharide 33* and pentasaccharide 73* are immunogenic in rabbit and induced cross-reactive antibodies.

Example 82: ELISA

The end point titer of rabbit sera were analyzed by ELISA. High binding ninety six well polystyrene microtiter plates (Corning, USA) were coated overnight at 4° C. with CSP-5 (50 μl of 10 μg/ml per well) in PBS, pH 7.2. The plates were washed thrice with PBS containing 0.1% Tween-20 (PBST) and blocked with 10% FCS in PBS at 37° C. for 1 hr. After washing thrice with PBST, the plate was incubated with the individual and pooled rabbit serum (n=3) at different dilutions in duplicate or triplicates at 37° C. for 1 hr. The plate was washed 4-5 times with PBST and incubated with HRP conjugated goat anti-rabbit IgG antibodies (diluted 1 in 10,000 in PBS containing serum diluted in 10% FCS followed by incubation at 37° C. for 1 hr. The plate was washed thoroughly with PBST and developed using 3,3',5,5'-tetramethylbenzidine (Thermo Fisher Scientific, USA). The reaction was stopped by adding 2% $H_2SO_4$ and absorbance recorded at 450 nm.

Antibody Responses Analyzed by ELISA

Three groups of rabbit (n=3) were immunized with 10 μg of glycans equivalent conjugate on day 0, 14 and 28 subcutaneously, and the antibody responses were analyzed at different time point. The CSP-5 (Life Technologies, USA) polysaccharide specific endpoint antibody titer of the individual rabbit serum was determined. Immunization with tetrasaccharide and pentasaccharide conjugates induced high antibody titers (FIG. 10A). We further quantitated the polysaccharide specific immunoglobulins by endpoint (FIG. 10B). Endpoint titer was calculated as the reciprocal of the highest serum dilution that gave an absorbance value obtained with the preimmune sera (diluted 1:1000). The antibody response for individual animal of each groups were plotted as fold change at day 35. This analysis suggested that pentasaccharide 73* or conjugate 87* is more immunogenic compared to tetrasaccharide 33* or conjugate 58*c.

Example 83 Surface Binding of Anti-ST5 Glycan Conjugates Sera

The protective immunity against pneumococci is primarily antibody mediated and for an effective vaccine candidate the B cell epitopes should be accessible to the antibody. To investigate the accessibility of B cell epitope, we performed the flow cytometry for surface staining. The UV inactivated pneumococcal cells were incubated with preimmune and hyperimmune sera followed by the FITC-conjugated goat anti-rabbit antibodies. The stained bacteria were analyzed by flow cytometry. The flow cytometry data indicated that the pneumococcal cells incubated with hyperimmune sera exhibited the surface staining (tetrasaccharide; black histogram and pentasaccharide; gray histogram). We did not observe any staining with the preimmune sera (doted black histogram). This indicated that antibodies against the anti-ST5 glycans localized the epitope on the surface of pneumococci (FIG. 11) and considered to be a novel synthetic vaccine candidate.

Flow Cytometry Analysis:

S. pneumoniae serotype 5 cells were stained as previously described with minor modifications (Khan et al; 2015, Clin Vaccine Immunol. 22(1):99-107). Briefly, mid-logarithmic phase ($A_{600}$=0.3-0.4) pneumococcal cells were harvested by centrifuging at 6000×g. Cells were washed with PBS (pH 7.4) and UV inactivated for 10 min. The cell inactivation was confirmed by plating on blood agar plats. The cells were blocked with 2% BSA prepared in PBS at room temperature for 30 min followed by incubation with preimmunre and hyperimmune pooled sera (n=3) (diluted 1:100) at room temperature for 1 hr. FITC-conjugated goat anti-rabbit IgG (Life Technologies, USA) diluted 1:200 dilution in 0.5% BSA-PBS) was used as the secondary antibody. The stained cells were analyzed by flow cytometry (BD Bioscience).

Example 84: In Vitro Opsonophagocytic Killing Assay opsonophagocytic killing assay was performed as described previously (Romero-Steiner et al., CLINICAL AND DIAGNOSTIC LABORATORY IMMUNOLOGY 1997, 415-422). Briefly, ~4×10⁵ cell/ml HL-60 cells were differentiated into HL-60 cells were differentiated into phagocytic cells by using 0.8% Dimethylformamide (DMF) for 5-6 days before performing the assay. After differentiation the cells were harvested and counted by using a haemocytometer and resuspended in opsonophagocytic buffer (HBSS with $Ca^{++}$ and $Mg^{++}$ and 0.1% gelatin) at a density of 1×10⁷ cells/ml. Serotype 5 strain (1000 cfu) in 20 μl of opsonophagocytic buffer were incubated with 10 μl of pooled (n=3) anti-SP-5 tetrasaccharide conjugate (58*c) polyclonal sera (day 35). Preimmune sera (day 0), anti-$CRM_{197}$ and anti-Prevnar 13® sera were used as positive and negative controls and bacteria were preopsonized for 15 min at 37° C. After preopsonization 8 μl of baby rabbit complement and 40 μl differentiated HL-60 cells (1:400 ratio) were added with antibody treated pneumococci for 45 min at 37° C. and 5% $CO_2$ with intermittent shaking. The viable extracellular pneumococci were determined by plating serial dilutions on TSA plates in triplicates. The mean of 3 independent experiments was plotted as percent killing relative to the 'no sera' control.

Anti-ST5 (Tetrasaccharide) Antibodies Augment Uptake of Pneumococci by HL-60 Cells Anti-ST5 (tetrasaccharide) may facilitate clearance of pneumococci by phagocytosis. We performed opsonophagocytic killing assay to assess the functional relevance of the antibodies induced in response to immunization with ST5 (tetrasaccharide) conjugate 58*c. Differentiated HL-60 cells were incubated with serotype 5 bacteria pre-opsonized with either anti-ST5 (tetrasaccharide) or preimmune sera. The killing of pneumococci was assessed by plating method as described in the Material and Methods. The relative percent killing value obtained for polyclonal antibody against ST5 (tetrasaccharide) was greater than 50% compared to the preimmune sera (FIG. 12). We observed some basal level of killing (~25%) with the preimmune sera. The anti-prevnar 13® rabbit sera were used as a positive control. The OPKA data demonstrates that ST5 (tetrasaccharide) conjugate (58*c) generate neutralizing antibodies and promote the killing of pneumococci by differentiated HL-60 cells.

The invention claimed is:

1. A saccharide of general formula (I)

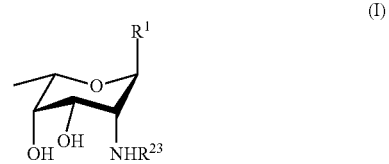

(I)

wherein
$R^1$ is selected from —$R^2$, —$R^4$,

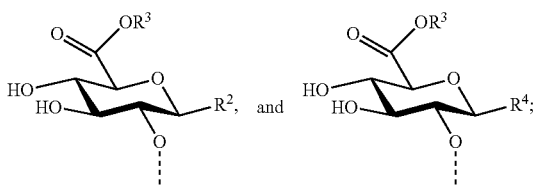

$R^2$ represents

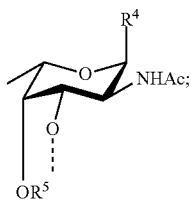

$R^3$ is selected from —H, —CH$_3$, —C$_2$H$_5$, —C$_3$H$_7$, —C$_4$H$_9$ and —CF$_3$;

$R^4$ represents $R^6$ or

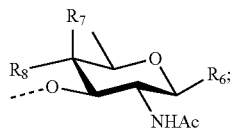

$R^5$ represents —H or

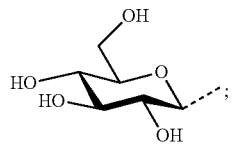

$R^6$ represents —O-L-NH$_2$;

$R^7$ and $R^8$ are independently of each other selected from —H and —OH and cannot be simultaneously —H;

$R^7$ and $R^8$ can form together with the carbon atom to which they are attached to a carbonyl group C=O;

$R^{23}$ is selected from —H, —C(O)CH$_3$, —C(O)CF$_3$ and —C(O)CCl$_3$;

-L- is selected from: —CH$_2$—, —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —(CH$_2$)$_9$—, —(CH$_2$)$_{10}$—, —CF$_2$—, —(CF$_2$)$_2$—, —(CF$_2$)$_3$—, —(CF$_2$)$_4$—, —(CF$_2$)$_5$—, —(CF$_2$)$_6$—, —(CF$_2$)$_7$—, —(CF$_2$)$_8$—, —(CF$_2$)$_9$—, —(CF$_2$)$_{10}$—, —(CH$_2$)$_2$—O—(CH$_2$)$_2$—, —CH$_2$—O—(CH$_2$)$_3$—, —(CH$_2$)$_3$—O—CH$_2$—, —CH$_2$—O—(CH$_2$)$_2$—, —(CH$_2$)$_2$—O—CH$_2$—, —(CH$_2$)$_3$—O—(CH$_2$)$_2$—, —(CH$_2$)$_2$—O—(CH$_2$)$_3$—, —(CH$_2$)$_4$—O—CH$_2$—, —CH$_2$—O—(CH$_2$)$_4$—, -L$^a$-, -L$^a$-L$^e$-, -L$^a$-L$^b$-L$^e$-, -L$^a$-L$^b$-L$^d$-L$^c$-L$^e$, -L$^a$-L$^d$-L$^e$;

wherein

-L$^a$- is selected from: —(CH$_2$)$_m$—, —(CF$_2$)$_m$—, —(CH$_2$—CH$_2$—O)$_m$—C$_2$H$_4$—, —(CH$_2$—CH$_2$—O)$_m$—CH$_2$—, —(CR$^{10}$R$^{11}$)$_m$—,

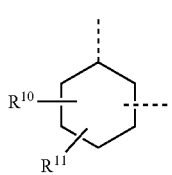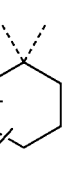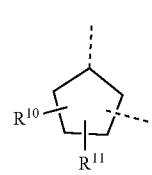

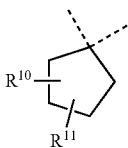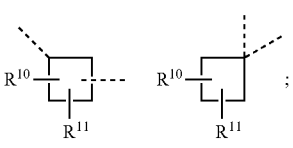

-L$^b$- and -L$^c$- are independently of each other selected from: —O—, —S—, —NH—C(O)—NH—, —NH—C(S)—NH—, —NH—C(O)—, —C(O)—NH—, —NH—C(O)—O—, —NR$^9$—, —NR$^{18}$—, —SO$_2$—,

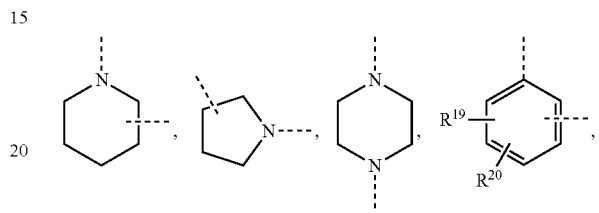

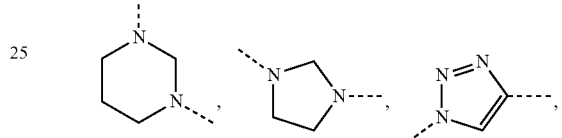

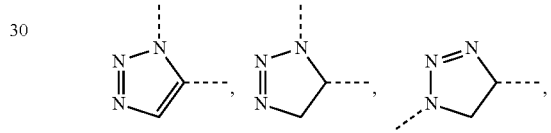

-L$^d$- represents —(CH$_2$)$_n$—, —(CF$_2$)$_n$—, —(CR$^{12}$R$^{13}$)$_n$—, —(CH$_2$—CH$_2$—O)$_n$—C$_2$H$_4$—, —(CH$_2$—CH$_2$—O)$_n$—CH$_2$—,

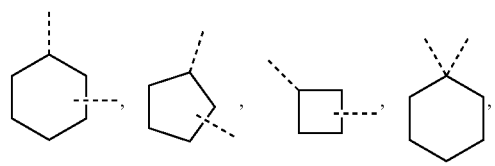

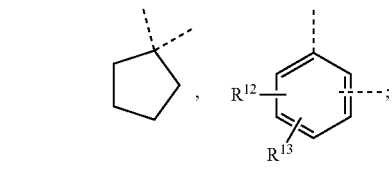

-L$^e$- is selected from: —(CH$_2$)$_{p1}$—, —(CF$_2$)$_{p1}$—, —C$_2$H$_4$—(O—CH$_2$—CH$_2$)$_{p1}$—, —CH$_2$—(O—CH$_2$—CH$_2$)$_{p1}$—, —(CH$_2$)$_{p1}$—O—(CH$_2$)$_{p2}$—, —(CH$_2$)$_{p1}$—S—(CH$_2$)$_{p2}$—, —(CR$^{14}$R$^{15}$)$_{p1}$—, —(CR$^{14}$R$^{15}$)$_{p1}$—O—(CR$^{21}$R$^{22}$)$_{p2}$—, —(CR$^{14}$R$^{15}$)$_{p1}$—S—(CR$^{21}$R$^{22}$)$_{p2}$—,

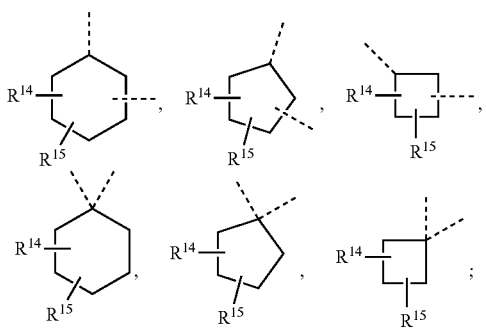

$R^9$ and $R^{18}$ are independently of each other selected from: —$CH_3$, —$C_2H_5$, —$C_3H_7$, and —C(O)$CH_3$;

$R^{10}$, $R^{11}$, $R^{12}$, $R^{13}$, $R^{14}$, $R^{15}$, $R^{16}$, $R^{17}$, $R^{19}$, $R^{20}$, $R^{21}$ and $R^{22}$ are independently of each other selected from: —H, —F, —Cl, —$CH_3$, —$C_2H_5$, —$C_3H_7$, —$C_5H_9$, —$C_6H_{13}$, —$OCH_3$, —$OC_2H_5$, —$CH_2F$, —$CHF_2$, —$CF_3$, —C(O)—$NH_2$, —$SCH_3$, —$SC_2H_5$, —NHC(O)$CH_3$, —N($CH_3$)$_2$ and —N($C_2H_5$)$_2$;

m, n, p1 and p2 are independently of each other an integer selected from 1, 2, 3, 4, 5, 6, 7, 8, 9, and 10;

and pharmaceutically acceptable salts thereof.

2. The saccharide according to claim 1, wherein $R^1$ represents

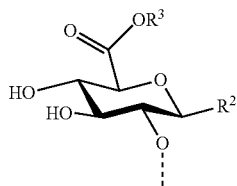

and $R^2$ and $R^3$ have the meanings as defined in claim 1.

3. The saccharide according to claim 1, wherein $R^4$ represents $R^6$.

4. The saccharide according to claim 1 of general formula (III)

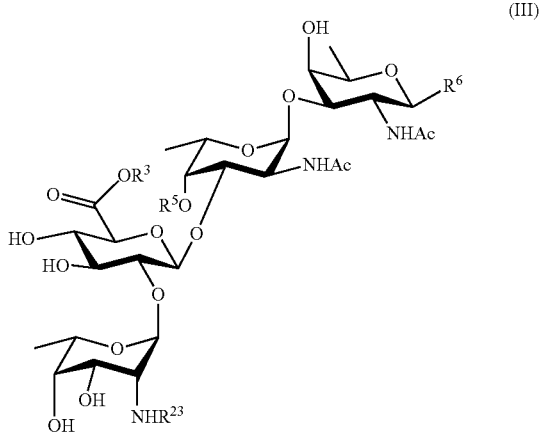

wherein $R^3$, $R^5$, $R^6$ and $R^{23}$ have the meanings as defined in claim 1.

5. The saccharide according to claim 1 of the formula 72

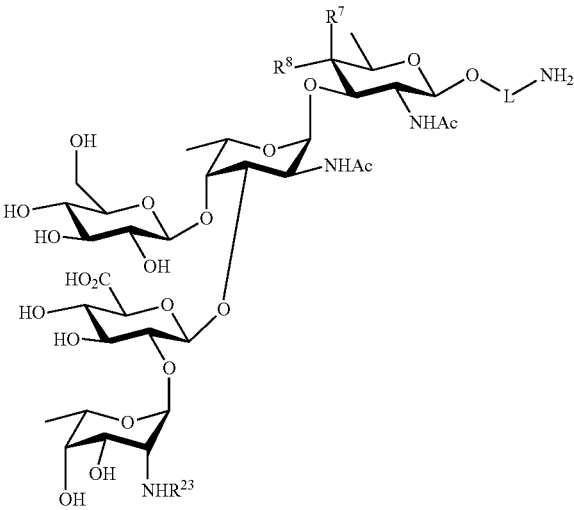

wherein L, $R^7$, $R^8$ and $R^{23}$ have the meanings as defined in claim 1.

6. The saccharide according to claim 1, wherein $R^3$ represents —H and $R^{23}$ represents —C(O)$CH_3$.

7. The saccharide according to claim 1 selected from the group consisting of:

5-amino-pentanyl 2-N-acetyl-α-L-pneumosaminopyranosyl-(1→2)-β-D-glucopyranosyluronate (27*), 5-amino-pentanyl 2-N-acetyl-α-L-pneumosaminopyranosyl-(1→2)-β-D-glucopyranosyluronate-(1→3)-2-N-acetyl-α-L-fucosaminopyranosyl-(1→3)-2-N-acetyl-β-D-fucosaminopyranoside (33*), 5-amino-pentanyl 2-N-acetyl-α-L-pneumosaminopyranosyl-(1→2)-β-D-glucopyranosyluronate-(1→3)-2-N-acetyl-α-L-fucosaminopyranosyl-(1→3)-[β-D-glucopyranosyl-(1→4)]-2-N-acetyl-β-D-fucosaminopyranoside (73*), 5-amino-pentanyl 2-N-acetyl-α-L-pneumosaminopyranosyl-(1→2)-β-DD-glucopyranosyluronate-(1→3)-2-N-acetyl-α-L-fucosaminopyranosyl-(1→3)-β-D-glucopyranosyl-(1→4)]-2-N-acetyl-3-D-quinovosaminopyranoside (85*), and 5-amino-pentanyl 2-N-acetyl-α-L-pneumosaminopyranosyl-(1→2)-β-D-glucopyranosyluronate-(1→3)-2-N-acetyl-α-L-fucosaminopyranosyl-(1→3)-[β-D-glucopyranosyl-(1→4)]-2-acetamido-2,5-dideoxy-β-D-xylo-hexos-4-uloside (88*).

8. An intermediate compound of formula (IX), 36, 41, 63, 68*, 70 or 70a:

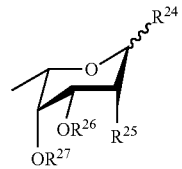

wherein
$R^{24}$ is selected from

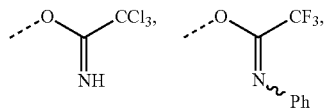

—F, —Cl, —Br, —I, —$SR^{28}$, —$SeR^{29}$, —$OPO_3R^{30}{}_2$;

$R^{25}$ is selected from —$N_3$, -NBn$_2$, -NBnCbz;
$R^{26}$ and $R^{27}$ are independently of each other selected from —H, -Bn,

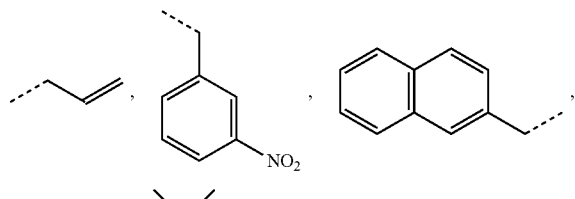

Si(CH$_3$)$_3$, —Si(CH$_2$CH$_3$)$_3$, —C(O)CH$_3$, —C(O)Ph,

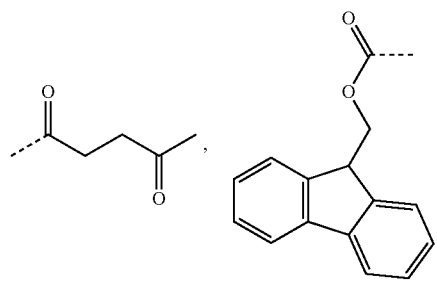

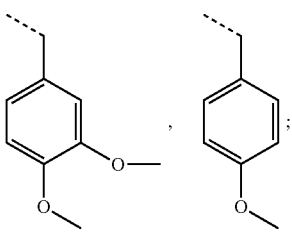

or $R^{26}$ and $R^{27}$ can form together

$R^{28}$ is selected from: —CH$_3$, —CH$_2$CH$_3$, -Ph,

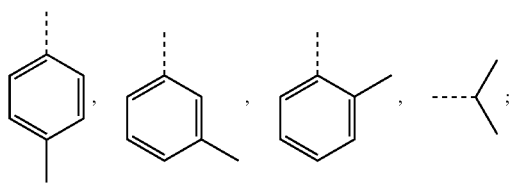

$R^{29}$ represents -Ph;
$R^{30}$ represents —CH$_2$CH$_2$CH$_2$CH$_3$;

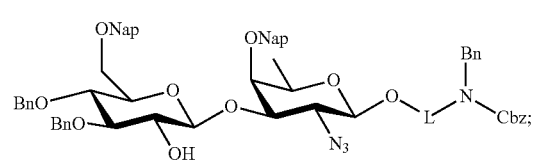

wherein L has the meanings as defined in claim 1;

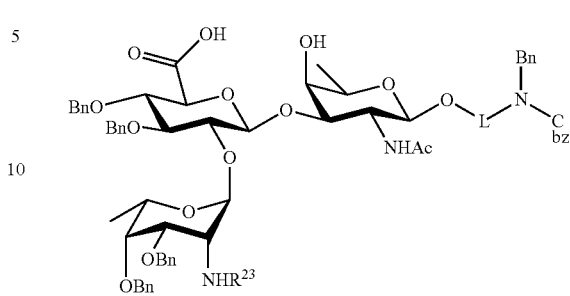

wherein L and $R^{23}$ have the meanings as defined in claim 1;

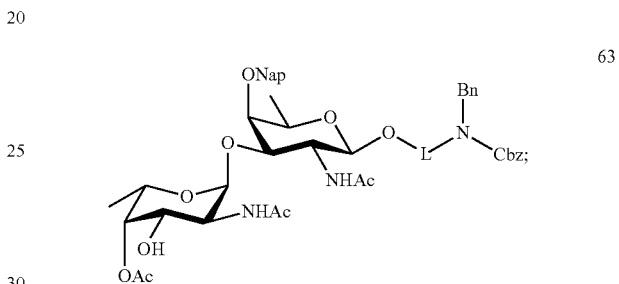

wherein L has the meanings as defined in claim 1;

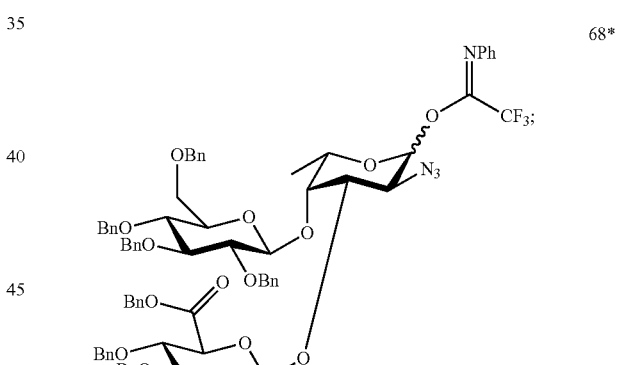

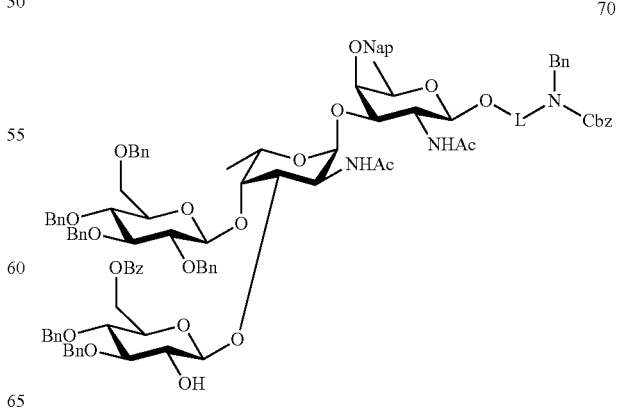

wherein L has the meanings as defined in claim 1;

or

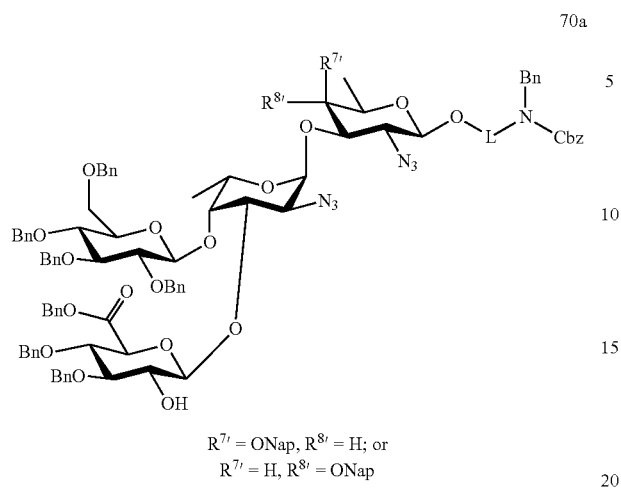

70a $R^{7\prime}$ = ONap, $R^{8\prime}$ = H; or
$R^{7\prime}$ = H, $R^{8\prime}$ = ONap wherein L has the meanings as defined in claim 1.

9. The intermediate according to claim 8 is selected from the group consisting of the saccharides 36, 41, 63, 70, 70a, wherein L is —$C_5H_{10}$— and/or $R^{23}$ is $CH_3CO$—.

10. A conjugate comprising the saccharide according to claim 1.

11. The conjugate according to claim 10 selected from the group consisting of the conjugates of the formulae (X), (XI) and (XII):

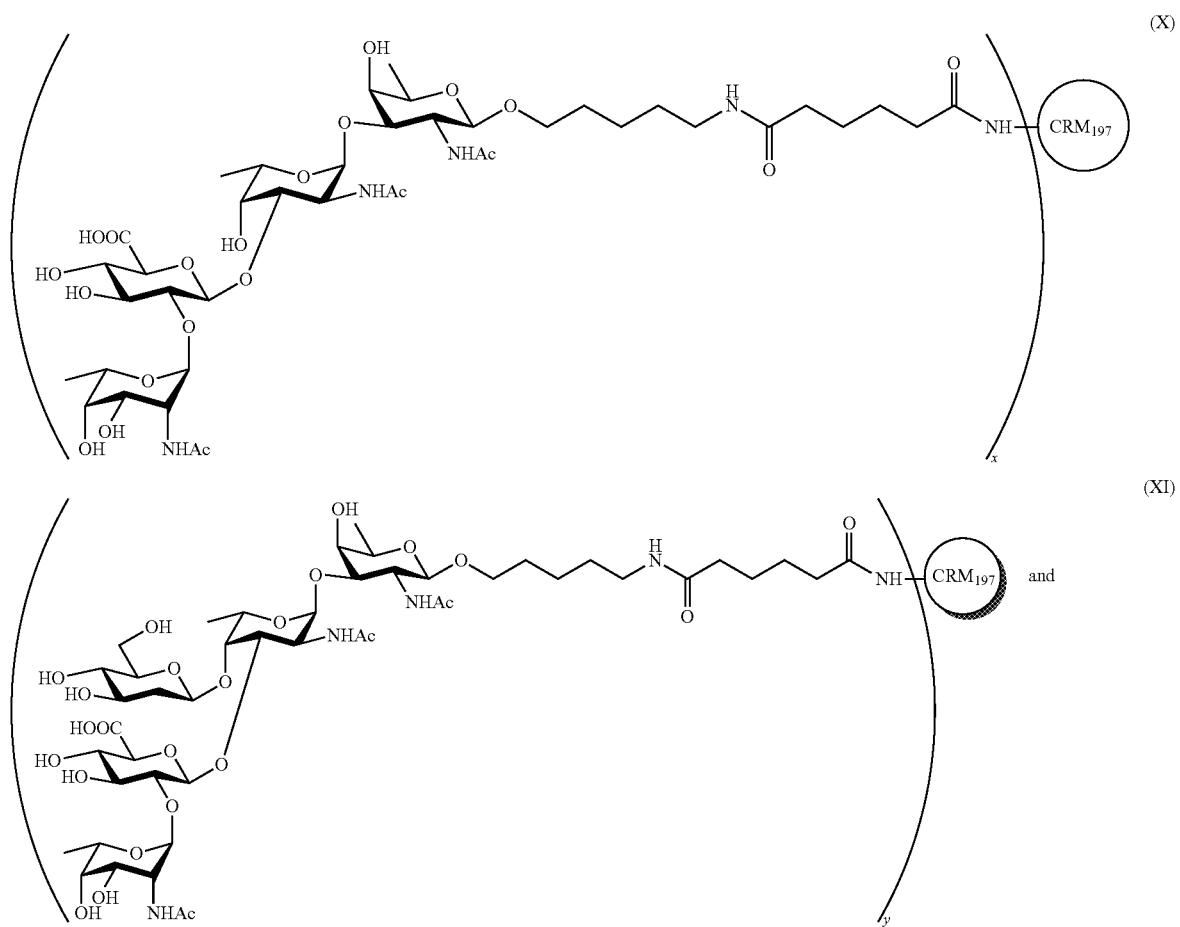

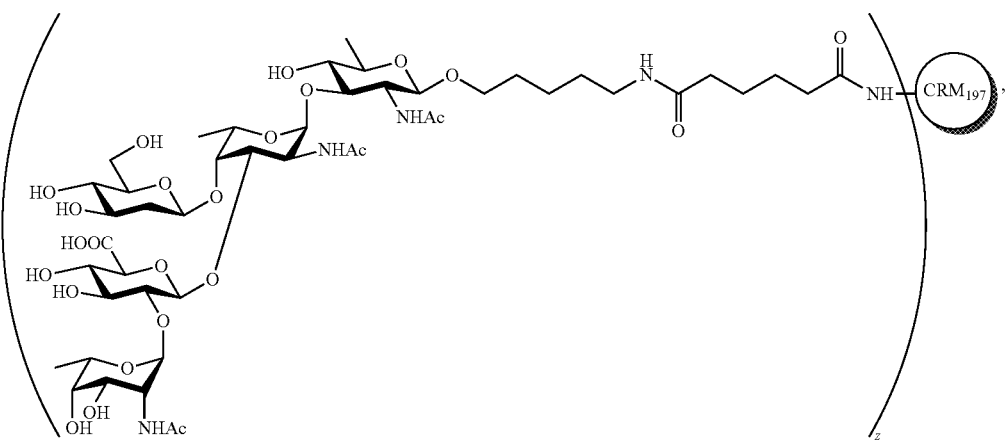
(XII)
wherein x, y and z are independently integer from 1 to 20.
12. The conjugate according to claim 10 selected from the group consisting of 58*a, 58*b, 58*c and 87*:
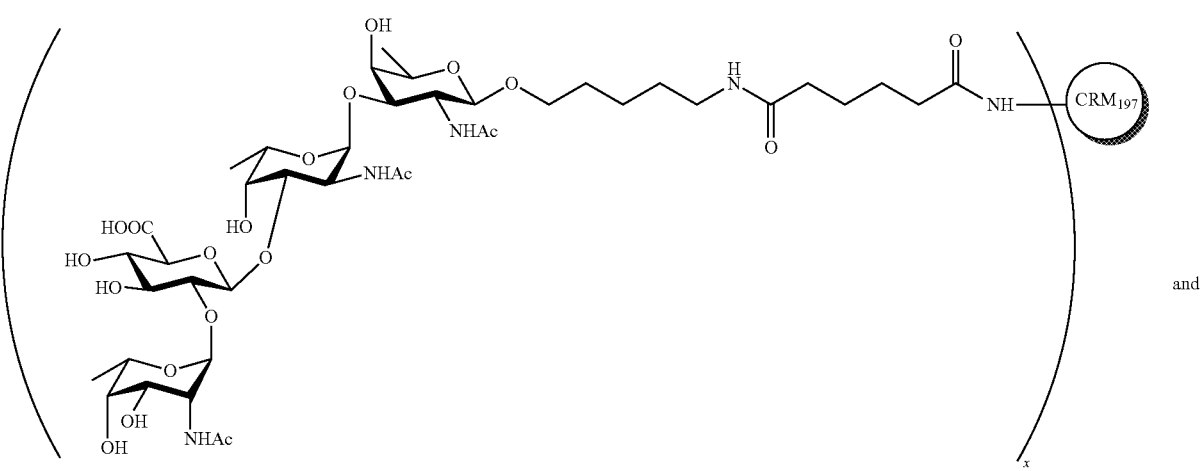
58*a, x = 7
58*b, x = 8
58*c, x = 11.2
87*
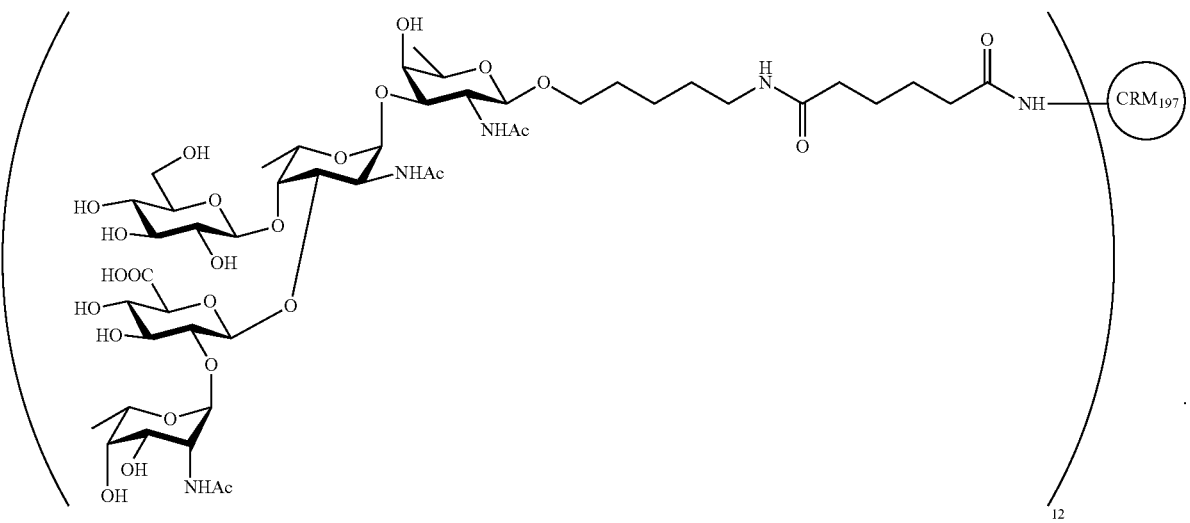

13. A method for raising a protective immune response in a human or animal host comprising administering to the human or animal host a saccharide according to claim 1 or a conjugate comprising the saccharide.

14. A method for prevention and/or treatment of diseases associated with bacteria containing N-acetyl-L-pneumosamine in their capsular polysaccharide comprising administering to a patient a saccharide according to claim 1 or a conjugate comprising the saccharide.

15. The method according to claim 14, wherein the bacteria is *Streptococcus pneumoniae* serotype 5.

16. The method according to claim 14, wherein the diseases associated with the bacteria are selected from pneumonia, meningitis, otitis media, bacteremia and acute exacerbation of chronic bronchitis, sinusitis, arthritis and conjunctivitis.

17. A pharmaceutical composition comprising the conjugate according to claim 10 together with at least one pharmaceutically acceptable cryoprotectant, lyoprotectant, excipient and/or diluent.

18. The pharmaceutical composition according to claim 17 further comprising at least one of antigens of other *Streptococcus pneumoniae* serotypes.

19. An immunological assays comprising a saccharide of claim 1 conjugated to a solid support, wherein the assay is configured for detection of antibodies against bacteria containing N-acetyl-L-pneumosamine in their capsular polysaccharide.

20. A pharmaceutical composition comprising the saccharide according claim 1 together with at least one pharmaceutically acceptable cryoprotectant, lyoprotectant, excipient and/or diluent.

21. The saccharide according to claim 1, wherein the linker -L- represents —$(CH_2)_m$—, wherein m is an integer selected from 1, 2, 3, 4, 5, 6, 7, 8, 9, and 10.

* * * * *